US008633353B2

(12) United States Patent
Ratcliffe et al.

(10) Patent No.: US 8,633,353 B2
(45) Date of Patent: Jan. 21, 2014

(54) PLANTS WITH IMPROVED WATER DEFICIT AND COLD TOLERANCE

(75) Inventors: Oliver J. Ratcliffe, Oakland, CA (US); Jacqueline Heard, Webster Groves, MO (US); Roderick W. Kumimoto, Norman, OK (US); Peter P. Repetti, Emeryville, CA (US); T. Lynne Reuber, San Mateo, CA (US); Robert Creelman, Castro Valley, CA (US); Frederick D. Hempel, Sunol, CA (US); Neal L. Gutterson, Oakland, CA (US); Roger Canales, Bernburg (DE)

(73) Assignee: Mendel Biotechnology, Inc., Hayward, CA (US)

( * ) Notice: Subject to any disclaimer, the term of this patent is extended or adjusted under 35 U.S.C. 154(b) by 753 days.

(21) Appl. No.: 11/981,813

(22) Filed: Oct. 30, 2007

(65) Prior Publication Data

US 2008/0163397 A1   Jul. 3, 2008

Related U.S. Application Data

(60) Continuation-in-part of application No. 10/675,852, filed on Sep. 30, 2003, now abandoned, and a continuation-in-part of application No. 11/479,226, filed on Jun. 30, 2006, now Pat. No. 7,858,848, and a continuation-in-part of application No. 11/725,235, filed on Mar. 16, 2007, now Pat. No. 7,601,893, and a continuation-in-part of application No. 11/728,567, filed on Mar. 26, 2007, now Pat. No. 7,635,800, and a continuation-in-part of application No. 11/069,255, filed on Feb. 28, 2005, now Pat. No. 8,558,059, and a continuation-in-part of application No. 10/374,780, filed on Feb. 25, 2003, now Pat. No. 7,511,190, and a continuation-in-part of application No. 10/546,266, filed as application No. PCT/US2004/005654 on Feb. 25, 2004, now Pat. No. 7,659,446, which is a continuation-in-part of application No. 10/374,780, and a continuation-in-part of application No. 10/675,852, application No. 11/981,813, which is a continuation-in-part of application No. 10/412,699, filed on Apr. 10, 2003, now Pat. No. 7,345,217, which is a continuation-in-part of application No. 10/374,780, application No. 11/981,813, which is a continuation-in-part of application No. 11/642,814, filed on Dec. 20, 2006, now Pat. No. 7,825,296, which is a division of application No. 10/666,642, filed on Sep. 18, 2003, now Pat. No. 7,196,245, application No. 11/981,813, which is a continuation-in-part of application No. 10/714,887, filed on Nov. 13, 2003, now abandoned, which is a continuation-in-part of application No. 10/666,642, application No. 11/981,813, which is a continuation-in-part of application No. 11/435,388, filed on May 15, 2006, now Pat. No. 7,663,025, which is a continuation-in-part of application No. PCT/US2004/037584, filed on Nov. 12, 2004, which is a continuation-in-part of application No. 10/714,887, application No. 11/981,813, which is a continuation-in-part of application No. PCT/US2006/034615, filed on Aug. 31, 2006, and a continuation-in-part of application No. 11/705,903, filed on Feb. 12, 2007, now Pat. No. 7,868,229, which is a continuation-in-part of application No. PCT/US2006/034615.

(60) Provisional application No. 60/961,403, filed on Jul. 20, 2007, provisional application No. 60/713,952, filed on Aug. 31, 2005.

(51) Int. Cl.
*A01H 1/00* (2006.01)

(52) U.S. Cl.
USPC ............ 800/278; 800/287; 800/289; 800/290

(58) Field of Classification Search
None
See application file for complete search history.

(56) References Cited

U.S. PATENT DOCUMENTS

| 6,121,513 | A  | 9/2000  | Zhang et al.     |
|-----------|----|---------|------------------|
| 6,235,975 | B1 | 5/2001  | Harada et al.    |
| 6,320,102 | B1 | 11/2001 | Harada et al.    |
| 6,476,212 | B1 | 11/2002 | Lalgudi et al.   |
| 6,495,742 | B1 | 12/2002 | Shinozaki et al. |
| 6,545,201 | B1 | 4/2003  | Harada et al.    |
| 6,664,446 | B2 | 12/2003 | Heard et al.     |

(Continued)

FOREIGN PATENT DOCUMENTS

| AR | PO70102784 | 1/2008  |
|----|------------|---------|
| CA | 2302828    | 10/2000 |

(Continued)

OTHER PUBLICATIONS

Bowie et al, Science 247:1306-1310, 1990.*

(Continued)

*Primary Examiner* — Stuart F Baum
(74) *Attorney, Agent, or Firm* — Jeffrey M. Libby; Yifan Mao

(57) ABSTRACT

The present invention provides nucleic acid constructs, including plasmids, expression vectors or expression cassettes comprising polynucleotides encoding CCAAT-binding transcription factor polypeptides that have the ability to increase a plant's tolerance to abiotic stress. Polynucleotides encoding functional CCAAT-binding transcription factors were incorporated into expression vectors, introduced into plants, and ectopically expressed. The encoded polypeptides of the invention significantly increased the cold and water deficit tolerance of the transgenic plants, as compared to tolerance to these stresses of control plants.

22 Claims, 5 Drawing Sheets

(56) References Cited

U.S. PATENT DOCUMENTS

Figure 1:
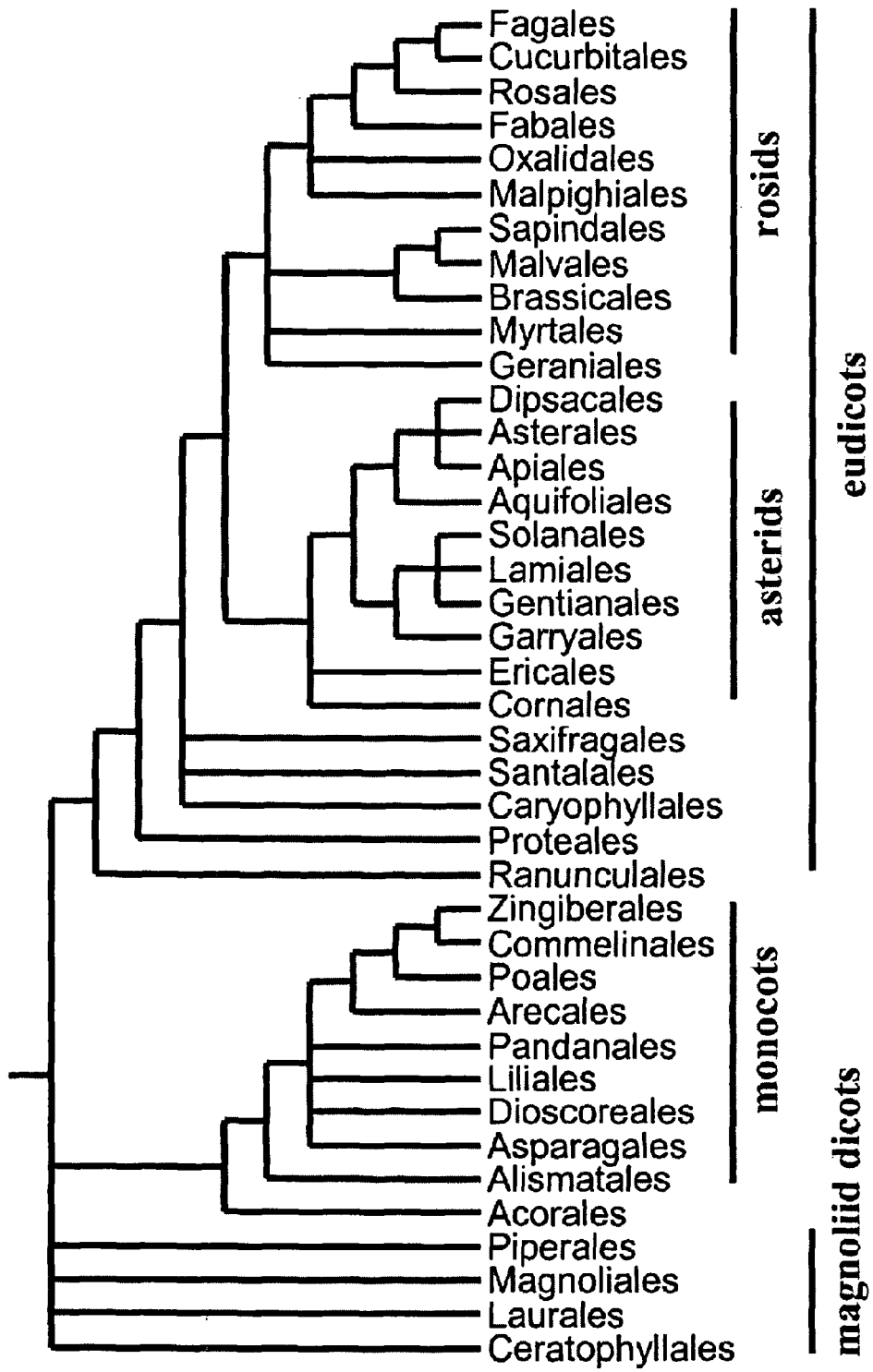

| | | |
|---|---|---|
| 6,677,504 B2 | 1/2004 | da Costa e Silva et al. |
| 6,706,866 B1 | 3/2004 | Thomashow et al. |
| 6,717,034 B2 | 4/2004 | Jiang et al. |
| 6,781,035 B1 | 8/2004 | Harada et al. |
| 6,825,397 B1 | 11/2004 | Lowe et al. |
| 6,835,540 B2 | 12/2004 | Broun et al |
| 6,946,586 B1 | 9/2005 | Fromm et al. |
| 7,109,393 B2 | 9/2006 | Gutterson et al. |
| 7,135,616 B2 | 11/2006 | Heard et al. |
| 7,193,129 B2 | 3/2007 | Reuber et al. |
| 7,196,245 B2 | 3/2007 | Jiang et al. |
| 7,223,904 B2 | 5/2007 | Heard et al. |
| 7,238,860 B2 | 7/2007 | Ratcliffe et al. |
| 7,345,217 B2 | 3/2008 | Zhang et al. |
| 7,511,190 B2 | 3/2009 | Sherman et al. |
| 7,598,429 B2 | 10/2009 | Heard et al. |
| 7,601,893 B2 | 10/2009 | Reuber et al. |
| 7,635,800 B2 | 12/2009 | Ratcliffe et al. |
| 7,659,446 B2 | 2/2010 | Sherman et al. |
| 7,663,025 B2 | 2/2010 | Heard et al. |
| 7,692,067 B2 | 4/2010 | Creelman et al. |
| 2001/0051335 A1 | 12/2001 | Lalgudi et al. |
| 2002/0023281 A1 | 2/2002 | Gorlach et al. |
| 2002/0040489 A1 | 4/2002 | Gorlach et al. |
| 2003/0041356 A1 | 2/2003 | Reuber et al. |
| 2003/0061637 A1 | 3/2003 | Jiang et al. |
| 2003/0093837 A1 | 5/2003 | Keddie |
| 2003/0101481 A1 | 5/2003 | Zhang et al. |
| 2003/0121070 A1 | 6/2003 | Adam et al. |
| 2003/0126638 A1 | 7/2003 | Allen et al. |
| 2003/0131386 A1 | 7/2003 | Samaha et al. |
| 2003/0188330 A1 | 10/2003 | Heard |
| 2004/0009476 A9 | 1/2004 | Harper et al. |
| 2004/0016022 A1 | 1/2004 | Lowe et al. |
| 2004/0019927 A1 | 1/2004 | Sherman et al. |
| 2004/0031072 A1 | 2/2004 | La Rosa et al. |
| 2004/0034888 A1 | 2/2004 | Liu et al. |
| 2004/0098764 A1 | 5/2004 | Heard et al. |
| 2004/0123338 A1 | 6/2004 | Fincher et al. |
| 2004/0123339 A1 | 6/2004 | Conner et al. |
| 2004/0123343 A1 | 6/2004 | La Rosa et al. |
| 2004/0128712 A1 | 7/2004 | Jiang et al. |
| 2004/0172684 A1 | 9/2004 | Kovalic et al. |
| 2004/0181830 A1 | 9/2004 | Kovalic et al. |
| 2004/0214272 A1 | 10/2004 | La Rosa et al. |
| 2004/0216190 A1 | 10/2004 | Kovalic et al. |
| 2004/0229367 A1 | 11/2004 | Berka et al. |
| 2004/0259145 A1 | 12/2004 | Wood et al. |
| 2005/0022266 A1 | 1/2005 | Wu |
| 2005/0086718 A1 | 4/2005 | Heard et al. |
| 2005/0097638 A1 | 5/2005 | Jiang et al. |
| 2005/0155117 A1 | 7/2005 | Century et al. |
| 2005/0172364 A1 | 8/2005 | Heard et al. |
| 2006/0008874 A1 | 1/2006 | Creelman et al. |
| 2006/0015972 A1 | 1/2006 | Heard et al. |
| 2006/0162018 A1 | 7/2006 | Gutterson et al. |
| 2007/0022495 A1 | 1/2007 | Reuber et al. |
| 2007/0101454 A1 | 5/2007 | Jiang et al. |
| 2007/0184092 A1 | 8/2007 | Meyer et al. |
| 2007/0199107 A1 | 8/2007 | Ratcliffe et al. |
| 2007/0226839 A1 | 9/2007 | Gutterson et al. |
| 2008/0040973 A1 | 2/2008 | Nelson et al. |
| 2008/0104730 A1* | 5/2008 | Wu et al. ................ 800/278 |
| 2008/0155706 A1 | 6/2008 | Riechmann et al. |
| 2008/0172759 A1 | 7/2008 | da Costa e Silva et al. |
| 2008/0229448 A1 | 9/2008 | Libby et al. |
| 2008/0301836 A1 | 12/2008 | Century et al. |
| 2008/0301840 A1 | 12/2008 | Gutterson et al. |
| 2008/0301841 A1 | 12/2008 | Ratcliffe et al. |
| 2008/0313756 A1 | 12/2008 | Zhang et al. |
| 2009/0044297 A1 | 2/2009 | Andersen et al. |
| 2009/0049566 A1 | 2/2009 | Zhang et al. |
| 2009/0049573 A1 | 2/2009 | Dotson |
| 2009/0138981 A1 | 5/2009 | Repetti et al. |
| 2009/0151015 A1 | 6/2009 | Adam et al. |
| 2009/0183270 A1 | 7/2009 | Adams |
| 2009/0192305 A1 | 7/2009 | Riechmann et al. |
| 2009/0205063 A1 | 8/2009 | Zhang et al. |
| 2009/0265807 A1 | 10/2009 | Kumimoto et al. |
| 2009/0265813 A1 | 10/2009 | Gutterson et al. |
| 2009/0276912 A1 | 11/2009 | Sherman et al. |
| 2010/0071086 A1 | 3/2010 | Repetti et al. |
| 2010/0083395 A1 | 4/2010 | Reuber et al. |
| 2010/0083402 A1 | 4/2010 | Heard et al. |
| 2010/0107279 A1 | 4/2010 | Ratcliffe et al. |
| 2010/0162427 A1 | 6/2010 | Riechmann et al. |
| 2010/0175145 A1 | 7/2010 | Heard et al. |
| 2010/0186105 A1 | 7/2010 | Creelman et al. |
| 2010/0186106 A1 | 7/2010 | Creelman et al. |
| 2010/0192249 A1 | 7/2010 | Creelman et al. |
| 2010/0223689 A1 | 9/2010 | Creelman et al. |
| 2010/0281565 A1 | 11/2010 | Engler et al. |

FOREIGN PATENT DOCUMENTS

| | | |
|---|---|---|
| CL | 185107 | 2/2008 |
| DE | 19503359 | 2/1996 |
| EP | 1 033 405 | 9/2000 |
| EP | 1230345 | 8/2002 |
| EP | 1 420 630 | 2/2003 |
| EP | 1420630 | 2/2003 |
| EP | 1454993 | 9/2004 |
| EP | 1601758 | 9/2004 |
| EP | 0803572 | 10/2007 |
| GB | 2244272 | 11/1991 |
| GB | 2392444 | 3/2004 |
| WO | WO 98/37184 | 8/1998 |
| WO | WO 98/37755 | 9/1998 |
| WO | WO 98/58069 | 12/1998 |
| WO | WO 99/53016 A2 | 10/1999 |
| WO | WO 99/67405 | 12/1999 |
| WO | WO 00/28058 | 5/2000 |
| WO | WO 00/53724 A2 | 9/2000 |
| WO | WO 01/36598 A1 | 5/2001 |
| WO | WO 01/45493 A2 | 6/2001 |
| WO | WO 01/64022 | 9/2001 |
| WO | WO 01/77311 | 10/2001 |
| WO | WO 02/06499 | 1/2002 |
| WO | WO 02/16655 | 2/2002 |
| WO | WO 02/46442 | 6/2002 |
| WO | WO 02/057439 A2 | 7/2002 |
| WO | WO 02/079245 A2 | 10/2002 |
| WO | WO 03/000898 | 1/2003 |
| WO | WO 03/001902 | 1/2003 |
| WO | WO 03/002751 | 1/2003 |
| WO | WO 03/008540 | 1/2003 |
| WO | WO 03/014327 A2 | 2/2003 |
| WO | WO 03/020936 | 3/2003 |
| WO | WO 03/083042 | 10/2003 |
| WO | WO 2004/009820 | 1/2004 |
| WO | WO 2004/031349 A2 | 4/2004 |
| WO | WO 2004/076638 A2 | 9/2004 |
| WO | WO 2004/079006 | 9/2004 |
| WO | WO 2005/001050 | 1/2005 |
| WO | WO2005/033319 A2 | 4/2005 |
| WO | WO 2008/002480 A2 | 1/2008 |

OTHER PUBLICATIONS

McConnell et al, Nature 411 (6838):709-713, 2001.*
U.S. Appl. No. 09/533,030, filed Mar. 22, 2000, Keddie, James, et al.
U.S. Appl. No. 10/286,264, Jun. 25, 2008, Keddie, James, et al., office action.
U.S. Appl. No. 10/286,264, Mar. 10, 2009, Keddie, James, et al., office action.
U.S. Appl. No. 10/286,264, Aug. 11, 2006, Keddie, James, et al., office action.
U.S. Appl. No. 10/286,264, Oct. 7, 2005, Keddie, James, et al., office action.
U.S. Appl. No. 10/286,264, Jul. 26, 2007, Keddie, James, et al., office action.
U.S. Appl. No. 10/675,852, Apr. 14, 2008, Heard, J., et al., office action.

(56) References Cited

OTHER PUBLICATIONS

U.S. Appl. No. 11/069,255, Nov. 26, 2008, Heard, J., et al., office action.
U.S. Appl. No. 11/069,255, Mar. 19, 2008, Heard, J., et al., office action.
U.S. Appl. No. 11/069,255, Mar. 21, 2007, Heard, J., et al., office action.
U.S. Appl. No. 10/112,887, Sep. 28, 2004, Heard, J., et al., office action.
U.S. Appl. No. 09/533,030, Nov. 23, 2001, Keddie, James et al., office action.
U.S. Appl. No. 09/533,030, May 3, 2002, Keddie, James et al., office action.
U.S. Appl. No. 10/675,852, Feb. 25, 2009, Heard, J., et al., office action.
Asamizu, E., et al. (Apr. 28, 2000). Generation of 7137 non-redundant expressed sequence tags from a legume, Lotus japonicus. DNA Res. 7 (2), 127-130.
Bucher, P., and Trifonov, E.N. (Jun. 1988). CCAAT box revisited: bidirectionality, location and context. J Biomol Struct Dyn 5, 1231-1236.
Bucher, P. (Apr. 20, 1990). Weight matrix descriptions of four eukaryotic RNA polymerase II promoter elements derived from 502 unrelated promoter sequences. J Mol Biol 212, 563-578.
Chae, H.D., et al. (May 20, 2004). Cdk2-dependent phosphorylation of the NF-Y transcription factor is essential for the expression of the cell cycle-regulatory genes and cell cycle G1/S and G2/M transitions. Oncogene 23, 4084-4088.
Clarke, B., et al. (Mar. 2003). Arabidopsis genomic information for interpreting wheat EST sequences. Funct. Integr. Genomics 3 (1-2), 33-38.
Gelinas, R., et al. (Jan. 1985). Sequences of G gamma, A gamma, and beta genes of the Greek (A gamma) HPFH mutant: evidence for a distal CCAAT box mutation in the A gamma gene. Prog Clin Biol Res 191, 125-139.
Good, L.F., and Chen, K.Y. (May 1996). Cell cycle- and age-dependent transcriptional regulation of human thymidine kinase gene: the role of NF-Y in the CBP/tk binding complex. Biol Signals 5, 163-169.
Hiei, Y., et al. Efficient transformation of rice (Oryza sativa L.) mediated by Agrobacterium and sequence analysis of the boundaries of the T-DNA. Plant J. Aug. 1994; 6(2); 271-282.
Ito, T., et al. (Oct. 1995). A far-upstream sequence of the wheat histone H3 promoter functions differently in rice and tobacco cultured cells. Plant Cell Physiol 36, 1281-1289.
Johnson, P.F., and McKnight, S.L. (Jul. 1989). Eukaryotic transcriptional regulatory proteins. Annu Rev Biochem 58 799-839.
Jones, P.G., et al. (epub Nov. 26, 2002). Gene discovery and microarray analysis of cacao varieties. Planta 216 (2), 255-264.
Maity, S.N., and de Crombrugghe, B. (May 1998). Role of the CCAAT-binding protein CBF/NF-Y in transcription. Trends Biochem Sci 23, 174-178.
Mazon, M.J., Gancedo, J.M., and Gancedo, C. (Oct. 1982). Phosphorylation and inactivation of yeast fructose-bisphosphatase in vivo by glucose and by proton ionophores. A possible role for cAMP. Eur J Biochem 127, 605-608.
McNabb, D.S., Xing, Y., and Guarente, L. (Jan. 1995). Cloning of yeast HAP5: a novel subunit of a heterotrimeric complex required for CCAAT binding. Genes Dev 9, 47-58.
Olesen, J.T., and Guarente, L. (Oct. 1990). The HAP2 subunit of yeast CCAAT transcriptional activator contains adjacent domains for subunit association and DNA recognition: model for the HAP2/3/4 complex. Genes Dev 4, 1714-1729.
Rieping, M., and Schöffl, F. (Jan. 1992). Synergistic effect of upstream sequences, CCAAT box elements, and HSE sequences for enhanced expression of chimaeric heat shock genes in transgenic tobacco. Mol Gen Genet 231, 226-232.
Edwards, D., et al. (1998). Multiple genes encoding the conserved CCAAT-Box transcription factor complex are expressed in Arabidopsis. Plant Physiol. 117, pp. 1015-1022.
Edwards, et al. (1997). Arabidopsis thaliana mRNA for Hap3b transcription factor. GenBank Accession No. Y13724.
Gusmaroli (2002). Regulation of the Arabidopsis thaliana CCAAT-binding nuclear factor Y subunits. Gene 283, 41-48.
Gusmaroli, et al. (2001). Regulation of the CCAAT-Binding NF-Y subunits in Arabidopsis thaliana. Gene 264, 173-185.
Riechmann, et al. (2000). Arabidopsis transcription factors: genome-wide comparative analysis among eukaryotes. Science 290, 2105-2110.
Mantovani (Oct. 18, 1999). The molecular biology of the CCAAT-binding factor. Gene 239, 15-27.
Li, et al. (1999). Transcription factor NF-Y, CCAAT-binding chain B-maize, NCBI Sequence S22820.
Li, et al. (Mar. 1992). Evolutionary variation of the CCAAT-binding transcription factor NF-Y. Nucl. Acids Res. 20, 1087-1091.
Guo, et al. (2004). "Protein tolerance to random amino acid change". Proc. Natl. Acad. Sci. USA 101, 9205-9210.
Smolen, et al. (2002). Dominant Alleles of the basic Helix-Loop Helix Transcription Factor ATR2 Activate Stress-Responsive Genes in Arabidopsis. Gen vol. 161, pp. 1235-1246.
Liu, Q., et al. (1998). Two transcription factors, DREB1 and DREB2, with an EREBP/AP2 DNA binding domain separate two cellular signal . . . Plant Cell, vol. 10, pp. 1391-1406.
Fourgoux-Nicol, et al. (1999). Isolation of rapeseed genes expressed early and specifically during development of the male gametophyte. Plant Mol Biol 40, 857-872.
Eisen, et al. (1998). "Phylogenomics: Improving Functional Predictions for Uncharacterized Genes by Evolutionary Analysis". Genome Research 8, 163-167.
Rossini, et al. The maize golden2 gene defines a novel class of transcriptional regulators in plants. The Plant Cell vol. 13, May 2001, pp. 1231-1244, XP002962733.
Hill, et al. (1998). Functional analysis of conserved histidines in ADP glucose pyrophosphorylase from Escherichia coli. Biochem. Biophys. Res. Comm. 244, 573-577.
Rounsley, S.D., et al. (Aug. 1997) Database Embl, Arabidopsis thaliana chromosome II BAC T13E15 genomic seq, complete seq. XP002303794. Acc No. AC002388. Positions 57340-58040.
Rounsley, S.D., et al. (2000). Database EMBL Sep. 12, 1997. "Arabidopsis thaliana mRNA for Hap3a.." XP002315220 retrieved from EBI acc No. EM_PRO:ATHAP3A, acc No. Y13723.
Ohme-Takagi, M. and Singh, K. (Feb 1995) "Ethylene-inducible DNA binding proteins that interact with an . . . " Plant Cell, vol. 7, pp. 173-182, XP002108954. *Figs 5, 6*.
Buttner, M. and Singh, K. (May 27, 1997) "Arabidopsis thaliana ethylene-responsive.." Proc of the Natl Acad of Sciences, vol. 94, pp. 5961-5966, XP002108953.
Winicov, I. (Dec. 1998 ) "New molecular approaches to improving salt tolerance in crop plants." Annals of Botany, ACAD Press, vol. 82, No. 6, pp. 705-710, XP001007288.
Urao, T., et al. (Nov. 1993) "An Arabidopsis MYB homolog is induced by dehydration stress and its gene product binds to . . . " Plant Cell, vol. 5, pp. 1529-1539, XP002938159.
Kasuga Mie, et al. (Mar. 1999) "Improving plant drought, salt, and freezing tolerance by gene.." Nature Biotechnol vol. 17, No. 3, pp. 287-291, XP002173128.
Kaneko, t., et al. (Mar. 1, 2001) database trembl seq lib ebi, hinxton; "transcription factor hap5a-like (at5g50480) . . . " xp002302644 www.ebi.ac.UK Database accession No. Q9FGP7.
Kaneko, T., et al. (Apr. 9, 1999) EMBL SEQ LIB EBI, Hinxton;"Structural analysis of Arabidopsis thaliana chromosome 5. XL.; P1 clone : MBA10" www.EBI.AC.UK acc. No. AB025619.
Lotan, Tamar, et al. (Jun. 26, 1998). "Arabidopsis Leafy COTYLEDON1 is sufficient to induce embryo . . . " Cell, Cell Press, vol. 93, No. 7, pp. 1195-1205, XP002136428.
Albani, Diego et al., (Dec. 29, 1995) Cloning and characterization of a Brassica napus gene encoding a homologue of the B subunit of a heteromeric CCAAT-binding factor, Gene 167, pp. 209-213.
Arents, G., and Moudrianakis, E.N. (Nov. 21,1995). The histone fold: a ubiquitous architectural motif utilized in DNA compaction and protein dimerization. Proc Natl Acad Sci U S A 92, 11170-11174.

(56) References Cited

OTHER PUBLICATIONS

Caretti G, Motta MC, Mantovani R (Dec. 1999) NF-Y associates with H3-H4 tetramers and octamers by multiple mechanisms. Mol Cell Biol 19: 8591-8603.

Caretti, G., Salsi, V., Vecchi, C. Imbriano, C., and Mantovani, R. (Aug. 15, 2003). Dynamic recruitment of NF-Y and histone acetyltransferases on cell-cycle promoters. J Biol Chem 278, 30435-30440.

Cane, I.A., and Kay, S.A. (Dec. 1995). Multiple DNA-Protein complexes at a circadian-regulated promoter element. Plant Cell 7, 2039-2051.

Chattopadhyay C, et al. (Jul. 8, 2004) Human p32, interacts with B subunit of the CCAAT-binding factor, CBF/NF-Y, and inhibits CBF-mediated transcription activation in vitro. Nucleic Acids Res 32: 3632-3641.

Chang, Z.F., and Liu, C.J. (Jul. 8, 1994). Human thymidine kinase CCAAT-binding protein is NF-Y, whose A subunit expression is serum-dependent in human IMR-90 diploid fibroblasts. J Biol Chem 269, 17893-17898.

Chen, W. et al. (Mar. 2002). Expression profile matrix of *Arabidopsis* transcription factor genes suggests their putative functions in response to environmental stresses. Plant Cell 14, 559-574.

Ayele, M., et al. (Apr. 2005). Whole genome shotgun sequencing of *Brassica oleracea* and its application to gene discovery and annotation in *Arabidopsis*. Genome Res. 15 (4), 487-495.

Bezhani, S., Sherameti, I., Pfannschmidt, T., and Oelmuller, R. (Jun. 29, 2001). A repressor with similarities to prokaryotic and eukaryotic DNA helicases controls the assembly of the CAAT box binding complex at a photosynthesis gene promoter. J Biol Chem 276, 23785-23789.

Bi, W., et al. (Oct. 17, 1997). DNA binding specificity of the CCAAT-binding factor CBF/NF-Y. J Biol Chem 272, 26562-26572.

Borrell, A.K., et al. (Jul. 2000). Does Maintaining Green Leaf Area in Sorghum Improve Yield under Drought? II. Dry Matter Production and Yield. Crop Science 40, 1037-1048.

Bowler, C., and Fluhr, R. (Jun. 2000). The role of calcium and activated oxygens as signals for controlling cross-tolerance. Trends Plant Sci 5, 241-246.

Bowie, et al. Science 247: 1306-1310 (1990).

Cooper, B., et al. (Oct. 2003). Identification of rice (*Oryza sativa*) proteins linked to the cyclin-mediated regulation of the cell cycle. Plant Mol. Biol. 53(3):273-9.

Coupland (Oct. 1995). Flower development. LEAFY blooms in aspen. Nature 377:482-483.

Coustry, F., Maity, S.N., and de Crombrugghe, B. (Jan. 6, 1995). Studies on transcription activation by the multimeric CCAAT-binding factor CBF. J Biol Chem 270, 468-475.

Coustry, F., Maity, S.N., Sinha, S., and de Crombrugghe, B. (Jun. 14, 1996). The transcriptional activity of the CCAAT-binding factor CBF is mediated by two distinct activation domains, one in the CBF-B subunit and the other in the CBF-C subunit. J Biol Chem 271, 14485-14491.

Coustry, F., Sinha, S., Maity, S.N., and Crombrugghe, B. (Apr. 1, 1998). The two activation domains of the CCAAT-binding factor CBF interact with the dTAFII110 component of the *Drosophila* TFIID complex. Biochem J 331 ( Pt 1), 291-297.

Coustry, F., Hu, Q., de Crombrugghe, B., and Maity, S.N. (Nov. 2, 2001). CBF/NF-Y functions both in nucleosomal disruption and transcription activation of the chromatin-assembled topoisomerase IIalpha promoter. Transcription activation by CBF/NF-Y in chromatin is dependent on the promoter structure. J Biol Chem 276, 40621-40630.

Covitz, P.A., et al. (Aug. 1998). Expressed sequence tags from a root-hair-enriched medicago truncatula cDNA library. Plant Physiol. 117(4):1325-32.

Crevillen P, Ventriglia T, Pinto F, Orea A, Merida A, Romero JM (Mar. 4, 2005) Differential pattern of expression and sugar regulation of *Arabidopsis thaliana* ADP-glucose pyrophosphorylase-encoding genes. J Biol Chem 280: 8143-8149.

Crookshanks, M., et al. (Sep. 18, 2001). The potato tuber transcriptome: analysis of 6077 expressed sequence tags. FEBS Lett. 506 (2), 123-126.

Currie, R.A. (Dec. 5, 1997). Functional interaction between the DNA binding subunit trimerization domain of NF-Y and the high mobility group protein HMG-I(Y). J Biol Chem 272, 30880-30888.

Daly et al. (Dec. 2001). Plant Systematics in the Age of Genomics. Plant Physiology 127:1328-1333.

Dang, V.D., Bohn, C., Bolotin-Fukuhara, M., and Daignan-Fornier, B. (Apr. 1996). The CCAAT box-binding factor stimulates ammonium assimilation in *Saccharomyces cerevisiae*, defining a new cross-pathway regulation between nitrogen and carbon metabolisms. J Bacteriol 178, 1842-1849.

di Silvio A, Imbriano C, Mantovani R (Jul. 1, 1999) Dissection of the NF-Y transcriptional activation potential. Nucleic Acids Res 27: 2578-2584.

Faniello MC, Bevilacqua MA, Condorelli G, de Crombrugghe B, Maity SN, Avvedimento VE, Cimino F, Costanzo F (Mar. 19, 1999) The B subunit of the CAAT-binding factor NFY binds the central segment of the Co-activator p300. J Biol Chem 274: 7623-7626.

Forsburg, S.L., and Guarente, L. (Feb. 1988). Mutational analysis of upstream activation sequence 2 of the CYC1 gene of *Saccharomyces cerevisiae*: a HAP2-HAP3-responsive site. Mol Cell Biol 8, 647-654.

Forsburg, S.L., and Guarente, L. (Aug. 1989). Identification and characterization of HAP4: a third component of the CCAAT-bound HAP2/HAP3 heteromer. Genes Dev 3, 1166-1178.

Franchini A, Imbriano C, Peruzzi E, Mantovani R, Ottaviani E (Feb. 2005) Expression of the CCAAT-binding factor NF-Y in *Caenorhabditis elegans*. J Mol Histol 36: 139-145.

Frontini M, Imbriano C, Manni I, Mantovani R (Feb. 2004) Cell cycle regulation of NF-YC nuclear localization. Cell Cycle 3: 217-222.

Fu, et al. (Aug. 2001). Expression of Arabidopsis GAI in Transgenic Rice Represses Multiple Gibberellin Responses. Plant Cell 13:1791-1802.

Gancedo, J.M. (Jun. 1998). Yeast carbon catabolite repression. Microbiol Mol Biol Rev 62, 334-361.

Gardiner, J., et al. (Apr. 2004). Anchoring 9,371 Maize Expressed Sequence Tagged Unigenes to the Bacterial Artificial Chromosome Contig Map by Two-Dimensional Overgo Hybridization. Plant Physiol. 134 (4), 1317-1326.

Gurtner A, et al. (Jul. 2003) Requirement for Down-Regulation of the CCAAT-binding Activity of the NF-Y Transcription Factor during Skeletal Muscle Differentiation. Mol Biol Cell 14: 2706-2715.

Guterman, I., et al. (Oct. 2002). Rose Scent: Genomics Approach to Discovering Novel Floral Fragrance-Related Genes. Plant Cell 14 (10), 2325-2338.

Haas, B., et al. (May 30, 2002). Full-length messenger RNA sequences greatly improve genome annotation. Genome Biology 2002, 3(6)research0029.1-0029.12.

Harmer, S., et al., (Dec. 15, 2000) Orchestrated Transcription of Key Pathways in *Arabidopsis* by the Circadian Clock. Science vol. 290, p. 2110.

Herwig, R., et al. (Aug. 2002). Construction of a 'unigene' cDNA clone set by oligonucleotide fingerprinting allows access to 25,000 potential sugar beet genes. Plant J. 32 (5), 845-857.

Hollung Kristin et al. (Jun. 1997) Developmental stress and ABA modulation of mRNA levels for bZIP transcription factors and Vp 1 in barley embryos and embryo-derived suspension cultures, Plant Molecular Biology, vol. 35, No. 5, pp. 561-571.

Kahle J, et al. (Jul. 2005) Subunits of the heterotrimeric transcription factor NF-Y are imported into the nucleus by distinct pathways involving importin beta and importin 13. Mol Cell Biol 25: 5339-5354.

Kater, et al. (Feb. 1998). Multiple AGAMOUS Homologs from Cucumber and Petunia Differ in Their Ability to Induce Reproductive Organ Fate. Plant Cell 10:171-182.

Kehoe, D.M., et al. (Aug. 1994). Two 10-bp regions are critical for phytochrome regulation of a Lemna gibba Lhcb gene promoter. Plant Cell 6, 1123-1134.

Kim, C.G., and Sheffery, M. (Aug. 1990). Physical characterization of the purified CCAAT transcription factor, alpha-CP1. J Biol Chem 265, 13362-13369.

(56) References Cited

OTHER PUBLICATIONS

Kim, I.S., et al. (Aug. 1996). Determination of functional domains in the C subunit of the CCAAT-binding factor (CBF) necessary for formation of a CBF-DNA complex: CBF-B interacts simultaneously with both the CBF-A and CBF-C subunits to form a heterotrimeric CBF molecule. Mol Cell Biol 16, 4003-4013.

Kusnetsov, V., et al. (Dec. 10, 1999). The assembly of the CAAT-box binding complex at a photosynthesis gene promoter is regulated by light, cytokinin, and the stage of the plastids. J Biol Chem 274, 36009-36014.

Kwong, R.W., et al. (Jan. 2003). LEAFY COTYLEDON1-Like defines a class of regulators essential for embryo development. Plant Cell 15, 5-18.

Lapik, Y.R., and Kaufman, L.S. (Jul. 2003). The *Arabidopsis* cupin domain protein AtPirin1 interacts with the G protein alpha-subunit GPA1 and regulates seed germination and early seedling development. Plant Cell 15, 1578-1590.

Lascaris R, et al. (Dec. 17, 2002) Hap4p overexpression in glucose-grown *Saccharomyces cerevisiae* induces cells to enter a novel metabolic state. Genome Biol. 4: R3.

Lazar et al. (Mar. 1988) Transforming Growth Factor alpha: Mutation of Aspartic Acid 47 and Leucine 48 Results in Different Biological Activities. Mol. Cell Biol. 8:1247-1252.

Lee, H., et al. (Feb. 18, 2003). Arabidopsis LEAFY COTYLEDON1 represents a functionally specialized subunit of the CCAAT binding transcription factor. Proc Natl Acad Sci U S A 100, 2152-2156.

Lee J H. et al. (Oct. 1995), Derepression of the activity of genetically engineered heat shock factor causes constitutive synthesis of heat shock proteins and increased themotolerance in transgenic *Arabidopsis*. Plant Journal, vol. 8, No. 4, pp. 603-612.

Levesque-Lemay M, et al. (Mar. 4, 2003) Expression of CCAAT-binding factor antisense transcripts in reproductive tissues affects plant fertility. Plant Cell Rep 21: 804-808.

Li, Q., et al. (Nov. 2, 1998). *Xenopus* NF-Y pre-sets chromatin to potentiate p300 and acetylation-responsive transcription from the *Xenopus* hsp70 promoter in vivo. Embo J 17, 6300-6315.

Lin, J.F., and Wu, S.H. (Aug. 2004). Molecular events in senescing *Arabidopsis* leaves. Plant J 39, 612-628.

Luger, K., et al. (Sep. 18, 1997). Crystal structure of the nucleosome core particle at 2.8 A resolution. Nature 389, 251-260.

Mandel et al. (Oct. 1992). Manipulation of flower structure in transgenic tobacco, Cell 71-133-143.

Mantovani, R. (Mar. 1998). A survey of 178 NF-Y binding CCAAT boxes. Nucleic Acids Res 26, 1135-1143.

Masiero, S., et al. (Jul. 19, 2002). Ternary complex formation between MADS-box transcription factors and the histone fold protein NF-YB. J Biol Chem 277, 26429-26435.

McNabb, D.S., et al. (Dec. 1997). The *Saccharomyces cerevisiae* Hap5p homolog from fission yeast reveals two conserved domains that are essential for assembly of heterotetrameric CCAAT-binding factor. Mol Cell Biol 17, 7008-7018.

McConnell, et al. (6838). Role of PHABULOSA and PHAVOLUTA in determining radial patterning in shoots; Nature 411, 709-713 (2001).

Meinke, D. (Dec. 4, 1992). A homeotic mutant of *Arabidopsis thaliana* with leafy cotyledons. Science 258, 1647-1650.

Meinke, D.W., et al. (Aug. 1994). Leafy Cotyledon Mutants of *Arabidopsis*. Plant Cell 6, 1049-1064.

Miyoshi, K., et al. (Nov. 2003). OsHAP3 genes regulate chloroplast biogenesis in rice. Plant J 36, 532-540.

Myers, R.M., Tilly, K., and Maniatis, T. (May 2, 1986). Fine structure genetic analysis of a beta-globin promoter. Science 232, 613-618.

Nakamura, Y., et al. (Dec. 31, 1997). Structural analysis of *Arabidopsis thaliana* chromosome 5. III. Sequence features of the regions of 1,191,918 by covered by seventeen physically assigned P1 clones. DNA Res. 4(6):401-414.

Nakshatri, H., et al. (Nov. 15, 1996). Subunit association and DNA binding activity of the heterotrimeric transcription factor NF-Y is regulated by cellular redox. J Biol Chem 271, 28784-28791.

Nandi et al. (Feb. 24, 2000). A conserved function for *Arabidopsis* Superman in regulating floral-whorl cell proliferation in rice, a monocotyledonous plant. Curr. Biol. 10:215-218.

Novillo, F., et al. (Mar. 16, 2004). CBF2/DREB1C is a negative regulator of CBF1/DREB1B and CBF3/DREB1A expression and plays a central role in stress tolerance in *Arabidopsis*. Proc Natl Acad Sci U S A 101, 3985-3990.

Parcy, F., et al. (Aug. 1997). The Abscisic Acid-INSENSITIVE3, FUSCA3, and Leafy COTYLEDON1 loci act in concert to control multiple aspects of *Arabidopsis* seed development. Plant Cell 9, 1265-1277.

Peng et al. (Dec. 1, 1997). The *Arabidopsis* GAI gene defines a signaling pathway that negatively regulates gibberellin responses. Genes and Development 11:3194-3205.

Peng et al. (Jul. 15, 1999). 'Green revolution' genes encode mutant gibberellin response modulators, Nature 400:256-261.

Pinkham, J.L., and Guarente, L. (Dec. 1985). Cloning and molecular analysis of the HAP2 locus: a global regulator of respiratory genes in *Saccharomyces cerevisiae*. Mol Cell Biol 5, 3410-3416.

Prandl R. et al., (May 1998) HSF3, a new heat shock factor from *Arabidopsis thaliana*, derepresses the heat shock response and confers thermotolerance when overexpressed in transgenic plants. Molecular and General Genetics, vol. 258, pp. 269-278.

Rizhsky, L., et al. (Nov. 2002). The combined effect of drought stress and heat shock on gene expression in tobacco. Plant Physiol 130, 1143-1151.

Romier, C., et al. (Jan. 10, 2003). The NF-YB/NF-YC structure gives insight into DNA binding and transcription regulation by CCAAT factor NF-Y. J Biol Chem 278, 1336-1345.

Sabehat, A., et al. (Jun. 1998). Expression of small heat-shock proteins at low temperatures. A possible role in protecting against chilling injuries. Plant Physiol 117, 651-658.

Salmi, M.L., et al. (Jul. 2005). Profile and analysis of gene expression changes during early development in germinating spores of *Ceratopteris richardii*. Plant Physiol. 138 (3), 1734-1745.

Salsi, V., et al. (Feb. 28, 2003). Interactions between p300 and multiple NF-Y trimers govern cyclin B2 promoter function. J Biol Chem 278, 6642-6650.

Sasaki, T., et al. (Nov. 21, 2002). The genome sequence and structure of rice chromosome 1. Nature 420 (6913), 312-316.

Seki, M., et al. (Jan. 2001). Monitoring the expression pattern of 1300 *Arabidopsis* genes under drought and cold stresses by using a full-length cDNA microarray. Plant Cell 13, 61-72.

Sinha S, et al. (Feb. 28, 1995) Recombinant rat CBF-C, the third subunit of CBF/NFY, allows formation of a protein-DNA complex with CBF-A and CBF-B and with yeast HAP2 and HAP3. Proc Natl Acad Sci U S A 92: 1624-1628.

Sinha, S., et al. (Jan. 1996). Three classes of mutations in the A subunit of the CCAAT-binding factor CBF delineate functional domains involved in the three-step assembly of the CBF-DNA complex. Mol Cell Biol 16, 328-337.

Surpin, M., et al. (May 2002). Signal transduction between the chloroplast and the nucleus. Plant Cell 14 Suppl, S327-338.

Suzuki et al. (Nov. 2001). Maize VP1 complements *Arabidopsis* abi3 and confers a novel ABA/auxin interaction in roots. Plant J. 28:409-418.

Tasanen, K., et al. (Jun. 5, 1992). Promoter of the gene for the multifunctional protein disulfide isomerase polypeptide. Functional significance of the six CCAAT boxes and other promoter elements. J Biol Chem 267, 11513-11519.

Testa A, et al. (Jan. 11, 2005) Chromatin immunoprecipitation (ChIP) on chip experiments uncover a widespread distribution of NF-Y binding CCAAT sites outside of core promoters. J Biol Chem 280: 13606-13615.

Thomas, H., and Howarth, C.J. (Feb. 2000). Five ways to stay green. J Exp Bot 51 Spec No, 329-337.

Vicient, C.M., et al. (Jun. 2000). Changes in gene expression in the leafy cotyledon1 (lec1) and fusca3 (fus3) mutants of *Arabidopsis thaliana* L. J Exp Bot 51, 995-1003.

Weigel and Nilsson (Oct. 12, 1995). A developmental switch sufficient for flower initiation in diverse plants. Nature 377:482-500.

Wendler, W.M., et al. (Mar. 28, 1997). Identification of pirin, a novel highly conserved nuclear protein. J Biol Chem 272, 8482-8489.

(56) References Cited

OTHER PUBLICATIONS

West, M., et al. (Dec. 1994). Leafy COTYLEDON1 Is an essential regulator of late embryogenesis and cotyledon identity in *Arabidopsis*. Plant Cell 6, 1731-1745.

Winicov Ilga et al., (Jun. 1999) Transgenic overexpression of the transcription factor Alfin1 enhances expression of the endogenous MsPRP2 gene in alfalfa and improves salinity tolerance of the plants. Plant Physiology vol. 120, No. 2, pp. 473-480.

Xing, Y, Fikes, J.D., and Guarente, L. (Dec. 1993). Mutations in yeast HAP2/HAP3 define a hybrid CCAAT box binding domain. Embo J 12, 4647-4655.

Xiong, L., et al. (Dec. 2001). Modulation of abscisic acid signal transduction and biosynthesis by an Sm-like protein in *Arabidopsis*. Dev Cell 1, 771-781.

Xiong, L., et al. (Aug. 1, 2001). FIERY1 encoding an inositol polyphosphate 1-phosphatase is a negative regulator of abscisic acid and stress signaling in *Arabidopsis*. Genes Dev 15, 1971-1984.

Yan, J., et al. (Aug. 2004). Overexpression of the *Arabidopsis* 14-3-3 protein GF14 lambda in cotton leads to a "stay-green" phenotype and improves stress tolerance under moderate drought conditions. Plant Cell Physiol 45, 1007-1014.

Yu, J., et al. (Feb. 2005). The Genomes of Oryza sativa: A History of Duplications. PloS Biol. 3 (2), E38: 266-281.

Yun, J., et al. (Sep. 19, 2003). Cdk2-dependent phosphorylation of the NF-Y transcription factor and its involvement in the p. 53-p. 21 signaling pathway. J Biol Chem 278, 36966-36972.

Zhang, S., et al. (Jun. 2002). Similarity of expression patterns of knotted1 and ZmLEC1 during somatic and zygotic embryogenesis in maize ( *Zea mays* L.). Planta 215, 191-194.

Zhou, Y., and Lee, A.S. (Mar. 4, 1998). Mechanism for the suppression of the mammalian stress response by genistein, an anticancer phytoestrogen from soy. J Natl Cancer Inst 90, 381-388.

Shinn, et al. (Dec. 1, 2001). Database SPTREMBL [Online] XP002962732 Database accession No. (Q94F45).

Nakamura, Y., et al. (Mar. 1, 2001). Database TREMBL SEQ LIB EBI, Hinxton; "Structural analysis of *Arabidopsis* . . . " XP002302645 WWW.EBI.AC.UK Database acc No. Q9FMV5.

Database UniProt [Online] (May 1, 2000). "Putative CCAAT-binding transcription factor subunit.." retrieved from EBI accession No. UNIPROT: Database acc No. Q9SLGO.

NCBI accession No. AA660543 (gi:2604587) (Nov. 11, 1997); Covitz, P.A., et al. "00429 MtRHE *Medicago truncatula* cDNA 5' similar to CCAAT box DNA binding transcription factor, mRNA sequence"; (*Medicago truncatula*) (publication: see Plant Physiol. 117 (4), 1325-1332, 1998).

NCBI accession No. AAAA01000016 (gi:19924325) (pos. 61435-62623) (Apr. 4, 2002); Yu, J., et al. "*Oryza sativa* (indica cultivar-group) scaffold000016, whole genome shotgun sequence"; (*Oryza sativa*) (publication: see PloS Biol. 3 (2), E38, 2005, The Genomes of *Oryza sativa*: A History of Duplications).

NCBI accession No. AAAA01001199 (gi:19925508) (pos. 24979-25653) (Apr. 4, 2002); Yu, J., et al. "*Oryza sativa* (indica cultivar-group) scaffold001199, whole genome shotgun sequence"; (*Oryza sativa*) (publication: see PloS Biol. 3 (2), E38, 2005, The Genomes of *Oryza sativa*: A History of Duplications).

NCBI accession No. AAAA01003638 (gi:19927947) (Apr. 4, 2002); Yu, J., et al. "*Oryza sativa* (indica cultivar-group) scaffold003638, whole genome shotgun sequence"; (*Oryza sativa*) (publication: see PloS Biol. 3 (2), E38, 2005, The Genomes of *Oryza sativa*: A History of Duplications).

NCBI accession No. AAAA01006073 (gi:19930383) (Apr. 4, 2002); Yu, J., et al. "*Oryza sativa* (indica cultivar-group) scaffold006073, whole genome shotgun sequence"; (*Oryza sativa*) (publication: see PloS Biol. 3 (2), E38, 2005, The Genomes of *Oryza sativa*: A History of Duplications).

NCBI accession No. AAAA01008870 (gi:19933180) (Apr. 4, 2002); Yu, J., et al. "*Oryza sativa* (indica cultivar-group) scaffold008870, whole genome shotgun sequence"; (*Oryza sativa*) (publication: see PloS Biol. 3 (2), E38, 2005, The Genomes of *Oryza sativa*: A History of Duplications).

NCBI accession No. AAAA01009782 (gi:19934092) (Apr. 4, 2002); Yu, J., et al. "*Oryza sativa* (indica cultivar-group) scaffold009782, whole genome shotgun sequence"; (*Oryza sativa*) (publication: see PloS Biol. 3 (2), E38, 2005, The Genomes of *Oryza sativa*: A History of Duplications).

NCBI acc. No. AAAA01015835 (gi: 19945865) (Apr 4 2002); Yu,J., et al. "*Oryza sativa* (indica cultivar-group) scaffold015835, whole genome shotgun sequence"; source: *Oryza sativa* (indica cultivar-group); Title: "The Genomes of *Oryza sativa* : A History of Duplications" (PLoS Biol. 3 (2), E38 (2005)).

NCBI accession No. AAAA01015884 (gi:19945953) (Apr. 4, 2002); Yu, J., et al. "*Oryza sativa* (indica cultivar-group) scaffold015884, whole genome shotgun sequence"; (*Oryza sativa*) (publication: see PloS Biol. 3 (2), E38, 2005, The Genomes of *Oryza sativa* : A History of Duplications).

NCBI accession No. AAK95562 (gi:15321716) (Aug. 28, 2001); Lowe, K.S. et al "Leafy cotyledon1" (*Zea mays*).

NCBI accession No. AAL27657 (gi:16902050) (Nov. 10, 2001); Lowe, K.S., et al. "CCAAT-box binding factor HAP3 B domain" (*Glycine max*.).

NCBI accession No. AAL27658 (gi:16902052) (Nov. 10, 2001); Lowe, K.S., et al. "CCAAT-box binding factor HAP3 B domain" (*Glycine max*.).

NCBI accession No. AAL27659 (gi:16902054) (Nov. 10, 2001); Lowe, K.S., et al. "CCAAT-box binding factor HAP3 B domain" (*Vernonia galamensis*).

NCBI accession No. AAL27660 (gi:16902056) (Nov. 10, 2001); Lowe, K.S. et al. "CCAAT-box binding factor HAP3 B domain" (*Argemone mexicana*).

NCBI accession No. AAL27661 (gi:16902058) (Nov. 10, 2001); Lowe, K.S. et al. "CCAAT-box binding factor HAP3 B domain" (*Triticum aestivum*).

NCBI accession No. AAL49943 (gi:17979253) (Dec. 26, 2001); Shinn, P. et al., "At2g37060/T2N18.18 [*Arabidopsis thaliana*]".

NCBI accession No. AAN01148 (gi:22536010) (Aug. 29, 2002); Kwong, R.W., et al. "LEC1-like protein" (*Phaseolus coccineus*) (note: the original submission and latest update are provided for examination) (publication: see Plant Cell 15 (1), 5-18, 2003, Leafy COTYLEDON1-Like Defines a Class of Regulators Essential for Embryo Development).

NCBI accession No. AAO33918 (gi:28274147) (Feb. 8, 2003); Adams, K.L., et al. "Putative CCAAT-binding transcription factor"; (*Gossypium barbadense*).

NCBI accession No. AAO33919 (gi:28274149) (Feb. 8, 2003); Adams, K.L., et al. "Putative CCAAT-binding transcription factor" *Gossypium barbadense*.

NCBI accession No. AAO72650 (gi:29367577) (Mar. 30, 2003); Cooper, B., et al. "CCAAT-binding transcription factor-like protein" (*Oryza sativa*) (note: the original submission and latest update are provided for examination) (publication: see Plant Mol. Biol. 53 (3), 273-279, 2003, Identification of rice (*Oryza sativa*) proteins linked to the cyclin-mediated regulation of the cell cycle).

NCBI accession No. AB025628 (gi:4589434) (pos. 69357-69929) (Apr. 20, 1999); Nakamura, Y., "*Arabidopsis thaliana* genomic DNA, chromosome 5, P1 clone: MNJ7, complete sequence" (note: the original submission and latest update are provided for examination, see gene id: MNJ7.23, protein id: BAB09090.1, gi:9758792 marked on p. 7/29).

NCBI accession No. AC000106 (gi:1785951) (Jan. 21 1997); Osborne, B.I., et al., "*Arabidopsis thaliana* chromosome 1" (note: two versions are presented for review, gi:1785951 submitted Jan. 21, 1997; and, gi:2342673 submitted Sep. 17, 1997).

NCBI accession No. AC002388 (gi:2282009) (Jul. 28, 1997); Rounsley, S.D., et al., "*Arabidopsis thaliana* clone T13E15" (note: two versions are presented for review, gi:2282009 submitted Jul. 28, 1997; and, gi:20196917 submitted Apr. 18, 2002).

NCBI accession No. AC005770 (gi:3694645) (pos 56423-57963) (Oct. 3, 1998); Rounsley, S.D., et al., "*Arabidopsis thaliana* clone T7F6" (note: two versions are presented for review, gi:3694645 submitted Oct. 3, 1998; and, gi:20197440 submitted Apr. 18, 2002, see gene At2g38870, gi:20197447 marked on p. 2/35).

NCBI accession No. AC006260 (gi:4071012) (pos 40445-41633)(Dec. 29, 1998); Lin, X., et al., "*Arabidopsis thaliana* clone

(56) References Cited

OTHER PUBLICATIONS

T2N18" (note: two versions are presented for review, gi:4071012 submitted Dec. 29, 1998; and, gi:20197714 submitted Apr. 18, 2002, see p. 6 of 28, gene At2g37070, gi:4371294).
NCBI acc. No. AC007063 (gi: 4389532) (Mar 11 1999); Lin,X., et al. "*Arabidopsis thaliana* clone T10F5, * Sequencing in Progress *, 4 unordered pieces"; source: *Arabidopsis thaliana* (thale cress); Title: "*Arabidopsis thaliana* 'TAMU' BAC 'T10F5' genomic sequence near marker 'GPC6'" (Unpublished).
NCBI acc. No. AC104284 (gi: 17402732) (Dec 7 2001); Chow,T.-Y., et al. "*Oryza sativa* (japonica cultivar-group) chromosome 5 clone OJ1735C10, * Sequencing in Progress *, 7 ordered pieces"; source: *Oryza sativa* (japonica cultivar-group); Title: "*Oryza sativa* BAC OJ1735C10 genomic sequence" (Unpublished).
NCBI accession No. AC120529 (gi:20503070) (pos. 90470-91129) (May 8, 2002); Buell, C., et al. "*Oryza sativa* (japonica cultivar-group) chromosome 3 clone OSJNBa0039N21, complete sequence"; (*Oryza sativa*) (note: two versions are presented for review, gi:20503070 submitted May 8, 2002; and, gi:34447241 submitted Sep. 4, 2003, see protein id: 41469085, marked on p. 6/53).
NCBI accession No. AC122165 (gi:21104913) (pos. 113095-113208 in latest version) (May 23, 2002); Shaull, S., et al. "*Medicago truncatula* clone mth2-32m22, complete sequence"; (*Medicago truncatula*) (note: two versions are presented for review, gi:21104913 submitted May 23, 2002; and, gi:71274322 submitted on Jul. 27, 2005).
NCBI accession No. AF193440 (gi:6289056) (Nov. 9, 1999); Gherraby, W., et al., "*Arabidopsis thaliana* heme activated protein (HAP5c) mRNA, complete cds".
NCBI accession No. AF410176 (gi:15321715) (Aug. 28, 2001); Lowe, K.S., et al. "*Zea mays* leafy cotyledon) (Lec1) mRNA, complete cds"; (*Zea mays*).
NCBI accession No. AF533650 (gi:22536009) (Aug. 29, 2002); Kwong, R.W., et al. "*Phaseolus coccineus* LEC1-like protein mRNA, complete cds"; (*Phaseolus coccineus*) (note: the original submission and latest update are provided for examination).
NCBI accession No. AI442376 (gi:4295745) (Feb. 19, 1999); Shoemaker, R., et al. "Sa26b07.y1 Gm-c1004 *Glycine max* cDNA clone Genome systems clone ID: Gm-c1004-398 5' similar to TR:023634 023634 transcription factor; mRNA sequence" (publication: see Plant Cell 15 (1), 5-18, 2003, Leafy COTYLEDON1-Like Defines a Class of Regulators Essential for Embryo Development).
NCBI accession No. AI442765 (gi:4298466) (Feb. 19, 1999); Shoemaker, R., et al. "Sa26b07.x1 Gm-c1004 *Glycine max* cDNA clone genome systems clone ID: Gm-c1004-398 3' similar to TR:023634 023634 transcription factor; mRNA sequence"; (*Glycine max*).
NCBI accession No. AI486503 (gi:4381874) (Mar. 9, 1999); Alcala, J., et al. "EST244824 tomato ovary, TAMU *Lycopersicon esculentum* cDNA clone cLED6C8, mRNA sequence"; (*Lycopersicon esculentum*).
NCBI accession No. AI495007 (gi:4396010) (Mar. 11, 1999); Shoemaker, R., et al. "Sa89f03.y1 Gm-c1004 *Glycine max* cDNA clone genome systems clone ID: Gm-c1004-6486 5' similar to TR:023310 023310 CCAATt-binding transcription factor subunit A.; mRNA sequence"; (*Glycine max*).
NCBI accession No. AI725612 (gi:5044464) (Jun. 11, 1999); Blewitt, M., et al., "BNLGHi12445 Six-day Cotton fiber *Gossypium hirsutum* cDNA 5' similar to CCAAT-binding transcription factor subunit A (CBF-A) (NF-Y Protein Chain B) (NFYB) (CAAT-Box DNA binding protein subunit B), mRNA sequence"; (*Gossypium hirsutum*).
NCBI accession No. AI728916 (gi:5047768) (Jun. 11, 1999); Blewitt, M., et al, "BNLGHi12022 Six-day Cotton fiber *Gossypium hirsutum* cDNA 5' similar to (Y13723) Transcription factor [*Arabidopsis thaliana*], mRNA sequence"; (*Gossypium hirsutum*).
NCBI accession No. AI731250 (gi:5050102) (Jun. 11, 1999); Blewitt, M., et al., "BNLGHi9010 Six-day Cotton fiber *Gossypium hirsutum* cDNA 5' similar to (X59714) CAAT-box DNA binding protein subunit B (NF-YB) [*Zea mays*], mRNA sequence"; (*Gossypium hirsutum*).

NCBI accession No. AI731275 (gi:5050127) (Jun. 11, 1999); Blewitt, M., et al., "BNLGHi9078 Six-day Cotton fiber *Gossypium hirsutum* cDNA 5' similar to (X59714) CAAT-box DNA binding protein subunit B (NF-YB) [*Zea mays*], mRNA sequence"; (*Gossypium hirsutum*).
NCBI accession No. AI782351 (gi:5280392) (Jun. 29, 1999); D'Ascenzo, M., et al., "EST263230 tomato susceptible, Cornell *Lycopersicon esculentum* cDNA clone cLES18L2, mRNA sequence"; (*Lycopersicon esculentum*).
NCBI accession No. AI900024 (gi:5605926) (Jul. 27, 1999); Shoemaker, R., et al., "sb97g11.y1 Gm-c1012 *Glycine max* cDNA clone Genome Systems clone ID: Gm-c1012-669 5' similar to SW:CBFA_ Maize P25209 CCAAT-binding transcription factor subunit A; mRNA sequence"; (*Glycine max*).
NCBI accession No. AI965590 (gi:5760227) (Aug. 23, 1999); Shoemaker, R., et al., "sc74b05.y1 Gm-c1018 *Glycine max* cDNA clone Genome Systems clone ID: Gm-c1018-586 5' similar to SW:CBFA_ Maize P25209 CCAAT-binding transcription factor subunit A; mRNA sequence"; (*Glycine max*).
NCBI accession No. AI966550 (gi:5761187) (Aug. 23, 1999); Shoemaker, R., et al., "sc51h01.y1 Gm-c1015 *Glycine max* cDNA clone Genome Systems Clone ID: Gm-c1015-1130 5' similar to TR:023633 023633 Transcription factor; mRNA sequence"; (*Glycine max*).
NCBI accession No. AJ487398 (gi:22022152) (Jul. 30, 2002); Gebhardt, C., et al., "AJ487398 *Solanum tuberosum* cv. Provita *Solanum tuberosum* cDNA clone P1e4, mRNA sequence"; (*Solanum tuberosum*).
NCBI accession No. AJ501023 (gi:22081956) (Aug. 1, 2002); Manthey, K., et al., "AJ501023 MTAMP *Medicago truncatula* cDNA clone mtgmadc120001h01, mRNA sequence"; (*Medicago truncatula*) (note: the original submission and latest update are provided for examination).
NCBI accession No. AJ501814 (gi:22082742) (Aug. 1, 2002); Manthey, K., et al., "AJ501814 MTAMP *Medicago truncatula* cDNA clone mtgmadc120012b08, mRNA sequence"; (*Medicago truncatula*) (note: the original submission and latest update are provided for examination).
NCBI accession No. AL132966 (gi:6434215) (pos. 15052-16661) (Nov. 15, 1999); Bloecker, H., et al., "*Arabidopsis thaliana* DNA chromosome 3, BAC clone F4P12" (note: the original submission and latest update are provided for examination, see gene F4P12 40, protein id gi:CAB6764.1 marked on p. 4/66).
NCBI accession No. AL387357 (gi:9687108) (Aug. 3, 2000); Journet, E.P., et al, "MtBC42A04F1 MtBC *Medicago truncatula* cDNA clone MtBC42A04 T3, mRNA sequence"; (*Medicago truncatula*) (note: the original submission and latest update are provided for examination).
NCBI accession No. AL506199 (gi:12032414) (Jan. 4, 2001); Michalek, W., et al., "AL506199 *Hordeum vulgare* Baarke developing caryopsis (3.-15.DAP) *Hordeum vulgare* subsp. Vulgare cDNA clone HY02F18T 5', mRNA sequence"; (*Hordeum vulugare*).
NCBI accession No. AL509098 (gi:12035601) (Jan. 4, 2001); Michalek, W., et al., "AL509098 *Hordeum vulgare* Barke developing caryopsis (3.-15.DAP) *Hordeum vulgare* subsp. Vulgare cDNA clone HY10L07V 5', mRNA sequence"; (*Hordeum vulgare* ).
NCBI accession No. AL830693 (gi:21842473) (Jul. 16, 2002); Sprunck, S., et al., "AL830693 q:242 *Triticum aestivum* cDNA clone D05_q242_plate_10, mRNA sequence"; (*Triticum aestivum*).
NCBI accession No. AP003246 (gi:13027276) (pos. 28048-28351) (Feb. 21, 2001); Sasaki, T., et al., "*Oryza sativa* (japonica cultivar-group) genomic DNA, chromosome 1, PAC clone: P0423A12"; (*Oryza sativa*) (note: two versions are presented for review, gi:21104640 submitted Feb. 21, 2001; and, gi:21104640 submitted May 22, 2002, see protein id BAB93258.1 marked on p. 14/50) (publication: see Nature 420 (6913), 312-316, 2002, the genome sequence and structure office chromosome 1).
NCBI acc. No. NP_030436 (gi: 18404885) (Jan 29 2002);, et al. "putative CCAAT-binding transcription factor subunit"; source: Unknown.; Title: "".
NCBI acc. No. NP_199575 (gi: 15238156) (Aug. 21 2001); Tabata,S., et al. "putative protein [*Arabidopsis thaliana*]"; source:

(56) References Cited

OTHER PUBLICATIONS

*Arabidopsis thaliana* (thale cress); Title: "Sequence and analysis of chromosome 5 of the plant *Arabidopsis thaliana*" (Nature 408 (6814), 823-826 (2000)).
NCBI acc. No. NP_193190 (gi: 15233475) (Aug. 21 2001); Mayer,K., et al. "CCAAT-binding transcription factor subunit A(CBF-A) [*Arabidopsis thaliana*]"; source: *Arabidopsis thaliana* (thale cress); Title: "Sequence and analysis of chromosome 4 of the plant *Arabidopsis thaliana*" (Nature 402 (6763), 769-777 (1999)).
NCBI acc. No. NP_001031500 (gi: 79324546) (Nov. 3 2005);, et al. "unknown protein [*Arabidopsis thaliana*]"; source: *Arabidopsis thaliana* (thale cress); Title: "" ( ).
NCBI acc. No. NP_178981 (gi: 15225440) (Aug. 21 2001); Lin,X., et al. "putative CCAAT-box binding trancription factor [*Arabidopsis thaliana*]"; source: *Arabidopsis thaliana* (thale cress); Title: "Sequence and analysis of chromosome 2 of the plant *Arabidopsis thaliana*" (Nature 402 (6763), 761-768 (1999)).
NCBI acc. No. NP_190902 (gi: 15231796) (Aug. 21 2001); Salanoubat,M., et al. "transcription factor NF-Y, CCAAT-binding-like protein [*Arabidopsis thaliana*]"; source: *Arabidopsis thaliana* (thale cress); Title: "Sequence and analysis of chromosome 3 of the plant *Arabidopsis thaliana*" (Nature 408 (6814), 820-822 (2000)).
NCBI accession No. AP003266 (gi:13027296)(pos. 83090-83330) (Feb. 21, 2001); Sasaki, T., et al., "*Oryza sativa* (japonica cultivar-group) genomic DNA, chromosome 1, PAC clone:P0492G09"; (*Oryza sativa* ) (note: two versions are presented for review, gi:13027296 submitted Feb. 21, 2001; and, gi:15408784 submitted Aug. 31, 2001, see protein id BAB54190.1 marked on p. 6/47) (publication: see Nature 420 (6913), 312-316, 2002, The genome sequence and structure office chromosome 1).
NCBI accession No. AP003271 (gi:13027301) (pos. 154362-155761) (Feb. 21, 2001); Sasaki, T., et al., "*Oryza sativa* (japonica cultivar-group) genomic DNA, chromosome 1, PAC clone: P0506B12"; (*Oryza sativa* ) ) (note: two versions are presented for review, gi:13027301 submitted Feb. 21, 2001; and, gi:20160789 submitted Apr. 16, 2002, see protein id: BAD73383.1, gi:56201933 marked on p. 3/45) (publication: see Nature 420 (6913), 312-316, 2002, The genome sequence and structure of rice chromosome 1).
NCBI accession No. AP004179 (gi:15718436) (pos. 36798-37036) (Sep. 20, 2001); Sasaki, T., et al., "*Oryza sativa* (japonica cultivar-group) genomic DNA, chromosome 2, BAC clone: OJ1124_G07"; (*Oryza sativa* ) ) (note: two versions are presented for review, gi:15718436 submitted Sep. 20, 2001; and, gi:45735881 submitted Mar. 25, 2004, see protein id BAD12927.1, gi:45735894 marked on p. 6/32).
NCBI accession No. AP004366 (gi:17046146) (pos. 72619-74018) (Nov. 21, 2001); Sasaki, T., et al., "*Oryza sativa* (japonica cultivar-group) genomic DNA, chromosome 1, PAC clone: P0460004"; (*Oryza sativa* ) ) (note: two versions are presented for review, gi:17046146 submittedd Nov. 21, 2001; and, gi:20805242 submitted May 15, 2002, see protein id: BAD73788.1, gi:56202329 marked on p. 12/46) (publication: see Nature 420 (6913), 312-316, 2002, The genome sequence and structure of rice chromosome 1).
NCBI accession No. AP005193 (gi:20975319) (pos. 56389-57063) (May 17, 2002); Sasaki, T., et al., "*Oryza sativa* (japonica cultivar-group) genomic DNA, chromosome 7, PAC clone: P0493C06"; (*Oryza sativa* ) ) (note: two versions are presented for review, gi:20975319 submitted May 17, 2002; and, gi:38142450 submitted Oct. 31, 2003, see protein id: BAD31143.1, gi:50508657 marked on p. 7/50).
NCBI accession No. AT002114 (gi:5724898) (Aug. 10, 1999); Ryu, S.W., et al., "AT002114 Flower bud cDNA *Brassica rapa* subsp. Pekinesis cDNA clone RF0417, mRNA sequence".
NCBI accession No. AU088581 (gi:7378310) (Mar. 31, 2000); Sasaki, T., et al., "AU88581 Rice Callus *Oryza sativa* (japonica cultivar-group) cDNA clone C52742, mRNA sequence"; (*Oryza sativa* ).
NCBI accession No. AV411210 (gi:7740371) (May 9, 2000); Asamizu, E., et al, "AV411210 *Lotus japonicus* young plants (two-week old) *Lotus corniculatus* var. japonicus cDNA clone MWM203a04_r 5', mRNA sequence"; (*Lotus corniculatus*) (publication: see DNA Res. 7 (2), 127-130, 2000, Generation of 7137 non-redundant expressed sequence tags from a legume, *Lotus japonicus*).
NCBI accession No. AV420653 (gi:7749830) (May 9, 2000); Asamizo, E., et al, "AV420653 *Lotus japonicus* young plants (two-week old) *Lotus corniculatus* var. japonicus cDNA clone MWM184h05_r 5', mRNA sequence"; (*Lotus corniculatus*) (publication: see DNA Res. 7 (2), 127-130, 2000, Generation of 7137 non-redundant expressed sequence tags from a legume, *Lotus japonicus*).
NCBI accession No. AV424305 (gi:7781090) (May 12, 2000); Asamizo, E., et al, "AV424305 *Lotus japonicus* young plants (two-week old) *Lotus corniculatus* var. japonicus cDNA clone MWM038e02_r 5', mRNA sequence"; (*Lotus corniculatus*) (publication: see Dna Res. 7 (2), 127-130, 2000, Generation of 7137 non-redundant expressed sequence tags from a legume, *Lotus japonicus*).
NCBI accession No. AV425835 (gi:7784165) (May 12, 2000); Asamizo, E., et al, "AV425835 *Lotus japonicus* young plants (two-week old) *Lotus corniculatus* var. japonicus cDNA clone MWM059e05_r 5', mRNA sequence"; (*Lotus corniculatus*) (publication: see DNA Res. 7 (2), 127-130, 2000, Generation of 7137 non-redundant expressed sequence tags from a legume, *Lotus japonicus*).
NCBI accession No. AV632044 (gi:10775364) (Oct. 11, 2000); Asamizo, E., et al, "AV632044 *Chlamydomonas reinhardtii* 5% CO2 *Chlamydomonas reinhardtii* cDNA clone HC003b12_r 5', mRNA sequence"; (*Chlamydomonas reinhardtii*) (publication: see DNA Res. 7 (5), 305-307, 2000, Generation of expressed sequence tags from low-CO2 and high-0O2 adapted cells of *Chlamydomonas reinhardtii*).
NCBI accession No. AV632945 (gi:10776265) (Oct. 11, 2000); Asamizo, E., et al, "AV632945 *Chlamydomonas reinhardtii* 5% CO2 *Chlamydomonas reinhardtii* cDNA clone HC014f12_r 5', mRNA sequence"; (*Chlamydomonas reinhardtii*) (publication: see DNA Res. 7 (5), 305-307, 2000, Generation of expressed sequence tags from low-CO2 and high-CO2 adapted cells of *Chlamydomonas reinhardtii*).
NCBI accession No. AW035570 (gi:5894326) (Sep. 15, 1999); Alcala, J., et al., "EST281308 tomato callus, TAMU *Lycopersicon esculentum* cDNA clone cLEC39F2 similar to CAAT-box DNA binding protein subunit B (NF-YB), putative, mRNA sequence"; (*Lycopersicon esculentum*).
NCBI accession No. AW043377 (gi:5903906) (Sep. 18, 1999); Whetten, R.W., "ST32F09 Pine TriplEx shoot tip library *Pinus taeda* cDNA clone ST32F09, mRNA sequence"; (*Pinus taeda*).
NCBI accession No. AW132359 (gi:6133966) (Oct. 27, 1999); Shoemaker, R., et al., "se03b02.y1 Gm-c1013 *Glycine max* cDNA clone Genome Systems clone ID: Gm-c1013-2404 5' similar to SW:CBFA_Maize P25209 CCAAT-binding transcription factor subunit A; mRNA sequence"; (*Glycine max*).
NCBI accession No. AW200790 (gi:6481519) (Nov. 30, 1999); Shoemaker, R., et al., "se93e11.y1 Gm-c1027 *Glycine max* cDNA clone Genome Systems clone ID: Gm-c1027-357 5' similar to TR:023310 023310 CCAAT-binding transcription factor subunit A; mRNA sequence"; (*Glycine max*).
NCBI accession No. AW201996 (gi:6482782) (Nov. 30, 1999); Shoemaker, R., et al., "sf09g11.y1 Gm-c1027 *Glycine max* cDNA clone Genome Systems clone ID: Gm-c1027-1821 5' similar to TR:023310 023310 CCAAT-binding transcription factor subunit A; mRNA sequence"; (*Glycine max*).
NCBI accession No. AW348165 (gi:6845875) (Feb. 1, 2000); Vodkin, L., et al., "GM210001A21D7 Gm-r1021 *Glycine max* cDNA clone Gm-r1021-158 3', mRNA sequence"; (*Glycine max*).
NCBI accession No. AW395227 (gi:6913697) (Feb. 7, 2000); Shoemaker, R., et al., "sh45e04.y1 Gm-c1017 *Glycine max* cDNA clone Genome Systems clone ID: Gm-c1017-4663 5' similar to TR:Q9ZQC3 Q9ZQC3 Putative CCAAT-binding transcription factor; mRNA sequence"; (*Glycine max*).
NCBI accession No. AW397727 (gi:6916197) (Feb. 7, 2000); Shoemaker, R., et al., "sg83f04.y1 Gm-c1026 *Glycine max* cDNA clone Genome Systems clone ID: Gm-c1026-344 5' similar to TR:023634 023634 transcription factor; mRNA sequence"; (*Glycine max*).

(56) References Cited

OTHER PUBLICATIONS

NCBI accession No. AW432980 (gi:6964287) (Feb. 11, 2000); Shoemaker, R., et al., "si03a01.y1 Gm-c1029 *Glycine max*cDNA clone Genome Systems clone ID: Gm-c1029-97 5' similar to TR:081130 081130 CCAAT-box binding factor HAP3 homolog; mRNA sequence"; (*Glycine max*).
NCBI accession No. AW459387 (gi:7029546) (Feb. 24, 2000); Shoemaker, R., et al., "sh23f03.y1 Gm-c1016 *Glycine max*cDNA clone Genome Systems clone ID: Gm-c1016-5622 5' similar to TR:Q9ZQC3 Q9ZQC3 Putative CCAAT-binding transcription factor; mRNA sequence"; (*Glycine max*).
NCBI accession No. AW570530 (gi:7235201) (Mar. 13, 2000); Shoemaker, R., et al., "sj63c01.y1 Gm-c1033 *Glycine max*cDNA clone Genome Systems clone ID: Gm-c1033-1945 5' similar to SW:CBFA_Maize P25209 CCAAT-binding transcription factor subunit A; mRNA sequence"; (*Glycine max*).
NCBI accession No. AW597630 (gi:7285143) (Mar. 22, 2000); Shoemaker, R., et al., "sj96g06.y1 Gm-c1023 *Glycine max*cDNA clone Genome Systems clone ID: Gm-c1023-2483 5' similar to TR:Q9ZQC3 Q9ZQC3 Putative CCAAT-binding transcription factor; mRNA sequence"; (*Glycine max*).
NCBI accession No. AW621652 (gi:7333299) (Mar. 28, 2000); Van der Hoeven, R.S., et al., "EST312450 tomato root during/after fruit set, Cornell University *Lycopersicon esculentum* cDNA clone cLEX12N12 5', mRNA sequence"; (*Lycopersicon esculentum*).
NCBI accession No. AW625817 (gi:7338844) (Mar. 28, 2000); Van der Hoeven, R.S., et al., "EST319724 tomato radicle, 5 d post-imbibition, Cornell University *Lycopersicon esculentum* cDNA clone cLEZ17A3 5', mRNA sequence"; (*Lycopersicon esculentum*).
NCBI accession No. AW648378 (gi:7409616) (Apr. 4, 2000); Alcala, J., et al., "EST326832 tomato germinating seedlings, TAMU *Lycopersicon esculentum* cDNA clone cLEI4I18 5', mRNA sequence"; (*Lycopersicon esculentum*).
NCBI accession No. AW648379 (gi:7409617) (Apr. 4, 2000); Alcala, J., et al., "EST326833 tomato germinating seedlings, TAMU *Lycopersicon esculentum* cDNA clone cLEI4I22 5', mRNA sequence"; (*Lycopersicon esculentum*).
NCBI accession No. AW688588 (gi:7563324) (Apr. 14, 2000); He, X.-Z., et al., "NF009C11ST1F1000 Developing stem *Medicago truncatula* cDNA clone NF009C11ST 5', mRNA sequence"; (*Medicago truncatula*).
NCBI accession No. AW719547 (gi:7614059) (Apr. 19, 2000); Freund, S., et al., "LjNEST6a3r *Lotus japonicus* nodule library, mature and immature nodules *Lotus corniculatus* var. japonicus cDNA 5', mRNA sequence"; (*Lotus corniculatus*).
NCBI accession No. AW720671 (gi:7615221) (Apr. 19, 2000); Colebatch, G., et al., "LjNEST6a3rc *Lotus japonicus* nodule library 5 and 7 week-old *Lotus corniculatus* var. japonicus cDNA 5', mRNA sequence"; (*Lotus corniculatus* ).
NCBI accession No. AW733618 (gi:7639292) (Apr. 24, 2000); Shoemaker, R., et al., "sk75h06.y1 Gm-c1016 *Glycine max* cDNA clone Genome systems clone ID: Gm-c1016-9972 5' similar to TR:Q9ZQC3 Q9ZQC3 Putative CCAAT-binding transcription factor, mRNA sequence"; (*Glycine max*).
NCBI accession No. AW738727 (gi:7647672) (Apr. 25, 2000); Van der Hoeven, R.S., et al., "EST340154 tomato flower buds, anthesis, Cornell University *Lycopersicon esculentum* cDNA clone cTOD8G22 5', mRNA sequence"; (*Lycopersicon esculentum*).
NCBI accession No. AW754604 (gi:7676324) (May 1, 2000); Whetten, R.W. et al., "PC04B12 Pine TriplEx pollen cone library *Pinus taeda* cDNA clone PC04B12, mRNA sequence"; (*Pinus taeda*).
NCBI accession No. AW756413 (gi:7685765) (May 3, 2000); Shoemaker, R., et al., "s121a12.y1 Gm-c1036 *Glycine max* cDNA clone Genome systems clone ID: Gm-c1036-1943 5' similar to TR:081130 081130 CCAAT-box binding factor HAP3 homolog, mRNA sequence"; (*Glycine max*).
NCBI accession No. AW760103 (gi:7691987) (May 4, 2000); Shoemaker, R., et al., "s158b03.y1 Gm-c1027 *Glycine max* cDNA clone Genome systems clone ID: Gm-c1027-5478 5' similar to TR:023310 023310 CCAAT-binding transcription factor subunit A, mRNA sequence"; (*Glycine max*).
NCBI accession No. AW775623 (gi:7765436) (May 9, 2000); Fedorova, M., et al., "EST334688 DSIL *Medicago truncatula* cDNA clone pDSIL-2K6, mRNA sequence"; (*Medicago truncatula*).
NCBI accession No. AW907348 (gi:8071558) (May 24, 2000); Van der Hoeven, R.S., et al., "EST343471 potato stolon, Cornell University *Solanum tuberosum* cDNA clone cSTA6D11, mRNA sequence"; (*Solanum tuberosum*).
NCBI accession No. AW931376 (gi:8106777) (May 30, 2000); Alcala, J., et al., "EST357219 tomato fruit mature green, TAMU *Lycopersicon esculentum* cDNA clone cLEF44N20 5', mRNA sequence"; (*Lycopersicon esculentum*).
NCBI accession No. AW931634 (gi:8107035) (May 30, 2000); Alcala, J., et al., "EST357477 tomato fruit mature green, TAMU *Lycopersicon esculentum* cDNA clone cLEF45F24 5', mRNA sequence"; (*Lycopersicon esculentum*).
NCBI accession No. AW980494 (gi:8172030) (Jun. 2, 2000); Fedorova, M., et al., "EST391647 GVN *Medicago truncatula* cDNA clone pGVN-55A17, mRNA sequence"; (*Medicago truncatula*).
NCBI accession No. AW981720 (gi:8173288) (Jun. 2, 2000); Whetten, R.W., et al., "PC15H07 pine Trip1Ex pollen cone library *Pinus taeda* cDNA clone PC15H07, mRNA sequence"; (*Pinus taeda*).
NCBI accession No. AX180950 (gi:15132741) (Aug. 9, 2001); Costa e Silva, O.D., et al., "Sequence 1 from Patent WO0145493"; (*Physcomitrella patens*) (note: the original submission and latest update are provided for examination) (publication: see WO 0145493-A1; Jun. 28, 2001).
NCBI accession No. AX180957 (gi:15132748) (Aug. 9, 2001); Costa e Silva, O.D., et al., "Sequence 8 from Patent WO0145493"; (*Physcomitrella patens*) (note: the original submission and latest update are provided for examination) (publication: see WO 0145493-A1; Jun. 28, 2001).
NCBI accession No. AX288144 (gi:17049846) (Nov. 22, 2001); da Costa Silva, O., et al., "Sequence 15 from Patent WO0177311"; (*Physcomitrella patens*) (note: the original submission and latest update are provided for examination) (publication: see WO 0177311-A 15; Oct. 18, 2001).
NCBI accession No. AX365282 (gi:18697024) (Feb. 16, 2002); Garnaat, C., et al., "Sequence 18 from Patent WO0206499"; (*Zea mays*) (note: the original submission and latest update are provided for examination) (publication: see WO 0206499-A 18; Jan. 24, 2002).
NCBI accession No. AX584259 (gi:27655760) (Jan. 11, 2003); Cahoon, R.E., et al., Sequence 1 from Patent WO02057439 (*Momordica charantia*) (note: the original submission and latest update are provided for examination) (publication: see WO 02057439-A 1; Jul. 25, 2002).
NCBI accession No. AX584261 (gi:27655761) (Jan. 11, 2003); Cahoon, R.E., et al., "Sequence 3 from patent WO2057439"; (*Eucalyptus grandis*) (note: the original submission and latest update are provided for examination) (publication: see WO 02057439-A 3; Jul. 25, 2002).
NCBI accession No. AX584263 (gi:27655762) (Jan. 11, 2003); Cahoon, R.E., et al., "Sequence 5 from Patent WO02057439"; (*Zea mays*) (note: the original submission and latest update are provided for examination) (publication: see WO 02057439-A 5; Jul. 25, 2002).
NCBI accession No. AX584265 (gi:27655763) (Jan. 11, 2003); Cahoon, R.E., et al., "Sequence 7 from Patent WO02057439"; (*Zea mays*) (note: the original submission and latest update are provided for examination) (publication: see WO 02057439-A 7; Jul. 25, 2002).
NCBI accession No. AX584267 (gi:27655764) (Jan. 11, 2003); Cahoon, R.E., et al., "Sequence 9 from patent WO02057439"; (*Oryza sativa*) (note: the original submission and latest update are provided for examination) (publication: see WO 02057439-A 9; Jul. 25, 2002).
NCBI accession No. AX584269 (gi:27655765) (Jan. 11, 2003); Cahoon, R.E., et al., "Sequence 11 from Patent WO02057439"; (*Oryza sativa*) (note: the original submission and latest update are provided for examination) (publication: see WO 02057439-A 11; Jul. 25, 2002).

(56) References Cited

OTHER PUBLICATIONS

NCBI accession No. AX584271 (gi:27655766) (Jan. 11, 2003); Cahoon, R.E. et al., "Sequence 13 from Patent WO02057439"; (*Glycine max*) (note: the original submission and latest update are provided for examination) (publication: see WO 02057439-A 13; Jul. 25, 2002).
NCBI accession No. AX584273 (gi:27655767) (Jan. 11, 2003); Cahoon, R.E., et al, "Sequence 15 from Patent WO02057439"; (*Glycine max*) (note: the original submission and latest update are provided for examination) (publication: see WO 02057439-A 15; Jul. 25, 2002).
NCBI accession No. AX584275 (gi:27655768) (Jan. 11, 2003); Cahoon, R.E., et al., "Sequence 17 from Patent WO02057439"; (*Glycine max*) (note: the original submission and latest update are provided for examination) (publication: see WO 02057439-A 17; Jul. 25, 2002).
NCBI accession No. AX584277 (gi:27655769) (Jan. 11, 2003); Cahoon, R.E., et al., "Sequence 19 from Patent WO02057439"; (*Glycine max*) (note: the original submission and latest update are provided for examination) (publication: see WO 02057439-A 19; Jul. 25, 2002).
NCBI accession No. AX584279 (gi:27655770) (Jan. 11, 2003); Cahoon, R.E., et al., "Sequence 21 from patent WO02057439"; (*Glycine max*) (note: the original submission and latest update are provided for examination) (publication: see WO 02057439-A 21; Jul. 25, 2002).
NCBI accession No. AX584281 (gi:27655771) (Jan. 11, 2003); Cahoon, R.E., et al., "Sequence 23 from patent WO02057439"; (*Triticum aestivum*) (note: the original submission and latest update are provided for examination) (publication: see WO 02057439-A 23; Jul. 25, 2002).
NCBI accession No. AX584283 (gi:27655772) (Jan. 11, 2003); Cahoon, R.E., et al., "Sequence 25 from patent WO02057439"; (*Triticum aestivum*) (note: the original submission and latest update are provided for examination) (publication: see WO 02057439-A 25; Jul. 25, 2002).
NCBI accession No. AX584285 (gi:27655773) (Jan. 11, 2003); Cahoon, R.E., et al., "Sequence 27 from patent WO02057439"; (*Triticum aestivum*) (note: the original submission and latest update are provided for examination) (publication: see WO 02057439-A 27; Jul. 25, 2002).
NCBI accession No. AX584287 (gi:27655774) (Jan. 11, 2003); Cahoon, R.E., et al., "Sequence 29 from patent WO02057439"; (*Canna indica*) (note: the original submission and latest update are provided for examination) (publication: see WO 02057439-A 29; Jul. 25, 2002).
NCBI accession No. AY112643 (gi:21217233) (May 26, 2002); Gardiner, J., et al., "Zea mays CL691_1 mRNA sequence"; (*Zea mays*) (note: the original submission and latest update are provided for examination) (publication: see Plant Physiol. 134 (4), 1317-1326 2004, Anchoring 9,371 maize expressed sequence tagged unigenes to the bacterial artificial chromosome contig map by two-dimensional overgo hybridization).
NCBI accession No. BAB64189 (gi:15408793) (Aug. 31, 2001); Sasaki, T., et al. "P0492G09.10" (*Oryza sativa*) (note: the original submission and latest update are provided for examination) (publication: see Nature 420 (6913), 312-316, 2002, The genome sequence and structure of rice chromosome 1).
NCBI accession No. BAB64190 (gi:15408794) (Aug. 31, 2001); Sasaki, T., et al. "Putative HAP3-like transcriptional-activator" (*Oryza sativa*) (note: the original submission and latest update are provided for examination) (publication: see Nature 420 (6913), 312-316, 2002, The genome sequence and structure of rice chromosome 1).
NCBI accession No. BAB89732 (gi:20160792) (Apr. 16, 2002); Sasaki, et al. "Putative CAAT-box DNA binding protein" (*Oryza sativa*) (note: the original submission and latest update are provided for examination) (publication: see Nature 420 (6913), 312-316, 2002, The genome sequence and structure of rice chromosome 1).

NCBI accession No. BAB92931 (gi:20805265) (May 15, 2002); Sasaki, T., et al. "Putative CAAT-box DNA binding protein" (*Oryza sativa*) (note: the original submission and latest update are provided for examination) (publication: see Nature 420 (6913), 312-316, 2002, The genome sequence and structure of rice chromosome 1).
NCBI accession No. BAB93257 (gi:21104666) (May 22, 2002); Sasaki, T., et al. "P0423A12.29" (*Oryza sativa*) (note: the original submission and latest update are provided for examination) (publication: see Nature 420 (6913), 312-316, 2002, The genome sequence and structure of rice chromosome 1).
NCBI accession No. BAB93258 (gi:21104667) (May 22, 2002); Sasaki, T., et al. "Putative HAP3-like transcriptional-activator"; (*Oryza sativa*) (note: the original submission and latest update are provided for examination) (publication: see Nature 420 (6913), 312-316, 2002, The genome sequence and structure of rice chromosome 1).
NCBI accession No. BAC76331 (gi:30409459) (May 6, 2003); Miyoshi, K., et al., "NF-YB [*Oryza sativa* (japonica cultivar-group)]" (note: the original submission and latest update are provided for examination) (publication: see Plant J. 36, 532-540, 2003, OsHAP3 genes regulate chloroplast biogenesis in rice).
NCBI accession No. BAC76332 (gi:30409461) (May 6, 2003); Miyoshi, K., et al., "NF-YB [*Oryza sativa* (japonica cultivar-group)]"; (note: the original submission and latest update are provided for examination) (publication: see Plant J. 36, 532-540, 2003, OsHAP3 genes regulate chloroplast biogenesis in rice).
NCBI accession No. BAC76333 (gi:30409463) (May 6, 2003); Miyoshi, K., et al., "NF-YB [*Oryza sativa* (japonica cultivar-group)]"; (note: the original submission and latest update are provided for examination) (publication: see Plant J. 36, 532-540, 2003, OsHAP3 genes regulate chloroplast biogenesis in rice).
NCBI accession No. BE021941 (gi:8284382) (Jun. 6, 2000); Shoemaker, R., et al., "sm64d05.y1 Gm-c1028 *Glycine max* cDNA clone Genome systems clone ID: Gm-c1028-8674 5' similar to TR:Q9ZQC3 Q9ZQC3 Putative CCAAT-binding transcription factor; mRNA sequence"; (*Glycine max*).
NCBI accession No. BE054369 (gi:13243855) (Jun. 8, 2000); Wing, R.A., et al., "GA_Ea0002A05f *Gossypium arboreum* 7-10 dpa fiber library *Gossypium arboreum* cDNA clone GA_Ea0002A05f, mRNA sequence"; (*Gossypium arboreum*) (note: two versions are presented for review, gi:13243855 submitted Jun. 8, 2000; and, gi:8381425 submitted on Jun. 8, 2000).
NCBI accession No. BE060015 (gi:8404381) (Jun. 9, 2000); Shoemaker, R., et al., "sn39h06.y1 Gm-c1027 *Glycine max* cDNA clone Genome systems clone ID: Gm-c1027-9684 5' similar to TR:023634 023634 transcription factor; mRNA sequence"; (*Glycine max* ).
NCBI accession No. BE121888 (gi:8513993) (Jun. 13, 2000); Grossman, A., et al., "894015G05.y1 *C. reinhardtii* cc-1690, normalized, Lambda ZapII *Chlamydomonas reinhardtii* cDNA, mRNA sequence"; (*Chlamydomonas reinhardtii*).
NCBI accession No. BE196056 (gi:13188584) (Jun. 26, 2000); Wing, R., et al., "HVSMEh0091D23f *Hordeum vulgare* 5-45 DAP spike EST library HVcDNA0009 (5 to 45 DAP) *Hordeum vulgare* subsp. Vulgare cDNA clone HVSMEh0091D23f, mRNA sequence"; (*Hordeum vulgare*) ) (note: two versions are presented for review, gi:13188584 submitted Jun. 26, 2000; and, gi:8708251 submitted Jun. 26, 2000).
NCBI accession No. BE210041 (gi:8826311) (Jun. 29, 2000); Shoemaker, R., et al., "so38b01.y1 Gm-c1039 *Glycine max* cDNA clone Genome systems clone ID: Gm-c1039-194 5' similar to TR:Q9ZQC3 Q9ZQC3 putative CCAAT-binding transcription factor; mRNA sequence"; (*Glycine max*).
NCBI accession No. BE356560 (gi:9298117) (Jul. 20, 2000); Cordonnier-Pratt, M., et al. "DG1_126_D05.b1_A002 Dark Grown 1 (DG1) Sorghum bicolor cDNA, mRNA sequence"; (*Sorghum bicolor*).
NCBI accession No. BE413647 (gi:9411493) (Jul. 24, 2000); Anderson, O.A., et al., "SCU001.E10.R990714 ITEC SCU Wheat Endosperm Library *Triticum aestivum* cDNA clone SCU001.E10, mRNA sequence"; (*Triticum aestivum*).

(56) References Cited

OTHER PUBLICATIONS

NCBI accession No. BE418716 (gi:9416562) (Jul. 24, 2000); Anderson, O.A., et al., "SCL074.B01R990724 ITEC SCL Wheat Leaf Library *Triticum aestivum* cDNA clone SCL074.B01, mRNA sequence"; (*Triticum aestivum*).
NCBI accession No. BE441135 (gi:9440635) (Jul. 25, 2000); Alcala, J., et al., "EST408405 tomato developing/immature green fruit *Lycopersicon esculentum* cDNA clone cLEM6C23 similar to *Zea mays* CAAT-box DNA binding protein subunit B, mRNA sequence"; (*Lycopersicon esculentum*).
NCBI accession No. BE441739 (gi:9441376) (Jul. 25, 2000); Grossman, A., et al., "925009A11.x1 *C. Reinhardtii* CC-2290, normalized, Lambda Zap II *Chlamydomonas reinhardtii* cDNA, mRNA sequence"; (*Chlamydomonas reinhardtii*).
NCBI accession No. BE496857 (gi:9695474) (Aug. 4, 2000); Anderson, O.D. et al., "WHE0761_D09_H17ZS Wheat heat-stressed seedling cDNA library *Triticum aestivum* cDNA clone WHE0761_D09_H17, mRNA sequence"; (*Triticum aestivum*).
NCBI accession No. BE516510 (gi:9740538) (Aug. 8, 2000); Anderson, O.D., et al., "WHE611_D10_H19ZA Wheat ABA-treated embryo cDNA library *Triticum aestivum* cDNA clone WHE611_D10_H19, mRNA sequence"; (*Triticum aestivum*).
NCBI accession No. BE603222 (gi:13191083) (Aug. 21, 2000); Wing, R., et al., "HVSMEh0102J16f *Hordeum vulgare* 5-45 DAP spike EST library HVcDNA0009 (5 to 4 DAP) *Hordeum vulgare* subsp. Vulgare cDNA clone HVSMEh0102J16f, mRNA sequence"; (*Hordeum vulgare*) ) (note: two versions are presented for review, gi:13191083 submitted Aug. 21, 2000; and, gi:9860783 submitted Aug. 21, 2000).
NCBI accession No. BE604847 (gi:9862117) (Aug. 21, 2000); Anderson, O.D., et al., "WHE1713-1716_D19_D19ZS Wheat heat stressed spike cDNA library *Triticum aestivum* cDNA clone WHE1713-1716_D19_D19, mRNA sequence"; (*Triticum aestivum*).
NCBI accession No. BE641101 (gi:9958761) (Sep. 1, 2000); Salmi, M.L., et al., "Cri2_2_E11_SP6 Ceratopteris Spore Library Ceratopteris richardii cDNA clone Crit_2_E11 5', mRNA sequence"; (*Ceratopteris richardii*) (publication: see Plant Physiol. 138 (3), 1734-1745, 2005, Profile and analysis of gene expression changes during early development in germinating spores of *Ceratopteris richardii*).
NCBI accession No. BE726750 (gi:10127934) (Sep. 14, 2000); Grossman, A., et al., "894093C12.y3 *C. Reinhardtii* CC-1690, normalized, Lambda Zap II *Chlamydomonas reinhardtii* cDNA, mRNA sequence"; (*Chlamydomonas reinhardtii*).
NCBI accession No. BE802539 (gi:10233651) (Sep. 20, 2000); Shoemaker, R, et al., "sr32f02.y1 Gm-c1050 *Glycine max* cDNA clone Genome systems clone ID: Gm-c1050-2068 5' similar to SW:CBFA_Maize P25209 CCAAT-binding transcription factor subunit A; mRNA sequence"; (*Glycine max*).
NCBI accession No. BE803572 (gi:10234684) (Sep. 20, 2000); Shoemaker, R, et al., "sr60e 1 1.y1 Gm-c1052 *Glycine max* cDNA clone Genome systems clone ID: Gm-c1052-165 5' similar to TR:Q9ZQC3 Q9ZQC3 Putative CCAAT-binding transcription factor; mRNA sequence"; (*Glycine max*).
NCBI accession No. BE804236 (gi:10235348) (Sep. 20, 2000); Shoemaker, R, et al., "sr77b04.y1 Gm-c1052 *Glycine max* cDNA clone Genome systems clone ID: Gm-c1052-1736 5' similar to SW:CBFA_Maize P25209 CCAAT-binding transcription factor subunit A; mRNA sequence"; (*Glycine max*).
NCBI accession No. BF065056 (gi:10841695) (Oct. 17, 2000); Wing, R., et al., "HV_CEb022M01f *Hordeum vulgare* seedling green leaf EST library HvcDNA 0005 (*Blumeria* challenged) *Hordeum vulgare* subsp. Vulgare cDNA clone HV_CEb0022M01f, mRNA sequence"; (*Hordeum vulgare*).
NCBI accession No. BF071234 (gi:10845982) (Oct. 17, 2000); Shoemaker, R, et al., "stO6h05.y1 Gm-c1065 *Glycine max* cDNA clone Genome systems clone ID: Gm-c1065-562 5' similar to TR:Q9ZQC3 Q9ZQC3 Putative CCAAT-binding transcription factor; mRNA sequence"; (*Glycine max*).

NCBI accession No. BF169598 (gi:11054215) (Oct. 30, 2000); Sederoff, R., "NXCI_125_B04_F NXCI (Nsf Xylem Compression wood Inclined) *Pinus taeda* cDNA clone NXCI_125_B04 5' similar to *Arabidopsis thaliana* sequence At2g37060 putative CCAAT-box binding transcription factor see http://mips.gsf.de/proj/thal/db/index.html, mRNA sequence"; (*Pinus taeda*).
NCBI accession No. BF263449 (gi:13260832) (Nov. 17, 2000); Wing, R, et al., "HV_CEa0006M10f *Hordeum vulgare* seedling green leaf EST library HvcDNA 0004 (*Blumeria* challenged) *Hordeum vulgare* subsp. Vulgare cDNA clone HV_CEa0006M10f, mRNA sequence"; (*Hordeum vulgare*) (note: two versions are presented for review, gi:13260832 submitted Nov. 17, 2000; and, gi:11194443 submitted Nov. 17, 2000).
NCBI accession No. BF263455 (gi:13260837) (Nov. 17, 2000); Wing, R, et al., "HV_CEa0006M16f *Hordeum vulgare* seedling green leaf EST library HvcDNA 0004 (*Blumeria challenged*) *Hordeum vulgare* subsp. Vulgare cDNA clone HV_CEa0006M16f, mRNA sequence"; (*Hordeum vulgare*) (note: two versions are presented for review, gi:13260837 submitted on Nov. 17, 2000; and gi:16334312 submitted Oct. 23, 2001).
NCBI accession No. BF270164 (gi:13247369) (Nov. 17, 2000); Wing, R, et al., "GA_Eb0007A21f *Gossypium arboreum* 7-10 dpa fiber library *Gossypium arboreum* cDNA clone GA_Eb0007A21f, mRNA sequence"; (*Gossypium arboreum*) (note: two versions are presented for review, gi:13247369 submitted Nov. 17, 2000; and, gi:11201159 submitted Nov. 17, 2000).
NCBI accession No. BF270944 (gi:11201939) (Nov. 17, 2000); Wing, R, et al., "GA_Eb0010B11f *Gossypium arboreum* 7-10 dpa fiber library *Gossypium arboreum* cDNA clone GA_Eb0010B11f, mRNA sequence"; (*Gossypium arboreum*).
NCBI accession No. BF291752 (gi:11222816) (Nov. 17, 2000); Akhunov, E., et al., "WHE2205_F04_K07ZS *Aegilops speltoides* anther cDNA library *Aegilops speltoides* cDNA clone WHE2205_F04_K07, mRNA sequence"; (*Aegilops speltoides*).
NCBI accession No. BF459554 (gi:11528732) (Dec. 4, 2000); Crookshanks, M., et al., "061A04 Mature tuber lambda ZAP *Solanum tuberosum* cDNA 5' similar to (AL132966) transcription factor NF-Y, CCAAT-binding . . . emb CAB7641.1, mRNA sequence"; (*Solanum tuberosum*) (publication: see FEBS Lett. 506 (2), 123-126, 2001, The potato tuber transcriptome: analysis of 6077 expressed sequence tags).
NCBI accession No. BF460267 (gi:11529424) (Dec. 4, 2000); Crookshanks, M., et al., "073E08 Mature tuber lambda ZAP *Solanum tuberosum* cDNA 5' similar to CCAAT-binding transcription factor subunit . . . sp P25209, mRNA sequence"; (*Solanum tuberosum*) (publication: see FEBS Lett. 506 (2), 123-126, 2001, The potato tuber transcriptome: analysis of 6077 expressed sequence tags).
NCBI accession No. BF517889 (gi:11606021) (Dec. 8, 2000); Sederoff, R., "NXSI_029_D01_F NXSI (Nsf Xylem Side wood Inclined) *Pinus taeda* cDNA clone NXSI_029_D01 5' similar to *Arabidopsis thaliana* sequence At2g37060 putative CCAAT-box binding transcription factor see http://mips.gsf.de/proj/thal/db/index.html, mRNA sequence"; (*Pinus taeda*).
NCBI accession No. BF585526 (gi:11677850) (Dec. 12, 2000); Cordonnier-Pratt, M., et al., "FM1_23_E09.g1_A003 Floral-Induced Meristem 1 (FM1) *Sorghum propinquum* cDNA, mRNA sequence"; (*Sorghum propinquum*).
NCBI accession No. BF585616 (gi:11677940) (Dec. 12, 2000); Cordonnier-Pratt, M., et al., "FM1_23_E09.b1_A003 Floral-Induced Meristem 1 (FM1) *Sorghum propinquum* cDNA, mRNA sequence"; (*Sorghum propinquum*).
NCBI accession No. BF595304 (gi:11687628) (Dec. 12, 2000); Shoemaker, R., et al, "su76f03.y1 Gm-c1055 *Glycine max* cDNA clone Genome Systems clone ID: gm-c1055-653 5' similar to TR:081130 081130 CCAAT-Box binding factor HAP3 homolog; mRNA sequence"; (*Glycine max*).
NCBI accession No. BF597252 (gi:11689576) (Dec. 12, 2000); Shoemaker, R., et al, "su96c06.y1 Gm-c1056 *Glycine soja* cDNA clone Genome Systems clone ID: gm-c1056-131 5' similar to TR:Q9zQC3 Q9ZQC3 Putative CCAAT-Box binding transcription factor; mRNA sequence"; (*Glycine soja*).

(56) References Cited

OTHER PUBLICATIONS

NCBI accession No. BF636140 (gi:11900298) (Dec. 19, 2000); Torrez-Jerez, I., et al, "NF060H09DT1F1079 Drought *Medicago truncatula* cDNA clone NF060H09DT 5', mRNA sequence"; (*Medicago truncatula*).

NCBI accession No. BF645376 (gi:11910505) (Dec. 20, 2000); Torres-Jerez, I., et al., "NF040B5EC1F1044 Elicted cell culture *Medicago truncatula* cDNA clone NF040B05EC 5', mRNA sequence"; (*Medicago truncatula*).

NCBI accession No. BF651151 (gi:11916281) (Dec. 20, 2000); Torres-Jerez, I., et al., "NF101H1OEC1F1090 Elicted cell culture *Medicago truncatula* cDNA clone NF101H10EC 5', mRNA sequence"; (*Medicago truncatula*).

NCBI accession No. BF715909 (gi:12015181) (Jan. 2, 2001); Shoemaker, R., et al., "saa11e08.y1 Gm-c1058 *Glycine soja* cDNA clone Genome systems clone ID: Gm-c1058-999 5' similar to TR:O23310 O23310 CCAAT-binding transcription factor subunit A; mRNA sequence"; (*Glycine soja*).

NCBI accession No. BF777951 (gi:12125851) (Jan. 12, 2001); Sederoff, R., "NXSI_079_C03_F NXSI (Nsf Xylem Side wood Inclined) *Pinus taeda* cDNA clone NXSI_079_C03 5' similar to *Arabidopsis thaliana* sequence At4g14540 CCAAT-binding transcription factor subunit A (CBF-A) see http://mips.gsf.de/proj/thal/db/index.html, mRNA sequence"; (*Pinus taeda*).

NCBI accession No. BG039303 (gi:12481888) (Jan. 24, 2001); Sederoff, R., "NXSI_097_E11_F NXSI (Nsf Xylem Side Wood Inclined) *Pinus taeda* cDNA clone NXSI_097_E11 5' similar to *Arabidopsis thaliana* sequence At2g37060 putative CCAAT-box binding transcription factor see http://mips.gsf.de/proj/thal/db/index.html, mRNA sequence"; (*Pinus taeda*).

NCBI accession No. BG135204 (gi:12635392) (Jan. 31, 2001); Van der Hoeven, R., et al., "EST468096 tomato crown gall *Lycopersicon esculentum* cDNA clone cTOE21D12 5' sequence, mRNA sequence"; (*Lycopersicon esculentum*).

NCBI accession No. BG263362 (gi:12865444) (Feb. 16, 2001); Anderson, O.D., et al., "WHE2341_B02_C03ZS Wheat pre-anthesis spike cDNA library *Triticum aestivum* cdNA clone WHE2341_B02_C03, mRNA sequence"; NCBI accession No. BG263362 (gi:12865444) (*Triticum aestivum*).

NCBI accession No. BG274786 (gi:13067446) (Feb. 21, 2001); Akhunov, E., et al., "WHE2234_C03 E06ZS *Aegilops speltoides* anther cDNA library *Aegilops speltoides* cDNA clone WHE2234_C03_E06, mRNA sequence"; (*Aegilops speltoides*).

NCBI accession No. BG314203 (gi:13116006) (Feb. 23, 2001); Anderson, 0.D., et al., "WHE2460_E10_I20ZS *Triticum monococcum* early reproductive apex cDNA library *Triticum monococcum* cDNA clone WHE2460_E10_120, mRNA sequence"; (*Triticum monococcum*).

NCBI accession No. BG318871 (gi:13128301) (Feb. 26, 2001); Sederoff, R., "NXPV_020_H08_F NXPV (Nsf Xylem Planings Wood Vertical) *Pinus taeda* cDNA clone NXPV_020_H08 5' similar to *Arabidopsis thaliana* sequence At4g14540 CCAAT-binding transcription factor subunit a (CBF-A) see http://mips.gsf.de/proj/thal/db/index.html, mRNA sequence"; (*Pinus taeda*).

NCBI accession No. BG350430 (gi:13179172) (Mar. 1, 2001); Crookshanks, M., et al., "091D09 mature tuber lambda ZAP *Solanum tuberosum* cDNA, mRNA sequence"; (*Solanum tuberosum*) (publication: see FEBS Lett. 506 (2), 123-126, 2001, The potato tuber transcriptome: analysis of 6077 expressed sequence tags).

NCBI accession No. BG350792 (gi:13179534) (Mar. 1, 2001); Crookshanks, M., et al., "098C07 mature tuber lambda ZAP *Solanum tuberosum* cDNA, mRNA sequence"; (*Solanum tuberosum*) (publication: see FEBS Lett. 506 (2), 123-126, 2001, The potato tuber transcriptome: analysis of 6077 expressed sequence tags).

NCBI accession No. BG362898 (gi:13251995) (Mar. 8, 2001); Shoemaker, R., et al., "sacl3e07.y1 Gm-c1040 *Glycine max* cDNA clone Genome systems clone ID: Gm-c1040-4453 5' similar to TR:023633 023633 Transcription factor; mRNA sequence"; (*Glycine max*).

NCBI accession No. BG363233 (gi:13252330) (Mar. 8, 2001); Shoemaker, R., et al., "sacl1h11.y1 Gm-c1040 *Glycine max* cDNA clone Genome Systems clone ID: Gm-c1040-4581 5' similar to TR: Q9ZQC3 Q9ZQC3 Putative CCAAT-binding transcription factor; mRNA sequence"; (*Glycine max*).

NCBI accession No. BG368375 (gi:13257476) (Mar. 8, 2001); Wing, R., et al., "HVSMEi0018C01f *Hordeum vulgare* 20 DAP spike EST library HvcDNA0010 (20 DAP) *Hordeum vulgare* subsp. vulgare cDNA clone HVSMEi0018C01f, mRNA sequence"; (*Hordeum vulgare*) ) (note: two versions are presented for review, gi:13257476 submitted Mar. 8, 2001; and, gi:16325230 submitted Oct. 22, 2001).

NCBI accession No. BG440251 (gi:13349902) (Mar. 15, 2001); Wing, R.A., et al., "GA_Ea006K20f *Gossypium arboreum* 7-10 dpa fiber library *Gossypium arboreum* cDNA clone GA_Ea0006K20f, mRNA sequence"; (*Gossypium arboreum*).

NCBI accession No. BG445358 (gi:13355010) (Mar. 15, 2001); Wing, R.A., et al., "GA_Ea0027N18f *Gossypium arboreum* 7-10 dpa fiber library *Gossypium arboreum* cDNA clone GA_Ea0027N18f, mRNA sequence"; (*Gossypium arboreum*).

NCBI accession No. BG526135 (gi:16949604) (Nov. 16, 2001); Brandle, J.E., et al., "57-6 Stevia field grown leaf cDNA *Stevia rebaudiana* cDNA 5', mRNA sequence"; (*Stevia rebaudiana*).

NCBI accession No. BG551755 (gi:13563535) (Apr. 9, 2001); Shoemaker, R., "sad42f11.y1 Gm-c1075 *Glycine max* cDNA clone Genome systems clone ID: Gm-c1075-669 5' similar to TR:081130 081130 CCAAT-Box binding factor HAP3 homolog; mRNA sequence"; (*Glycine max*).

NCBI accession No. BG589029 (gi:13607169) (Apr. 12, 2001); Harrison, M.J., et al., "EST490838 MHRP-*Medicago truncatula* cDNA clone pMHRP-59024, mRNA sequence"; (*Medicago truncatula*).

NCBI accession No. BG594268 (gi:13612408) (Apr. 12, 2001); Van der Hoeven, R., et al., "EST492946 cSTS *Solanum tuberosum* cDNA clone cSTS7A17 5' sequence, mRNA sequence"; (*Solanum tuberosum*).

NCBI accession No. BG599785 (gi:13616921) (Apr. 12, 2001); Van der Hoeven, R., et al., "EST504680 cSTS *Solanum tuberosum* cDNA clone cSTS26G12 5' sequence, mRNA sequence"; (*Solanum tuberosum*).

NCBI accession No. BG642751 (gi:13777673) (Apr. 24, 2001); Van der Hoeven, R., et al., "EST510945 tomato shoot/meristem *Lycopersicon esculentum* cDNA clone cTOF25F23 5' sequence, mRNA sequence"; (*Lycopersicon esculentum*).

NCBI accession No. BG644353 (gi:13779465) (Apr. 24, 2001); VandenBosch, K., et al., "EST505972 KV3 *Medicago truncatula* cDNA clone pKV3-37C23 5' end, mRNA sequence"; (*Medicago truncatula*).

NCBI accession No. BG662094 (gi:13884016) (Apr. 30, 2001); Poulsen, C., et al., "Ljirnpest38-110-g8 Ljirnp Lambda HybriZap two-hybrid library *Lotus corniculatus* var. japonicus cDNA clone LP110-38-g8 5' similar to homolog of transcription factor NF-Y, CCAAT-binding-like protein, mRNA sequence"; (*Lotus corniculatus*).

NCBI accession No. BG832836 (gi:14189478) (May 22, 2001); Sederoff, R., "NXPV_081_C10_F NXPV (Nsf Xylem Planings wood Vertical) *Pinus taeda* cDNA clone NXPV_081_C10 5' similar to *Arabidopsis thaliana* sequence At4g14540 CCAAT-binding transcription factor subunit A (CBF-A) see http://mips.gsf.de/proj/thal/db/index.html, mRNA sequence"; (*Pinus taeda*).

NCBI accession No. BG846124 (gi:14227308) (May 29, 2001); Grossman, A., et al., "1024012C11.y1 C. Reinhardtii CC-1690, normalized, Lambda Zap II *Chlamydomonas reinhardtii* cDNA, mRNA sequence"; (*Chlamydomonas reinhardtii*).

NCBI accession No. BG847452 (gi:14228636) (May 29, 2001); Grossman, A., et al., "1024017D03.y1 C. Reinhardtii CC-1690, normalized, Lambda Zap II *Chlamydomonas reinhardtii* cDNA, mRNA sequence"; (*Chlamydomonas reinhardtii*).

NCBI accession No. BG850688 (gi:14231872) (May 29, 2001); Grossman, A., et al., "1024029A11.y1 C. Reinhardtii CC-1690, normalized, Lambda Zap II *Chlamydomonas reinhardtii* cDNA, mRNA sequence"; (*Chlamydomonas reinhardtii*).

NCBI accession No. BG850689 (gi:14231873) (May 29, 2001); Grossman, A., et al., "1024029A11.y2 C. Reinhardtii CC-1690, normalized, Lambda Zap II *Chlamydomonas reinhardtii* cDNA, mRNA sequence"; (*Chlamydomonas reinhardtii*).

(56) References Cited

OTHER PUBLICATIONS

NCBI accession No. BG857007 (gi:14238191) (May 29, 2001); Grossman, A., et al., "1024049D01.y1 C. Reinhardtii CC-1690, normalized, Lambda Zap II *Chlamydomonas reinhardtii* cDNA, mRNA sequence"; (*Chlamydomonas reinhardtii*).
NCBI accession No. BG858372 (gi:14239556) (May 29, 2001); Grossman, A., et al., "1024057C11.y1 C. Reinhardtii CC-1690, normalized, Lambda Zap II *Chlamydomonas reinhardtii* cDNA, mRNA sequence"; (*Chlamydomonas reinhardtii*).
NCBI accession No. BG890447 (gi:14267556) (May 30, 2001); Van der Hoeven, R., et al., "EST516298 cSTD *Solanum tuberosum* cDNA clone cSTD18M6 5' sequence, mRNA sequence"; (*Solanum tuberosum*).
NCBI accession No. BH966788 (gi:23448014) (Oct. 1, 2002); Delehaunty, K., et al., "odi26h12.b1 *B.oleracea*002 *Brassica oleracea* genomic, genomic survey sequence"; (*Brassica oleracea*).
NCBI accession No. BI129814 (gi:18013785) (Dec. 31, 2001); Hertzberg, M., et al., "G095P88Y *Populus cambium* cDNA library *Populus tremula* x *Populus tremuloides* cDNA, mRNA sequence"; (*Populus tremula* x *Populus tremuloides*).
NCBI accession No. BI176409 (gi:14642220) (Jul. 9, 2001); Restrepo, S, et al., "EST521199 P. Infestans-challenged potato leaf, compatible reaction *Solanum tuberosum* cDNA clone PPCAC88 5' sequence similar to CCAAT-box binding transcription factor gene_ id:MNJ7.26 (*Arabdiopsis thaliana*), mRNA sequence"; (*Solanum tuberosum*).
NCBI accession No. BI206716 (gi:14684440) (Jul. 11, 2001); Van der Hoeven, R., et al., "EST524756 cTOS *Lycopersicon esculentum* cDNA clone cTOS11H10 5' end, mRNA sequence"; (*Lycopersicon esculentum*).
NCBI accession No. BI207873 (gi:14685597) (Jul. 11, 2001); Van der Hoeven, R., et al., "EST525913 cTOS *Lycopersicon esculentum* cDNA clone cTOS15I16 5' end, mRNA sequence"; (*Lycopersicon esculentum*).
NCBI accession No. BI268123 (gi:14873755) (Jul. 18, 2001); Korth, K., et al., "NF116D11IN1F1094 Insect herbivory *Medicago truncatula* cDNA clone NF116D11IN 5', mRNA sequence"; (*Medicago truncatula*).
NCBI accession No. BI271802 (gi:14880590) (Jul. 18, 2001); Torres-Jerez, I., et al., "NF013D06FL1F1057 Developing flower *Medicago truncatula* cDNA clone NF013D06FL 5', mRNA sequence"; (*Medicago truncatula*).
NCBI accession No. BI309186 (gi:14983513) (Jul. 20, 2001); Grusak, M.A., et al., "EST530596 GPOD *Medicago truncatula* cDNA clone pGPOD-10P10 5' end, mRNA sequence"; (*Medicago truncatula*).
NCBI accession No. BI311277 (gi:14985604) (Jul. 20, 2001); Grusak, M.A., et al., "EST5313027 GESD *Medicago truncatula* cDNA clone pGESD10M10 5' end, mRNA sequence"; (*Medicago truncatula*).
NCBI accession No. BI316766 (gi:14991093) (Jul. 20, 2001); Shoemaker, R., et al., "saf73a12.y1 Gm-c1078 *Glycine max* cDNA clone Genome systems clone ID: Gm-c1078-1584 5' similar to TR: Q9ZQC3 Q9ZQC3 Putative CCAAT-Binding transcription factor; mRNA sequence"; (*Glycine max*).
NCBI accession No. BI406257 (gi:15185671) (Aug. 14, 2001); Crookshanks, M., et al., "158C12 Mature tuber lambda Zap *Solanum tubersum* cDNA, mRNA sequence"; (*Solanum tuberosum*) (publication: see FEBS Lett. 506 (2), 123-126, 2001, The potato tuber transcriptome: analysis of 6077 expressed sequence tags).
NCBI accession No. BI419749 (gi:15190772) (Aug. 15, 2001); Colebatch, G., et al., "LjNEST14e12r *Lotus japonicus* nodule library 5 and 7 week-old *Lotus corniculatus* var. japonicus cDNA 5', mRNA sequence"; (*Lotus corniculatus* var. japonicus).
NCBI accession No. BI423967 (gi:15199704) (Aug. 16, 2001); Shoemaker, R., et al., "sah64c11.y1 Gm-c1049 *Glycine max* cDNA clone Genome systems clone ID: Gm-c1049-3189 5' similar to TR:023310 023310 CCAAT-binding transcription factor subunit A; mRNA sequence"; (*Glycine max*).

NCBI accession No. BI469382 (gi:15285491) (Aug. 24, 2001); Shoemaker, R., et al., "saillb10.y1 Gm-c1053 *Glycine max* cDNA clone Genome systems clone ID: Gm-c1053-2779 5' similar to TR:023310 023310 CCAAT-Binding transcription factor subunit A; mRNA sequence"; (*Glycine max*).
NCBI accession No. BI480208 (gi:15315976) (Aug. 27, 2001); Akhunov, E., et al., "WHE2403_H07_P13ZS Wheat 3-6 DAP seed cDNA library *Triticum aestivum* cDNA clone WHE2403_H07_ P13, mRNA sequence"; (*Triticum aestivum*).
NCBI accession No. BI531782 (gi:15372356) (Aug. 29, 2001); Grossman, A., et al., "1024116E03.y1 C. Reinhardtii CC-1690, normalized, Lambda Zap II *Chlamydomonas reinhardtii* cDNA, mRNA sequence"; (*Chlamydomonas reinhardtii*).
NCBI accession No. BI531808 (gi:15372382) (Aug. 29, 2001); Grossman, A., et al., "1024116G03.y1 C. Reinhardtii cc-1690, normalized, Lambda Zap II *Chlamydomonas reinhardtii* cDNA, mRNA sequence"; (*Chlamydomonas reinhardtii*).
NCBI accession No. BI718232 (gi:15693927) (Sep. 19, 2001); Grossman, A., et al., "1031024F10.y1 C. Reinhardtii cc-1690, stress II (normalized), Lambda Zap II *Chlamydomonas reinhardtii* cDNA, mRNA sequence"; (*Chlamydomonas reinhardtii*).
NCBI accession No. BI719728 (gi:15695423) (Sep. 19, 2001); Grossman, A., et al., "1031045D08.y1 C. Reinhardtii cc-1690, stress II (normalized), Lambda Zap II *Chlamydomonas reinhardtii* cDNA, mRNA sequence"; (*Chlamydomonas reinhardtii*).
NCBI accession No. BI875221 (gi:16073225) (Oct. 11, 2001); Grossman, A., et al., "963122G10.y1 C. Reinhardtii cc-1690, stress condition I, normalized, Lambda Zap II *Chlamydomonas reinhardtii* cDNA, mRNA sequence"; (*Chlamydomonas reinhardtii*).
NCBI accession No. BI952722 (gi:16296768) (Oct. 19, 2001); Wing, R., et al., "HVSMEm0007I19f *Hordeum vulgare* green seedling EST library HvcDNA0014 (*Blumeria* infected) *Hordeum vulgare* subsp. Vulgare cDNA clone HVSMEm0007I19f, mRNA sequence"; (*Hordeum vulgare*).
NCBI accession No. BI953657 (gi:16298505) (Oct. 19, 2001); Wing, R., et al., "HVSMEm0013M03f *Hordeum vulgare* green seedling EST library HvcDNA0014 (*Blumeria*infected) *Hordeum vulgare* subsp. Vulgare cDNA clone HVSMEm0013M03f, mRNA sequence"; (*Hordeum vulgare*).
NCBI accession No. BI967397 (gi:16341802) (Oct. 23, 2001); Vodkin, L., et al., "GM830001B20E03 Gm-r1083 *Glycine max* cDNA clone Gm-r1083-222 3', mRNA sequence"; (*Glycine max*).
NCBI accession No. BI972318 (gi:16346723) (Oct. 23, 2001); Shoemaker, R., et al., "sag90a01.y1 Gm-c1084 *Glycine max* cDNA clone Genome Systems clone ID: Gm-c1084-1178 5' similar to TR: Q9ZQC3 Q9ZQC3 Putative CCAAT-Binding Transcription Factor; mRNA sequence"; (*Glycine max*).
NCBI accession No. BJ208385 (gi:19946503) (Apr. 4, 2002); Ogihara, Y., et al., "BJ208385 Y. Ogihara unpublished cDNA library, Wh *Triticum aestivum* cDNA clone wh8a18 5', mRNA sequence"; (*Triticum aestivum*).
NCBI accession No. BJ208815 (gi:19947041) (Apr. 4, 2002); Ogihara, Y., et al., "BJ208815 Y. Ogihara unpublished cDNA library, Wh *Triticum aestivum* cDNA clone wh10p16 5', mRNA sequence"; (*Triticum aestivum*).
NCBI accession No. BJ210400 (gi:19949034) (Apr. 4, 2002); Ogihara, Y., et al., "BJ210400 Y. Ogihara unpublished cDNA library, Wh *Triticum aestivum* cDNA clone wh27122 5', mRNA sequence"; (*Triticum aestivum*).
NCBI accession No. BJ210722 (gi:19949459) (Apr. 4, 2002); Ogihara, Y., et al., "BJ210722 Y. Ogihara unpublished cDNA library, Wh *Triticum aestivum* cDNA clone wh29f24 5', mRNA sequence"; (*Triticum aestivum*).
NCBI accession No. BJ215658 (gi:19954285) (Apr. 4, 2002); Ogihara, Y., et al., "BJ215658 Y. Ogihara unpublished cDNA library, Wh *Triticum aestivum* cDNA clone wh8a18 3', mRNA sequence"; (*Triticum aestivum*).
NCBI accession No. BJ217966 (gi:19957482) (Apr. 4, 2002); Ogihara, Y., et al., "BJ217966 Y. Ogihara unpublished cDNA library, Wh *Triticum aestivum* cDNA clone wh29f24 3', mRNA sequence"; (*Triticum aestivum*).

(56) References Cited

OTHER PUBLICATIONS

NCBI accession No. BJ234039 (gi:20051078) (Apr. 5, 2002); Ogihara, Y., et al., "BJ234039 Y. Ogihara unpublished cDNA library, Wh *Triticum aestivum* cDNA clone whe8e16 5', mRNA sequence"; (*Triticum aestivum*).
NCBI accession No. BJ236476 (gi:20052449) (Apr. 5, 2002); Ogihara, Y., et al., "BJ236476 Y. Ogihara unpublished cDNA library, Wh *Triticum aestivum* cDNA clone whe21n09 5', mRNA sequence" (*Triticum aestivum*).
NCBI accession No. BJ248969 (gi:20059585) (Apr. 5, 2002); Ogihara, Y., et al., "BJ248969 Y. Ogihara unpublished cDNA library, Wh *Triticum aestivum* cDNA clone whf8n09 5', mRNA sequence"; (*Triticum aestivum*).
NCBI accession No. BJ255219 (gi:20079277) (Apr. 8, 2002); Ogihara, Y., et al., "BJ255219 Y. Ogihara unpublished cDNA library, Wh *Triticum aestivum* cDNA clone whf8n09 3', mRNA sequence"; (*Triticum aestivum*).
NCBI accession No. BJ463462 (gi:21141969) (May 23, 2002); Sato, K., et al., "BJ463462 K. Sato unpublished cDNA library, cv. Haruna Nijo germination shoots *Hordeum vulgare* subsp. Vulgare cDNA clone bags32a01 5', mRNA sequence"; (*Hordeum vulgare* subsp. Vulgare).
NCBI accession No. BJ482187 (gi:21160648) (May 23, 2002); Sato, K., et al., "BJ482187 K. Sato unpublished cDNA library, strain H602 adult, heading stage top three leaves *Hordeum vulgare* subsp. Spontaneum cDNA clone bah6302 5', mRNA sequence"; (*Hordeum vulgare*).
NCBI accession No. BJ555744 (gi:27237564) (Dec. 18, 2002); Hoshino, A., et al., "BJ555744 *Ipomoea nil* mixture of flower and flower bud *Ipomoea nil* cDNA clone jm18c02 5', mRNA sequence"; (*Ipomoea nil*).
NCBI accession No. BJ571596 (gi:27253424) (Dec. 18, 2002); Hoshino, A., et al., "BJ571596 *Ipomoea nil* mixture of flower and flower bud *Ipomoea nil* cDNA clone jm18c02 3', mRNA sequence"; (*Ipomoea nil*).
NCBI accession No. BJ575345 (gi:27257173) (Dec. 18, 2002); Hoshino, A., et al., "BJ575345 *Ipomoea nil* mixture of flower and flower bud *Ipomoea nil* cDNA clone jm29j19 3', mRNA sequence"; (*Ipomoea nil*).
NCBI accession No. BM109471 (gi:17070418) (Nov. 26, 2001); Van der Hoeven, R., et al., "EST557007 potato roots *Solanum tuberosum* cDNA clone cPRO4E20 5' end, mRNA sequence"; (*Solanum tuberosum*).
NCBI accession No. BM134935 (gi:17143059) (Nov. 28, 2001); Anderson, O.D., et al., "WHE0460_A02_A03ZS Wheat Fusarium graminearum infected spike cDNA library *Triticum aestivum* cDNA clone WHE0460_A02_A03, mRNA sequence"; (*Triticum aestivum*).
NCBI accession No. BM139923 (gi:21638877) (Jul. 1, 2002); Wang, G., et al., "Gm-R115 Soybean root reverse subtractive cDNA library *Glycine max* cDNA clone Gm-R115, mRNA sequence"; (*Glycine max*).
NCBI accession No. BM268414 (gi:17931454) (Dec. 18, 2001); Wen, T.J., et al., "MEST395-C12.univ ISUM5-RN *Zea mays* cDNA clone MEST395-C12 3', mRNA sequence"; (*Zea mays*).
NCBI accession No. BM269434 (gi:17932474) (Dec. 18, 2001); Wen, T.J., et al., "MEST409-G11. Univ ISUM5-RN *Zea mays* cDNA clone MEST409-G11 3', mRNA sequence"; (*Zea mays*).
NCBI accession No. BM308208 (gi:18039914) (Jan. 2, 2002); Shoemaker, R., et al., "sak43a12.y1 Gm-c1036 *Glycine max* cDNA clone Soybean Clone ID: Gm-c1036-5783 5' similar to TR:081130 081130 CCAAT-Box Binding Factor HAP3 Homolog; mRNA sequence"; (*Glycine max*).
NCBI accession No. BM331836 (gi:18161997) (Jan. 16, 2002); Wen, T.J., et al., "MEST171-B11.T3 ISUM5-RN *Zea mays* cDNA clone MEST171-B11 3', mRNA sequence"; (*Zea mays*).
NCBI accession No. BM337630 (gi:18167790) (Jan. 16, 2002); Wen, T.J., et al., "MEST215-B12.T3 ISUM-RN *Zea mays* cDNA clone MEST215-B12 3', mRNA sequence"; (*Zea mays*).

NCBI accession No. BM341107 (gi:18171267) (Jan. 16, 2002); Wen, T.J., et al., "MEST330-D11.T3 ISUM-RN *Zea mays* cDNA clone MEST330-D11 3', mRNA sequence"; (*Zea mays*).
NCBI accession No. BM341536 (gi:18171696) (Jan. 16, 2002); Wen, T.J., et al., "MEST336-C11.T3 ISUM5-RN *Zea mays* cDNA clone MEST336-C11 3', mRNA sequence"; (*Zea mays*).
NCBI accession No. BM349646 (gi:18174258) (Jan. 16, 2002); Wen, T.J., et al., "MEST253-D11.T3 ISUM5-RN *Zea mays* cDNA clone MEST253-D11 3', mRNA sequence".
NCBI accession No. BM525962 (gi:18730588) (Feb. 19, 2002); Shoemaker, R., et al., "sak74b11.y1 gm-c1036 *Glycine max* cDNA clone Soybean clone ID: Gm-c1036-8542 5' similar to TR: Q9ZQC3 Q9ZQC3 Putative CCAAT-Binding Transcription factor; mRNA sequence"; (*Glycine max*).
NCBI accession No. BM528842 (gi:18735577) (Feb. 19, 2002); Shoemaker, R., et al., "sak69b03.y1 Gm-c1036 *Glycine max* cDNA clone Soybean clone ID: Gm-c10368141 5' similar to TR:081130 0811130 CCAAT-Box Binding Factor HAP3 Homolog, mRNA sequence"; (*Glycine max*).
NCBI accession No. BM887558 (gi:19271302) (Mar. 8, 2002); Shoemaker, R., et al., "sam40c09.y1 Gm-c1068 *Glycine max* cDNA clone Soybean clone ID: Gm-c10687050 5' similar to TR:Q9ZQC3 Q9ZQC3 Putative CCAAT-Box Binding Transcription Factor, mRNA sequence"; (*Glycine max*).
NCBI accession No. BM888735 (gi:19272479) (Mar. 8, 2002); Walbot, V., "952068E04.y1 952—BMS tissue from Walbot Lab (reduced rRNA) *Zea mays* cDNA, mRNA sequence"; (*Zea mays*).
NCBI accession No. BM892103 (gi:19347223) (Mar. 11, 2002); Shoemaker, R., et al., "sam48d03.y1 Gm-c1069 *Glycine max* cDNA clone Soybean clone ID: Gm-c1069-2478 5' similar to TR:Q9ZQC3 Q9ZQC3 Putative CCAAT-Binding Factor, mRNA sequence"; (*Glycine max*).
NCBI accession No. BM896169 (gi:19351637) (Mar. 11, 2002); Walbot, V., "952067E04 .xl 952—BMS tissue from Walbot Lab (reduced rRNA) *Zea mays* cDNA, mRNA sequence"; (*Zea mays*).
NCBI accession No. BQ046483 (gi:19820469) (Mar. 29, 2002); Zhang, P., et al., "EST595601 P. Infestans-challenged potato leaf, incompatible reaction *Solanum tuberosum* cDNA clone BPLI114J14 5' end, mRNA sequence"; (*Solanum tuberosum*).
NCBI accession No. BQ104671 (gi:20154333) (Apr. 16, 2002); Guterman, I., et al., "fc0546.e Rose Petals (Fragrant Cloud) Lambda Zap Express Library Rosa hybrid cultivar cDNA clone fc0546.e 5', mRNA sequence"; (Rosa hybrid cultivar) (publication: see Plant Cell 14 (10), 2325-2338, 2002, Rose Scent: Genomics Approach to Discovering Novel Floral Fragrance-Related Genes).
NCBI accession No. BQ105902 (gi:20155564) (Apr. 16, 2002); Guterman, I., et al., "fc0632.e Rose Petals (Fragrant Cloud) Lambda Zap Express Library Rosa hybrid cultivar cDNA clone fc0632.e 5', mRNA sequence"; (Rosa hybrid cultivar) (publication: see Plant Cell 14 (10), 2325-2338, 2002, Rose Scent: Genomics Approach to Discovering Novel Floral Fragrance-Related Genes).
NCBI accession No. BQ164458 (gi:20301515) (Apr. 24, 2002); Walbot, V., et al., "1091020E11.y3 1091—Immature ear with common ESTs screened by Schmidt lab *Zea mays* cDNA, mRNA sequence"; (*Zea mays*).
NCBI accession No. BQ255423 (gi:20456176) (May 6, 2002); VandenBosch, K., "MTNAL55TKN KVKC *Medicago truncatula* cDNA clone pKVKC-12E7, mRNA sequence"; (*Medicago truncatula*).
NCBI accession No. BQ296537 (gi:20812059) (May 16, 2002); Shoemaker, R., et al., "san93f01.y2 Gm-c1052 glycine max cDNA clone Soybean clone ID: Gm-c10527178 5' similar to TR: Q9ZQC3 Q9ZQC3 putative CCAAT-binding transcription factor; mRNA sequence"; (*Glycine max*).
NCBI accession No. BQ405785 (gi:21093472) (May 22, 2002); Wing, R.A., et al., "GA_Ed0086G12f *Gossypium arboreum* 7-10 dpa fiber library *Gossypium arboreum* cDNA clone GA_Ed0086G12f, mRNA sequence"; (*Gossypium arboreum*).
NCBI accession No. BQ488908 (gi:21333528) (Jun. 7, 2002); Bellin, D., et al., "95-E9134-006-006-M23-T3 Sugar beet MPIZ-ADIS-006 Lambda Zap II Library *Beta vulgaris* cDNA clone M-23-6, mRNA sequence"; (*Beta vulgaris*).

(56) References Cited

OTHER PUBLICATIONS

NCBI accession No. BQ505705 (gi:21364574) (Jun. 10, 2002); Buell, C.R., et al., "EST613120 Generation of a set of potato cDNA clones for microarray analyses mixed potato tissues *Solanum tuberosum* cDNA clone STMGF80 5' end, mRNA sequence"; (*Solanum tuberosum*) (note: two versions are presented for review, gi:21364574 submitted Jun. 10, 2002; and, gi:21921628 submitted Jul. 22, 2002).
NCBI accession No. BQ505706 (gi:21364575) (Jun. 10, 2002); Buell, C.R., et al., "EST613121 Generation of a set of potato cDNA clones for microarray analyses mixed potato tissues *Solanum tuberosum* cDNA clone STMGF80 3' end, mRNA sequence"; (*Solanum tuberosum*) (note: two versions are presented for review, gi:21364575 submitted Jun. 10, 2002; and, gi:21921629 submitted Jul. 22, 2002).
NCBI accession No. BQ507074 (gi:21365943) (Jun. 10, 2002); Buell, C.R., et al., "EST614489 Generation of a set of potato cDNA clones for microarray analyses mixed potato tissues *Solanum tuberosum* cDNA clone STMG023 3' end, mRNA sequence"; (*Solanum tuberosum*) (note: two versions are presented for review, gi:21365943 submitted Jun. 10, 2002; and, gi:21922914 submitted Jul. 22, 2002).
NCBI accession No. BQ508506 (gi:21367375) (Jun. 10, 2002); Buell, C.R., et al., "EST615921 Generation of a set of potato cDNA clones for microarray analyses mixed potato tissues *Solanum tuberosum* cDNA clone STMGW70 5' end, mRNA sequence"; (*Solanum tuberosum*) (note: two versions are presented for review, gi:21367375 submitted Jun. 10, 2002; and, gi:21924285 submitted Jul. 22, 2002).
NCBI accession No. BQ508507 (gi:21367376) (Jun. 10, 2002); Buell, C.R., et al., "EST615922 Generation of a set of potato cDNA clones for microarray analyses mixed potato tissues *Solanum tuberosum* cDNA clone STMGW70 3' end, mRNA sequence"; (*Solanum tuberosum*) (note: two versions are presented for review, gi:21367376 submitted Jun. 10, 2002; and, gi:21924286 submitted Jul. 22, 2002).
NCBI accession No. BQ510555 (gi:21369424) (Jun. 10, 2002); Buell, C.R., et al., "EST617970 Generation of a set of potato cDNA clones for microarray analyses mixed potato tissues *Solanum tuberosum* cDNA clone STMHL13 5' end, mRNA sequence"; (*Solanum tuberosum*) (note: two versions are presented for review, gi:21369424 submitted Jun. 10, 2002; and, gi:21926247 submitted Jul. 22, 2002).
NCBI accession No. BQ511879 (gi:21370748) (Jun. 10, 2002); Buell, C.R., et al., "EST619294 Generation of a set of potato cDNA clones for microarray analyses mixed potato tissues *Solanum tuberosum* cDNA clone STMHU61 5' end, mRNA sequence"; (*Solanum tuberosum*) (note: two versions are presented for review, gi:21370748 submitted Jun. 10, 2002; and, gi:21927514 submitted Jul. 22, 2002).
NCBI accession No. BQ592365 (gi:26121948) (Dec. 6, 2002); Herwig, R., et al., "E012681-024-020-H10-SP6 MPIZ-ADIS-024-developing root *Beta vulgaris* cDNA clone 024020-H10 5', mRNA sequence"; (*Beta vulgaris*) (publication: see Plant J. 32 (5), 845-857, 2002, Construction of a 'unigene' cDNA clone set by oligonucleotide fingerprinting allows access to 25,000 potential sugar beet genes).
NCBI accession No. BQ606328 (gi:21555594) (Jun. 25, 2002); Clarke, B., et al., "BRY_2180 wheat EST endosperm library *Triticum aestivum* cDNA 5', mRNA sequence"; (*Triticum aestivum*) (publication: see Funct. Integr. Genomics 3 (1-2), 33-38, 2003, *Arabidopsis* genomic information for interpreting wheat EST sequences).
NCBI accession No. BQ629472 (gi:21677121) (Jul. 2, 2002); Shoemaker, R., et al., "saq02e06.y1 Gm-c1045 Glycine max cDNA clone Soybean clone ID: Gm-c1045-3660 5' similar to TR: Q9ZQC3 Q9ZQC3 Putative CCAAT-Binding Transcription Factor, mRNA sequence"; (*Glycine max*).
NCBI accession No. BQ667936 (gi:21809618) (Jul. 15, 2002); Walbot, V., "946102B01.y1 946—tassel primordium prepared by Schmidt lab *Zea mays* cDNA, mRNA sequence"; (*Zea mays*).

NCBI accession No. BQ744755 (gi:21891542) (Jul. 17, 2002); Walbot, V., "946111A02.y1 946—tassel primordium prepared by Schmidt lab *Zea mays* cDNA, mRNA sequence"; (*Zea mays*).
NCBI accession No. BQ757780 (gi:21966252) (Jul. 26, 2002); Hedley, P., et al., "EBem10_SQ005_D11_R embryo, 2 Day germination, no treatment, cv Optic, EBem10 *Hordeum vulgare* subsp. Vulgare cDNA clone EBem10_SQ005_D11 5', mRNA sequence"; (*Hordeum vulgare*).
NCBI accession No. BQ799965 (gi:22014931) (Jul. 30, 2002); Abbal, P., et al., "EST 2134 Green Grape berries Lambda Zap II Library *Vitis vinifera* cDNA clone GT203H05 3', mRNA sequence"; (*Vitis vinifera*).
NCBI accession No. BQ816666 (gi:22065967) (Aug. 1, 2002); Grossman, A., et al, "1030059C09.y1 *C. Reinhardtii* CC-1690, Deflgellation (normalized), Lambda Zap II *Chlamydomonas reinhardtii* cDNA, mRNA sequence"; (*Chlamydomonas reinhardtii*).
NCBI accession No. BQ838221 (gi:22142539) (Aug. 8, 2002); Anderson, O.D., et al., "WHE2907_H09_P17ZS Wheat aluminum-stressed root tip cDNA library *Triticum aestivum* cDNA clone WHE2907_H09_P17, mRNA sequence"; (*Triticum aestivum*).
NCBI accession No. BQ857127 (gi:22242592) (Aug. 14, 2002); Kozik, A., et al., "QGB6K24.yg.abl QG_ABCDI lettuce salinas *Lactuca sativa* cDNA clone QGB6K24, mRNA sequence"; (*Lactuca sativa*).
NCBI accession No. BQ862671 (gi:22248136) (Aug. 14, 2002); Kozik, A., et al., "QGC21L19.yg.abl QG_ABCDI lettuce salinas *Lactuca sativa* cDNA clone QGC21L19, mRNA sequence"; (*Lactuca sativa*).
NCBI accession No. BQ875352 (gi:22264573) (Aug. 15, 2002); Kozik, A., et al., "QGI7N22.yg.abl QG_ABCDI lettuce salinas *Lactuca sativa* cDNA clone QGI7N22, mRNA sequence"; (*Lactuca sativa*).
NCBI accession No. BQ911236 (gi:22310015) (Aug. 19, 2002); Kozik, A., et al., "QHA16J13.yg.abl QG_ABCDI sunflower RHA801 *Helianthus annus* cDNA clone QHA16J13, mRNA sequence"; (*Helianthus annus*).
NCBI accession No. BQ990941 (gi:22410476) (Aug. 21, 2002); Kozik, A., et al., "QGF21I11.yg.abl QG_EFGHJ lettuce serriola *Lactuca serriola* cDNA clone QGF21I11, mRNA sequence"; (*Lactuca serriola*).
NCBI accession No. BQ996905 (gi:22431301) (Aug. 22, 2002); Kozik, A., et al., "QGG14CO3.yg.abl QG_EFGHJ lettuce serriola *Lactuca serriola* cDNA clone QGG14CO3, mRNA sequence"; (*Lactuca serriola*).
NCBI accession No. BU008142 (gi:22442537) (Aug. 22, 2002); Kozik, A., et al., "QGH6K04.yg.abl QG_EFGHJ lettuce serriola *Lactuca serriola* cDNA clone QGH6K04, mRNA sequence"; (*Lactuca serriola*).
NCBI accession No. BU013962 (gi:22448357) (Aug. 22, 2002); Kozik, A., et al., "QGJ6B02.yg.abl QG_EFGHJ lettuce serriola *Lactuca serriola* cDNA clone QGJ6B02, mRNA sequence"; (*Lactuca serriola*).
NCBI accession No. BU016847 (gi:22452367) (Aug. 23, 2002); Kozik, A., et al., "QHE14C23.yg.abl QG_EFGHJ sunflower RHA280 *Helianthus annuus* cDNA clone QHE14C23, mRNA sequence"; (*Helianthus annuus*).
NCBI accession No. BU051043 (gi:22491120) (Aug. 26, 2002); Walbot, V., "1111037G04.y2 1111—Unigene III from Maize Genome Project *Zea mays* cDNA, mRNA sequence"; (*Zea mays*).
NCBI accession No. BU090324 (gi:22540481) (Aug. 29, 2002); Shoemaker, R., et al., "sr70c10.y1 Gm-c1052 *Glycine max* cDNA clone Genome systems clone ID: Gm-c1052-1099 5' similar to SW: CBFA_Maize P25209 CCAAT-binding transcription factor subunit A; mRNA sequence"; (*Glycine max*).
NCBI accessino No. BU097938 (gi:22545579) (Aug. 29, 2002); Walbot, V., et al., "946122D01.y1 946—tassel primodium prepared by Schmidt lab *Zea mays* cDNA, mRNA sequence"; (*Zea mays*).
NCBI accession No. BU238020 (gi:22749845) (Sep. 6, 2002); Singh, J.A., et al, "Ds01_14a12_A Ds01_AAFCj_ECORC_cold_stressed_Flixweed_seedlings *Descurainia sophia* cDNA clone Ds01_14a12, mRNA sequence"; (*Descurainia sophia*).

(56) References Cited

OTHER PUBLICATIONS

NCBI accession No. BU499457 (gi:22819367) (Sep. 12, 2002); Walbot, V., "946175D02.y1 946—tassel primordium prepared by Schmidt lab *Zea mays* cDNA, mRNA sequence"; (*Zea mays*).
NCBI accession No. BU551072 (gi:22933933) (Sep. 16, 2002); Vodkin, L, et al., "GM880006B11G05 Gm-r1088 *Glycine max* cDNA clone Gm-r1088-2241 3', mRNA sequence"; (*Glycine max*).
NCBI accession No. BU653821 (gi:23366001) (Sep. 30, 2002); Grossman, A., et al., "1112109C03.y1 *C. Reinhardtii* cc-1690 (mt+), cc-1691 (mt−), Gamete (normalized), Lambda Zap II *Chlamydomonas reinhardtii* cDNA, mRNA sequence"; (*Chlamydoonas reinhardtii*).
NCBI accession No. BU655174 (gi:23367356) (Sep. 30, 2002); Grossman, A., et al., "1112118C09.y1 *C. Reinhardtii* cc-1690 (mt+), cc-1691 (mt−), Gamete (normalized), Lambda Zap II *Chlamydomonas reinhardtii* cDNA, mRNA sequence"; (*Chlamydomonas reinhardtii*).
NCBI accession No. BU871529 (gi:24063053) (Oct. 16, 2002); Unneberg, P., et al., Q031E12 *Populus* flower cDNA library *Populus trichocarpa* cDNA 5', mRNA sequence (*Populus trichocarpa*).
NCBI accession No. BU880488 (gi:24072012) (Oct. 16, 2002); Unneberg, P., et al., "UM49TGO9 *Populus* flower cDNA library *Populus trichocarpa* cDNA 5', mRNA sequence"; (*Populus trichocarpa*).
NCBI accession No. BU881483 (gi:24073007) (Oct. 16, 2002); Unneberg, P., et al., "UM63TC12 *Populus* flower cDNA library *Populus trichocarpa* cDNA 5', mRNA sequence"; (*Populus trichocarpa*).
NCBI accession No. BU896236 (gi:24107443) (Oct. 17, 2002); Unneberg, P., et al., "X037F04 *Populus* wood cDNA library *Populus tremulax Populus tremuloides* cDNA 5', mRNA sequence"; (*Populus tremula x Populus tremuloides*).
NCBI accession No. BU997198 (gi:24274181) (Oct. 23, 2002); Zhang, H., et al., "HI07D15r HI *Hordeum vulgare* subsp. Vulgare cDNA clone HI07D15 5', mRNA sequence"; (*Hordeum vulgare*).
NCBI accession No. BZ505711 (gi:27026128) (Dec. 16, 2002); Ayele, M., et al., "BONBC73TF BO__1.y__2__KB_tot *Brassica oleracea* genomic clone BONBC73, genomic survey sequence"; (*Brassica oleracea*) (publication: see Genome Res. 15 (4), 487-495, 2005, Whole genome shotgun sequencing of *Brassica oleracea* and its application to gene discovery and annotation in *Arabidopsis*).
NCBI accession No. BZ635584 (gi:28084146) (Jan. 29, 2003); Whitelaw, C.A. et al., "OGCAF48TC ZM__0.7__1.5__KB *Zea mays* genomic clone ZMMBMa0126G24, genomic survey sequence"; (*Zea mays*).
NCBI accession No. BZ635588 (gi:28084150) (Jan. 29, 2003); Whitelaw, C.A., et al., "OGCAF48TM ZM__0.71__5__KB *Zea mays* genomic clone ZMMBMa0126G24, genomic survey sequence"; (*Zea mays*).
NCBI accession No. BZ707196 (gi:28427237) (Feb. 19, 2003); Whitelaw, C.A. et al., "OGEBD41TC ZM__0.7__1.5__KB *Zea mays* genomic clone ZMMBMa0222G10, genomic survey sequence"; (*Zea mays*).
NCBI accession No. BZ733904 (gi:28710230) (Mar. 3, 2003); Whitelaw, C.A. et al., "OGFAN93TC ZM__0.7__1.5__KB *Zea mays* genomic clone ZMMBMa0240O18, genomic survey sequence"; (*Zea mays*).
NCBI accession No. BZ733911 (gi:28710244) (Mar. 3, 2003); Whitelaw, C.A. et al., "OGFAN93TM ZM__0.71.5__KB *Zea mays* genomic clone ZMMBMa0240O18, genomic survey sequence"; (*Zea mays*).
NCBI accession No. CA026619 (gi:24303993) (Oct. 23, 2002); Radchuk, V., et al., "HZ56G24r HZ *Hordeum vulgare* subsp. Vulgare cDNA clone HZ56G24 5', mRNA sequence"; (*Hordeum vulgare*).
NCBI accession No. CA688065 (gi:25278629) (Nov. 25, 2002); Tingey, S.V., et al., "w1m96.pk037.k9 w1m96 *Triticum aestivum* cDNA clone w1m96.pk037.k9 5' end, mRNA sequence"; (*Triticum aestivum*).
NCBI accession No. CA753815 (gi:25797854) (Nov. 27, 2002); Bohnert, H.J., et al., "BR040003000__PLATE__A05__33__034.abl OA *Oryza sativa* (japonica cultivar-group) cDNA clone BR040003000__PLATE__A05__33__34.abl similar to putative CAAT-box DNA binding protein [*Oryza sativa* (japonica cultivar-group)] gi:20805265:dbj:BAB92931.1 (AP004366) putative CAAT-box DNA binding protein [*Oryza sativa* (japonica cultivar-group)], mRNA sequence"; (*Oryza sativa*).
NCBI accession No. CA785249 (gi:26048796) (Dec. 4, 2002); Shoemaker, R., et al., "sau26h11.y1 Gm-c1062 *Glycine max* cDNA clone Soybean Clone ID: Gm-c1062-9574 5' similar to TR: 023310 023310 CCAAT-binding transcription factor subunit A., mRNA sequence"; (*Glycine max*.).
NCBI accession No. CA795038 (gi:26052114) (Dec. 5, 2002); Jones, P.G., et al., "Cac__BL__208 Cac__BL (Bean and Leaf from Amelonardo type Cacao) *Theobroma cacao* cDNA clone Cac__BL__208 5', mRNA sequence"; (*Theobroma cacao*) (publication: see Planta 216 (2), 255-264, 2002, Gene discovery and microarray analysis of cacao varieties).
NCBI accession No. CA801742 (gi:26058828) (Dec. 5, 2002); Shoemaker, R., et al., "sat17b11.y1 Gm-c1036 *Glycine max* cDNA clone Soybean Clone ID: Gm-c1036-13894 5' similar to TR: 081130 081130 CCAAT-Box binding transcription factor HAP3 Homolog, mRNA sequence"; (*Glycine max*.).
NCBI accession No. CA802391 (gi:26059477) (Dec. 5, 2002); Shoemaker, R., et al., "sau35c03.y1 Gm-c1071 *Glycine max* cDNA clone Soybean Clone ID: Gm-c1071-2813 5' similar to SW:CBFA__Maize P25209 CCAAT-binding transcription factor subunit A., mRNA sequence"; (*Glycine max*.).
NCBI accession No. CA802515 (gi:26059601) (Dec. 5, 2002); Shoemaker, R., et al., "sau37e09.y1 Gm-c1071 *Glycine max* cDNA clone Soybean Clone ID: Gm-c1071-3281 5' similar to TR: 023633 023633 transcription factor, mRNA sequence"; (*Glycine max*.).
NCBI accession No. CA820519 (gi:26269456) (Dec. 9, 2002); Shoemaker, R., et al., "sau90c06.y1 Gm-c1048 *Glycine max* cDNA clone Soybean Clone ID: Gm-c1048-3180 5' similar to TR: O23310 O23310 CCAAT-binding transcription factor subunit A., mRNA sequence"; (*Glycine max*.).
NCBI accession No. CA828166 (gi:26456583) (Dec. 11, 2002); Walbot, V., "1114024G02.y2 1114—Unigene IV from Maize Genome Project *Zea mays* cDNA, mRNA sequence"; (*Zea mays*).
NCBI accession No. CA829931 (gi:26557696) (Dec. 12, 2002); Walbot, V., "3529__1__1__1__A10.y__1 3529—2 mm ear tissue from Schmidt and Hake labs *Zea mays* cDNA, mRNA sequence"; (*Zea mays*).
NCBI accession No. CA832165 (gi:26559930) (Dec. 12, 2002); Walbot, V., "1117028F06.y1 1117—Unigene V from Maize Genome Project *Zea mays* cDNA, mRNA sequence"; (*Zea mays*).
NCBI accession No. CA897002 (gi:27383993) (Dec. 27, 2002); Bui, A.Q., et al., "PCEP0404 Scarlet Runner Bean Embryo-Proper Region *Phaseolus coccineus* cDNA 5' similar to AB025628: contains similarity to CCAAT-box binding transcription factor gene__id:MNJ7.26 [*Arabidopsis thaliana*]; Identical to At5g47670: LEC1-like [AF533650], mRNA sequence"; (*Phaseolus coccineus*).
NCBI accession No. CA902393 (gi:27389385) (Dec. 27, 2002); Bui, A.Q., et al., "PCS03217F Scarlet Runner Bean Suspensor Region Trip1Ex2 *Phaseolus coccineus* cDNA 5' similar to AB025628: contains similarity to CCAAT-box binding transcription factor gene__id:MNJ7.26 [*Arabidopsis thaliana*]; Identical to At5g47670: LEC1-like [AF533650], mRNA sequence"; (*Phaseolus coccineus*).
NCBI accession No. CA902394 (gi:27389386) (Dec. 27, 2002); Bui, A.Q., et al., "PCSC12889 Scarlet Runner Bean Suspensor Region Trip1Ex2 *Phaseolus coccineus* cDNA 5' similar to AB025628: contains similarity to CCAAT-box binding transcription factor gene__id:MNJ7.26 [*Arabidopsis thaliana*]; Identical to At5g47670: LEC1-like [AF533650], mRNA sequence"; (*Phaseolus coccineus*).
NCBI accession No. CA902402 (gi:27389394) (Dec. 27, 2002); Bui, A.Q., et al. "PCSC08658 Scarlet Runner Bean Suspensor Region Trip1Ex2 *Phaseolus coccineus* cDNA 5' similar to P25209: CBFA__Maize CCAAT-binding transcription factor subunit A (CBF-A) [*Arabidopsis thaliana*]; similar to At3g53340: Non-LEC1-type AHAP3, mRNA sequence"; (*Phaseolus coccineus*).
NCBI accession No. CA902403 (gi:27389395) (Dec. 27, 2002); Bui, A.Q., et al., "PCSC08738 Scarlet Runner Bean Suspensor Region Trip1Ex2 *Phaseolus coccineus* cDNA 5' similar to P25209: CBFA__

(56) References Cited

OTHER PUBLICATIONS

Maize CCAAT-binding transcription factor subunit A (CBF-A) [*Arabidopsis thaliana*]; similar to At3g53340: Non-LEC1-type AHAP3, mRNA sequence"; (*Phaseolus coccineus*).
NCBI accession No. CA902404 (gi:27389396) (Dec. 27, 2002); Bui, A.Q., et al., "PCSC14305 Scarlet Runner Bean Suspensor Region Trip1Ex2 *Phaseolus coccineus* cDNA 5' similar to P25209: CBFA_Maize CCAAT-binding transcription factor subunit A (CBF-A) [*Arabidopsis thaliana*]; similar to At3g53340: Non-LEC1 type AHAP3, mRNA sequence"; (*Phaseolus coccineus*).
NCBI accession No. CA902413 (gi:27389405) (Dec. 27, 2002); Bui, A.Q., et al. "PCSC08277 Scarlet Runner Bean Suspensor Region Trip1Ex2 Phaseolus coccineus cDNA 5' similar to P25209: CBFA_Maize CCAAT-binding transcription factor subunit A (CBF-A) [*Arabidopsis thaliana*]; Identical to At3g53340: Non-LEC1-type AHAP3, mRNA sequence"; (*Phaseolus coccineus*).
NCBI accession No. CA919789 (gi:27406719) (Dec. 27, 2002); VanderBosch, K., et al., "EST637507 MTUS Medicago truncatula cDNA clone MTUS-18B7, mRNA sequence"; (*Medicago truncatula*).
NCBI accession No. CA923822 (gi:27410752) (Dec. 27, 2002); Ranjan, P., et al., "MTU7CL.P15.D04 Aspen leaf cDNA Library Populus tremuloides cDNA, mRNA sequence"; (*Populus tremuloides*).
NCBI accession No. CA935541 (gi:27424021) (Dec. 30, 2002); Shoemaker, R., et al., "sau55g04.y1 Gm-c1071 Glycine max cDNA clone Soybean Clone ID: Gm-c1071-4927 5' similar to Tr:08113 081130 CCAAT-Box Binding Factor HAP3 Homolog, mRNA sequence"; (*Glycine max*).
NCBI accession No. CAA42234 (gi:22380) (Apr. 21, 1993); Li, X.Y., et al. "CA-box DNA binding protein subunit B (NF-YB)" (*Zea mays*) (note: the original submission and latest update are provided for examination) (publication: see Nucleic Acids Res. 20 (5), 1087-1091, 1992, Evolutionary variation of the CCAAT-binding transcription factor NF-Y).
NCBI accession No. CAA74051 (gi:2398527) (Sep. 16, 1997); Edwards, D., "Transcription factor [*Arabidopsis thaliana*]" (note: the original submission and latest update are provided for examination).
NCBI accession No. CAC37695 (gi:13928060) (May 2, 2001); Masiero, S., et al. "NFYB1 protein" (*Oryza sativa*) (note: the original submission and latest update are provided for examination).
NCBI accession No. CB077569 (gi:27891006) (Jan. 24, 2003); Levesque, M.P., et al., "hj56d09.g1 *Hedyotis terminalis* flower—Stage 2 (Nybg) Hedyotis terminalis cDNA clone hj56d09, mRNA sequence"; (*Hedyotis terminalis*).
NCBI accession No. CB090548 (gi:27914740) (Jan. 27, 2003); Brenner, E.D., et al., "gy76g12.g1 *Cycad* Leaf Library (Nybg) *Cycas rumphii* cDNA clone gy76g12, mRNA sequence"; (*Cycas rumphii*).
NCBI accession No. CB290512 (gi:28615969) (Feb. 28, 2003); Close, T.J., et al., "UCRCS01 01bh12_b1 Washington Navel orange cold acclimated flavedo & albedo cDNA library *Citrus sinensis* cDNA clone UCRCS01_01bh12, mRNA sequence"; (*Citrus sinensis*).
NCBI accession No. CB290513 (gi:28615970) (Feb. 28, 2003); Close, T.J., et al., "UCRCS01_01bh12_g1 Washington Navel orange cold acclimated flavedo & albedo cDNA library *Citrus sinensis* cDNA clone UCRCS01_01bh12, mRNA sequence"; (*Citrus sinensis*).
NCBI accession No. CB347686 (gi:28968653) (Mar. 14, 2003); Goes da Silva, F., et al., "CAB2SG0003_IaF_CO7 Cabernet Sauvignon Berry—CAB2SG *Vitis vinifera* cDNA clone CAB2SG0003_IaF_CO7 5', mRNA sequence"; (*Vitis vinifera*) (note: two versions are presented for review, gi:28968653 submitted Mar. 14, 2003; and, gi:29782405 submitted Apr. 10, 2003).
NCBI accession No. CB347754 (gi:28968721) (Mar. 14, 2003); Goes da Silva, F., et al., "CAB2SG0003_IaR_C07 Cabernet Sauvignon BerrY—CAB2SG *Vitis vinifera* cDNA clone CAB2SG0003_IaR_C07 3', mRNA sequence"; (*Vitis vinifera*) (note: two versions are presented for review, gi:28968721 submitted Mar. 14, 2003; and, gi:29782446 submitted Apr. 10, 2003).

NCBI accession No. CB350611 (gi:28985378) (Mar. 17, 2003); Wen, T.J., et al., "MEST253-D11.univ ISUM5-RN *Zea mays* cDNA clone MEST253-D11 3', mRNA sequence"; (*Zea mays*).
NCBI accession No. CB351460 (gi:28987093) (Mar. 17, 2003); Walbot, V., "3529_1_39_1_B01.y_1 3529—2 mm ear tissue from Schmidt and Hake labs *Zea mays* cDNA, mRNA sequence"; (*Zea mays*).
NCBI accession No. CB351633 (gi:28987436) (Mar. 17, 2003); Walbot, V.,. "3529_1_42_1_E05.y_1 3529—2 mm ear tissue from Schmidt and Hake labs *Zea mays* cDNA, mRNA sequence"; (*Zea mays*).
NCBI accession No. P25209 (gi:115840) (Apr. 23, 1993); Li, X.Y., et al. "CCAAT-binding transcription factor subunit A (CBF-A) (NF-Y protein chain B) (NF-YB) (CAAT-box DNA binding protein subunit B)" (*Zea mays*) (note: the original submission and latest update are provided for examination) (publication: see Nucleic Acids Res. 20 (5), 1087-1091, 1992, Evolutionary variation of the CCAAT-binding transcription factor NF-Y).
NCBI accession No. S22820 (gi:7443522) (Apr. 5, 2000); Li, X.Y., et al. "Transcription factor NF-Y, CCAAT-binding, chain B—maize" (*Zea mays*) (note: the original submission and latest update are provided for examination) (publication: see Nucleic Acids Res. 20 (5), 1087-1091, 1992, Evolutionary variation of the CCAAT-binding transcription factor NF-Y).
NCBI accession No. X59714 (gi:22379) (Apr. 21, 1993); Benoist, C., "*Z.mays* mRNA for CAAT-box DNA binding protein subunit B (NF-YB)"; (*Zea mays*) (note: the original submission and latest update are provided for examination) (publication: see Nucleic Acids Res. 20 (5), 1087-1091, 1992, Evolutionary variation of the CCAAT-binding transcription factor NF-Y).
NCBI accession No. Y13723 (gi:2398526) (Sep. 16, 1997); Edwards, D., "*Arabidopsis thaliana* mRNA for Hap3a transcription factor" (note: the original submission and latest update are provided for examination).
NCBI accession No. Y13724 (gi:2398528) (Sep. 16, 1997); Edwards, D., "*Arabidopsis thaliana* mRNA for Hap3b transcription factor" (note: the original submission and latest update are provided for examination).
NCBI accession No. Z97336 (gi:2244788) (pos. 102664-103149) (Jul. 6, 1997); Bevan, M., et al., "*Arabidopsis thaliana* DNA chromosome 4, ESSA I contig fragment No. 1" (note: the original submission and latest update are provided for examination, see gene d13310w, protein id CAB10233.1 marked on p. 21-22/47).
Database TREMBL Accession No. AB025619; (Apr. 9, 1999) "*Arabidopsis thaliana* genomic DNA, chromosome 5, P1 clone: MBA10".
Database TREMBL Sequence Library TREMBL Accession No. Q9FGJ3 (Mar. 1, 2001); protein: "Similarity to CCAAT-box binding transcription factor" (origin-gene: AT5g47640).
Database TREMBL Sequence Library TREMBL Accession No. Q9FGP7 (Mar. 1, 2001); protein: "Transcription factor Hap5a-like" (origin-gene: At5g50480).
Database TREMBL Sequence Library TREMBL Accession No. Q9FMV5 (Mar. 1, 2001); protein: "Transcription factor Hap5a-like protein" (origin-gene: At5g63470) (publication: see DNA Res. 4:401-414, 1997, Structural analysis of *Arabidopsis thaliana* chromosome 5 . . . ).
Database TREMBL Sequence Library TREMBL Accession No. Q9LFI3 (Oct. 1, 2000); protein: "Transcription factor NF-Y, CCAAT-binding-like protein" (origin-gene: At3g53340).
Database TREMBL Sequence Library TREMBL Accession No. Q9SLGO (May 1, 2000); protein: "Putative CCAAT-binding transcription factor subunit" (origin-gene: At2g38880) (publication: see Genome Biol. 3:RESEARCH0029-RESEARCH0029, 2002, Full-length messenger RNA sequences greatly improve genome annotation).
Database TREMBL Sequence Library TREMBL Accession No. Q9ZQC3 (May 1, 1999); protein: "Putative CCAAT-box binding transcription factor" (origin-gene: At2g37060).
Database TREMBL Sequence Library TREMBL Accession No. 023634 (Jan. 1, 1998); protein: "Transcription factor [fragment]" (origin-gene: hap3b).

(56) References Cited

OTHER PUBLICATIONS

Database TREMBL Sequence Library TREMBL Accession No. O23310 (Jan. 1, 1998); protein: "CCAAT-binding transcription factor subunit A (CBF-A)".
Database TREMBL Sequence Library TREMBL Accession No. O81130 (Nov. 1, 1998); protein: "CCAAT-box binding factor HAP3 homolog"; (publication: see Cell 93:1195-1205, 1998, "*Arabidopsis* Leafy Cotyledon1 is sufficient to induce embryo development in vegetative cells").
U.S. Appl. No. 09/733,089, filed Dec. 11, 2000, Lutfiyya.
U.S. Appl. No. 09/474,435, filed Dec. 28, 1999, Monsanto Co., et al.
U.S. Appl. No. 09/532,591, filed Mar. 22, 2000, Samaha, R. et al.
U.S. Appl. No. 09/533,648, filed Mar. 22, 2000, Riechmann, Jose Luis et al.
U.S. Appl. No. 10/290,627, filed Nov. 7, 2002, Riechmann, Jose Luis et al.
U.S. Appl. No. 09/713,994, filed Nov. 16, 2000, Keddie, James et al.
U.S. Appl. No. 09/837,944, filed Apr. 18, 2001, Creelman, Robert et al.
U.S. Appl. No. 09/594,214, filed Jun. 14, 2000, Jones, J. et al.
U.S. Appl. No. 10/456,882, filed Jun. 6, 2003, Riechmann, Jose Luis et al.
U.S. Appl. No. 10/171,468, filed Jun. 14, 2002, Creelman, Robert et al.
U.S. Appl. No. 09/394,519, filed Sep. 13, 1999, Zhang, J. et al.
U.S. Appl. No. 09/627,348, filed Jul. 28, 2000, Thomashow, Michael et al.
U.S. Appl. No. 09/489,376, filed Jan. 21, 2000, Heard, J. et al.
U.S. Appl. No. 09/489,230, filed Jan. 21, 2000, Broun, P. et al.
U.S. Appl. No. 09/506,720, filed Feb. 17, 2000, Keddie, James et al.
U.S. Appl. No. 09/533,030, filed Mar. 22, 2000, Keddie, James et al.
U.S. Appl. No. 09/533,392, filed Mar. 22, 2000, Jiang, C-Z, et al.
U.S. Appl. No. 12/526,042, filed Feb. 7, 2008, Repetti, Peter P. et al.
U.S. Appl. No. 12/721,304, filed Mar. 10, 2010, Creelman, Robert et al.
U.S. Appl. No. 12/988,789, filed Oct. 20, 2010, Chen, Jianxin, et al.
U.S. Appl. No. 12/689,010, filed Jan. 18, 2010, Powell, Ann L.T. et al.
U.S. Appl. No. 12/732,911, filed Mar. 26, 2010, Armstrong, Joshua I. et al.
U.S. Appl. No. 12/917,303, filed Nov. 1, 2010, Jiang, C-Z., et al.
U.S. Appl. No. 12/922,834, filed Sep. 15, 2010, Khanna, Rajnish, et al.
U.S. Appl. No. 12/902,887, filed Oct. 12, 2010, Armstrong, Joshua, et al.

\* cited by examiner

| | | | | | |
|---|---|---|---|---|---|
| Zm | G3434 | (12) | REQDRFLPIAN|ISRIMKKAVPAN | ---------- | -GKIAKDA|KETLQ|ECVSE|FISFVT |
| Os | G3395 | (38) | REQDRFLPIAN|ISRIMKKAVPAN | ---------- | -GKIAKDA|KETLQ|ECVSE|FISFVT |
| Gm | G3470 | (4)  | REQDRYLPIAN|ISRIMKKALPPN | ---------- | -GKIAKDA|KDTMQ|ECVSE|FISFIT |
| Gm | G3471 | (6)  | REQDRYLPIAN|ISRIMKKALPPN | ---------- | -GKIAKDA|KDTMQ|ECVSE|FISFIT |
| At | G481  | (2)  | REQDRYLPIAN|ISRIMKKALPPN | ---------- | -GKIGKDA|KDTVQ|ECVSE|FISFIT |
| Gm | G3875 | (8)  | REQDRFLPIAN|ISRIMKKALPAN | ---------- | -GKIAKDA|KETVQ|ECVSE|FISFVT |
| At | G1364 | (14) | REQDRFLPIAN|ISRIMKRGLPAN | ---------- | -GKIAKDA|KEIVQ|ECVSE|FISFVT |
| At | G2345 | (22) | REQDRFLPIAN|ISRIMKRGLPLN | ---------- | -GKIAKDA|KETMQ|ECVSE|FISFVT |
| Gm | G3876 | (10) | REQDRFLPIAN|ISRIMKKAIPAN | ---------- | -GKIAKDA|KETVQ|ECVSE|FISFIT |
| Zm | G3866 | (42) | REQDRFLPIAN|ISRIMKKAIPAN | GKTIPANGKTIPANG | KIAKDA|KETVQ|ECVSE|FISFIT |
| Gm | G3475 | (16) | REQDRFLPIAN|VSRIMKKALPAN | ---------- | -AKISKDA|KETVQ|ECVSE|FISFIT |
| Gm | G3478 | (26) | REQDRFLPIAN|VSRIMKKALPAN | ---------- | -AKISKDA|KETVQ|ECVSE|FISFIT |
| Gm | G3476 | (20) | REQDRFLPIAN|VSRIMKKALPAN | ---------- | -AKISKDA|KETVQ|ECVSE|FISFIT |
| At | G482  | (28) | REQDRFLPIAN|VSRIMKKALPAN | ---------- | -AKISKDA|KETVQ|ECVSE|FISFIT |
| At | G485  | (18) | REQDRFLPIAN|VSRIMKKALPAN | ---------- | -AKISKDA|KETMQ|ECVSE|FISFIT |
| Zm | G3435 | (30) | REQDRFLPIAN|VSRIMKKALPAN | ---------- | -AKISKDA|KETVQ|ECVSE|FISFIT |
| Zm | G3436 | (34) | REQDRFLPIAN|VSRIMKKALPAN | ---------- | -AKISKDA|KETVQ|ECVSE|FISFIT |
| Os | G3397 | (36) | REQDRFLPIAN|VSRIMKKALPAN | ---------- | -AKISKDA|KETVQ|ECVSE|FISFIT |
| Os | G3398 | (40) | REQDRFLPIAN|VSRIMKRALPAN | ---------- | -AKISKDA|KETVQ|ECVSE|FISFIT |
| Gm | G3474 | (24) | REQDRFLPIAN|VSRIMKKALPAN | ---------- | -AKISKEA|KETVQ|ECVSE|FISFIT |
| Gm | G3472 | (32) | REQDRFLPIAN|VSRIMKKALPAN | ---------- | -AKISKEA|KETVQ|ECVSE|FISFIT |
| Os | G3396 | (44) | REQDRFLPIAN|IGRIMRRAVPEN | ---------- | -GKIAKDS|KESVQ|ECVSE|FISFIT |
| Os | G3429 | (46) | --TNAELPMAN|LVRLIKKVLPGK | ---------- | -AKIGGAA|KGLTHDCAVE|FVGFVG |

Fig. 4A

| | | |
|---|---|---|
| Zm G3434 | (12) | SEASDKCQKEKRKTINGDDLLWAMATLGFEEYVEPLKIYLQKYKE |
| Os G3395 | (38) | SEASDKCQKEKRKTINGEDLLFAMGTLGFEEYVDPLKIYLHKYRE |
| Gm G3470 | (4)  | SEASEKCQKEKRKTINGDDLLWAMATLGFEDYIEPLKVYLARYRE |
| Gm G3471 | (6)  | SEASDKCQKEKRKTINGDDLLWAMATLGFEDYIEPLKVYLARYRE |
| At G481  | (2)  | SEASDKCQKEKRKTVNGDDLLWAMATLGFEDYLEPLKIYLARYRE |
| Gm G3875 | (8)  | SEASDKCQREKRKTINGDDLLWAMATLGFEDYIDPLKIYLTRYRE |
| At G1364 | (14) | SEASDKCQREKRKTINGDDLLWAMATLGFEDYMEPLKVYLMRYRE |
| At G2345 | (22) | SEASDKCQREKRKTINGDDLLWAMATLGFEDYIDPLKVYLMRYRE |
| Gm G3876 | (10) | SEASDKCQREKRKTINGDDLLWAMATLGFEDYIEPLKVYLQKYRE |
| Zm G3866 | (42) | SEASDKCQREKRKTINGDDLLWAMTTLGFEDYVEPLKGYLQRFRE |
| Zm G3475 | (16) | GEASDKCQREKRKTINGDDLLWAMTTLGFEDYVEPLKGYLQRFRE |
| Gm G3478 | (26) | GEASDKCQREKRKTINGDDLLWAMTTLGFEDYVEPLKIYLQRFRE |
| Gm G3476 | (20) | GEASDKCQREKRKTINGDDLLWAMTTLGFEDYVEPLKVYLQRFRE |
| At G482  | (28) | GEASDKCQREKRKTINGDDLLWAMTTLGFEDYVEPLKVYLQRFRE |
| At G485  | (18) | GEASDKCQREKRKTINGDDLLWAMTTLGFEDYVEPLKVYLQKYRE |
| Zm G3435 | (30) | GEASDKCQREKRKTINGDDLLWAMTTLGFEDYVEPLKHYLHKFRE |
| Zm G3436 | (34) | GEASDKCQREKRKTINGDDLLWAMTTLGFEDYVEPLKLYLHKFRE |
| Os G3397 | (36) | GEASDKCQREKRKTINGDDLLWAMTTLGFEDYVDPLKHYLHKFRE |
| Os G3398 | (40) | GEASDKCQREKRKTINGDDLLWAMTTLGFEDYIDPLKLYLHKFRE |
| Gm G3474 | (24) | GEASDKCQKEKRKTINGDDLLWAMTTLGFEDYVDPLKLYLHKYRE |
| Gm G3472 | (32) | GEASDKCQKEKRKTINGDDLLWAMTTLGFEDYVEPLKVYLHKYRE |
| Os G3396 | (44) | SEASDKCLKEKRKTINGDDLIWSMGTLGFEDYVEPLKLYLRLYRE |
| Os G3429 | (46) | DEASEKAKAEHRRTVAPEDYLGSFGDLGFDRYVDPMDAYIHGYRE |

Fig. 4B

PLANTS WITH IMPROVED WATER DEFICIT AND COLD TOLERANCE

RELATIONSHIP TO COPENDING APPLICATIONS

This application (the "present application") claims the benefit of U.S. provisional application 60/961,403, filed 20 Jul. 2007 (expired); and, the present application is a continuation-in-part application of U.S. non-provisional application Ser. No. 10/675,852, filed 30 Sep. 2003 (pending); and, the present application is a continuation-in-part application of U.S. non-provisional application Ser. No. 11/479,226, filed 30 Jun. 2006 (issued as U.S. Pat. No. 7,858,848); and, the present application is a continuation-in-part application of U.S. non-provisional application Ser. No. 11/725,235, filed 16 Mar. 2007 (issued as U.S. Pat. No. 7,601,893); and, the present application is a continuation-in-part application of U.S. non-provisional application Ser. No. 11/728,567, filed 26 Mar. 2007 (issued as U.S. Pat. No. 7,635,800); and, the present application is a continuation-in-part application of U.S. non-provisional application Ser. No. 11/069,255, filed 28 Feb. 2005 (pending); and, the present application is a continuation-in-part application of U.S. non-provisional application Ser. No. 10/374,780, filed 25 Feb. 2003 (issued as U.S. Pat. No. 7,511,190); and, the present application is a continuation-in-part application of U.S. non-provisional application Ser. No. 10/546,266, filed 19 Aug. 2005 (issued as U.S. Pat. No. 7,659,446), which is a '371 National Stage filing of PCT application PCT/US2004005654, filed 25 Feb. 2004 (expired), which is a continuation-in-part of both U.S. non-provisional application Ser. No. 10/374,780, filed 25 Feb. 2003 (issued as U.S. Pat. No. 7,511,190) and U.S. non-provisional application Ser. No. 10/675,852, filed 30 Sep. 2003 (pending); and, the present application is a continuation-in-part application of U.S. non-provisional application Ser. No. 10/412,699, filed 10 Apr. 2003 (issued as U.S. Pat. No. 7,345,217), and U.S. non-provisional application Ser. No. 10/412,699 also is a continuation-in-part application of U.S. non-provisional application Ser. No. 10/374,780, filed 25 Feb. 2003 (issued as U.S. Pat. No. 7,511,190); and, the present application is a continuation-in-part application of U.S. non-provisional application Ser. No. 11/642,814, filed 20 Dec. 2006 (issued as U.S. Pat. No. 7,825,296), which is a divisional application of U.S. non-provisional application Ser. No. 10/666,642, filed 18 Sep. 2003 (issued as U.S. Pat. No. 7,196,245); and, the present application is a continuation-in-part application of U.S. non-provisional application Ser. No. 10/714,887, filed 13 Nov. 2003 (pending), which is a continuation-in-part application of U.S. non-provisional application Ser. No. 10/666,642, filed 18 Sep. 2003 (issued as U.S. Pat. No. 7,196,245); and, the present application is a continuation-in-part application of U.S. non-provisional application Ser. No. 11/435,388, filed 15 May 2006 (issued as U.S. Pat. No. 7,663,025), which is a continuation-in-part application of PCT application PCT/US04/37584, filed 12 Nov. 2004 (expired), which is a continuation-in-part of U.S. non-provisional application Ser. No. 10/714,887, filed 13 Nov. 2003 (pending); and, the present application is a continuation-in-part of International Application No. PCT/US2006/34615, filed 31 Aug. 2006 (expired), which claims priority from U.S. provisional application 60/713,952, filed 31 Aug. 2005 (expired); and, the present application is a continuation-in-part application of U.S. non-provisional application Ser. No. 11/705,903, filed 12 Feb. 2007 (issued as U.S. Pat. No. 7,868,229), which is a continuation-in-part application of PCT application PCT/US2006/34615, filed 31 Aug. 2006 (expired), which claims the benefit of U.S. provisional application 60/713,952, filed 31 Aug. 2005 (expired). The entire contents of each of these applications are hereby incorporated by reference.

JOINT RESEARCH AGREEMENT

The claimed invention, in the field of functional genomics and the characterization of plant genes for the improvement of plants, was made by or on behalf of Mendel Biotechnology, Inc. and Monsanto Company as a result of activities undertaken within the scope of a joint research agreement in effect on or before the date the claimed invention was made.

FIELD OF THE INVENTION

The present invention relates to plant genomics and plant improvement, increasing tolerance to abiotic stresses, and improving the appearance and yield of plants.

BACKGROUND OF THE INVENTION

Water deficit is a common component of many plant stresses. Water deficit occurs in plant cells when the whole plant transpiration rate exceeds the water uptake. In addition to drought, other stresses, such as salinity and low temperature, produce cellular dehydration (McCue and Hanson, 1990).

Heat stress often accompanies conditions of low water availability. Heat itself is seen as an interacting stress and adds to the detrimental effects caused by water deficit conditions. Evaporative demand exhibits near exponential increases with increases in daytime temperatures and can result in high transpiration rates and low plant water potentials (Hall et al., 2000). High-temperature damage to pollen almost always occurs in conjunction with drought stress, and rarely occurs under well-watered conditions. Thus, separating the effects of heat and drought stress on pollination is difficult. Combined stress can alter plant metabolism in novel ways; therefore, understanding the interaction between different stresses may be important for the development of strategies to enhance stress tolerance by genetic manipulation.

"Chilling sensitivity" describes many types of physiological damage produced at low, but above freezing, temperatures. Typical chilling damage includes wilting, necrosis, chlorosis or leakage of ions from cell membranes. The underlying mechanisms of chilling sensitivity are not completely understood yet, but probably involve the level of membrane saturation and other physiological deficiencies. By some estimates, chilling accounts for monetary losses in the United States second only to drought and flooding.

Based on the commonality of many aspects of cold, drought, and salt stress responses, genes that increase tolerance to cold or salt stress can also improve drought stress protection. In fact, this has already been demonstrated for some transcription factors, such as AtCBF/DREB1, and for other genes such as OsCDPK7 (Saijo et al., 2000), or AVP1 (a vacuolar pyrophosphatase-proton-pump, Gaxiola et al., 2001).

This study identifies polynucleotides encoding another group of transcription factors that can improve tolerance to cold and/or water deficit conditions. The protein sequences of the invention, which belong to the CCAAT-binding family of transcription factors, have been introduced into transgenic plants that were then found to have greater tolerance to cold and water deficit stress than control plants. Thus, important polynucleotide and polypeptide sequences for producing commercially valuable plants and crops as well as the methods for making them and using them were discovered. Other aspects and embodiments of the invention are described below and can be derived from the teachings of this disclosure as a whole.

SUMMARY OF THE INVENTION

The present invention pertains to a nucleic acid construct, such as an expression vector or cassette, a plasmid or another DNA preparation that comprises a recombinant polynucleotide encoding a HAP3-like (or NF-YB) transcription factor found within the CCAAT binding-transcription factor family (also known as the NF-Y family; Mantovani, 1999). Comprised within each highly conserved central B domain of any of these proteins is found a conserved protein-protein and DNA-binding interaction module within the "histone fold motif" or "HFM". The conserved B domains of the present transcription factors responsible for these functions are closely-related to the B domain of G481, SEQ ID NO: 2, in that they are at least about 78%, 80%, 81, 82%, 83%, 84%, 85%, 86%, 87%, 91%, 93%, 95%, 97%, 98%, or 100% identical to the G481 B domain. When the expression vector or cassette is introduced into a plant to produce a transgenic plant, the transgenic plant that results is capable of overexpressing the polypeptide, at which point the transgenic plant becomes more tolerant to cold or a water deficit condition than a control plant. Examples of water deficit conditions include heat, salt, drought, desiccation, dehydration, high sugar concentration, or freezing. Examples of control plants include wild-type plants or plants transformed with an "empty" expression vector that does not comprise the recombinant polynucleotide.

The invention also pertains to a transgenic plant comprising the nucleic acid construct comprising the recombinant polynucleotide encoding the CCAAT family transcription factor polypeptide having the conserved B domain that is at least about 78%, 80%, 81, 82%, 83%, 84%, 85%, 86%, 87%, 91%, 93%, 95%, 97%, 98%, or 100% identical to a conserved B domain of SEQ ID NO: 2, wherein the transgenic plant has more tolerance to cold or a water deficit condition than a control plant.

The invention is also directed to a method for increasing the cold or water deficit tolerance of a plant, the method comprising the steps of introducing into a nucleic acid construct to produce a transgenic plant. The nucleic acid construct comprises the recombinant polynucleotide encoding the CCAAT family transcription factor polypeptide having the conserved B domain that is at least 78%, 80%, 81, 82%, 83%, 84%, 85%, 86%, 87%, 91%, 93%, 95%, 97%, 98%, or 100% identical to a conserved B domain of SEQ ID NO: 2. When the transgenic plant overexpresses the polypeptide, the transgenic plant will then have more tolerance to cold or a water deficit condition than a control plant.

BRIEF DESCRIPTION OF THE SEQUENCE LISTING AND DRAWINGS

The Sequence Listing provides exemplary polynucleotide and polypeptide sequences of the invention. The traits associated with the use of the sequences are included in the Examples.

CD-ROMs Copy 1 and Copy 2, and the CRF copy (Copy 3) of the Sequence Listing under CFR Section 1.821(e), are read-only memory computer-readable compact discs. Each contains a copy of the Sequence Listing in ASCII text format. The Sequence Listing is named "MBI0071CIP.ST25.txt", the electronic file of the Sequence Listing contained on each of these CD-ROMs was created on 19 Oct. 2007, and each copy of the Sequence Listing is 159 kilobytes in size. These copies of the Sequence Listing on the three CD-ROM discs submitted with this application are hereby incorporated by reference in their entirety.

FIG. 1 shows a conservative estimate of phylogenetic relationships among the orders of flowering plants (modified from Soltis et al., 1997). Those plants with a single cotyledon (monocots) are a monophyletic clade nested within at least two major lineages of dicots; the eudicots are further divided into rosids and asterids. *Arabidopsis* is a rosid eudicot classified within the order Brassicales; rice is a member of the monocot order Poales. FIG. 1 was adapted from Daly et al., 2001.

Figure 2:
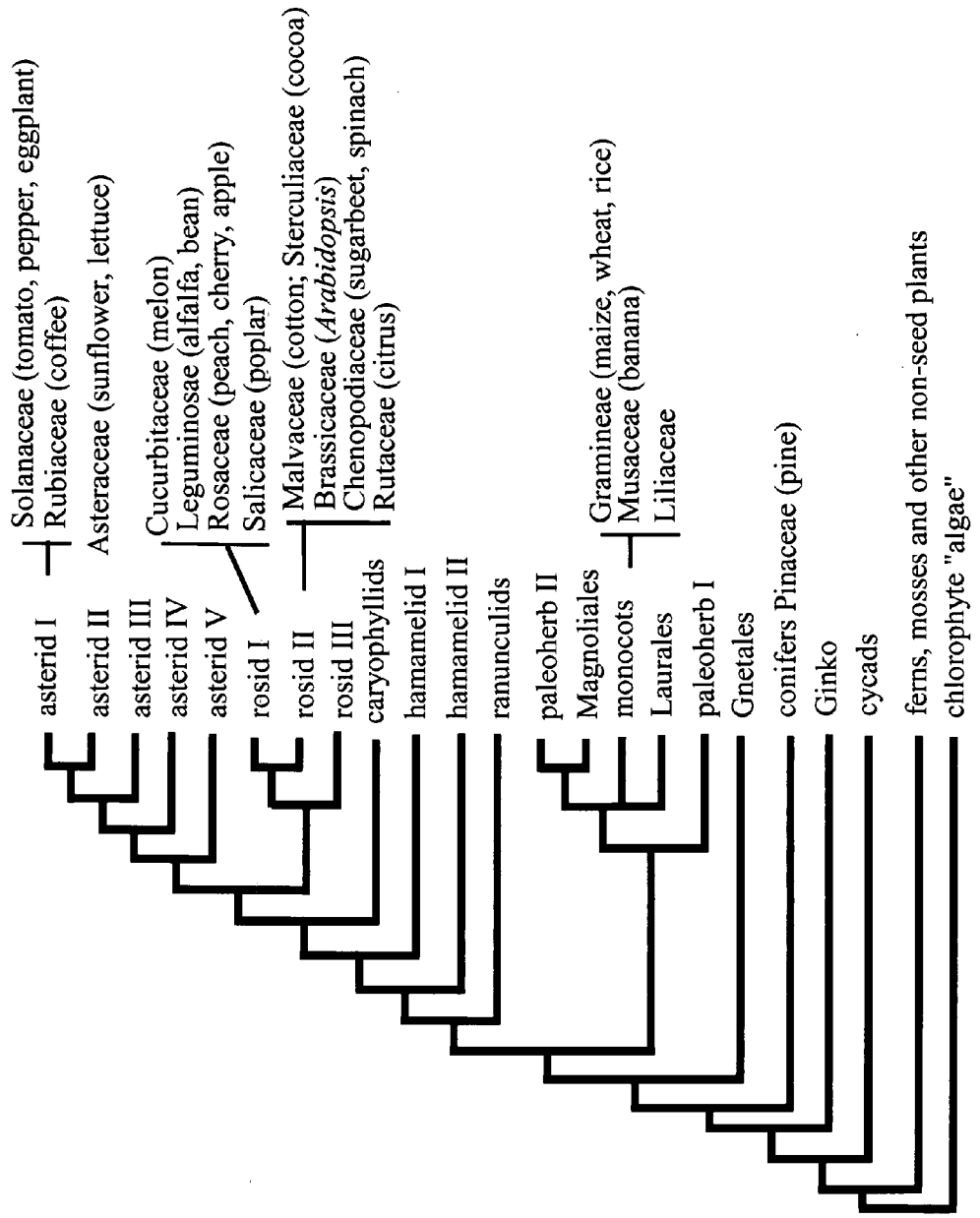

FIG. 2 shows a phylogenic dendogram depicting phylogenetic relationships of higher plant taxa, including clades containing tomato and *Arabidopsis*; adapted from Ku et al., 2000; and Chase et al., 1993.

Figure 3:
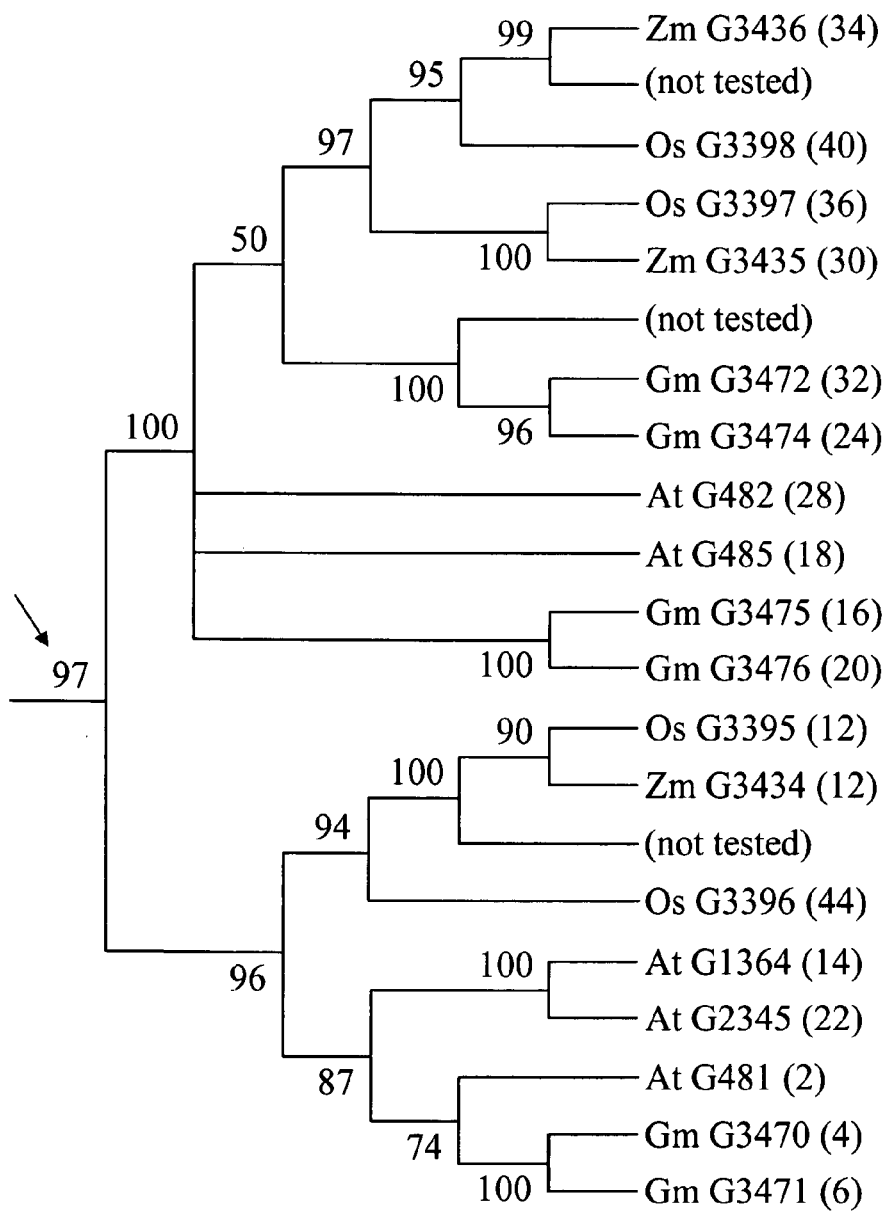

FIG. 3 illustrates the phylogenic relationship of a number of sequences within the G482 subclade. The phylogenetic tree and multiple sequence alignments of G481 and related full length proteins were constructed using ClustalW (CLUSTAL W Multiple Sequence Alignment Program version 1.83, 2003) and MEGA2 (www.megasoftware.net) software. The ClustalW multiple alignment parameters were:

Gap Opening Penalty: 10.00
Gap Extension Penalty: 0.20
Delay divergent sequences: 30%
DNA Transitions Weight: 0.50
Protein weight matrix: Gonnet series
DNA weight matrix: IUB
Use negative matrix: OFF.

A FastA formatted alignment was then used to generate a phylogenetic tree in MEGA2 using the neighbor joining algorithm and a p-distance model. A test of phylogeny was done via bootstrap with 100 replications and Random Speed set to default. Cut off values of the bootstrap tree were set to 50%. G482 subclade transcription factors of the broader non-LEC1-like clade of transcription factors found in the L1L-related CCAAT transcription factor family are derived from a common single strong node (arrow). The sequences shown in FIG. 3 have been introduced into plants, including sequences from both monocots and eudicots, most of these sequences have conferred increased cold or water deficit tolerance when the sequences were overexpressed. The sequences of FIG. 3 that conferred improved cold or water deficit tolerance in *Arabidopsis* plants have B domains with at least 78% identity to the B domain of G481. SEQ ID NOs: of the sequences found in FIG. 3 are provided in the parentheses.

FIGS. 4A and 4B provide a sequence alignment of the conserved B domains of HAP3 polypeptides from *Arabidopsis*, soybean, rice, and corn. SEQ ID NOs of sequences in FIGS. 4A to 4B are found within the parentheses after the Gene Identification Numbers (GIDs; e.g., "G481", "G482", etc.). Members of the G482 subclade are shown above the horizontal lines in FIGS. 4A to 4B. Conserved residues constituting the backbone structure (Maity and de Crombrugghe, 1998; Zemzoumi et al., 1999) of the histone fold matrix (Gusmaroli et al., 2002; Edwards et al., 1998) are shown in the boxes in FIGS. 4A and 4B and are also found in SEQ ID NO: 114.

DETAILED DESCRIPTION

The present invention relates to polynucleotides and polypeptides for modifying phenotypes of plants, particularly those associated with increased cold and/or water deficit tolerance with respect to a control plant (for example, a wild-type plant or a plant transformed with an "empty" vector lacking a gene of interest). Throughout this disclosure, various information sources are referred to and/or are specifically incorporated. The information sources include scientific journal articles, patent documents, textbooks, and World Wide Web browser-inactive page addresses. While the reference to these information sources clearly indicates that they can be used by one of skill in the art, each and every one of the information sources cited herein are specifically incorporated in their entirety, whether or not a specific mention of "incorporation by reference" is noted. The contents and teachings of each and every one of the information sources can be relied on and used to make and use embodiments of the invention.

As used herein and in the appended claims, the singular forms "a", "an", and "the" include the plural reference unless the context clearly dictates otherwise. Thus, for example, a reference to "a host cell" includes a plurality of such host cells, and a reference to "a stress" is a reference to one or more stresses and equivalents thereof known to those skilled in the art, and so forth.

DEFINITIONS

"Polynucleotide" is a nucleic acid molecule comprising a plurality of polymerized nucleotides, e.g., at least about 15 consecutive polymerized nucleotides. A polynucleotide may be a nucleic acid, oligonucleotide, nucleotide, or any fragment thereof. In many instances, a polynucleotide comprises a nucleotide sequence encoding a polypeptide (or protein) or a domain or fragment thereof. Additionally, the polynucleotide may comprise a promoter, an intron, an enhancer region, a polyadenylation site, a translation initiation site, 5' or 3' untranslated regions, a reporter gene, a selectable marker, or the like. The polynucleotide can be single-stranded or double-stranded DNA or RNA. The polynucleotide optionally comprises modified bases or a modified backbone. The polynucleotide can be, e.g., genomic DNA or RNA, a transcript (such as an mRNA), a cDNA, a PCR product, a cloned DNA, a synthetic DNA or RNA, or the like. The polynucleotide can be combined with carbohydrate, lipids, protein, or other materials to perform a particular activity such as transformation or form a useful composition such as a peptide nucleic acid (PNA). The polynucleotide can comprise a sequence in either sense or antisense orientations. "Oligonucleotide" is substantially equivalent to the terms amplimer, primer, oligomer, element, target, and probe and is preferably single-stranded.

A "recombinant polynucleotide" is a polynucleotide that is not in its native state, e.g., the polynucleotide comprises a nucleotide sequence not found in nature, or the polynucleotide is in a context other than that in which it is naturally found, e.g., separated from nucleotide sequences with which it typically is in proximity in nature, or adjacent (or contiguous with) nucleotide sequences with which it typically is not in proximity. For example, the sequence at issue can be cloned into a nucleic acid construct, or otherwise recombined with one or more additional nucleic acid.

An "isolated polynucleotide" is a polynucleotide, whether naturally occurring or recombinant, that is present outside the cell in which it is typically found in nature, whether purified or not. Optionally, an isolated polynucleotide is subject to one or more enrichment or purification procedures, e.g., cell lysis, extraction, centrifugation, precipitation, or the like.

"Gene" or "gene sequence" refers to the partial or complete coding sequence of a gene, its complement, and its 5' or 3' untranslated regions. A gene is also a functional unit of inheritance, and in physical terms is a particular segment or sequence of nucleotides along a molecule of DNA (or RNA, in the case of RNA viruses) involved in producing a polypeptide chain. The latter may be subjected to subsequent processing such as chemical modification or folding to obtain a functional protein or polypeptide. A gene may be isolated, partially isolated, or found with an organism's genome. By way of example, a transcription factor gene encodes a transcription factor polypeptide, which may be functional or require processing to function as an initiator of transcription.

Operationally, genes may be defined by the cis-trans test, a genetic test that determines whether two mutations occur in the same gene and that may be used to determine the limits of the genetically active unit (Rieger et al., 1976). A gene generally includes regions preceding ("leaders"; upstream) and following ("trailers"; downstream) the coding region. A gene may also include intervening, non-coding sequences, referred to as "introns", located between individual coding segments, referred to as "exons". Most genes have an associated promoter region, a regulatory sequence 5' of the transcription initiation codon (there are some genes that do not have an identifiable promoter). The function of a gene may also be regulated by enhancers, operators, and other regulatory elements.

A "polypeptide" is an amino acid sequence comprising a plurality of consecutive polymerized amino acid residues e.g., at least about 15 consecutive polymerized amino acid residues. In many instances, a polypeptide comprises a polymerized amino acid residue sequence that is a transcription factor or a domain or portion or fragment thereof. Additionally, the polypeptide may comprise: (i) a localization domain; (ii) an activation domain; (iii) a repression domain; (iv) an oligomerization domain; (v) a protein-protein interaction domain; (vi) a DNA-binding domain; or the like. The polypeptide optionally comprises modified amino acid residues, naturally occurring amino acid residues not encoded by a codon, non-naturally occurring amino acid residues.

"Protein" refers to an amino acid sequence, oligopeptide, peptide, polypeptide or portions thereof whether naturally occurring or synthetic.

"Portion", as used herein, refers to any part of a protein used for any purpose, but especially for the screening of a library of molecules which specifically bind to that portion or for the production of antibodies.

A "recombinant polypeptide" is a polypeptide produced by translation of a recombinant polynucleotide. A "synthetic polypeptide" is a polypeptide created by consecutive polymerization of isolated amino acid residues using methods well known in the art. An "isolated polypeptide," whether a naturally occurring or a recombinant polypeptide, is more enriched in (or out of) a cell than the polypeptide in its natural state in a wild-type cell, e.g., more than about 5% enriched, more than about 10% enriched, or more than about 20%, or more than about 50%, or more, enriched, i.e., alternatively denoted: 105%, 110%, 120%, 150% or more, enriched relative to wild type standardized at 100%. Such an enrichment is not the result of a natural response of a wild-type plant. Alternatively, or additionally, the isolated polypeptide is separated from other cellular components with which it is typically associated, e.g., by any of the various protein purification methods herein.

"Homology" refers to sequence similarity between a reference sequence and at least a fragment of a newly sequenced clone insert or its encoded amino acid sequence.

"Identity" or "similarity" refers to sequence similarity between two polynucleotide sequences or between two polypeptide sequences, with identity being a more strict comparison. The phrases "percent identity" and "% identity" refer to the percentage of sequence similarity found in a comparison of two or more polynucleotide sequences or two or more polypeptide sequences. "Sequence similarity" refers to the percent similarity in base pair sequence (as determined by any suitable method) between two or more polynucleotide sequences. Two or more sequences can be anywhere from 0 to 100% similar. Identity or similarity can be determined by comparing a position in each sequence that may be aligned for purposes of comparison. When a position in the compared sequence is occupied by the same nucleotide base or amino acid, then the molecules are identical at that position. A degree of similarity or identity between polynucleotide sequences is a function of the number of identical, matching or corresponding nucleotides at positions shared by the polynucleotide sequences. A degree of identity of polypeptide sequences is a function of the number of identical amino acids at corresponding positions shared by the polypeptide sequences. A degree of homology or similarity of polypeptide sequences is a function of the number of amino acids at corresponding positions shared by the polypeptide sequences.

By "substantially identical" is meant an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein assayed. (e.g., as described herein). Preferably, such a sequence has at least 78% or greater identity with a listed sequence of the invention, such as at least 78% or greater identity with the B domain of SEQ ID NO: 2 or at least 80% or greater identity with the B domain of SEQ ID NO: 2, or at least 83% or greater identity with the B domain of SEQ ID NO: 2, or at least 85% or greater identity with the B domain of SEQ ID NO: 2, or at least 91% or greater identity with the B domain of SEQ ID NO: 2, or at least 93% or greater identity with the B domain of SEQ ID NO: 2.

"Alignment" refers to a number of nucleotide bases or amino acid residue sequences aligned by lengthwise comparison so that components in common (i.e., nucleotide bases or amino acid residues at corresponding positions) may be visually and readily identified. The fraction or percentage of components in common is related to the homology or identity between the sequences. Alignments such as those of FIGS. 4A to 4B may be used to identify conserved B domains and relatedness within these domains. An alignment may suitably be determined by means of computer programs known in the art, such as MACVECTOR software (1999) (Accelrys, Inc., San Diego, Calif.).

A "conserved domain" or "conserved region" as used herein refers to a region in heterologous polynucleotide or polypeptide sequences where there is a relatively high degree of sequence identity between the distinct sequences. With respect to polynucleotides encoding presently disclosed polypeptides, a conserved domain is preferably at least nine base pairs (bp) in length. Transcription factor sequences that possess or encode for conserved domains that have a minimum percentage identity and have comparable biological activity to the present polypeptide sequences, thus being members of the same clade or subclade of transcription factor polypeptides, are encompassed by the invention. Overexpression in a transformed plant of a polypeptide that comprises, for example, a conserved domain having DNA-binding, activation or nuclear localization activity results in the transformed plant having similar improved traits as other transformed plants overexpressing other members of the same clade or subclade of transcription factor polypeptides.

A fragment or domain can be referred to as outside a conserved domain, outside a consensus sequence, or outside a consensus DNA-binding site that is known to exist or that exists for a particular polypeptide class, family, or sub-family. In this case, the fragment or domain will not include the exact amino acids of a consensus sequence or consensus DNA-binding site of a transcription factor class, family or sub-family, or the exact amino acids of a particular transcription factor consensus sequence or consensus DNA-binding site. Furthermore, a particular fragment, region, or domain of a polypeptide, or a polynucleotide encoding a polypeptide, can be "outside a conserved domain" if all the amino acids of the fragment, region, or domain fall outside of a defined conserved domain(s) for a polypeptide or protein. Sequences having lesser degrees of identity but comparable biological activity are considered to be equivalents.

As one of ordinary skill in the art recognizes, conserved domains may be identified as regions or domains of identity to a specific consensus sequence (see, for example, Riechmann et al., 2000a, 2000b). Thus, by using alignment methods well known in the art, the conserved domains of the plant polypeptides may be determined.

The conserved B domains for many of the polypeptide sequences of the invention are listed in Table 2. Also, the polypeptides of FIGS. 4A to 4B and Table 2 have conserved B domains specifically indicated by amino acid coordinate start and stop sites. A comparison, of the regions of these polypeptides allows one of skill in the art (see, for example, Reeves and Nissen, 1995) to identify domains or conserved B domains for any of the polypeptides listed or referred to in this disclosure.

"Complementary" refers to the natural hydrogen bonding by base pairing between purines and pyrimidines. For example, the sequence A-C-G-T (5'→3') forms hydrogen bonds with its complements A-C-G-T (5'→3') or A-C-G-U (5'→3'). Two single-stranded molecules may be considered partially complementary, if only some of the nucleotides bond, or "completely complementary" if all of the nucleotides bond. The degree of complementarity between nucleic acid strands affects the efficiency and strength of hybridization and amplification reactions. "Fully complementary" refers to the case where bonding occurs between every base pair and its complement in a pair of sequences, and the two sequences have the same number of nucleotides.

The terms "highly stringent" or "highly stringent condition" refer to conditions that permit hybridization of DNA strands whose sequences are highly complementary, wherein these same conditions exclude hybridization of significantly mismatched DNAs. Polynucleotide sequences capable of hybridizing under stringent conditions with the polynucleotides of the present invention may be, for example, variants of the disclosed polynucleotide sequences, including allelic or splice variants, or sequences that encode orthologs or paralogs of presently disclosed polypeptides. Nucleic acid hybridization methods are disclosed in detail by Kashima et al., 1985, Sambrook et al., 1989, and by Haymes et al., 1985, which references are incorporated herein by reference.

In general, stringency is determined by the temperature, ionic strength, and concentration of denaturing agents (e.g., formamide) used in a hybridization and washing procedure (for a more detailed description of establishing and determining stringency, see the section "Identifying Polynucleotides or Nucleic Acids by Hybridization", below). The degree to which two nucleic acids hybridize under various conditions of stringency is correlated with the extent of their similarity.

Thus, similar nucleic acid sequences from a variety of sources, such as within a plant's genome (as in the case of paralogs) or from another plant (as in the case of orthologs) that may perform similar functions can be isolated on the basis of their ability to hybridize with known related polynucleotide sequences. Numerous variations are possible in the conditions and means by which nucleic acid hybridization can be performed to isolate related polynucleotide sequences having similarity to sequences known in the art and are not limited to those explicitly disclosed herein. Such an approach may be used to isolate polynucleotide sequences having various degrees of similarity with disclosed polynucleotide sequences, such as, for example, encoded transcription factors having 78% or greater identity with the conserved B domain of disclosed sequences.

The terms "paralog" and "ortholog" are defined below in the section entitled "Orthologs and Paralogs". In brief, orthologs and paralogs are evolutionarily related genes that have similar sequences and functions. Orthologs are structurally related genes in different species that are derived by a speciation event. Paralogs are structurally related genes within a single species that are derived by a duplication event.

The term "equivalog" describes members of a set of homologous proteins that are conserved with respect to function since their last common ancestor. Related proteins are grouped into equivalog families, and otherwise into protein families with other hierarchically defined homology types. This definition is provided at the Institute for Genomic Research (TIGR) World Wide Web (www) website, "tigr.org" under the heading "Terms associated with TIGRFAMs".

In general, the term "variant" refers to molecules with some differences, generated synthetically or naturally, in their base or amino acid sequences as compared to a reference (native) polynucleotide or polypeptide, respectively. These differences include substitutions, insertions, deletions or any desired combinations of such changes in a native polynucleotide of amino acid sequence.

With regard to polynucleotide variants, differences between presently disclosed polynucleotides and polynucleotide variants are limited so that the nucleotide sequences of the former and the latter are closely similar overall and, in many regions, identical. Due to the degeneracy of the genetic code, differences between the former and latter nucleotide sequences may be silent (i.e., the amino acids encoded by the polynucleotide are the same, and the variant polynucleotide sequence encodes the same amino acid sequence as the presently disclosed polynucleotide. Variant nucleotide sequences may encode different amino acid sequences, in which case such nucleotide differences will result in amino acid substitutions, additions, deletions, insertions, truncations or fusions with respect to the similar disclosed polynucleotide sequences. These variations may result in polynucleotide variants encoding polypeptides that share at least one functional characteristic. The degeneracy of the genetic code also dictates that many different variant polynucleotides can encode identical and/or substantially similar polypeptides in addition to those sequences illustrated in the Sequence Listing.

Also within the scope of the invention is a variant of a nucleic acid listed in the Sequence Listing, that is, one having a sequence that differs from the one of the polynucleotide sequences in the Sequence Listing, or a complementary sequence, that encodes a functionally equivalent polypeptide (i.e., a polypeptide having some degree of equivalent or similar biological activity) but differs in sequence from the sequence in the Sequence Listing, due to degeneracy in the genetic code. Included within this definition are polymorphisms that may or may not be readily detectable using a particular oligonucleotide probe of the polynucleotide encoding polypeptide, and improper or unexpected hybridization to allelic variants, with a locus other than the normal chromosomal locus for the polynucleotide sequence encoding polypeptide.

"Allelic variant" or "polynucleotide allelic variant" refers to any of two or more alternative forms of a gene occupying the same chromosomal locus. Allelic variation arises naturally through mutation, and may result in phenotypic polymorphism within populations. Gene mutations may be "silent" or may encode polypeptides having altered amino acid sequence. "Allelic variant" and "polypeptide allelic variant" may also be used with respect to polypeptides, and in this case the terms refer to a polypeptide encoded by an allelic variant of a gene.

"Splice variant" or "polynucleotide splice variant" as used herein refers to alternative forms of RNA transcribed from a gene. Splice variation naturally occurs as a result of alternative sites being spliced within a single transcribed RNA molecule or between separately transcribed RNA molecules, and may result in several different forms of mRNA transcribed from the same gene. Thus, splice variants may encode polypeptides having different amino acid sequences, which may or may not have similar functions in the organism. "Splice variant" or "polypeptide splice variant" may also refer to a polypeptide encoded by a splice variant of a transcribed mRNA.

As used herein, "polynucleotide variants" may also refer to polynucleotide sequences that encode paralogs and orthologs of the presently disclosed polypeptide sequences. "Polypeptide variants" may refer to polypeptide sequences that are paralogs and orthologs of the presently disclosed polypeptide sequences.

Differences between presently disclosed polypeptides and polypeptide variants are limited so that the sequences of the former and the latter are closely similar overall and, in many regions, identical. Presently disclosed polypeptide sequences and similar polypeptide variants may differ in amino acid sequence by one or more substitutions, additions, deletions, fusions and truncations, which may be present in any combination. These differences may produce silent changes and result in a functionally equivalent polypeptides. Thus, it will be readily appreciated by those of skill in the art, that any of a variety of polynucleotide sequences is capable of encoding the polypeptides and homolog polypeptides of the invention. A polypeptide sequence variant may have "conservative" changes, wherein a substituted amino acid has similar structural or chemical properties. Deliberate amino acid substitutions may thus be made on the basis of similarity in polarity, charge, solubility, hydrophobicity, hydrophilicity, and/or the amphipathic nature of the residues, as long as a significant amount of the functional or biological activity of the polypeptide is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine. More rarely, a variant may have "non-conservative" changes, e.g., replacement of a glycine with a tryptophan. Similar minor variations may also include amino acid deletions or insertions, or both. Related polypeptides may comprise, for example, additions and/or deletions of one or more N-linked or O-linked glycosylation sites, or an addition and/or a deletion of one or more cysteine residues. Guidance in determining which and how many amino acid residues may be substituted, inserted or deleted without abolishing functional or biological activity may be found using computer programs well known in the art, for example, DNASTAR software (see U.S. Pat. No. 5,840, 544 to Hawkins, 1998).

"Fragment", with respect to a polynucleotide, refers to a clone or any part of a polynucleotide molecule that retains a usable, functional characteristic. Useful fragments include oligonucleotides and polynucleotides that may be used in hybridization or amplification technologies or in the regulation of replication, transcription or translation. A "polynucleotide fragment" refers to any subsequence of a polynucleotide, typically, of at least about 9 consecutive nucleotides, preferably at least about 30 nucleotides, more preferably at least about 50 nucleotides, of any of the sequences provided herein. Exemplary polynucleotide fragments are the first sixty consecutive nucleotides of the polynucleotides listed in the Sequence Listing. Exemplary fragments also include fragments that comprise a region that encodes a conserved B domain of a polypeptide. Exemplary fragments also include fragments that comprise a conserved domain of a polypeptide.

Fragments may also include subsequences of polypeptides and protein molecules, or a subsequence of the polypeptide. Fragments may have uses in that they may have antigenic potential. In some cases, the fragment or domain is a subsequence of the polypeptide which performs at least one biological function of the intact polypeptide in substantially the same manner, or to a similar extent, as does the intact polypeptide. For example, a polypeptide fragment can comprise a recognizable structural motif or functional domain such as a DNA-binding site or domain that binds to a DNA promoter region, an activation domain, or a domain for protein-protein interactions, and may initiate transcription. Fragments can vary in size from as few as 3 amino acid residues to the full length of the intact polypeptide, but are preferably at least about 30 amino acid residues in length and more preferably at least about 60 amino acid residues in length.

The invention also encompasses production of DNA sequences that encode polypeptides and derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding polypeptides or any fragment thereof.

"Derivative" refers to the chemical modification of a nucleic acid molecule or amino acid sequence. Chemical modifications can include replacement of hydrogen by an alkyl, acyl, or amino group or glycosylation, pegylation, or any similar process that retains or enhances biological activity or lifespan of the molecule or sequence.

The term "plant" includes whole plants, shoot vegetative organs/structures (for example, leaves, stems and tubers), roots, flowers and floral organs/structures (for example, bracts, sepals, petals, stamens, carpels, anthers and ovules), seed (including embryo, endosperm, and seed coat) and fruit (the mature ovary), plant tissue (for example, vascular tissue, ground tissue, and the like) and cells (for example, guard cells, egg cells, and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, horsetails, psilophytes, lycophytes, bryophytes, and multicellular algae (see for example, FIG. 1, adapted from Daly et al., 2001, FIG. 2, adapted from Ku et al., 2000; and see also Tudge, 2000.

A "control plant" as used in the present invention refers to a plant cell, seed, plant component, plant tissue, plant organ or whole plant used to compare against transformed, transgenic or genetically modified plant for the purpose of identifying an enhanced phenotype in the transformed, transgenic or genetically modified plant. A control plant may in some cases be a transformed or transgenic plant line that comprises an empty vector or marker gene, but does not contain the recombinant polynucleotide of the present invention that is expressed in the transformed, transgenic or genetically modified plant being evaluated. In general, a control plant is a plant of the same line or variety as the transformed, transgenic or genetically modified plant being tested. A suitable control plant would include a genetically unaltered or non-transgenic plant of the parental line used to generate a transformed or transgenic plant herein.

"Transformation" refers to the transfer of a foreign polynucleotide sequence into the genome of a host organism such as that of a plant or plant cell. Typically, the foreign genetic material has been introduced into the plant by human manipulation, but any method can be used as one of skill in the art recognizes. Examples of methods of plant transformation include *Agrobacterium*-mediated transformation (De Blaere et al., 1987) and biolistic methodology (Klein et al, 1987).

A "transformed plant", which may also be referred to as a "transgenic plant" or "transformant", generally refers to a plant, a plant cell, plant tissue, seed or calli that has been through, or is derived from a plant that has been through, a transformation process in which a nucleic acid construct that contains at least one foreign polynucleotide sequence is introduced into the plant. The nucleic acid construct, which may be an expression vector or expression cassette, a plasmid, or a DNA preparation, contains genetic material that is not found in a wild-type plant of the same species, variety or cultivar. The genetic material may include a regulatory element, a transgene (for example, a foreign transcription factor sequence), an insertional mutagenesis event (such as by transposon or T-DNA insertional mutagenesis), an activation tagging sequence, a mutated sequence, a homologous recombination event or a sequence modified by chimeraplasty. In some embodiments the regulatory and transcription factor sequence may be derived from the host plant, but by their incorporation into an expression vector of cassette, represent an arrangement of the polynucleotide sequences not found a wild-type plant of the same species, variety or cultivar.

An "untransformed plant" is a plant that has not been through the transformation process.

A "stably transformed" plant, plant cell or plant tissue has generally been selected and regenerated on a selection media following transformation.

A nucleic acid construct such as a plasmid, an expression vector or expression cassette typically comprises a polypeptide-encoding sequence operably linked (i.e., under regulatory control of) to appropriate inducible or constitutive regulatory sequences that allow for the controlled expression of polypeptide. The expression vector or cassette can be introduced into a plant by transformation or by breeding after transformation of a parent plant. A plant refers to a whole plant as well as to a plant part, such as seed, fruit, leaf, or root, plant tissue, plant cells or any other plant material, e.g., a plant explant, as well as to progeny thereof, and to in vitro systems that mimic biochemical or cellular components or processes in a cell.

"Wild type" or "wild-type", as used herein, refers to a plant cell, seed, plant component, plant tissue, plant organ or whole plant that has not been genetically modified or treated in an experimental sense. Wild-type cells, seed, components, tissue, organs or whole plants may be used as controls to compare levels of expression and the extent and nature of trait modification with cells, tissue or plants of the same species in which a polypeptide's expression is altered, e.g., in that it has been knocked out, overexpressed, or ectopically expressed.

A "trait" refers to a physiological, morphological, biochemical, or physical characteristic of a plant or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, e.g. by measuring tolerance to water deficit or particular salt or sugar concentrations, or by the observation of the expression level of a gene or genes, e.g., by employing Northern analysis, RT-PCR, microarray gene expression assays, or reporter gene expression systems, or by agricultural observations such as increased cold or water deficit tolerance or an increased yield. Any technique can be used to measure the amount of, comparative level of, or difference in any selected chemical compound or macromolecule in the transformed or transgenic plants, however.

"Trait modification" refers to a detectable difference in a characteristic in a plant ectopically expressing a polynucleotide or polypeptide of the present invention relative to a plant not doing so, such as a wild-type plant. In some cases, the trait modification can be evaluated quantitatively. For example, the trait modification can entail at least about a 2% increase or decrease, or an even greater difference, in an observed trait as compared with a control or wild-type plant. It is known that there can be a natural variation in the modified trait. Therefore, the trait modification observed entails a change of the normal distribution and magnitude of the trait in the plants as compared to control or wild-type plants.

When two or more plants have "similar morphologies", "substantially similar morphologies", "a morphology that is substantially similar", or are "morphologically similar", the plants have comparable forms or appearances, including analogous features such as overall dimensions, height, width, mass, root mass, shape, glossiness, color, stem diameter, leaf size, leaf dimension, leaf density, internode distance, branching, root branching, number and form of inflorescences, and other macroscopic characteristics, and the individual plants are not readily distinguishable based on morphological characteristics alone.

"Modulates" refers to a change in activity (biological, chemical, or immunological) or lifespan resulting from specific binding between a molecule and either a nucleic acid molecule or a protein.

The term "transcript profile" refers to the expression levels of a set of genes in a cell in a particular state, particularly by comparison with the expression levels of that same set of genes in a cell of the same type in a reference state. For example, the transcript profile of a particular polypeptide in a suspension cell is the expression levels of a set of genes in a cell knocking out or overexpressing that polypeptide compared with the expression levels of that same set of genes in a suspension cell that has normal levels of that polypeptide. The transcript profile can be presented as a list of those genes whose expression level is significantly different between the two treatments, and the difference ratios. Differences and similarities between expression levels may also be evaluated and calculated using statistical and clustering methods.

With regard to gene knockouts as used herein, the term "knockout" refers to a plant or plant cell having a disruption in at least one gene in the plant or cell, where the disruption results in a reduced expression or activity of the polypeptide encoded by that gene compared to a control cell. The knockout can be the result of, for example, genomic disruptions, including transposons, tilling, and homologous recombination, antisense constructs, sense constructs, RNA silencing constructs, or RNA interference. A T-DNA insertion within a gene is an example of a genotypic alteration that may abolish expression of that gene.

"Ectopic expression" or "altered expression" in reference to a polynucleotide indicates that the pattern of expression in, e.g., a transformed or transgenic plant or plant tissue, is different from the expression pattern in a wild-type plant or a reference plant of the same species. The pattern of expression may also be compared with a reference expression pattern in a wild-type plant of the same species. For example, the polynucleotide or polypeptide is expressed in a cell or tissue type other than a cell or tissue type in which the sequence is expressed in the wild-type plant, or by expression at a time other than at the time the sequence is expressed in the wild-type plant, or by a response to different inducible agents, such as hormones or environmental signals, or at different expression levels (either higher or lower) compared with those found in a wild-type plant. The term also refers to altered expression patterns that are produced by lowering the levels of expression to below the detection level or completely abolishing expression. The resulting expression pattern can be transient or stable, constitutive or inducible. In reference to a polypeptide, the terms "ectopic expression" or "altered expression" further may relate to altered activity levels resulting from the interactions of the polypeptides with exogenous or endogenous modulators or from interactions with factors or as a result of the chemical modification of the polypeptides.

The term "overexpression" as used herein refers to a greater expression level of a gene in a plant, plant cell or plant tissue, compared to expression in a wild-type plant, cell or tissue, at any developmental or temporal stage for the gene. Overexpression can occur when, for example, the genes encoding one or more polypeptides are under the control of a strong promoter (e.g., the cauliflower mosaic virus 35S transcription initiation region (SEQ ID NO: 107). Overexpression may also under the control of an inducible or tissue specific promoter. The choice of inducible or tissue-specific promoters may include, for example, the LTP1 epidermal-specific promoter (SEQ ID NO: 108), the SUC2 vascular-specific promoter (SEQ ID NO: 109), the ARSK1 root-specific promoter (SEQ ID NO: 110), the RD29A stress inducible promoter (SEQ ID NO: 111), the AS1 emergent leaf primordia-specific promoter (SEQ ID NO: 112), or the RBCS3 leaf- or photosynthetic-tissue specific-promoter (SEQ ID NO: 113). Many of these promoters have been used with polynucleotide sequences of the invention to produce transgenic plants. These or other inducible or tissue-specific promoters may be incorporated into a nucleic acid construct comprising a transcription factor polynucleotide of the invention, where the promoter is operably linked to the transcription factor polynucleotide, can be envisioned and produced. Thus, overexpression may occur throughout a plant, in specific tissues of the plant, or in the presence or absence of particular environmental signals, depending on the promoter used.

Overexpression may take place in plant cells normally lacking expression of polypeptides functionally equivalent or identical to the present polypeptides. Overexpression may also occur in plant cells where endogenous expression of the present polypeptides or functionally equivalent molecules normally occurs, but such normal expression is at a lower level. Overexpression thus results in a greater than normal production, or "overproduction" of the polypeptide in the plant, cell or tissue.

The term "transcription regulating region" refers to a DNA regulatory sequence that regulates expression of one or more genes in a plant when a transcription factor having one or more specific binding domains binds to the DNA regulatory sequence. Transcription factors possess at least one conserved domain. The transcription factors also comprise an amino acid subsequence that forms a transcription activation domain that regulates expression of one or more genes that modulate tolerance to cold or water deficit in a plant when the transcription factor binds to the regulating region.

"Yield" or "plant yield" refers to increased plant growth, increased crop growth, increased biomass, and/or increased plant product production, and is dependent to some extent on temperature, plant size, organ size, planting density, light, water and nutrient availability, and how the plant copes with various stresses, such as through temperature acclimation and water or nutrient use efficiency.

"Planting density" refers to the number of plants that can be grown per acre. For crop species, planting or population density varies from a crop to a crop, from one growing region to another, and from year to year. Using corn as an example, the average prevailing density in 2000 was in the range of 20,000-25,000 plants per acre in Missouri, USA. A desirable higher population density (a measure of yield) would be at least 22,000 plants per acre, and a more desirable higher population density would be at least 28,000 plants per acre, more preferably at least 34,000 plants per acre, and most preferably at least 40,000 plants per acre. The average prevailing densities per acre of a few other examples of crop plants in the USA in the year 2000 were: wheat 1,000,000-1,500,000; rice 650,000-900,000; soybean 150,000-200,000, canola 260,000-350,000, sunflower 17,000-23,000 and cotton 28,000-55,000 plants per acre (U.S. Pat. Appl. No. 20030101479, Cheikh et al., 2003). A desirable higher population density for each of these examples, as well as other valuable species of plants, would be at least 10% higher than the average prevailing density or yield.

DESCRIPTION OF THE SPECIFIC EMBODIMENTS

Transcription Factors Modify Expression of Endogenous Genes

A transcription factor may include, but is not limited to, any polypeptide that can activate or repress transcription of a single gene or a number of genes. As one of ordinary skill in the art recognizes, transcription factors can be identified by the presence of a region or domain of structural similarity or identity to a specific consensus sequence or the presence of a specific consensus DNA-binding motif (see, for example, Riechmann et al., 2000a). The plant transcription factors of the present invention are transcription factors.

Generally, transcription factors are involved in cell differentiation and proliferation and the regulation of growth. Accordingly, one skilled in the art would recognize that by expressing the present sequences in a plant, one may change the expression of autologous genes or induce the expression of introduced genes. By affecting the expression of similar autologous sequences in a plant that have the biological activity of the present sequences, or by introducing the present sequences into a plant, one may alter a plant's phenotype to one with improved traits related to Improved cold or water deficit tolerance. The sequences of the invention may also be used to transform a plant and introduce desirable traits not found in the wild-type cultivar or strain. Plants may then be selected for those that produce the most desirable degree of over- or under-expression of target genes of interest and coincident trait improvement.

The sequences of the present invention may be from any species, particularly plant species, in a naturally occurring form or from any source whether natural, synthetic, semi-synthetic or recombinant. The sequences of the invention may also include fragments of the present amino acid sequences. Where "amino acid sequence" is recited to refer to an amino acid sequence of a naturally occurring protein molecule, "amino acid sequence" and like terms are not meant to limit the amino acid sequence to the complete native amino acid sequence associated with the recited protein molecule.

In addition to methods for modifying a plant phenotype by employing one or more polynucleotides and polypeptides of the invention described herein, the polynucleotides and polypeptides of the invention have a variety of additional uses. These uses include their use in the recombinant production (i.e., expression) of proteins; as regulators of plant gene expression, as diagnostic probes for the presence of complementary or partially complementary nucleic acids (including for detection of natural coding nucleic acids); as substrates for further reactions, e.g., mutation reactions, PCR reactions, or the like; as substrates for cloning e.g., including digestion or ligation reactions; and for identifying exogenous or endogenous modulators of the transcription factors. The polynucleotide can be, e.g., genomic DNA or RNA, a transcript (such as an mRNA), a cDNA, a PCR product, a cloned DNA, a synthetic DNA or RNA, or the like. The polynucleotide can comprise a sequence in either sense or antisense orientations.

Expression of genes that encode polypeptides that modify expression of endogenous genes, polynucleotides, and proteins are well known in the art. In addition, transformed or transgenic plants comprising isolated polynucleotides encoding transcription factors may also modify expression of endogenous genes, polynucleotides, and proteins. Examples include Peng et al., 1997 and Peng et al., 1999. In addition, many others have demonstrated that an *Arabidopsis* transcription factor expressed in an exogenous plant species elicits the same or very similar phenotypic response. See, for example, Fu et al., 2001; Nandi et al., 2000; Coupland, 1995; and Weigel and Nilsson, 1995).

In another example, Mandel et al., 1992b, and Suzuki et al., 2001, teach that a transcription factor expressed in another plant species elicits the same or very similar phenotypic response of the endogenous sequence, as often predicted in earlier studies of *Arabidopsis* transcription factors in *Arabidopsis* (see Mandel et al., 1992a; Suzuki et al., 2001). Other examples include Müller et al., 2001; Kim et al., 2001; Kyozuka and Shimamoto, 2002; Boss and Thomas, 2002; He et al., 2000; and Robson et al., 2001.

In yet another example, Gilmour et al., 1998, teach an *Arabidopsis* AP2 transcription factor, CBF1, which, when overexpressed in transgenic plants, increases plant freezing tolerance. Jaglo et al., 2001, further identified sequences in Brassica napus which encode CBF-like genes and that transcripts for these genes accumulated rapidly in response to low temperature. Transcripts encoding CBF-like proteins were also found to accumulate rapidly in response to low temperature in wheat, as well as in tomato. An alignment of the CBF proteins from *Arabidopsis*, B. napus, wheat, rye, and tomato revealed the presence of conserved consecutive amino acid residues, PKK/RPAGRxKFxETRHP (SEQ ID NO: 115) and DSAWR (SEQ ID NO: 116), which bracket the AP2/EREBP DNA binding domains of the proteins and distinguish them from other members of the AP2/EREBP protein family. (Jaglo et al., 2001).

Transcription factors mediate cellular responses and control traits through altered expression of genes containing cis-acting nucleotide sequences that are targets of the introduced transcription factor. It is well appreciated in the art that the effect of a transcription factor on cellular responses or a cellular trait is determined by the particular genes whose expression is either directly or indirectly (e.g., by a cascade of transcription factor binding events and transcriptional changes) altered by transcription factor binding. In a global analysis of transcription comparing a standard condition with one in which a transcription factor is overexpressed, the resulting transcript profile associated with transcription factor overexpression is related to the trait or cellular process controlled by that transcription factor. For example, the PAP2 gene and other genes in the MYB family have been shown to control anthocyanin biosynthesis through regulation of the expression of genes known to be involved in the anthocyanin biosynthetic pathway (Bruce et al., 2000; and Borevitz et al., 2000). Further, global transcript profiles have been used successfully as diagnostic tools for specific cellular states (e.g., cancerous vs. non-cancerous; Bhattacharjee et al., 2001; and Xu et al., 2001). Consequently, it is evident to one skilled in the art that similarity of transcript profile upon overexpression of different transcription factors would indicate similarity of transcription factor function.

Polypeptides and Polynucleotides of the Invention

The present invention includes transcription factors (TFs), and isolated or recombinant polynucleotides encoding the polypeptides, or novel sequence variant polypeptides or polynucleotides encoding novel variants of polypeptides derived from the specific sequences provided in the Sequence Listing; the recombinant polynucleotides of the invention may be incorporated in nucleic acid constructs for the purpose of producing transformed plants. Also provided are methods for accelerating the time for a plant to flower, as compared to a control plant. These methods are based on the ability to alter the expression of critical regulatory molecules that may be conserved between diverse plant species. Related conserved regulatory molecules may be originally discovered in a model system such as *Arabidopsis* and homologous, functional molecules then be discovered in other plant species. The latter may then be used to confer improved water deficit and or/cold tolerance in diverse plant species.

Exemplary polynucleotides encoding the polypeptides of the invention were identified in the *Arabidopsis thaliana* GenBank database using publicly available sequence analysis programs and parameters. Sequences initially identified were then further characterized to identify sequences comprising specified sequence strings corresponding to sequence motifs present in families of known polypeptides. In addition, further exemplary polynucleotides encoding the polypeptides of the invention were identified in the plant GenBank database using publicly available sequence analysis programs and parameters. Sequences initially identified were then further characterized to identify sequences comprising specified sequence strings corresponding to sequence motifs present in families of known polypeptides.

Additional polynucleotides of the invention were identified by screening *Arabidopsis thaliana* and/or other plant cDNA libraries with probes corresponding to known polypeptides under low stringency hybridization conditions. Additional sequences, including full length coding sequences, were subsequently recovered by the rapid amplification of cDNA ends (RACE) procedure using a commercially available kit according to the manufacturer's instructions. Where necessary, multiple rounds of RACE are performed to isolate 5' and 3' ends. The full-length cDNA was then recovered by a routine end-to-end polymerase chain reaction (PCR) using primers specific to the isolated 5' and 3' ends. Exemplary sequences are provided in the Sequence Listing.

The HAP3/NF-YB Sub-Group of the CCAAT Binding Factor Family

G481 (AT2G38880; also known as HAP3A and NF-YB1) from *Arabidopsis* is a member of the HAP3/NF-YB subgroup of the CCAAT binding factor family (CCAAT) of transcription factors. This gene and related sequences were selected for further study based on our original finding of hyperosmotic stress conferred by 35S::G481 lines, (SEQ ID NOs: 1-2), and salt tolerance conferred by constitutive overexpression of its paralog G482 (SEQ ID NOs: 27-28). Thus, the goal of the research program described herein was to determine the extent to which other proteins from the CCAAT family, both in *Arabidopsis* and other plant species, have similar functions.

The CCAAT Family Members Under Study

Transcriptional regulation of most eukaryotic genes occurs through the binding of transcription factors to sequence specific binding sites in their promoter regions. Many of these protein binding sites have been conserved through evolution and are found in the promoters of diverse eukaryotic organisms. One element that shows a high degree of conservation is the CCAAT-box (Gelinas et al., 1985). The CCAAT family of transcription factors, also be referred to as the "CAAT", "CAAT-box" "CCAAT-box binding," "HAP" or "NF-Y" family, are characterized by their ability to bind to the CCAAT-box element located 80 to 300 bp 5' from a transcription start site (Gelinas et al., 1985). This cis-acting regulatory element is found in all eukaryotic species and present in the promoter and enhancer regions of approximately 30% of genes (Bucher and Trifonov, 1988; Bucher, 1990). The element can function in either orientation, and operates alone, or in possible cooperation with other cis regulatory elements (Tasanen et al., 1992).

The present invention pertains to a nucleic acid construct that comprises a recombinant polynucleotide encoding a HAP3 (or NF-YB) protein found within the CCAAT family transcription factor family. HAP3 proteins contain an amino-terminal A domain, a central B domain and a carboxy-terminal C domain. Outside of the B domain, non-paralogous *Arabidopsis* HAP-3 like proteins are quite divergent in sequence and in overall length. It is therefore reasonable to assume that the A and C domains may provide a degree of functional specificity to each member of the HAP3 subfamily. However, as shown in the present analysis, sequences that are closely related to one of the transcription factors presently being studied, G481 or SEQ ID NO: 2, have similar functions in plants when the sequences are overexpressed.

Structural Features and Assembly of the NF-Y Subunits.

NF-Y is one of the most heavily studied transcription factor complexes and an extensive literature has accumulated regarding its structure, regulation, and putative roles in various different organisms. Each of the three subunits comprises a region which has been evolutionarily conserved (Li et al., 1992; Mantovani, 1999). In the NF-YA subunits, this conserved region is at the C-terminus, in the NF-YB proteins it is centrally located, and in the NF-YC subunits it is at the N-terminus The NF-YB and NF-YC subunits bear some similarity to histones; the conserved regions of both these subunits contain a "histone fold motif" (HFM), which is an ancient domain of about 65 amino acids. The HFM has a high degree of structural conservation across all histones and comprises three or four α-helices (four in the case of the NF-Y subunits) which are separated by short loops (L)/strand regions (Arents and Moudrianakis, 1995). In the histones, this HFM domain mediates dimerization and formation of non sequence-specific interactions with DNA (Arents and Moudrianakis, 1995).

Comprised within the larger highly conserved B domain (Lee et al., 2003) of the HAP3-like NF-YB transcription factors is found a "conserved protein-protein and DNA-binding interaction module" within their "histone fold motif" or "HFM" (Gusmaroli et al., 2002; Romier et al. (2003). The HFM, is thus "specific and required for HAP function" (Edwards et al., 1998), comprising two highly conserved subdomains within the B domain that are responsible for both subunit interaction and binding DNA. The B domain of HAP3 transcription factors is necessary and sufficient for the activity of another related HAP3 protein, LEC1 (Lee et al., 2003). According to Gusmaroli et al., 2002, "all residues that constitute the backbone structure of the HFMs are conserved, and residues such as AtNF-YB-10 N38, K58 and Q62, involved in CCAAT-binding, and E67 and E75, involved in NF-YA association (Maity and de Crombrugghe, 1998; Zemzoumi et al., 1999), are maintained". These conserved residues constituting the backbone structure of the HFMs are shown in the boxes that appear in FIGS. 4A and 4B and are represented by SEQ ID NO: 114.

Plant CCAAT binding transcription factors potentially bind DNA as heterotrimers composed of HAP2-like, HAP3-like and HAP5-like subunits. The heterotrimer is also referenced in the public literature as Nuclear Factor Y (NF-Y), which comprises an NF-YA subunit (corresponding to the HAP2-like subunit), an NF-YB subunit (corresponding to the HAP3-like subunit) and an NF-YC subunit (corresponding to the HAP5-like subunit) (Mantovani, 1999; Gusmaroli et al., 2001; Gusmaroli et al., 2002). All subunits contain regions that are required for DNA binding and subunit association. The subunit proteins appear to lack activation domains; therefore, that function must come from proteins with which they interact on target promoters. No proteins that provide the activation domain function for CCAAT binding factors have been confirmed in plants, although a pair of recent publications implicate CCT-domain containing proteins as having such a role (Ben-Naim et al., 2006; Wenkel et al., 2006). In yeast, however, the HAP4 protein provides the primary activation domain (McNabb et al., 1995; Olesen and Guarente, 1990).

Like their mammalian counterparts, plant CCAAT binding factors most likely bind DNA as heterotrimers composed of HAP2-like, HAP3-like and HAP5-like subunits. All subunits contain regions that are required for DNA binding and subunit association. However, regions that might have an activation domain function are less apparent than in the mammalian proteins, where Q-rich regions within the HAP2 and HAP5 subunits are thought to fulfill such a role. Nonetheless, some of the HAP2 and HAP5 class proteins that we have identified do have Q-rich regions within the N and C-termini. However, these regions have not been confirmed yet as having such activation domain properties. In yeast, the HAP4 protein provides the primary activation domain (McNabb et al., 1995; Olesen and Guarente, 1990). Although, HAP4 subunits do not exist in plants, it is possible that the activation domain function is provided by some other factor that interacts with the HAP complex.

Role of LEC1-Like Proteins

The functions of at least two of the *Arabidopsis* CCAAT-box genes have been genetically determined by others working in this field. These genes, LEAFY COTYLEDON 1 (LEC1, G620) and LEAFY COTYLEDON 1-LIKE (L1L, G1821) have critical roles in embryo development and seed maturation (Lotan et al., 1998; Kwong et al., 2003) and encode proteins of the HAP3 (NF-YB) class. LEC1 has multiple roles in and is critical for normal development during both the early and late phases of embryogenesis (Meinke, 1992; Meinke et al., 1994; West et al., 1994; Parcy et al., 1997; Vicient et al., 2000). Mutant lec1 embryos have cotyledons that exhibit leaf-like characteristics such as trichomes. The gene is required to maintain suspensor cell fate and to specify cotyledon identity in the early morphogenesis phase. Through overexpression studies, LEC1 activity has been shown sufficient to initiate embryo development in vegetative cells (Lotan et al., 1998). Additionally, lec1 mutant embryos are desiccation intolerant and cannot survive seed dry-down (but can be artificially rescued in the laboratory). This phenotype reflects a role for LEC1 at later stages of seed maturation; the gene initiates and/or maintains the maturation phase, prevents precocious germination, and is required for acquisition of desiccation tolerance during seed maturation. L1L appears to be a paralog of, and partially redundant with LEC1. Like LEC1, L1L is expressed during embryogenesis, and genetic studies have demonstrated that L1L can complement lec1 mutants (Kwong et al., 2003). A number of groups have now begun to elaborate details of the mechanism of LEC1 action in embryonic cell fate control. For example, Casson and Lindsey, 2006, proposed that LEC1 requires auxin and sucrose to promote cell division and embryonic differentiation.

Role of Non-LEC1-Like Proteins; HAP3 (NF-YB) Genes Affecting Chloroplast Development in Rice The first functional analysis of non-LEC1 like HAP3 proteins has now also been published (Miyoshi et al., 2003). These authors used antisense and RNAi approaches to reduce the activity of three non-LEC1-like HAP3 proteins from rice (OsHAP3A, OsHAP3B and OsHAP3C). These genes are ubiquitously expressed under normal conditions, and repression of these transcripts using antisense and RNAi techniques resulted in plants that were pale in coloration. This phenotype was found to be associated with aberrant plastid development (both chloroplasts and amyloplasts were affected) and a decrease in the expression of nuclear encoded photosynthesis related genes such as RBCS3 and CAB. However, it remains to be determined whether these phenotypes were due to the HAP3-like proteins having a direct role in the regulation of such genes and in chloroplast development, or whether the defects seen in the experimental plants were secondary effects relating from deficiencies in some other process.

HAP3 (NF-YB) proteins have a modular structure and are comprised of three distinct domains: an amino-terminal A domain, a central B domain and a carboxy-terminal C domain. There is very little sequence similarity between HAP3 proteins within the A and C domains suggesting that those regions could provide a degree of functional specificity to each member of the HAP3 subfamily. The B domain is a highly conserved region that specifies DNA binding and subunit association. Lee et al., 2003, performed an elegant series of domain swap experiments between the LEC1 and a non-LEC1 like HAP3 protein (At4g14540, G485) to demonstrate that the B domain of LEC1 is necessary and sufficient, within the context of the rest of the protein, to confer its activity in embryogenesis. Furthermore, these authors identified a specific defining residue within the B domain (Asp-55) that is required for LEC1 activity and which is sufficient to confer LEC1 function to a non-LEC1 like B domain.

There is very little sequence similarity between HAP3 proteins in the A and C domains; it is therefore reasonable to assume that the A and C domains could provide a degree of functional specificity to each member of the HAP3 subfamily. The B domain is the conserved region that specifies DNA binding and subunit association.

Phylogenetic trees based on sequential relatedness of the HAP3 genes are shown in FIG. 3. The present invention encompasses the G482 subclade within the non-LEC1-like clade of HAP3 (NF-YB) proteins, for which a representative number of monocot and eudicot species, including members from eudicot and monocot species, have been shown to confer increased cold or water deficit tolerance in plants when overexpressed (shown in Tables 1-3 in Example IV).

In FIGS. 4A and 4B, the B domains of G482 subclade members of the HAP3 polypeptides from *Arabidopsis*, soybean, rice, and corn are aligned with the similar domain of G481. The B domains of the sequences in this non-LEC1-like "G482 subclade" are generally distinguished by the conserved residues within the HFM and larger B domain comprised within the subsequence SEQ ID NO: 114:

Asn (Xaa)$_{19-26}$ Lys (Xaa)$_3$ Gln (Xaa)$_4$ Glu (Xaa)$_7$ Glu where Xaa can be any amino acid residue. Within the G482 subclade, the A and C domains (not shown in FIGS. 4A and 4B) are more variable than the B domain in both length and sequence identity. SEQ ID NOs of the sequences listed in FIGS. 4A and 4B are found with the parentheses.

Overexpression of the G482 subclade polypeptides comprising a central conserved domain containing this subsequence have been shown to confer increased cold and/or water deficit tolerance in transgenic plants, as compared to a non-transformed plant that does not overexpress the polypeptide.

Orthologs and Paralogs

Homologous sequences as described above can comprise orthologous or paralogous sequences. Several different methods are known by those of skill in the art for identifying and defining these functionally homologous sequences. General methods for identifying orthologs and paralogs, including phylogenetic methods, sequence similarity and hybridization methods, are described herein; an ortholog or paralog, including equivalogs, may be identified by one or more of the methods described below.

As described by Eisen, 1998, evolutionary information may be used to predict gene function. It is common for groups of genes that are homologous in sequence to have diverse, although usually related, functions. However, in many cases, the identification of homologs is not sufficient to make specific predictions because not all homologs have the same function. Thus, an initial analysis of functional relatedness based on sequence similarity alone may not provide one with a means to determine where similarity ends and functional relatedness begins. Fortunately, it is well known in the art that protein function can be classified using phylogenetic analysis of gene trees combined with the corresponding species. Functional predictions can be greatly improved by focusing on how the genes became similar in sequence (i.e., by evolutionary processes) rather than on the sequence similarity itself (Eisen, 1998). In fact, many specific examples exist in which gene function has been shown to correlate well with gene phylogeny (Eisen, 1998). Thus, "[t]he first step in making functional predictions is the generation of a phylogenetic tree representing the evolutionary history of the gene of interest and its homologs. Such trees are distinct from clusters and other means of characterizing sequence similarity because they are inferred by techniques that help convert patterns of similarity into evolutionary relationships .... After the gene tree is inferred, biologically determined functions of the various homologs are overlaid onto the tree. Finally, the structure of the tree and the relative phylogenetic positions of genes of different functions are used to trace the history of functional changes, which is then used to predict functions of [as yet] uncharacterized genes" (Eisen, 1998).

Within a single plant species, gene duplication may cause two copies of a particular gene, giving rise to two or more genes with similar sequence and often similar function known as paralogs. A paralog is therefore a similar gene formed by duplication within the same species. Paralogs typically cluster together or in the same clade (a group of similar genes) when a gene family phylogeny is analyzed using programs such as CLUSTAL (Thompson et al., 1994; Higgins et al., 1996). Groups of similar genes can also be identified with pair-wise BLAST analysis (Feng and Doolittle, 1987). For example, a clade of very similar MADS domain transcription factors from *Arabidopsis* all share a common function in flowering time (Ratcliffe et al., 2001), and a group of very similar AP2 domain transcription factors from *Arabidopsis* are involved in tolerance of plants to freezing (Gilmour et al., 1998). Analysis of groups of similar genes with similar function that fall within one clade can yield sub-sequences that are particular to the clade. These sub-sequences, known as consensus sequences, can not only be used to define the sequences within each clade, but define the functions of these genes; genes within a clade may contain paralogous sequences, or orthologous sequences that share the same function (see also, for example, Mount, 2001).

Transcription factor gene sequences are conserved across diverse eukaryotic species lines (Goodrich et al., 1993; Lin et al., 1991; Sadowski et al., 1988). Plants are no exception to this observation; diverse plant species possess transcription factors that have similar sequences and functions. Speciation, the production of new species from a parental species, gives rise to two or more genes with similar sequence and similar function. These genes, termed orthologs, often have an identical function within their host plants and are often interchangeable between species without losing function. Because plants have common ancestors, many genes in any plant species will have a corresponding orthologous gene in another plant species. Once a phylogenic tree for a gene family of one species has been constructed using a program such as CLUSTAL (Thompson et al., 1994; Higgins et al., 1996) potential orthologous sequences can be placed into the phylogenetic tree and their relationship to genes from the species of interest can be determined. Orthologous sequences can also be identified by a reciprocal BLAST strategy. Once an orthologous sequence has been identified, the function of the ortholog can be deduced from the identified function of the reference sequence.

By using a phylogenetic analysis, one skilled in the art would recognize that the ability to predict similar functions conferred by closely-related polypeptides is predictable. This predictability has been confirmed by our own many studies in which we have found that a wide variety of polypeptides have orthologous or closely-related homologous sequences that function as does the first, closely-related reference sequence. For example, distinct transcription factors, including:

(i) AP2 family *Arabidopsis* G47 (found in U.S. Pat. No. 7,135,616 to Heard et al., 2006), a phylogenetically-related sequence from soybean, and two phylogenetically-related homologs from rice all can confer greater tolerance to drought, hyperosmotic stress, or delayed flowering as compared to control plants;

(ii) Myb-related *Arabidopsis* G682 (found in U.S. Pat. No. 7,223,904 to Heard et al., 2006) and numerous phylogenetically-related sequences from eudicots and monocots can confer greater tolerance to heat, drought-related stress, cold, and salt as compared to control plants;

(iii) WRKY family *Arabidopsis* G1274 (found in U.S. Pat. No. 7,196,245 to Jiang et al., 2006) and numerous closely-related sequences from eudicots and monocots have been shown to confer increased water deprivation tolerance, and (iv) AT-hook family soy sequence G3456 (found in U.S. Pat. Appl. No. 20040128712, Jiang et al., 2004) and numerous phylogenetically-related sequences from eudicots and monocots, increased biomass compared to control plants when these sequences are overexpressed in plants.

The polypeptides sequences belong to distinct clades or subclades of polypeptides that include members from diverse species. Many of the G482 subclade member sequences derived from both eudicots and monocots that have been introduced into plants have been shown to confer greater tolerance to cold and/or water deficit conditions relative to control plants when the sequences were overexpressed, including most of the sequences shown in Table 2. These studies each demonstrate, in accord with the teachings of Goodrich et al., 1993, Lin et al., 1991, and Sadowski et al., 1988, that evolutionarily conserved genes from diverse species are likely to function similarly (i.e., by regulating similar target sequences and controlling the same traits), and that some polynucleotides from one species may be transformed into closely-related or distantly-related plant species to confer or improve traits.

At the nucleotide level, the sequences of the invention will typically share at least about 30% or 40% nucleotide sequence identity, preferably at least about 50%, about 60%, about 70% or about 80% sequence identity, and more preferably about 85%, about 90%, about 95% or about 97% or more sequence identity to one or more of the listed full-length sequences, or to a region of a listed sequence excluding or outside of the region(s) encoding a known consensus sequence or consensus DNA-binding site, or outside of the region(s) encoding one or all conserved domains. The degeneracy of the genetic code enables major variations in the nucleotide sequence of a polynucleotide while maintaining the amino acid sequence of the encoded protein.

At the polypeptide level, the sequences of the invention will typically share at least about 42%, at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84% sequence identity, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% or about 100% amino acid sequence identity to one or more of the listed full-length sequences, or to a listed sequence but excluding or outside of the known consensus sequence or consensus DNA-binding site, or to a B domain (e.g., SEQ ID NOs: 47-69) of a sequence of the invention, said B domain being required for DNA binding and subunit association.

Percent identity can be determined electronically, e.g., by using the MEGALIGN program (DNASTAR, Inc. Madison, Wis.). The MEGALIGN program can create alignments between two or more sequences according to different methods, for example, the clustal method (see, for example, Higgins and Sharp, 1988. The clustal algorithm groups sequences into clusters by examining the distances between all pairs. The clusters are aligned pairwise and then in groups. Other alignment algorithms or programs may be used, including FASTA, BLAST, or ENTREZ, FASTA and BLAST, and which may be used to calculate percent similarity. These are available as a part of the GCG sequence analysis package (University of Wisconsin, Madison, Wis.), and can be used with or without default settings. ENTREZ is available through the National Center for Biotechnology Information. In one embodiment, the percent identity of two sequences can be determined by the GCG program with a gap weight of 1, e.g., each amino acid gap is weighted as if it were a single amino acid or nucleotide mismatch between the two sequences (see U.S. Pat. No. 6,262,333 to Endege, 2001).

Software for performing BLAST analyses is publicly available, e.g., through the National Center for Biotechnology Information (see internet website at www.ncbi.nlm.nih-.gov/). This algorithm involves first identifying high scoring sequence pairs (HSPs) by identifying short words of length W in the G3876 sequence, which either match or satisfy some positive-valued threshold score T when aligned with a word of the same length in a database sequence. T is referred to as the neighborhood word score threshold (Altschul, 1990; Altschul et al., 1993). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, 1989). Unless otherwise indicated for comparisons of predicted polynucleotides, "sequence identity" refers to the % sequence identity generated from a tblastx using the NCBI version of the algorithm at the default settings using gapped alignments with the filter "off" (see, for example, internet website at www.ncbi.nlm.nih.gov/).

Other techniques for alignment are described by Doolittle, 1996. Preferably, an alignment program that permits gaps in the sequence is utilized to align the sequences. The Smith-Waterman is one type of algorithm that permits gaps in sequence alignments (see Shpaer, 1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

The percentage similarity between two polypeptide sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between polynucleotide sequences can also be counted or calculated by other methods known in the art, e.g., the Jotun Hein method (see, for example, Hein, 1990). Identity between sequences can also be determined by other methods known in the art, e.g., by varying hybridization conditions (see U.S. Pat. Appl. No. 20010010913, Hillmann, 2001).

Thus, the invention provides methods for identifying a sequence similar or paralogous or orthologous or homologous to one or more polynucleotides as noted herein, or one or more target polypeptides encoded by the polynucleotides, or otherwise noted herein and may include linking or associating a given plant phenotype or gene function with a sequence. In the methods, a sequence database is provided (locally or across an internet or intranet) and a query is made against the sequence database using the relevant sequences herein and associated plant phenotypes or gene functions.

In addition, one or more polynucleotide sequences or one or more polypeptides encoded by the polynucleotide sequences may be used to search against a BLOCKS (Bairoch et al., 1997), PFAM, and other databases which contain previously identified and annotated motifs, sequences and gene functions. Methods that search for primary sequence patterns with secondary structure gap penalties (Smith et al., 1992) as well as algorithms such as Basic Local Alignment Search Tool (BLAST; Altschul, 1990; Altschul et al., 1993), BLOCKS (Henikoff and Henikoff, 1991), Hidden Markov Models (HMM; Eddy, 1996; Sonnhammer et al., 1997), and the like, can be used to manipulate and analyze polynucleotide and polypeptide sequences encoded by polynucleotides. These databases, algorithms and other methods are well known in the art and are described in Ausubel et al., 1997, and in Meyers, 1995.

A further method for identifying or confirming that specific homologous sequences control the same function is by comparison of the transcript profile(s) obtained upon overexpression or knockout of two or more related polypeptides. Since transcript profiles are diagnostic for specific cellular states, one skilled in the art will appreciate that genes that have a highly similar transcript profile (e.g., with greater than 50% regulated transcripts in common, or with greater than 70% regulated transcripts in common, or with greater than 90% regulated transcripts in common) will have highly similar functions. Fowler and Thomashow, 2002, have shown that three paralogous AP2 family genes (CBF1, CBF2 and CBF3) are induced upon cold treatment, and each of which can condition improved freezing tolerance, and all have highly similar transcript profiles. Once a polypeptide has been shown to provide a specific function, its transcript profile becomes a diagnostic tool to determine whether paralogs or orthologs have the same function.

Furthermore, methods using manual alignment of sequences similar or homologous to one or more polynucleotide sequences or one or more polypeptides encoded by the polynucleotide sequences may be used to identify regions of similarity and conserved domains characteristic of a particular transcription factor family. Such manual methods are well-known to those with skill in the art and can include, for example, comparisons of tertiary structure between a polypeptide sequence encoded by a polynucleotide that comprises a known function and a polypeptide sequence encoded by a polynucleotide sequence that has a function not yet determined. Such examples of tertiary structure may comprise predicted alpha helices, beta-sheets, amphipathic helices, leucine zipper motifs, zinc finger motifs, proline-rich regions, cysteine repeat motifs, and the like.

Orthologs and paralogs of presently disclosed polypeptides may be cloned using compositions provided by the present invention according to methods well known in the art. cDNAs can be cloned using mRNA from a plant cell or tissue that expresses one of the present sequences. Appropriate mRNA sources may be identified by interrogating Northern blots with probes designed from the present sequences, after which a library is prepared from the mRNA obtained from a positive cell or tissue. Polypeptide-encoding cDNA is then isolated using, for example, PCR, using primers designed from a presently disclosed gene sequence, or by probing with a partial or complete cDNA or with one or more sets of degenerate probes based on the disclosed sequences. The cDNA library may be used to transform plant cells. Expression of the cDNAs of interest is detected using, for example, microarrays, Northern blots, quantitative PCR, or any other technique for monitoring changes in expression. Genomic clones may be isolated using similar techniques to those.

Examples of orthologs of the *Arabidopsis* polypeptide sequences and their functionally similar orthologs are listed in FIGS. 4A to 4B and Tables 1-3, and the Sequence Listing. In addition to the sequences in FIGS. 4A to 4B and Tables 1-3 and the Sequence Listing, the invention encompasses isolated nucleotide sequences that are phylogenetically and structurally similar to sequences listed in the Sequence Listing) and can function in a plant by improving water deficit tolerance and/or increased tolerance to cold when ectopically expressed in a plant.

Since a significant number of these sequences are phylogenetically and sequentially related to each other and have been shown to increase tolerance to cold and/or water deficit conditions, one skilled in the art would predict that other similar, phylogenetically related sequences derived from the same ancestral sequence would also perform similar functions when ectopically expressed.

Identifying Polynucleotides or Nucleic Acids by Hybridization

Polynucleotides homologous to the sequences illustrated in the Sequence Listing and tables can be identified, e.g., by hybridization to each other under stringent or under highly stringent conditions. Single stranded polynucleotides hybridize when they associate based on a variety of well characterized physical-chemical forces, such as hydrogen bonding, solvent exclusion, base stacking and the like. The stringency of a hybridization reflects the degree of sequence identity of the nucleic acids involved, such that the higher the stringency, the more similar are the two polynucleotide strands. Stringency is influenced by a variety of factors, including temperature, salt concentration and composition, organic and non-organic additives, solvents, etc. present in both the hybridization and wash solutions and incubations (and number thereof), as described in more detail in the references cited below (e.g., Sambrook et al., 1989; Berger and Kimmel, 1987; and Anderson and Young, 1985).

Encompassed by the invention are polynucleotide sequences that are capable of hybridizing to the claimed polynucleotide sequences, including any of the polynucleotides within the Sequence Listing, and fragments thereof under various conditions of stringency (see, for example, Wahl and Berger, 1987; and Kimmel, 1987). In addition to the nucleotide sequences listed in the Sequence Listing, full length cDNA, orthologs, and paralogs of the present nucleotide sequences may be identified and isolated using well-known methods. The cDNA libraries, orthologs, and paralogs of the present nucleotide sequences may be screened using hybridization methods to determine their utility as hybridization target or amplification probes.

With regard to hybridization, conditions that are highly stringent, and means for achieving them, are well known in the art. See, for example, Sambrook et al., 1989; Berger, 1987, pages 467-469; and Anderson and Young, 1985.

Stability of DNA duplexes is affected by such factors as base composition, length, and degree of base pair mismatch. Hybridization conditions may be adjusted to allow DNAs of different sequence relatedness to hybridize. The melting temperature (Tm) is defined as the temperature when 50% of the duplex molecules have dissociated into their constituent single strands. The melting temperature of a perfectly matched duplex, where the hybridization buffer contains formamide as a denaturing agent, may be estimated by the following equations:

DNA-DNA:

$$Tm(°C.)=81.5+16.6(\log [Na+])+0.41(\% G+C)-0.62(\% \text{ formamide})-500/L \quad (I)$$

DNA-RNA:

$$Tm(°C.)=79.8+18.5(\log [Na+])+0.58(\% G+C)+0.12(\% G+C)2-0.5(\% \text{ formamide})-820/L \quad (II)$$

RNA-RNA:

$$Tm(°C.)=79.8+18.5(\log [Na+])+0.58(\% G+C)+0.12(\% G+C)2-0.35(\% \text{ formamide})-820/L \quad (III)$$

where L is the length of the duplex formed, [Na$^+$] is the molar concentration of the sodium ion in the hybridization or washing solution, and % G+C is the percentage of (guanine+cytosine) bases in the hybrid. For imperfectly matched hybrids, approximately 1° C. is required to reduce the melting temperature for each 1% mismatch.

Hybridization experiments are generally conducted in a buffer of pH between 6.8 to 7.4, although the rate of hybridization is nearly independent of pH at ionic strengths likely to be used in the hybridization buffer (Anderson and Young, 1985). In addition, one or more of the following may be used to reduce non-specific hybridization: sonicated salmon sperm DNA or another non-complementary DNA, bovine serum albumin, sodium pyrophosphate, sodium dodecylsulfate (SDS), polyvinyl-pyrrolidone, ficoll and Denhardt's solution. Dextran sulfate and polyethylene glycol 6000 act to exclude DNA from solution, thus raising the effective probe DNA concentration and the hybridization signal within a given unit of time. In some instances, conditions of even greater stringency may be desirable or required to reduce non-specific and/or background hybridization. These conditions may be created with the use of higher temperature, lower ionic strength and higher concentration of a denaturing agent such as formamide.

Stringency conditions can be adjusted to screen for moderately similar fragments such as homologous sequences from distantly related organisms, or to highly similar fragments such as genes that duplicate functional enzymes from closely related organisms. The stringency can be adjusted either during the hybridization step or in the post-hybridization washes. Salt concentration, formamide concentration, hybridization temperature and probe lengths are variables that can be used to alter stringency (as described by the formula above). As a general guideline, high stringency is typically performed at Tm-5° C. to Tm-20° C., moderate stringency at Tm-20° C. to Tm-35° C. and low stringency at Tm-35° C. to Tm-50° C. for duplex >150 base pairs. Hybridization may be performed at low to moderate stringency (25-50° C. below Tm), followed by post-hybridization washes at increasing stringencies. Maximum rates of hybridization in solution are determined empirically to occur at Tm-25° C. for DNA-DNA duplex and Tm-15° C. for RNA-DNA duplex. Optionally, the degree of dissociation may be assessed after each wash step to determine the need for subsequent, higher stringency wash steps.

High stringency conditions may be used to select for nucleic acid sequences with high degrees of identity to the disclosed sequences. An example of stringent hybridization conditions obtained in a filter-based method such as a Southern or Northern blot for hybridization of complementary nucleic acids that have more than 100 complementary residues is about 5° C. to 20° C. lower than the thermal melting point (Tm) for the specific sequence at a defined ionic strength and pH. Conditions used for hybridization may include about 0.02 M to about 0.15 M sodium chloride, about 0.5% to about 5% casein, about 0.02% SDS or about 0.1% N-laurylsarcosine, about 0.001 M to about 0.03 M sodium citrate, at hybridization temperatures between about 50° C. and about 70° C. More preferably, high stringency conditions are about 0.02 M sodium chloride, about 0.5% casein, about 0.02% SDS, about 0.001 M sodium citrate, at a temperature of about 50° C. Nucleic acid molecules that hybridize under stringent conditions will typically hybridize to a probe based on either the entire DNA molecule or selected portions, e.g., to a unique subsequence, of the DNA.

Stringent salt concentration will ordinarily be less than about 750 mM NaCl and 75 mM trisodium citrate. Increasingly stringent conditions may be obtained with less than about 500 mM NaCl and 50 mM trisodium citrate, to even greater stringency with less than about 250 mM NaCl and 25 mM trisodium citrate. Low stringency hybridization can be obtained in the absence of organic solvent, e.g., formamide, whereas high stringency hybridization may be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. with formamide present. Varying additional parameters, such as hybridization time, the concentration of detergent, e.g., sodium dodecyl sulfate (SDS) and ionic strength, are well known to those skilled in the art. Various levels of stringency are accomplished by combining these various conditions as needed.

The washing steps that follow hybridization may also vary in stringency; the post-hybridization wash steps primarily determine hybridization specificity, with the most critical factors being temperature and the ionic strength of the final wash solution. Wash stringency can be increased by decreasing salt concentration or by increasing temperature. Stringent salt concentration for the wash steps will preferably be less than about 30 mM NaCl and 3 mM trisodium citrate, and most preferably less than about 15 mM NaCl and 1.5 mM trisodium citrate.

Thus, hybridization and wash conditions that may be used to bind and remove polynucleotides with less than the desired homology to the nucleic acid sequences or their complements that encode the present polypeptides include, for example:

6×SSC at a temperature of 65° C.;

50% formamide, 4×SSC at 42° C.; or 0.1×SSC, 0.2×SSC, 0.5×SSC, 1×SSC, 2×SSC, or 0.2×SSC to 2×SSC, with 0.1% SDS, at a temperature of 50° C., 55° C., 60° C., 65° C., or 50° C. to 65° C.;

with, for example, two wash steps of 10-30 minutes each. Useful variations on these conditions will be readily apparent to those skilled in the art.

A person of skill in the art would not expect substantial variation among polynucleotide species encompassed within the scope of the present invention because the highly stringent conditions set forth in the above formulae yield structurally similar polynucleotides.

If desired, one may employ wash steps of even greater stringency, including about 0.2×SSC, 0.1% SDS at 65° C. and washing twice, each wash step being about 30 minutes, or about 0.1×SSC, 0.1% SDS at 65° C. and washing twice for 30 minutes. The temperature for the wash solutions will ordinarily be at least about 25° C., and for greater stringency at least about 42° C. Hybridization stringency may be increased further by using the same conditions as in the hybridization steps, with the wash temperature raised about 3° C. to about 5° C., and stringency may be increased even further by using the same conditions except the wash temperature is raised about 6° C. to about 9° C. For identification of less closely related homologs, wash steps may be performed at a lower temperature, e.g., 50° C.

An example of a low stringency wash step employs a solution and conditions of at least 25° C. in 30 mM NaCl, 3 mM trisodium citrate, and 0.1% SDS over 30 minutes. Greater stringency may be obtained at 42° C. in 15 mM NaCl with 1.5 mM trisodium citrate, and 0.1% SDS over 30 minutes. Even higher stringency wash conditions are obtained at 65° C.-68° C. in a solution of 15 mM NaCl, 1.5 mM trisodium citrate, and 0.1% SDS. Wash procedures will generally employ at least two final wash steps. Additional variations on these conditions will be readily apparent to those skilled in the art (see, for example, U.S. Pat. Appl. No. 20010010913, Hillmann, 2001).

Stringency conditions can be selected such that an oligonucleotide that is perfectly complementary to the coding oligonucleotide hybridizes to the coding oligonucleotide with at least about a 5-10× higher signal to noise ratio than the ratio for hybridization of the perfectly complementary oligonucleotide to a nucleic acid encoding a polypeptide known as of the filing date of the application. It may be desirable to select conditions for a particular assay such that a higher signal to noise ratio, that is, about 15× or more, is obtained. Accordingly, a subject nucleic acid will hybridize to a unique coding oligonucleotide with at least a 2× or greater signal to noise ratio as compared to hybridization of the coding oligonucleotide to a nucleic acid encoding known polypeptide. The particular signal will depend on the label used in the relevant assay, e.g., a fluorescent label, a colorimetric label, a radioactive label, or the like. Labeled hybridization or PCR probes for detecting related polynucleotide sequences may be produced by oligolabeling, nick translation, end-labeling, or PCR amplification using a labeled nucleotide.

Encompassed by the invention are polynucleotide sequences that are capable of hybridizing to the claimed polynucleotide sequences, including any of the polynucleotides within the Sequence Listing, and fragments thereof under various conditions of stringency (see, for example, Wahl and Berger, 1987, pages 399-407; and Kimmel, 1987). In addition to the nucleotide sequences in the Sequence Listing, full length cDNA, orthologs, and paralogs of the present nucleotide sequences may be identified and isolated using well-known methods. The cDNA libraries, orthologs, and paralogs of the present nucleotide sequences may be screened using hybridization methods to determine their utility as hybridization target or amplification probes.

Vectors, Promoters, and Expression Systems

The present invention includes recombinant nucleic acid constructs comprising one or more of the nucleic acid sequences herein. The constructs typically comprise a vector, such as a plasmid, a cosmid, a phage, a virus (e.g., a plant virus), a bacterial artificial chromosome (BAC), a yeast artificial chromosome (YAC), or the like, into which a nucleic acid sequence of the invention has been inserted, in a forward or reverse orientation. In a preferred aspect of this embodiment, the construct further comprises regulatory sequences, including, for example, a promoter, operably linked to the sequence. Large numbers of suitable vectors, cassettes and promoters are known to those of skill in the art, and are commercially available.

General texts that describe molecular biological techniques useful herein, including the use and production of vectors, cassettes and promoters and many other relevant topics, include Berger and Kimmel, 1987, Sambrook et al., 1989, and Ausubel, 1997-2001. Any of the identified sequences can be incorporated into a cassette or vector, e.g., for expression in plants. A number of expression vectors or cassettes suitable for stable transformation of plant cells or for the establishment of transgenic plants have been described including those described in Weissbach and Weissbach, 1989, and Gelvin et al., 1990. Specific examples include those derived from a Ti plasmid of *Agrobacterium tumefaciens*, as well as those disclosed by Herrera-Estrella et al., 1983, Bevan 1984, Klee 1985, for dicotyledonous plants.

Alternatively, non-Ti vectors can be used to transfer the DNA into monocotyledonous plants and cells by using free DNA delivery techniques. Such methods can involve, for example, the use of liposomes, electroporation, microprojectile bombardment, silicon carbide whiskers, and viruses. By using these methods transgenic plants such as wheat, rice (Christou, 1991, and corn (Gordon-Kamm, 1990) can be produced. An immature embryo can also be a good target tissue for monocots for direct DNA delivery techniques by using the particle gun (Weeks et al., 1993; Vasil, 1993; Wan and Lemeaux, 1994, and for *Agrobacterium*-mediated DNA transfer (Ishida et al., 1996).

Typically, plant transformation vectors include one or more cloned plant coding sequence (genomic or cDNA) under the transcriptional control of 5' and 3' regulatory sequences and a dominant selectable marker. Such plant transformation vectors typically also contain a promoter (e.g., a regulatory region controlling inducible or constitutive, environmentally- or developmentally-regulated, or cell- or tissue-specific expression), a transcription initiation start site, an RNA processing signal (such as intron splice sites), a transcription termination site, and/or a polyadenylation signal.

A potential utility for the transcription factor polynucleotides disclosed herein is the isolation of promoter elements from these genes that can be used to program expression in plants of any genes. Each transcription factor gene disclosed herein is expressed in a unique fashion, as determined by promoter elements located upstream of the start of translation, and additionally within an intron of the transcription factor gene or downstream of the termination codon of the gene. As is well known in the art, for a significant portion of genes, the promoter sequences are located entirely in the region directly upstream of the start of translation. In such cases, typically the promoter sequences are located within 2.0 kb of the start of translation, or within 1.5 kb of the start of translation, frequently within 1.0 kb of the start of translation, and sometimes within 0.5 kb of the start of translation.

The promoter sequences can be isolated according to methods known to one skilled in the art.

Examples of constitutive plant promoters which can be useful for expressing the TF sequence include: the cauliflower mosaic virus (CaMV) 35S promoter, which confers constitutive, high-level expression in most plant tissues (see, e.g., Odell et al., 1985); the nopaline synthase promoter (An et al., 1988); and the octopine synthase promoter (Fromm et al., 1989).

A variety of plant gene promoters that regulate gene expression in response to environmental, hormonal, chemical, developmental signals, and in a tissue-active manner can be used for expression of a TF sequence in plants. Choice of a promoter is based largely on the phenotype of interest and is determined by such factors as tissue (e.g., seed, fruit, root, pollen, vascular tissue, flower, carpel, etc.), inducibility (e.g., in response to wounding, heat, cold, drought, light, pathogens, etc.), timing, developmental stage, and the like. Numerous known promoters have been characterized and can favorably be employed to promote expression of a polynucleotide of the invention in a transgenic plant or cell of interest. For example, tissue specific promoters include: seed-specific promoters (such as the napin, phaseolin or DC3 promoter described in U.S. Pat. No. 5,773,697 to Tomes, 1998), fruit-specific promoters that are active during fruit ripening (such as the dru 1 promoter (U.S. Pat. No. 5,783,393 to Kellogg, 1998), or the 2A11 promoter (U.S. Pat. No. 4,943,674 to Houck and Pear, 1990) and the tomato polygalacturonase promoter (Bird et al., 1988), root-specific promoters, such as those disclosed in U.S. Pat. No. 5,618,988 to Hauptmann, et al., 1997, U.S. Pat. No. 5,837,848 to Ely, 1998, and U.S. Pat. No. 5,905,186 to Thomas et al., 1999, pollen-active promoters such as PTA29, PTA26 and PTA13 (U.S. Pat. No. 5,792,929 to Mariani, 1998), promoters active in vascular tissue (Ringli and Keller, 1998), flower-specific (Kaiser et al., 1995), pollen (Baerson et al., 1994), carpels (Ohl et al., 1990), pollen and ovules (Baerson et al., 1993), auxin-inducible promoters (such as that described in van der Kop et al., 1999 or Baumann et al., 1999), cytokinin-inducible promoter (Guevara-Garcia, 1998), promoters responsive to gibberellin (Shi et al., 1998, Willmott et al., 1998) and the like. Additional promoters are those that elicit expression in response to heat (Ainley et al., 1993), light (e.g., the pea rbcS-3A promoter, Kuhlemeier et al., 1989, and the maize rbcS promoter, Schaffner and Sheen, 1991); wounding (e.g., wunI, Siebertz et al., 1989); pathogens (such as the PR-1 promoter described in Buchel et al., 1999, and the PDF1.2 promoter described in Manners et al., 1998), and chemicals such as methyl jasmonate or salicylic acid (Gatz, 1997). In addition, the timing of the expression can be controlled by using promoters such as those acting at senescence (Gan and Amasino, 1995); or late seed development (Odell et al., 1994).

Plant expression vectors or cassettes can also include RNA processing signals that can be positioned within, upstream or downstream of the coding sequence. In addition, the expression vectors can include additional regulatory sequences from the 3'-untranslated region of plant genes, e.g., a 3' terminator region to increase mRNA stability of the mRNA, such as the PI-II terminator region of potato or the octopine or nopaline synthase 3' terminator regions.

Expression Hosts

The present invention also relates to host cells which are transduced with vectors of the invention, and the production of polypeptides of the invention (including fragments thereof) by recombinant techniques. Host cells are genetically engineered (i.e., nucleic acids are introduced, e.g., transduced, transformed or transfected) with the vectors of this invention, which may be, for example, a cloning vector or an expression vector comprising the relevant nucleic acids herein. The vector is optionally a plasmid, a viral particle, a phage, a naked nucleic acid, etc. The engineered host cells can be cultured in conventional nutrient media modified as appropriate for activating promoters, selecting transformants, or amplifying the relevant gene. The culture conditions, such as temperature, pH and the like, are those previously used with the host cell selected for expression, and will be apparent to those skilled in the art and in the references cited herein, including, Sambrook, 1989 and Ausubel, 1997-2001.

The host cell can be a eukaryotic cell, such as a yeast cell, or a plant cell, or the host cell can be a prokaryotic cell, such as a bacterial cell. Plant protoplasts are also suitable for some applications. For example, the DNA fragments are introduced into plant tissues, cultured plant cells or plant protoplasts by standard methods including electroporation (Fromm et al., 1985, infection by viral vectors such as cauliflower mosaic virus (CaMV) (Hohn et al., 1982; and U.S. Pat. No. 4,407,956 to Howell, 1983), high velocity ballistic penetration by small particles with the nucleic acid either within the matrix of small beads or particles, or on the surface (Klein et al., 1987), use of pollen as vector (PCT Pat. Publ. No. WO8501856, De Wet), or use of *Agrobacterium tumefaciens* or *A. rhizogenes* carrying a T-DNA plasmid in which DNA fragments are cloned. The T-DNA plasmid is transmitted to plant cells upon infection by *Agrobacterium tumefaciens*, and a portion is stably integrated into the plant genome (Horsch et al., 1984; Fraley et al., 1983).

The cell can include a nucleic acid of the invention that encodes a polypeptide, wherein the cell expresses a polypeptide of the invention. The cell can also include vector sequences, or the like. Furthermore, cells and transgenic plants that include any polypeptide or nucleic acid above or throughout this specification, e.g., produced by transduction of a vector of the invention, are an additional feature of the invention.

For long-term, high-yield production of recombinant proteins, stable expression can be used. Host cells transformed with a nucleotide sequence encoding a polypeptide of the invention are optionally cultured under conditions suitable for the expression and recovery of the encoded protein from cell culture. The protein or fragment thereof produced by a recombinant cell may be secreted, membrane-bound, or contained intracellularly, depending on the sequence and/or the vector used. As will be understood by those of skill in the art, expression vectors containing polynucleotides encoding mature proteins of the invention can be designed with signal sequences which direct secretion of the mature polypeptides through a prokaryotic or eukaryotic cell membrane.

EXAMPLES

It is to be understood that this invention is not limited to the particular devices, machines, materials and methods described. Although particular embodiments are described, equivalent embodiments may be used to practice the invention.

The invention, now being generally described, will be more readily understood by reference to the following examples, which are included merely for purposes of illustration of certain aspects and embodiments of the present invention and are not intended to limit the invention. It will be recognized by one of skill in the art that a polypeptide that is associated with a particular first trait may also be associated with at least one other, unrelated and inherent second trait which was not predicted by the first trait.

Example I

Project Types and Vector and Cloning Information

A number of constructs were used to modulate the activity of sequences of the invention. An individual project was defined as the analysis of lines for a particular construct (for example, this might include plant lines that constitutively overexpress G482 or another subclade polypeptide). Generally, a full-length wild-type version of a gene or its cDNA was directly fused to a promoter that drove its expression in transgenic plants, except as noted in Table 1. Such a promoter could be the native promoter of that gene, or the CaMV 35S promoter which drives constitutive expression. Alternatively, a promoter that drives tissue specific or conditional expression could be used in similar studies. A direct fusion approach has the advantage of allowing for simple genetic analysis if a given promoter-polynucleotide line is to be crossed into different genetic backgrounds at a later date.

As an alternative to plant transformation with a direct fusion construct, some plant lines were transformed with a two component expression system in which a kanamycin resistant 35S::LexA-GAL4-TA driver line was established and then supertransformed with an opLexA::transcription factor construct carrying a sulfonamide resistance gene for each of the transcription factors of interest.

The first component vector, the "driver" vector or construct (P6506) contained a transgene carrying a 35S::LexA-GAL4-transactivation domain (TA) (SEQ ID NO: 77) along with a kanamycin resistance selectable marker. Having established a driver line containing the 35S::LexA-GAL4-transactivation domain component, the transcription factors of the invention could be expressed by super-transforming or crossing in a second construct carrying a sulphonamide resistance selectable marker and the transcription factor polynucleotide of interest cloned behind a LexA operator site (opLexA::TF). For example, the two constructs P6506 (35S::LexA-GAL4 TA; SEQ ID NO: 77) and P5072 (opLexA::G482; SEQ ID NO: 80) together constituted a two-component system for expression of G482 from the 35S promoter. A kanamycin resistant transgenic line containing P6506 was established, and this was then supertransformed with the P5072 construct containing a genomic clone of G482 and a sulfonamide resistance marker. For each transcription factor that was overexpressed with a two component system, the second construct carried a sulfonamide selectable marker and was contained within vector backbone pMEN53.

A summary of constructs that have been used in these studies is provided as follows. Generally, a direct promoter fusion nucleic acid construct may be prepared by fusing a promoter sequence, such as constitutive, tissue-specific or inducible promoter, include those found in the sequence listing, to the nucleic acid sequence found in the below listed PIDs. Alternatively, a two component expression system may be prepared to overexpress particular sequences of the invention, as noted below.

P46 (SEQ ID NO: 70) contains a G481 cDNA clone which incorporates native UTR and was derived from a cDNA library. P46 was used to prepare a 35S::G481 direct promoter-fusion construct that carries a kanamycin resistance marker.

The two constructs P5287 (LTP1::LexA-GAL4 TA; SEQ ID NO: 71) and P6812 (opLexA::G481; SEQ ID NO: 72) together constitute a two-component system for expression of G481 from the LTP1 promoter. A kanamycin resistant transgenic line containing P5287 was established, and this was then supertransformed with the P6812 construct containing a cDNA clone of G481 and a sulfonamide resistance marker.

P21522 (SEQ ID NO: 73) contains a G481 cDNA clone and was used to prepare SUC2::G481 direct promoter-fusion construct that carries a kanamycin resistance marker.

The two constructs P5311 (ARSK1::LexA-GAL4 TA; SEQ ID NO: 74) and P6812 (opLexA::G481; SEQ ID NO: 72) together constitute a two-component system for expression of G481 from the ARSK1 promoter. A kanamycin resistant transgenic line containing P5311 was established, and this was then supertransformed with the P6812 construct containing a cDNA clone of G481 and a sulfonamide resistance marker.

The two constructs P9002 (RD29A::LexA-GAL4 TA; SEQ ID NO: 75) and P6812 (opLexA::G481; SEQ ID NO: 72) together constitute a two-component system for expression of G481 from the RD29A promoter. A kanamycin resistant transgenic line containing P9002 was established, and this was then supertransformed with the P6812 construct containing a cDNA clone of G481 and a sulfonamide resistance marker.

The two constructs P5319 (AS1::LexA-GAL4 TA; SEQ ID NO: 76) and P6812 (opLexA::G481; SEQ ID NO: 72) together constitute a two-component system for expression of G481 from the AS1 promoter. A kanamycin resistant transgenic line containing P5319 was established, and this was then supertransformed with the P6812 construct containing a cDNA clone of G481 and a sulfonamide resistance marker.

The two constructs P6506 (35S::LexA-GAL4 TA; SEQ ID NO: 77) and P6812 (opLexA::G481; SEQ ID NO: 72) together constitute a two-component system for expression of G481 from the 35S promoter. P6812 contains the same cDNA clone that is present in P46. A kanamycin resistant transgenic line containing P6506 was established, and this was then supertransformed with the P6812 construct containing a cDNA clone of G481 and a sulfonamide resistance marker.

P25281 (SEQ ID NO: 78) was used to prepare a 35S::G481-GFP (Green Fluorescent Protein) fusion directly fused to the 35S promoter and a KanR marker.

P47 (SEQ ID NO: 79) was used to prepare a 35S::G482 direct promoter fusion construct that carried a KanR marker.

The two constructs P6506 (35S::LexA-GAL4 TA; SEQ ID NO: 77) and P5072 (opLexA::G482; SEQ ID NO: 80) together constitute a two-component system for expression of G482 from the 35S promoter. A kanamycin resistant transgenic line containing P6506 was established, and this was then supertransformed with the P5072 construct containing a cDNA clone of G482 and a sulfonamide resistance marker.

P1441 (SEQ ID NO: 81) contains a G485 cDNA clone and was used to prepare a 35S::G485 direct promoter fusion construct that carried a KanR marker.

The two constructs P6506 (35S::LexA-GAL4 TA; SEQ ID NO: 77) and P4190 (opLexA::G485; SEQ ID NO: 82) together constitute a two-component system for expression of G485 from the 35S promoter. A kanamycin resistant transgenic line containing P6506 was established, and this was then supertransformed with the P4190 construct containing a cDNA clone of G485 and a sulfonamide resistance marker.

P26044 (SEQ ID NO: 83) was used to prepare a 35S::G485-(9A)-CFP (9A=a linker comprising nine alanine residues; CFP=cyan fluorescent protein) fusion directly fused to the 35S promoter and that carried a KanR marker.

The two constructs P6506 (35S::LexA-GAL4 TA; SEQ ID NO: 77) and P4357 (opLexA::G1364; SEQ ID NO: 84) together constitute a two-component system for expression of G1364 from the 35S promoter. A kanamycin resistant transgenic line containing P6506 was established, and this was then supertransformed with the P4357 construct containing a genomic clone of G1364 and a sulfonamide resistance marker.

The two constructs P5284 (RBCS3::LexA-GAL4 TA; SEQ ID NO: 85) and P4357 (opLexA::G1364; SEQ ID NO: 84) together constitute a two-component system for expression of G1364 from the RBCS3 promoter. A kanamycin resistant transgenic line containing P5284 was established, and this was then supertransformed with the P4357 construct containing a genomic clone of G1364 and a sulfonamide resistance marker.

The two constructs P9002 (RD29A::LexA-GAL4 TA; SEQ ID NO: 75) and P4357 (opLexA::G1364; SEQ ID NO: 84) together constitute a two-component system for expression of G1364 from the RD29A promoter. A kanamycin resistant transgenic line containing P9002 (line 5) was established, and this was then supertransformed with the P4357 construct containing a genomic clone of G1364 and a sulfonamide resistance marker.

P26108 (SEQ ID NO: 86) was used to prepare a 35S::G1364-(9A)-CFP fusion directly fused to the 35S promoter, and that carried a KanR marker.

The two constructs P6506 (35S::LexA-GAL4TA; SEQ ID NO: 77) and P8079 (opLexA::G2345; SEQ ID NO: 87) together constitute a two-component system for expression of G2345 from the 35S promoter. A kanamycin resistant transgenic line containing P6506 was established, and this was then supertransformed with the P8079 construct containing a genomic clone of G2345 and a sulfonamide resistance marker.

P21253 (SEQ ID NO: 88) was used to prepare a G3395 cDNA clone 35S::G3395 direct promoter-fusion construct carrying a kanamycin resistance marker.

P23304 (SEQ ID NO: 89) was used to prepare a 35S::G3396 cDNA direct promoter-fusion that carried a KanR marker.

P21265 (SEQ ID NO: 90) contains a G3397 cDNA clone, and was used to prepare a 35S::G3397 direct promoter-fusion construct that carried a KanR marker.

P21252 (SEQ ID NO: 91) contains a G3398 cDNA clone, and was used to prepare a 35S::G3398 direct promoter-fusion construct that carried a KanR marker.

P21251 (SEQ ID NO: 92) contains a G3429 cDNA clone, and was used to prepare a 35S::G3429 direct promoter-fusion construct carrying a kanamycin resistance marker.

P21466 (SEQ ID NO: 93) contains a G3434 cDNA clone, and was used to prepare a 35S::G3434 direct promoter-fusion construct carrying a kanamycin resistance marker.

P21314 (SEQ ID NO: 94) contains a G3435 cDNA clone, and was used to prepare a 35S::G3435 direct promoter-fusion construct carrying a kanamycin resistance marker.

P21381 (SEQ ID NO: 95) contains a G3436 cDNA clone, and was used to prepare a 35S::G3436 direct promoter-fusion construct carrying a kanamycin resistance marker.

P21341 and P21471 (SEQ ID NOs: 96 and 97) each contain a G3470 cDNA clone, and are used to prepare 35S::G3470 direct promoter-fusion constructs carrying a kanamycin resistance marker.

P21342 (SEQ ID NO: 98) contains a G3471 cDNA clone, and was used to prepare a 35S::G3471 direct promoter-fusion construct carrying a kanamycin resistance marker.

P21348 (SEQ ID NO: 99) contains a G3472 cDNA clone, and was used to prepare a 35S::G3472 direct promoter-fusion construct carrying a kanamycin resistance marker.

P21344 (SEQ ID NO: 100) contains a G3474 cDNA clone, and was used to prepare a 35S::G3474 direct promoter-fusion construct carrying a kanamycin resistance marker.

P21347 (SEQ ID NO: 101) contains a G3475 cDNA clone, and was used to prepare a 35S::G3475 direct promoter-fusion construct carrying a kanamycin resistance marker.

P21345 (SEQ ID NO: 102) contains a G3476 cDNA clone, and was used to prepare a 35S::G3476 direct promoter-fusion construct carrying a kanamycin resistance marker.

P21350 (SEQ ID NO: 103) contains a G3478 cDNA clone, and was used to prepare a 35S::G3478 direct promoter-fusion construct carrying a kanamycin resistance marker.

P27818 (SEQ ID NO: 104) contains a G3866-GFP C-terminal protein fusion and was fused to the 35S promoter.

P26609 (SEQ ID NO: 105) was used to prepare a 35S::G3875 direct promoter fusion. The construct carries kanR and contains a cDNA clone of G3875. The clone within this construct apparently encodes a slightly truncated form of the protein.

P25657 (SEQ ID NO: 106) was used to prepare a 35S::G3876 direct fusion that carried a KanR marker. The construct contains a cDNA clone.

For the present study, the expression constructs used to generate lines of transgenic *Arabidopsis* plants constitutively overexpressing G482 subclade polypeptides are listed in Table 1. Compilations of the sequences of promoter fragments and the expressed transgene sequences within the PIDs are also provided in the Sequence Listing.

TABLE 1

G482 subclade polynucleotide expression constructs

| Species/Gene Identifier (GID) | SEQ ID NO: of GID | Promoter/expression system | PID Construct 1 (components) | PID Construct 2 (components) | SEQ ID NO: of PID(s) | Project type |
|---|---|---|---|---|---|---|
| At/G481 | 2 | Constitutive 35S | P46 (for 35S::G481) | | 70 | Direct promoter-fusion |
| | | Epidermal-specific LTP1 | P5287 (LTP1::LexA-GAL4 TA) | P6812 (opLexA::G481) | 71, 72 | Two component supertransformation |
| | | Vascular-specific SUC2 | P21522 (for SUC2::G481) | | 73 | Direct promoter-fusion |
| | | Root-specific | P5311 (ARSK1::LexA- | P6812 (opLexA::G481) | 74, 72 | Two component supertransformation |

TABLE 1-continued

G482 subclade polynucleotide expression constructs

| Species/Gene Identifier (GID) | SEQ ID NO: of GID | Promoter/expression system | PID Construct 1 (components) | PID Construct 2 (components) | SEQ ID NO: of PID(s) | Project type |
|---|---|---|---|---|---|---|
| | | ARSK1 | GAL4 TA) | | | |
| | | Stress inducible RD29A | P9002 (RD29A::LexA-GAL4 TA) | P6812 (opLexA::G481) | 75, 72 | Two component supertransformation |
| | | Emergent leaf primordial-specific AS1 | P5319 (AS1::LexA-GAL4 TA) | P6812 (opLexA::G481) | 76, 72 | Two component supertransformation |
| | | Constitutive 35S | P6506 (35S::LexA-GAL4 TA) | P6812 (opLexA::G481) | 77, 72 | Two component supertransformation |
| | | Constitutive 35S/GFP fusion | P25281 (for 35S::G481-GFP fusion) | | 78 | Direct promoter-protein-GFP fusion |
| At/G482 | 28 | Constitutive 35S | P47 (for 35S::G482) | | 79 | Direct promoter-fusion |
| | | Constitutive 35S | P6506 (35S::LexA-GAL4 TA) | P5072 (opLexA::G482) | 77, 80 | Two component supertransformation |
| At/G485 | 18 | Constitutive 35S | P1441 (for 35S::G485) | | 81 | Direct promoter-fusion |
| | | Constitutive 35S | P6506 (35S::LexA-GAL4 TA) | P4190 (opLexA::G485) | 77, 82 | Two component supertransformation |
| | | Emergent leaf primordial-specific AS1 | P5319 (AS1::LexA-GAL4 TA) | P4190 (opLexA::G485) | 76, 82 | Two component supertransformation |
| | | Constitutive 35S/CFP fusion | P26044 (for 35S::G485-(9A)-CFP) | | 83 | Direct promoter-fusion |
| At/G1364 | 14 | Constitutive 35S | P6506 (35S::LexA-GAL4 TA) | P4357 (opLexA::G1364) | 77, 84 | Two component supertransformation |
| | | Leaf-specific RBCS3 | P5284 (RBCS3::LexA-GAL4 TA) | P4357 (opLexA::G1364) | 85, 84 | Two component supertransformation |
| | | Stress inducible RD29A | P9002 (RD29A::LexA-GAL4 TA) | P4357 (opLexA::G1364) | 75, 84 | Two component supertransformation |
| | | Constitutive 35S/CFP fusion | P26108 (for 35S::G1364-(9A)-CFP fusion) | | 86 | Direct promoter-fusion |
| At/G2345 | 22 | Constitutive 35S | P6506 (35S::LexA-GAL4 TA) | P8079 (opLexA::G2345) | 77, 87 | Two component supertransformation |
| Os/G3395 | 38 | Constitutive 35S | P21253 (for 35S::G3395) | | 88 | Direct promoter-fusion |
| Os/G3396 | 44 | Constitutive 35S | P23304 (for 35S::G3396) | | 89 | Direct promoter-fusion |
| Os/G3397 | 36 | Constitutive 35S | P21265 (for 35S::G3397) | | 90 | Direct promoter-fusion |
| Os/G3398 | 40 | Constitutive 35S | P21252 (for 35S::G3398) | | 91 | Direct promoter-fusion |
| Os/G3429 | 46 | Constitutive 35S | P21251 (for 35S::G3429) | | 92 | Direct promoter-fusion |
| Zm/G3434 | 12 | Constitutive 35S | P21466 (for 35S::G3434) | | 93 | Direct promoter-fusion |
| Zm/G3435 | 30 | Constitutive 35S | P21314 (for 35S::G3435) | | 94 | Direct promoter-fusion |
| Zm/G3436 | 34 | Constitutive 35S | P21381 (for 35S::G3436) | | 95 | Direct promoter-fusion |
| Gm/G3470 | 4 | Constitutive 35S | P21341 (for 35S::G3470) | | 96 | Direct promoter-fusion |
| Gm/G3470 | 4 | Constitutive 35S | P21471 (for 35S::G3470) | | 97 | Direct promoter-fusion |
| Gm/G3471 | 6 | Constitutive 35S | P21342 (for 35S::G3471) | | 98 | Direct promoter-fusion |
| Gm/G3472 | 32 | Constitutive 35S | P21348 (for 35S::G3472) | | 99 | Direct promoter-fusion |

TABLE 1-continued

G482 subclade polynucleotide expression constructs

| Species/ Gene Identifier (GID) | SEQ ID NO: of GID | Promoter/ expression system | PID Construct 1 (components) | PID Construct 2 (components) | SEQ ID NO: of PID(s) | Project type |
|---|---|---|---|---|---|---|
| Gm/G3474 | 24 | Constitutive 35S | P21344 (35S::G3474) | | 100 | Direct promoter-fusion |
| Gm/G3475 | 16 | Constitutive 35S | P21347 (for 35S::G3475) | | 101 | Direct promoter-fusion |
| Gm/G3476 | 20 | Constitutive 35S | P21345 (for 35S::G3476) | | 102 | Direct promoter-fusion |
| Gm/G3478 | 26 | Constitutive 35S | P21350 (for 35S::G3478) | | 103 | Direct promoter-fusion |
| Zm/G3866 | 42 | Constitutive 35S | P26587 (for 35S::G3866 fused at the C-terminus with the GAL4 TA) | | 104 | Direct promoter-fusion |
| Gm/G3875 | 8 | Constitutive 35S | P26609 (for 35S::G3875) | | 105 | Direct promoter-fusion |
| Zm/G3876 | 10 | Constitutive 35S | P25657 (for 35S::G3876) | | 106 | Direct promoter-fusion |
| LexA-GAL4 TA in driver construct | — | Constitutive 35S | P6506 (35S::LexA-GAL4 TA) | | 77 | Driver construct |

Species abbreviations: At—*Arabidopsis thaliana*; Gm—*Glycine max*; Os—*Oryza sativa*; Zm—*Zea mays*

Example II

Transformation

Transformation of *Arabidopsis* was performed by an *Agrobacterium*-mediated protocol based on the method of Bechtold and Pelletier, 1998. Unless otherwise specified, all experimental work was performed with the *Arabidopsis* Columbia ecotype.

Plant Preparation:

*Arabidopsis* seeds were sown on mesh covered pots. The seedlings were thinned so that 6-10 evenly spaced plants remained on each pot 10 days after planting. The primary bolts were cut off a week before transformation to break apical dominance and encourage auxiliary shoots to form. Transformation was typically performed at 4-5 weeks after sowing.

Bacterial Culture Preparation:

*Agrobacterium* stocks were inoculated from single colony plates or from glycerol stocks and grown with the appropriate antibiotics until saturation. On the morning of transformation, the saturated cultures were centrifuged and bacterial pellets were re-suspended in Infiltration Media (0.5× MS, 1× B5 Vitamins, 5% sucrose, 1 mg/ml benzylaminopurine riboside, 200 µl/L Silwet L77) until an $A_{600}$ reading of 0.8 was reached.

Transformation and Seed Harvest:

the *Agrobacterium* solution was poured into dipping containers. All flower buds and rosette leaves of the plants were immersed in this solution for 30 seconds. The plants were laid on their side and wrapped to keep the humidity high. The plants were kept this way overnight at 4° C., after which the pots were turned upright, unwrapped, and moved to the growth racks.

The plants were maintained on the growth rack under 24-hour light until seeds were ready to be harvested. Seeds were harvested when 80% of the siliques of the transformed plants were ripe, approximately 5 weeks after the initial transformation. This seed was deemed T0 seed, since it was obtained from the T0 generation, and was later plated on selection plates (either kanamycin or sulfonamide). Resistant plants that were identified on such selection plates comprised the T1 generation.

Example III

Methods Used in Plate- and Soil-Based Physiology Assays

Unless otherwise stated, all experiments are performed with the *Arabidopsis thaliana* ecotype Columbia (col-0). Assays are usually performed on non-selected segregating T2 populations (in order to avoid the extra stress of selection). Control plants for assays on lines containing direct promoter-fusion constructs are Col-0 plants transformed an empty transformation vector (pMEN65). Controls for 2-component lines (generated by supertransformation) are the background promoter-driver lines (i.e. promoter::LexA-GAL4 TA lines), into which the supertransformations were initially performed. All assays are performed in tissue culture. Growing the plants under controlled temperature and humidity on sterile medium produced uniform plant material that had not been exposed to additional stresses (such as water stress) which could cause variability in the results obtained. All assays were designed to detect plants that are more tolerant or less tolerant to the particular stress condition and were developed with reference to the following publications: Jang et al., 1997, Smeekens, 1998, Liu and Zhu, 1997, Saleki et al., 1993, Wu et al., 1996, Zhu et al., 1998, Alia et al., 1998, Xin and Browse, 1998, Leon-Kloosterziel et al., 1996. Where possible, assay conditions were originally tested in a blind experiment with controls that had phenotypes related to the condition tested.

Plate-based physiological assays representing a variety of cold and water deficit-stress related conditions were used as a pre-screen to identify abiotic stress tolerant plant lines from each project (i.e. lines from transformation with a particular construct), many of which were tested in subsequent soil-based assays. Typically, ten or more lines were transformed with each construct and subjected to plate assays, from which the best three lines were selected for subsequent soil based assays.

Seed Treatment.

Prior to plating, seed for all experiments were surface sterilized with:

(1) a five minute incubation with mixing in 70% ethanol;

(2) a 20 minute incubation with mixing in 30% bleach, 0.01% triton-X 100; and (3) five rinses with sterile water.

After this treatment, the seeds were re-suspended in 0.1% sterile agarose and stratified at 4° C. for 3-4 days.

Germination Assays.

All germination assays followed modifications of the same basic protocol. Sterile seeds were sown on a conditional medium that had a basal composition of 80% MS+Vitamins. Plates were incubated at 22° C. under 24-hour light (120-130 µE m−2 s−1) in a growth chamber. Evaluation of germination and seedling vigor was performed five days after planting. For assessment of root development, seedlings germinated on 80% MS+Vitamins+1% sucrose were transferred to square plates at seven days after planting. Evaluation was performed five days after transfer following growth in a vertical position. Qualitative differences were recorded including lateral and primary root length, root hair number and length, and overall growth.

Water-deficit related plate-based germination assays were conducted in the conditional basal medium with 80% MS+Vitamins. Heat tolerance germination assays were conducted at 32° C. For the salt, mannitol and sugar sensing assays, the conditional basal medium was modified by adding one of the following for specific tolerance assays: NaCl (150 mM), mannitol (300 mM), or sucrose (9.4%).

Cold tolerance germination assays were conducted at 8° C.

Growth Assays.

Severe dehydration (a plate-based water deficit) assays were conducted by growing seedlings for 14 days on MS+Vitamins+1% Sucrose at 22° C. The plates were opened in a sterile laminar flow hood for three hours for hardening, and the seedlings were then removed from the media and dried for 2 hours on absorbent paper in the flow hood. After this time they were transferred back to plates and incubated at 22° C. for recovery. The plants were evaluated after five days.

For heat sensitivity growth assays, seeds were germinated and grown for seven days on MS+Vitamins+1% sucrose at 22° C., after which the seedlings were transferred to heat stress conditions by growing the seedlings at 32° C. for five days. The plants were transferred back to 22° C. for recovery and evaluated after a further 5 days.

Growth in cold conditions (chilling) was by germinating seeds and growing them for seven days on MS+Vitamins+1% sucrose at 22° C., The seedlings were then transferred to chilling conditions at 8° C. and the plants were evaluated after 10 days and 17 days in these conditions.

Soil-Based Drought Assays in Clay Pots.

The soil drought assay was based on the method of Haake et al., 2002. In the current procedure, *Arabidopsis* seedlings were first germinated on selection plates containing either kanamycin or sulfonamide. The seeds were sterilized by a two minute ethanol treatment followed by 20 minutes in 30% bleach/0.01% Tween and five washes in distilled water. The seeds were sown to MS agar in 0.1% agarose and stratified for three days at 4° C. before transfer to growth cabinets at 22° C. After seven days of growth on selection plates, the seedlings were transplanted to 3.5 inch diameter clay pots containing 80 g of a 50:50 mix of vermiculite:perlite topped with 80 g of ProMix. Typically, each pot contained 14 seedlings, and plants of the transgenic lines being tested and wild-type control plants were in separate pots. Pots containing the transgenic line and control pots were randomly interspersed in a growth room, maintained under 24-hour light conditions (18-23° C., and 90-100 µE m−2 s−1) and watered for a period of 14 days. Water was then withheld and the pots were placed on absorbent diaper paper for a period of 8-10 days to apply a drought treatment. After this period, a visual qualitative "drought score" from 0-6 was assigned to record the extent of visible drought stress symptoms. A score of "6" corresponded to no visible symptoms, whereas a score of "0" corresponded to extreme wilting and the leaves with a "crispy" texture. At the end of the drought period, the pots were re-watered and scored after 5-6 days; the number of surviving plants in each pot was counted, and the proportion of the total plants in the pot that survived was calculated.

Analysis of Results.

In a given experiment, we typically compared six or more pots of a transgenic line with six or more pots of the appropriate control. The mean drought score and mean proportion of plants surviving (survival rate) were calculated for pots of both the transgenic lines and wild type. In each case a p-value was calculated that indicated the significance of the difference between the two mean values. The p-value was calculated with a Mann-Whitney rank-sum test.

Example IV

Transcription Factor Polynucleotide and Polypeptide Sequences of the Invention, and Results Obtained with Plants Overexpressing these Sequences Table 2 shows the polypeptides identified by SEQ ID NO; Gene ID (GID) No.; the transcription factor family to which the polypeptide belongs, and conserved B domains of the polypeptide. The first column shows the polypeptide SEQ ID NO; the second column the species (abbreviated) and identifier (GID or "Gene IDentifier);

the third column shows percentage identity of each sequence to the G481 protein (the number of identical residues per the total number of residues in the subsequence used by the BLASTp algorithm for comparison appears in parentheses), the fourth column shows the amino acid coordinates of the conserved B domains of each transcription factor listed, the fifth column shows the B domain of each sequence; the sixth column lists each SEQ ID NO: of the respective B domains; and the seventh column shows the percentage identity of each of the B domains to the G481 B domains (the number of identical residues per the total number of residues in the subsequence used by the BLASTp algorithm for comparison appears in parentheses). The sequences are arranged in descending order of percentage identity to the G481 B domain. Percentage identities to the sequences listed in Table 2 were determined using BLASTP analysis with defaults of wordlength (W) of 3, an expectation (E) of 10, and the BLOSUM62 scoring matrix Henikoff & Henikoff (1989) *Proc. Natl. Acad. Sci. USA* 89:10915)*.

TABLE 2

Conserved domains of G481 and closely related sequences

| SEQ ID NO: | Species/ GID No., Accession No., or Identifier | Percent identity to the G481 protein* (number of identical residues per the total number of residues compared) | Domain in Amino Acid Coordinates | B Domain | B Domain SEQ ID NO: | Percent identity to G481 B domain* (number of identical residues per the total number of residues compared) |
|---|---|---|---|---|---|---|
| 2 | At/G481 | 100% (141/141) | 20-110 | REQDRYLPIANISRIMKKALPP NGKIGKDAKDTVQECVSEFIS FITSEASDKCQKEKRKTVNGD DLLWAMATLGFEDYLEPLKIY LARYRE | 47 | 100% (91/91) |
| 4 | Gm/G3470 | 75% (108/143) | 27-117 | REQDRYLPIANISRIMKKALPP NGKIAKDAKDTMQECVSEFIS FITSEASEKCQKEKRKTINGDD LLWAMATLGFEDYIEPLKVYL ARYRE | 48 | 93.4% (85/91) |
| 6 | Gm/G3471 | 75% (107/142) | 26-116 | REQDRYLPIANISRIMKKALPP NGKIAKDAKDTMQECVSEFIS FITSEASEKCQKEKRKTINGDD LLWAMATLGFEDYIEPLKVYL ARYRE | 49 | 93.4% (85/91) |
| 8 | Gm/G3875 | 78% (104/132) | 25-115 | REQDRYLPIANISRIMKKALPA NGKIADAKETVQECVSEFISF ITSEASDKCQREKRKTINGDD LLWAMATLGFEDYIDPLKIYL TRYRE | 50 | 91.2% (83/91) |
| 10 | Zm/G3876 | 72% (105/144) | 30-120 | REQDRFLPIANISRIMKKAIPA NGKIAKDAKETVQECVSEFISF ITSEASDKCQREKRKTINGDD LLWAMATLGFEDYIEPLKVYL QKYRE | 51 | 87.9% (80/91) |
| 12 | Zm/G3434 | 77% (97/125) | 18-108 | REQDRFLPIANISRIMKKAVPA NGKIAKDAKETLQECVSEFISF VTSEASDKCQKEKRKTINGDD LLWAMATLGFEEYVEPLKIYL QKYKE | 52 | 85.7% (78/91) |
| 14 | At/G1364 | 73% (97/132) | 29-119 | REQDRFLPIANISRIMKRGLPA NGKIAKDAKEIVQECVSEFISF VTSEASDKCQREKRKTINGDD LLWAMATLGFEDYMEPLKVY LMRYRE | 53 | 85.7% (78/91) |
| 16 | Gm/G3475 | 73% (85/115) | 23-113 | REQDRFLPIANVSRIMKKALP ANAKISKDAKETVQECVSEFIS FITGEASDKCQREKRKTINGD DLLWAMTTLGFEDYVEPLKG YLQRFRE | 54 | 84.6% (77/91) |
| 18 | At/G485 | 67% (90/133) | 20-110 | REQDRFLPIANVSRIMKKALP ANAKISKDAKETVQECVSEFIS FITGEASDKCQREKIRKTINGD DLLWAMTTLGFEDYVEPLKV YLQKYRE | 55 | 84.6% (77/91) |
| 20 | Gm/G3476 | 65% (87/132) | 26-116 | REQDRFLPIANVSRIMKKALP ANAKISKDAKETVQECVSEFIS FITGEASDKCQREKRKTINGD DLLWAMTTLGFEEYVEPLKIY LQRFRE | 56 | 84.6% (77/91) |
| 22 | At/G2345 | 70% (97/138) | 28-118 | REQDRFLPIANISRIMKRGLPL NGKIAKDAKETMQECVSEFIS FVTSEASDKCQREKRKTINGD DLLWAMATLGFEDYIDPLKV YLMRYRE | 56 | 84.6% (77/91) |

TABLE 2-continued

Conserved domains of G481 and closely related sequences

| SEQ ID NO: | Species/ GID No., Accession No., or Identifier | Percent identity to the G481 protein* (number of identical residues per the total number of residues compared) | Domain in Amino Acid Coordinates | B Domain | B Domain SEQ ID NO: | Percent identity to G481 B domain* (number of identical residues per the total number of residues compared) |
|---|---|---|---|---|---|---|
| 24 | Gm/G3474 | 65% (90/137) | 25-115 | REQDRFLPIANVSRIMKKALP ANAKISKEAKETVQECVSEFIS FITGEASDKCQKEKRKTINGD DLLWAMTTLGFEDYVDPLKI YLHKYRE | 58 | 84.6% (77/91) |
| 26 | Gm/G3478 | 70% (87/123) | 23-113 | REQDRFLPIANVSRIMKKALP ANAKISKDAKETVQECVSEFIS FITGEASDKCQREKRKTINGD DLLWAMTITLGFEDYVEPLKG YLQRFRE | 59 | 84.6% (77/91) |
| 28 | At/G482 | 69% (91/131) | 26-116 | REQDRFLPIANVSRIMKKALP ANAKISKDAKETMQECVSEFI SFVTGEASDKCQKEKRKTING DDLLWAMTTLGFEDYVEPLK VYLQRFRE | 60 | 83.5% (76/91) |
| 30 | Zm/G3435 | 68% (86/125) | 22-112 | REQDRFLPIANVSRIMKKALP ANAKISKDAKETVQECVSEFIS FITGEASDKCQREKRKTINGD DLLWAMTTLGFEDYVEPLKH YLHKFRE | 61 | 83.5% (76/91) |
| 32 | Gm/G3472 | 65% (90/137) | 25-115 | REQDRFLPIANVSRIMKKALP ANAKISKEAKETVQECVSEFIS FITGEASDKCQKEKRKTINGD DLLWAMTFFLGFEEYVEPLKV YLHKYRE | 62 | 83.5% (76/91) |
| 34 | Zm/G3436 | 59% (90/152) | 20-110 | REQDRFLPIANVSRIMKKALP ANAKISKDAKETVQECVSEFIS FITGEASDKCQREKRKTINGD DLLWAMTTLGFEDYVEPLKL YLHKFRE | 63 | 83.5% (76/91) |
| 36 | Os/G3397 | 58% (90/154) | 23-113 | REQDRFLPIANVSRIMKKALP ANAKISKDAKETVQECVSEFIS FITGEASDKCQREKRKTINGD DLLWAMTTLGFEDYVDPLKH YLHKFRE | 64 | 82.4% (75/91) |
| 38 | Os/G3395 | 69% (98/141) | 19-109 | REQDRFLPIANISRIMKKAVPA NGKIAKDAKETLQECVSEFISF VTSEASDKCQKEKRKTINGED LLFAMGTLGFEEYVDPLKIYL HKYRE | 65 | 82.4% (75/91) |
| 40 | Os/G3398 | 69% (91/136) | 20-110 | REQDRFLPIANVSRIMKRALP ANAKISKDAKETVQECVSEFIS FITGEASDKCQREKRKTINGD DLLWAMTTLGFEDYIDPLKLY LHKFRE | 66 | 81% (74/91) |
| 42 | Zm/G3866 | 69% (105/151) | 30-127 | REQDRFLPIANISRIMKKAIPA NGKTIPANGKIAKDAKETVQE CVSEFISFITSEASDKCQREKR KTINGDDLLWAMATLGFEDYI EPLKVYLQKYRE | 67 | 81.6% (80/98) |
| 44 | Os/G3396 | 74% (83/112) | 20-111 | KEQDRFLPIANIGRIMRRAVPE NGKIAKDSKESVQECVSEFISF ITSEASDKCLKEKRKTINGDDL IWSMGTLGFEDYVEPLKLYLR LYRE | 68 | 78.6% (71/91) |

TABLE 2-continued

Conserved domains of G481 and closely related sequences

| SEQ ID NO: | Species/ GID No., Accession No., or Identifier | Percent identity to the G481 protein* (number of identical residues per the total number of residues compared) | Domain in Amino Acid Coordinates | B Domain | B Domain SEQ ID NO: | Percent identity to G481 B domain* (number of identical residues per the total number of residues compared) |
|---|---|---|---|---|---|---|
| 46 | Os/G3429 | 42% (41/97) | 37-125 | TNAELPMANLVRLIKKVLPGK AKIGGAAKGLTHDCAVEFVG FVGDEASEKAKAEHRRTVAPE DYLGSFGDLGFDRYVDPMDA YIHGYRE | 69 | 43.5% (37/85) |

Species abbreviations:
At-*Arabidopsis thaliana*;
Gm-*Glycine max*;
Os-*Oryza sativa*;
Zm-*Zea mays*

The results of various water deficit-related assays are shown in Table 3. Of the twenty-three sequences that are phylogenetically and closely related to G482 and that have been overexpressed in plants, seventeen have demonstrated the ability to confer increased tolerance to water deprivation (water deficit). These positive results were obtained even though the expression levels for these sequences that would best confer water deprivation tolerance have not yet been optimized.

Three additional polypeptide sequences, G3875 (SEQ ID NO: 8), G3397 (SEQ ID NO: 36), and G3395, (SEQ ID NO: 38), produced weaker, yet positive results in water deficit assays as two of ten overexpressing lines showed greater tolerance to dehydration treatment, or one line of several tested showed greater tolerance in soil-based drought assays, than controls. Ectopic expression with other promoter-gene combinations has not been tested at Mendel Biotechnology.

Three sequences that are considered to fall within the G482 subclade, when expressed under the control of the 35S promoter, have not yet demonstrated the ability to confer increased tolerance to water deprivation. These include soy sequences G3474, G3475, and G3478 (SEQ ID NOs: 24, 16, and 26, respectively). However, ectopic expression with other promoter-gene combinations, and soil-based drought assays, have not yet been tested with the plants overexpressing any of these sequences.

TABLE 3

G482-subclade sequences overexpressed in plants that have shown improved water-deficit tolerance relative to control plants

| | | | Greater tolerance than controls to: | | | | | |
|---|---|---|---|---|---|---|---|---|
| Gene Identifier (Species) | SEQ ID NO: of GID | Expression system | At least one water deficit assay | Salt | Hyper-osmotic stress (mannitol, PEG) | Sucrose | Heat | Dehydration or drought |
| G481 (At) | 2 | 35S | + | | + | + | + | + |
| | | LTP1 | + | n/d | + | + | n/d | + |
| | | RBCS3 | + | | | | | + |
| | | SUC2 | + | | | | | + |
| | | ARSK1 | + | | | | | + |
| | | RD29A | + | | | | | + |
| | | GAL4 C-terminal fusion | + | + | | | + | + |
| | | GFP C-terminal fusion | + | + | + | + | n/d | + |
| G3470 (Gm) | 4 | 35S | + | + | + | + | + | + |
| G3471 (Gm) | 6 | 35S | + | | | + | | +** |
| G3875 (Gm) | 8 | 35S | +* | n/d | n/d | | | +* |
| G3475 (Gm) | 16 | 35S | | | | | | |
| G3876 (Zm) | 10 | 35S | + | n/d | n/d | | n/d | + |
| G3434 (Zm) | 12 | 35S | + | + | + | + | | + |

TABLE 3-continued

G482-subclade sequences overexpressed in plants that have shown improved water-deficit tolerance relative to control plants

| Gene Identifier (Species) | SEQ ID NO: of GID | Expression system | At least one water deficit assay | Salt | Hyper-osmotic stress (mannitol, PEG) | Sucrose | Heat | Dehydration or drought |
|---|---|---|---|---|---|---|---|---|
| G1364 (At) | 14 | 35S | + | | | | | + |
| | | RBCS3 | + | | + | | | |
| | | RD29A | + | + | | | | |
| | | CFP C-terminal fusion | + | n/d | n/d | | n/d | + |
| G485 (At) | 18 | 35S | + | + | + | + | | + |
| | | AS1 | + | n/d | n/d | n/d | n/d | + |
| | | CFP C-terminal fusion | + | | n/d | | n/d | + |
| G3476 (Gm) | 20 | 35S | + | | | | | + |
| G2345 (At) | 22 | 35S | + | | | | | + |
| G3474 (Gm) | 24 | 35S | | | | | | |
| G3478 (Gm) | 26 | 35S | | | | | | |
| G482 (At) | 28 | 35S | + | | + | | + | + |
| G3435 (Zm) | 30 | 35S | + | | | | | + |
| G3472 (Gm) | 32 | 35S | + | + | | | | |
| G3436 (Zm) | 34 | 35S | + | | | | + | |
| G3397 (Os) | 36 | 35S | +* | | | | | +* |
| G3395 (Os) | 38 | 35S | +* | | | | | +* |
| G3398 (Os) | 40 | 35S | + | | | | | + |
| G3866 (Zm) | 42, 115 | GAL4 C-terminal fusion | + | | | | | +*** |
| G3396 (Os) | 44 | GAL4 C-terminal fusion | + | | + | | | |
| G3429 (Os) | 46 | 35S | + | + | | | | |

Species abbreviations: At—*Arabidopsis thaliana*; Gm—*Glycine max*; Os—*Oryza sativa*; Zm—*Zea mays*
+ demonstrated greater water deficit tolerance than controls phenotype in more than two lines
+* demonstrated greater water deficit tolerance than controls in two lines
+** also reported in US patent application US20050022266 with constitutive overexpression in wilt, WUE and/or field assays (in US20050022266, G3866 = SEQ ID NO: 2, G3471 = SEQ ID NO: 6)

Sixteen of the G482 subclade sequences were found to confer increased cold tolerance during the germination or growth of *Arabidopsis* plants when the sequences were overexpressed (Table 4). Of these, G3471, G3435 and G3866 produced one or two lines that appeared to be more tolerant to cold. Five G482 subclade sequences, including *Arabidopsis* sequence G482, soy sequences G3472, G3474, G3478, and rice G3395 and G3398, have not yet demonstrated the ability to confer increased tolerance to cold during growth or germination. The rice G3429 sequence that did not confer improved cold tolerance, and while related to G481, is considered to be outside of the G482 subclade.

TABLE 4

G482-subclade sequences overexpressed in plants that have shown improved tolerance to cold conditions relative to control plants

| Gene Identifier (Species) | SEQ ID NO: of GID | Expression system | More tolerant to cold during germination and/or growth |
|---|---|---|---|
| G481 (At) | 2 | 35S | + |
| | | AS1 | + |
| | | LTP1 | + |
| | | RBCS3 | + |

TABLE 4-continued

G482-subclade sequences overexpressed in plants that have shown improved tolerance to cold conditions relative to control plants

| Gene Identifier (Species) | SEQ ID NO: of GID | Expression system | More tolerant to cold during germination and/or growth |
|---|---|---|---|
| | | SUC2 | + |
| | | GFP C-term fusion | + |
| G3470 (Gm) | 4 | 35S | + |
| G3471 (Gm) | 6 | 35S | +* |
| G3875 (Gm) | 8 | 35S | + |
| G3876 (Zm) | 10 | 35S | + |
| G3434 (Zm) | 12 | 35S | + |
| G1364 (At) | 14 | RD29A | + |
| | | RBCS3 | + |
| G3475 (Gm) | 16 | 35S | + |
| G485 (At) | 18 | 35S | + |
| | | AS1 | + |
| | | CFP C-term fusion | + |
| | | RBCS3 | + |
| | | RD29A | + |
| G3476 (Gm) | 20 | 35S | + |
| G2345 (At) | 22 | 35S | + |
| G3474 (Gm) | 24 | 35S | |
| G3478 (Gm) | 26 | 35S | |
| G482 (At) | 28 | 35S | |
| G3435 (Zm) | 30 | 35S | +* |
| G3472 (Gm) | 32 | 35S | |
| G3436 (Zm) | 34 | 35S | + |
| G3397 (Os) | 36 | 35S | + |
| G3395 (Os) | 38 | 35S | |
| G3398 (Os) | 40 | 35S | |
| G3866 (Zm) | 42 | 35S | +* |
| G3396 (Os) | 44 | 35S | + |
| G3429 (Os) | 46 | 35S | |

Species abbreviations: At—*Arabidopsis thaliana*; Gm—*Glycine max*; Os—*Oryza sativa*; Zm—*Zea mays*
+ demonstrated greater cold tolerance than controls in more than two lines
+* demonstrated greater cold tolerance in two lines than controls or substantially stronger cold tolerance than controls in at least one line
+** greater cold tolerance than controls observed in one line

Example V

Utilities of G482 Subclade and Phylogenetically-Related Sequences

The data obtained for water deprivation and cold tolerance in the above Examples indicate that G482 and related sequence overexpression can directly result in improved tolerance to cold, heat, salinity, water deficit conditions and/or freezing, as well as improved yield, quality, appearance, growth range, and/or water usage of crop plants, ornamental plants, and woody plants used in the food, ornamental, paper, pulp, lumber or other industries (for example, industries involved in bioremediation, or carbon sequestration).

Example VI

Transformation of Eudicots to Produce Increased Yield and/or Abiotic Stress Tolerance Crop species that overexpress polypeptides of the invention may produce plants with increased water deprivation, cold and/or nutrient tolerance and/or yield in both stressed and non-stressed conditions. Thus, polynucleotide sequences listed in the Sequence Listing recombined into, for example, one of the expression vectors of the invention, or another suitable expression vector, may be transformed into a plant for the purpose of modifying plant traits for the purpose of improving yield, appearance, and/or quality. The expression vector may contain a constitutive, tissue-specific or inducible promoter operably linked to the polynucleotide. The cloning vector may be introduced into a variety of plants by means well known in the art such as, for example, direct DNA transfer or *Agrobacterium tumefaciens*-mediated transformation. It is now routine to produce transgenic plants using most eudicot plants (see Weissbach and Weissbach, 1989, Gelvin et al., 1990; Herrera-Estrella et al., 1983; Bevan, 1984; and Klee, 1985). Methods for analysis of traits are routine in the art and examples are disclosed above.

Numerous protocols for the transformation of tomato and soy plants have been previously described, and are well known in the art. Gruber et al., 1993, and Glick and Thompson, 1993, describe several expression vectors and culture methods that may be used for cell or tissue transformation and subsequent regeneration. For soybean transformation, methods are described by Miki et al., 1993; and U.S. Pat. No. 5,563,055 to Townsend and Thomas, 1996.

There are a substantial number of alternatives to *Agrobacterium*-mediated transformation protocols, other methods for the purpose of transferring exogenous genes into soybeans or tomatoes. One such method is microprojectile-mediated transformation, in which DNA on the surface of microprojectile particles is driven into plant tissues with a biolistic device (see, for example, Sanford et al., 1987; Christou et al., 1992; Sanford, 1993; Klein et al., 1987; U.S. Pat. No. 5,015,580 to Christou et al, 1991; and U.S. Pat. No. 5,322,783 to Tomes et al., 1994).

Alternatively, sonication methods (see, for example, Zhang et al., 1991); direct uptake of DNA into protoplasts using $CaCl_2$ precipitation, polyvinyl alcohol or poly-L-ornithine (see, for example, Hain et al., 1985; Draper et al., 1982); liposome or spheroplast fusion (see, for example, Deshayes et al., 1985); Christou et al., 1987); and electroporation of protoplasts and whole cells and tissues (see, for example, Donn et al., 1990; D'Halluin et al., 1992; and Spencer et al., 1994) have been used to introduce foreign DNA and expression vectors into plants.

After a plant or plant cell is transformed (and the latter regenerated into a plant), the transformed plant may be crossed with itself or a plant from the same line, a non-transformed or wild-type plant, or another transformed plant from a different transgenic line of plants. Crossing provides the advantages of producing new and often stable transgenic varieties. Genes and the traits they confer that have been introduced into a tomato or soybean line may be moved into distinct line of plants using traditional backcrossing techniques well known in the art. Transformation of tomato plants may be conducted using the protocols of Koornneef et al., 1986, and in U.S. Pat. No. 6,613,962 to Vos et al., 2003, the latter method described in brief here. Eight day old cotyledon explants are precultured for 24 hours in Petri dishes containing a feeder layer of *Petunia hybrida* suspension cells plated on MS medium with 2% (w/v) sucrose and 0.8% agar supplemented with 10 μM α-naphthalene acetic acid and 4.4 μM 6-benzylaminopurine. The explants are then infected with a diluted overnight culture of *Agrobacterium tumefaciens* containing an expression vector comprising a polynucleotide of the invention for 5-10 minutes, blotted dry on sterile filter paper and cocultured for 48 hours on the original feeder layer plates. Culture conditions are as described above. Overnight cultures of *Agrobacterium tumefaciens* are diluted in liquid MS medium with 2% (w/v/) sucrose, pH 5.7) to an $OD_{600}$ of 0.8.

Following cocultivation, the cotyledon explants are transferred to Petri dishes with selective medium comprising MS medium with 4.56 μM zeatin, 67.3 μM vancomycin, 418.9 μM cefotaxime and 171.6 μM kanamycin sulfate, and cultured under the culture conditions described above. The explants are subcultured every three weeks onto fresh medium. Emerging shoots are dissected from the underlying callus and transferred to glass jars with selective medium without zeatin to form roots. The formation of roots in a kanamycin sulfate-containing medium is a positive indication of a successful transformation.

Transformation of soybean plants may be conducted using the methods found in, for example, U.S. Pat. No. 5,563,055 to Townsend et al., 1996), described in brief here. In this method soybean seed is surface sterilized by exposure to chlorine gas evolved in a glass bell jar. Seeds are germinated by plating on 1/10 strength agar solidified medium without plant growth regulators and culturing at 28° C. with a 16 hour day length. After three or four days, seed may be prepared for cocultivation. The seedcoat is removed and the elongating radicle removed 3-4 mm below the cotyledons.

Overnight cultures of *Agrobacterium tumefaciens* harboring the expression vector comprising a polynucleotide of the invention are grown to log phase, pooled, and concentrated by centrifugation. Inoculations are conducted in batches such that each plate of seed was treated with a newly resuspended pellet of *Agrobacterium*. The pellets are resuspended in 20 ml inoculation medium. The inoculum is poured into a Petri dish containing prepared seed and the cotyledonary nodes are macerated with a surgical blade. After 30 minutes the explants are transferred to plates of the same medium that has been solidified. Explants are embedded with the adaxial side up and level with the surface of the medium and cultured at 22° C. for three days under white fluorescent light. These plants may then be regenerated according to methods well established in the art, such as by moving the explants after three days to a liquid counter-selection medium (see U.S. Pat. No. 5,563,055 to Townsend et al., 1996).

The explants may then be picked, embedded and cultured in solidified selection medium. After one month on selective media transformed tissue becomes visible as green sectors of regenerating tissue against a background of bleached, less healthy tissue. Explants with green sectors are transferred to an elongation medium. Culture is continued on this medium with transfers to fresh plates every two weeks. When shoots are 0.5 cm in length they may be excised at the base and placed in a rooting medium.

Example VII

Transformation of Monocots to Produce Increased Yield or Abiotic Stress Tolerance Cereal plants such as, but not limited to, corn, wheat, rice, sorghum, or barley, or grasses such as, for example, *Miscanthus* or switchgrass, may be transformed with the present polynucleotide sequences, including monocot or eudicot-derived sequences such as those presented in the present Tables, cloned into a vector such as pGA643 and containing a kanamycin-resistance marker, and expressed constitutively under, for example, the CaMV 35S or COR15 promoters, or with tissue-specific or inducible promoters. The expression vectors may be one found in the Sequence Listing, or any other suitable expression vector may be similarly used. For example, pMEN020 may be modified to replace the NptII coding region with the BAR gene of *Streptomyces hygroscopicus* that confers resistance to phosphinothricin. The KpnI and BglII sites of the Bar gene are removed by site-directed mutagenesis with silent codon changes.

The cloning vector may be introduced into a variety of cereal plants by means well known in the art including direct DNA transfer or *Agrobacterium tumefaciens*-mediated transformation. The latter approach may be accomplished by a variety of means, including, for example, that of U.S. Pat. No. 5,591,616 to Hiei, 1997, in which monocotyledon callus is transformed by contacting dedifferentiating tissue with the *Agrobacterium* containing the cloning vector.

The sample tissues are immersed in a suspension of $3\times10^{-9}$ cells of *Agrobacterium* containing the cloning vector for 3-10 minutes. The callus material is cultured on solid medium at 25° C. in the dark for several days. The calli grown on this medium are transferred to Regeneration medium. Transfers are continued every 2-3 weeks (2 or 3 times) until shoots develop. Shoots are then transferred to Shoot-Elongation medium every 2-3 weeks. Healthy looking shoots are transferred to rooting medium and after roots have developed, the plants are placed into moist potting soil.

The transformed plants are then analyzed for the presence of the NPTII gene/kanamycin resistance by ELISA, using the ELISA NPTII kit from 5Prime-3Prime Inc. (Boulder, Colo.).

It is also routine to use other methods to produce transgenic plants of most cereal crops (Vasil, 1994) such as corn, wheat, rice, sorghum (Cassas et al., 1993), and barley (Wan and Lemeaux, 1994). DNA transfer methods such as the microprojectile method can be used for corn (Fromm et al., 1990; Gordon-Kamm et al., 1990; Ishida, 1996, wheat (Vasil et al., 1992; Vasil et al., 1993; Weeks et al., 1993), and rice (Christou, 1991; Hiei et al., 1994; Aldemita and Hodges, 1996; and Hiei et al., 1997). For most cereal plants, embryogenic cells derived from immature scutellum tissues are the preferred cellular targets for transformation (Hiei et al., 1997; Vasil, 1994). For transforming corn embryogenic cells derived from immature scutellar tissue using microprojectile bombardment, the A188XB73 genotype is the preferred genotype (Fromm et al., 1990; Gordon-Kamm et al., 1990). After microprojectile bombardment the tissues are selected on phosphinothricin to identify the transgenic embryogenic cells (Gordon-Kamm et al., 1990). Transgenic plants are regenerated by standard corn regeneration techniques (Fromm et al., 1990; Gordon-Kamm et al., 1990).

Example VIII

Expression and Analysis of Increased Yield or Abiotic Stress Tolerance in Non-Arabidopsis Species It is expected that structurally similar orthologs of the G482 subclade of polypeptide sequences, including those found in the Sequence Listing, can confer increased yield or increased tolerance to water deprivation and cold during germination or growth relative to control plants. As sequences of the invention have been shown to improve stress tolerance in a variety of plant species, it is also expected that these sequences will increase yield, appearance and/or quality of crop or other commercially important plant species.

Northern blot analysis, RT-PCR or microarray analysis of the regenerated, transformed plants may be used to show expression of a polypeptide or the invention and related genes that are capable of inducing abiotic stress tolerance, and/or larger size.

After a eudicot plant, monocot plant or plant cell has been transformed (and the latter regenerated into a plant) and shown to have greater size, improved planting density, that is, able to tolerate greater planting density with a coincident increase in yield, or tolerance to abiotic stress, or produce greater yield relative to a control plant under the stress conditions, the transformed monocot plant may be crossed with itself or a plant from the same line, a non-transformed or wild-type monocot plant, or another transformed monocot plant from a different transgenic line of plants.

The function of specific polypeptides of the invention, including closely-related orthologs, have been analyzed and may be further characterized and incorporated into crop plants. The ectopic overexpression of these sequences may be regulated using constitutive, inducible, or tissue specific regulatory elements. Genes that have been examined and have been shown to modify plant traits (including increasing yield and/or abiotic stress tolerance) encode polypeptides found in the Sequence Listing. In addition to these sequences, it is expected that newly discovered polynucleotide and polypeptide sequences closely related to polynucleotide and polypeptide sequences found in the Sequence Listing can also confer alteration of traits in a similar manner to the sequences found in the Sequence Listing, when transformed into any of a considerable variety of plants of different species, and including eudicots and monocots. The polynucleotide and polypeptide sequences derived from monocots (e.g., the rice sequences) may be used to transform both monocot and eudicot plants, and those derived from eudicots (e.g., the *Arabidopsis* and soy genes) may be used to transform either group, although it is expected that some of these sequences will function best if the gene is transformed into a plant from the same group as that from which the sequence is derived.

As an example of a first step to determine water deprivation-related tolerance, seeds of these transgenic plants may be subjected to germination assays to measure sucrose sensing, severe desiccation, freezing or drought. The methods for sucrose sensing, severe desiccation or drought assays are described above. Plants overexpressing sequences of the invention may be found to be more tolerant to high sucrose by having better germination, longer radicles, and more cotyledon expansion.

Plants that are more tolerant than controls to cold or water deprivation assays will generally have better survival rates than controls, or will recover better from these treatments than control plants. Therefore, the G482 subclade sequences of the invention may also be used to contribute to increased yield of commercially available plants.

It is expected that the same methods may be applied to identify other useful and valuable sequences of the present polypeptide clades, and the sequences may be derived from a diverse range of eudicot and monocot species of plants.

REFERENCES CITED

Ainley et al. (1993) *Plant Mol. Biol.* 22: 13-23
Aldemita and Hodges (1996) *Planta* 199: 612-617
Alia et al. (1998) *Plant J.* 16: 155-161
Altschul (1990) *J. Mol. Biol.* 215: 403-410
Altschul (1993) *J. Mol. Evol.* 36: 290-300
An et al. (1988) *Plant Physiol.* 88: 547-552
Anderson and Young (1985) "Quantitative Filter Hybridisation", In: Hames and Higgins, ed., *Nucleic Acid Hybridisation, A Practical Approach*. Oxford, IRL Press, 73-111
Arents and Moudrianakis (1995) *Proc. Natl. Acad. Sci. USA* 92: 11170-11174
Ausubel et al. (1997-2001; eds.) Current Protocols in Molecular Biology, John Wiley & Sons (1997 and supplements through 2001
Ausubel et al. (1997) Short Protocols in Molecular Biology, John Wiley & Sons, New York, N.Y., unit 7.7
Baerson et al. (1993) *Plant Mol. Biol.* 22: 255-267
Baerson et al. (1994) *Plant Mol. Biol.* 26: 1947-1959
Bairoch et al. (1997) *Nucleic Acids Res.* 25: 217-221
Baumann et al., (1999) *Plant Cell* 11: 323-334
Bechtold and Pelletier (1998) *Methods Mol. Biol.* 82: 259-266
Ben-Naim et al. (2006) *Plant J.* 46: 462-476
Berger and Kimmel (1987), "Guide to Molecular Cloning Techniques", in Methods in Enzymology, vol. 152, Academic Press, Inc., San Diego, Calif.
Bevan (1984) *Nucleic Acids Res.* 12: 8711-8721
Bhattachajee et al. (2001) *Proc. Natl. Acad. Sci. USA* 98: 13790-13795
Bi et al. (1997) *J. Biol. Chem.* 272: 26562-26572
Bird et al. (1988) *Plant Mol. Biol.* 11: 651-662
Borevitz et al. (2000) *Plant Cell* 12: 2383-2393
Boss and Thomas (2002) *Nature*, 416: 847-850
Bruce et al. (2000) *Plant Cell* 12: 65-79
Buchel et al. (1999) *Plant Mol. Biol.* 40: 387-396
Bucher and Trifonov (1988) *J. Biomol. Struct. Dyn.* 5: 1231-1236
Bucher (1990) *J. Mol. Biol.* 212: 563-578
Cassas et al. (1993) *Proc. Natl. Acad. Sci. USA* 90: 11212-11216
Casson and Lindsey (2006) *Plant Physiol.* 142: 526-541
Chase et al. (1993) *Ann. Missouri Bot. Gard.* 80: 528-580
Cheikh et al. (2003) U.S. Pat. Application No. 20030101479, published May 29, 2003
Christou et al. (1987) *Proc. Natl. Acad. Sci. USA* 84: 3962-3966
Christou (1991) *Bio/Technol.* 9:957-962
Christou et al. U.S. Pat. No. 5,015,580, issued May 14, 1991
Christou et al. (1992) *Plant. J.* 2: 275-281
Coupland (1995) *Nature* 377: 482-483
Coustry et al. (1995) *J. Biol. Chem.* 270: 468-475
Coustry et al. (1996) *J. Biol. Chem.* 271: 14485-14491
Coustry et al. (1998) *Biochem J.* 331(Pt 1): 291-297
Coustry et al. (2001) *J. Biol. Chem.* 276: 40621-40630
D'Halluin et al. (1992) *Plant Cell* 4: 1495-1505
Daly et al. (2001) *Plant Physiol.* 127: 1328-1333
De Blaere et al. (1987) *Meth. Enzymol.* 143:277)
De Wet, PCT Pat. Publication No. WO8501856, published May 9, 1985
Deshayes et al. (1985) *EMBO J.*: 4: 2731-2737
Doolittle, ed. (1996) *Methods in Enzymology*, vol. 266: "Computer Methods for Macromolecular Sequence Analysis" Academic Press, Inc., San Diego, Calif., USA
Donn et al. (1990) in Abstracts of VIIth International Congress on Plant Cell and Tissue Culture IAPTC, A2-38: 53
Draper et al. (1982) *Plant Cell Physiol.* 23: 451-458
Eddy (1996) *Curr. Opin. Str. Biol.* 6: 361-365
Edwards et al. (1998) *Plant Physiol.* 117: 1015-1022.
Ely, et al. U.S. Pat. No. 5,837,848, issued Nov. 17, 1998
Eisen (1998) *Genome Res.* 8: 163-167
Endege, et al., U.S. Pat. No. 6,262,333, issued Jul. 17, 2001
Feng and Doolittle (1987) *J. Mol. Evol.* 25: 351-360
Fraley et al. (1983) *Proc. Natl. Acad. Sci. USA* 80: 4803-4807
Forsburg and Guarente (1989) *Genes Dev.* 3: 1166-1178
Fowler and Thomashow (2002) *Plant Cell* 14: 1675-1690
Fromm et al. (1985) *Proc. Natl. Acad. Sci.* 82: 5824-5828
Fromm et al. (1989) *Plant Cell* 1: 977-984
Fromm et al. (1990) *Bio/Technol.* 8: 833-839
Fu et al. (2001) *Plant Cell* 13: 1791-1802
Gan and Amasino (1995) *Science* 270: 1986-1988
Gatz (1997) *Annu. Rev. Plant Physiol. Plant Mol. Biol.* 48: 89-108
Gaxiola et al. (2001) *Proc. Natl. Acad. Sci. USA* 98: 11444-11449
Gelvin et al. (1990) *Plant Molecular Biology Manual*, Kluwer Academic Publishers
Gilmour et al. (1998) *Plant J.* 16: 433-442

Gish and States (1993) *Nature Genetics* 3: 266-272
Glick and Thompson, eds. (1993) *Methods in Plant Molecular Biology and Biotechnology.* CRC Press., Boca Raton, Fla.
Goodrich et al. (1993) *Cell* 75: 519-530
Gordon-Kamm et al. (1990) *Plant Cell* 2: 603-618
Gruber et al. (1993) in *Methods in Plant Molecular Biology and Biotechnology*, p. 89-119
Guevara-Garcia (1998) *Plant Mol. Biol.* 38: 743-753
Gusmaroli et al. (2001) *Gene* 264: 173-185
Gusmaroli et al. (2002) *Gene* 283: 41-48
Haake et al. (2002) *Plant Physiol.* 130: 639-648
Hain et al. (1985) *Mol. Gen. Genet.* 199: 161-168
Hall et al. (2000) *Plant Physiol.* 123: 1449-1458
Hauptmann, et al., U.S. Pat. No. 5,618,988, issued Apr. 8, 1997
Hawkins et al. U.S. Pat. No. 5,840,544, issued Nov. 24, 1998
Haymes et al., *Nucleic Acid Hybridization: A Practical Approach*, IRL Press, Washington, D.C. (1985)
He et al. (2000) *Transgenic Res.* 9: 223-227
Heard et al., U.S. Pat. No. 7,135,616, issued Nov. 14, 2006
Hein (1990) *Methods Enzymol.* 183: 626-645
Henikoff & Henikoff (1989) *Proc. Natl. Acad. Sci. USA* 89:10915
Henikoff and Henikoff (1991) *Nucleic Acids Res.* 19: 6565-6572
Herrera-Estrella et al. (1983) *Nature* 303: 209
Hiei et al. (1994) *Plant J.* 6:271-282
Hiei et al. (1997) *Plant Mol. Biol.* 35:205-218
Hiei et al., U.S. Pat. No. 5,591,616, issued Jan. 7, 1997
Higgins et al. (1996) *Methods Enzymol.* 266: 383-402
Hillman et al., U.S. Pat. Appl. No. 20010010913, published Aug. 2, 2001
Hohn et al. (1982) *Molecular Biology of Plant Tumors*, Academic Press, New York, N.Y., pp. 549-560; US
Horsch et al. (1984) *Science* 233: 496-498
U.S. Pat. No. 4,943,674
Houck and Pear, U.S. Pat. No. 4,943,674, issued Jul. 24, 1990
Howell. U.S. Pat. No. 4,407,956, issued Oct. 4, 1983
Ishida et al. (1996) *Nature Biotechnol.* 14: 745-750
Jaglo et al. (2001) *Plant Physiol.* 127: 910-917
Jang et al. (1997) *Plant Cell* 9: 5-19
Jiang et al., U.S. Pat. Appl. No. 20040128712, published Jul. 1, 2004
Jiang et al., U.S. Pat. Appl. No. 20070033671, published Feb. 8, 2007 Kaiser et al. (1995) *Plant Mol. Biol.* 28: 231-243
Kashima et al. (1985) *Nature* 313: 402-404
Kellogg, et al., U.S. Pat. No. 5,783,393, issued Jul. 21, 1998
Kim et al. (1996) *Mol. Cell. Biol.* 16: 4003-4013
Kim et al. (2001) *Plant J.* 25: 247-259
Kim and Sheffrey (1990) *J. Biol. Chem.* 265: 13362-13369
Kimmel (1987) *Methods Enzymol.* 152: 507-511
Klee (1985) *Bio/Technology* 3: 637-642
Klein et al. (1987) *Nature* 327: 70-73
Klein et al, 1987; U.S. Pat. No. 4,945,050, issued Jul. 31, 1990
Koornneef et al. (1986) In *Tomato Biotechnology*: Alan R. Liss, Inc., 169-178
Ku et al. (2000) *Proc. Natl. Acad. Sci. USA* 97: 9121-9126
Kuhlemeier et al. (1989) *Plant Cell* 1: 471-478
Kwong (2003) *Plant Cell* 15: 5-18
Kyozuka and Shimamoto (2002) *Plant Cell Physiol.* 43: 130-135
Lee et al. (2003) *Proc. Natl. Acad. Sci. USA* 100: 2152-2156.
Leon-Kloosterziel et al. (1996) *Plant Physiol.* 110: 233-240
Li et al. (1992) *Nucleic Acids Res.* 20: 1087-1091
Lin et al. (1991) *Nature* 353: 569-571
Liu and Zhu (1997) *Proc. Natl. Acad. Sci. USA* 94: 14960-14964
Lotan et al. (1998) *Cell* 93: 1195-1205.
Luger et al. (1997) *Nature* 389: 251-260
Maity and de Crombrugghe (1998) *Trends Biochem. Sci.* 23: 174-178
Mandel (1992a) *Nature* 360: 273-277
Mandel et al. (1992b) *Cell* 71-133-143
Manners et al. (1998) *Plant Mol. Biol.* 38: 1071-1080
Mantovani (1999) *Gene* 239: 15-27
Mariani et al., U.S. Pat. No. 5,792,929, issued Aug. 11, 1998
McCue and Hanson (1990) *Trends Biotechnol.* 8: 358-362
McNabb et al. (1995) *Genes Dev.* 9: 47-58
McNabb et al. (1997) *Mol. Cell. Biol.* 17: 7008-7018
Meinke (1992) *Science* 258: 1647-1650
Meinke et al. (1994) *Plant Cell* 6: 1049-1064
Miki et al. (1993) in *Methods in Plant Molecular Biology and Biotechnology*, p. 67-88, Glick and Thompson, eds., CRC Press, Inc., Boca Raton
Miyoshi et al. (2003) *Plant J.* 36: 532-540
Mount (2001), in *Bioinformatics: Sequence and Genome Analysis*, Cold Spring Harbor Laboratory Press, Cold Spring Harbor, N.Y., p. 543
Müller et al. (2001) *Plant J.* 28: 169-179
Meyers (1995) Molecular Biology and Biotechnology, Wiley VCH, New York, N.Y., p 856-853
Nandi et al. (2000) *Curr. Biol.* 10: 215-218
Olesen and Guarente (1990) *Genes Dev.* 4: 1714-1729
Ohl et al. (1990) *Plant Cell* 2: 837-848
Odell et al. (1985) *Nature* 313: 810-812
Odell et al. (1994) *Plant Physiol.* 106: 447-458
Parcy et al. (1997) *Plant Cell* 9: 1265-1277
Peng et al. (1997) *Genes Development* 11: 3194-3205
Peng et al. (1999) *Nature* 400: 256-261
Ratcliffe et al. (2001) *Plant Physiol.* 126: 122-132
Reeves and Nissen (1995) *Prog. Cell Cycle Res.* 1: 339-349
Riechmann et al. (2000a) *Science* 290: 2105-2110
Riechmann and Ratcliffe (2000b) *Curr. Opin. Plant Biol.* 3: 423-434
Rieger et al. (1976) *Glossary of Genetics and Cytogenetics: Classical and Molecular,* 4th ed., Springer Verlag, Berlin
Ringli and Keller (1998) *Plant Mol. Biol.* 37: 977-988
Robson et al. (2001) *Plant J.* 28: 619-631
Romier et al. (2003) *J. Biol. Chem.* 278: 1336-1345
Sadowski et al. (1988) *Nature* 335: 563-564
Saijo et al. (2000) *Plant J.* 23: 319-327
Saleki et al. (1993) *Plant Physiol.* 101: 839-845
Sambrook et al. (1989) *Molecular Cloning: A Laboratory Manual,* 2nd Ed., Cold Spring Harbor Laboratory, Cold Spring Harbor, N.Y.
Sanford et al. (1987) *Part. Sci. Technol.* 5:27-37
Sanford (1993) *Methods Enzymol.* 217: 483-509
Schaffner and Sheen (1991) *Plant Cell* 3: 997-1012
Sherman et al., PCT publication WO2004076638, published Sep. 10, 2004
Shi et al. (1998) *Plant Mol. Biol.* 38: 1053-1060
Shpaer (1997) *Methods Mol. Biol.* 70: 173-187
Siebertz et al. (1989) *Plant Cell* 1: 961-968
Sinha et al. (1996) *Mol. Cell. Biol.* 16: 328-337
Smeekens (1998) *Curr. Opin. Plant Biol.* 1: 230-234
Smith et al. (1992) *Protein Engineering* 5: 35-51
Smith and Waterman (1981) *Adv. Appl. Math.* 2: 482-489
Soltis et al. (1997) *Ann. Missouri Bot. Gard.* 84: 1-49
Sonnhammer et al. (1997) *Proteins* 28: 405-420
Spencer et al. (1994) *Plant Mol. Biol.* 24: 51-61
Suzuki et al. (2001) *Plant J.* 28: 409-418
Tasanen et al. (1992) *J. Biol. Chem.* 267: 11513-11519

Thomas et al., U.S. Pat. No. 5,905,186, issued May 18, 1999
Thompson et al. (1994) *Nucleic Acids Res.* 22: 4673-4680
Tomes et al., U.S. Pat. No. 5,322,783, issued Jun. 21, 1994
Tomes et al. U.S. Pat. No. 5,773,697, issued Jun. 30, 1998
Townsend et al., U.S. Pat. No. 5,563,055, issued Oct. 8, 1996
Tudge (2000) in *The Variety of Life*, Oxford University Press, New York, N.Y. pp. 547-606
van der Kop et al. (1999) *Plant Mol. Biol.* 39: 979-990
Vasil et al. (1992) *Bio/Technol.* 10:667-674
Vasil et al. (1993) *Bio/Technol.* 11:1553-1558
Vasil (1994) *Plant Mol. Biol.* 25: 925-937
Vicient et al. (2000) *J. Exp. Bot.* 51: 995-1003
Vos et al. U.S. Pat. No. 6,613,962, issued Sep. 2, 2003
Wahl and Berger (1987) *Methods Enzymol.* 152: 399-407
Wan and Lemeaux (1994) *Plant Physiol.* 104: 37-48
Weeks et al. (1993) *Plant Physiol.* 102:1077-1084
Weigel and Nilsson (1995) *Nature* 377: 482-500
Weissbach and Weissbach (1989) *Methods for Plant Molecular Biology*, Academic Press
Wenkel et al. (2006) *Plant Cell.* 18: 2971-2984
West et al. (1994) *Plant Cell* 6: 1731-1745
Willmott et al. (1998) *Plant Molec. Biol.* 38: 817-825
Wu et al. (1996) *Plant Cell* 8: 617-627
Xin and Browse (1998) *Proc. Natl. Acad. Sci. USA* 95: 7799-7804
Xing et al. (1993) *EMBO J.* 12: 4647-4655
Xiong et al. (2001) *Genes Dev.* 15: 1971-1984.
Xu et al. (2001) *Proc. Natl. Acad. Sci. USA* 98: 15089-15094
Zemzoumi et al. (1999) *J. Mol. Biol.* 286: 327-337
Zhang et al. (1991) *Bio/Technology* 9: 996-997
Zhu et al. (1998) *Plant Cell* 10: 1181-1191

SEQUENCE LISTING

```
<160> NUMBER OF SEQ ID NOS: 116

<210> SEQ ID NO 1
<211> LENGTH: 832
<212> TYPE: DNA
<213> ORGANISM: Arabidopsis thaliana
<220> FEATURE:
<223> OTHER INFORMATION: G481

<400> SEQUENCE: 1
gagcgtttcg tagaaaaatt cgatttctct aaagccctaa aactaaaacg actatcccca      60
attccaagtt ctagggtttc catcttcccc aatctagtat aaatggcgga tacgccttcg     120
agcccagctg gagatggcgg agaaagcggc ggttccgtta gggagcagga tcgataccttt     180 cctatagcta atatcagcag gatcatgaag aaagcgttgc ctcctaatgg taagattgga     240
aaagatgcta aggatacagt tcaggaatgc gtctctgagt tcatcagctt catcactagc     300
gaggccagtg ataagtgtca aaaagagaaa aggaaaactg tgaatggtga tgatttgttg     360
tgggcaatgg caacattagg atttgaggat tacctggaac ctctaaagat atacctagcg     420
aggtacaggg agttggaggg tgataataag ggatcaggaa agagtggaga tggatcaaat     480
agagatgctg gtggcggtgt ttctggtgaa gaaatgccga gctggtaaaa gaagttgcaa     540
gtagtgatta agaacaatcg ccaaatgatc aagggaaatt agagatcagt gagttgttta     600
tagttgagct gatcgacaac tatttcgggt ttactctcaa tttcggttat gttagtttga     660
acgtttggtt tattgtttcc ggtttagttg gttgtattta aagatttctc tgttagatgt     720
tgagaacact tgaatgaagg aaaaatttgt ccacatcctg ttgttatttt cgattcactt     780
tcggaatttc atagctaatt tattctcatt taataccaaa tccttaaatt aa              832

<210> SEQ ID NO 2
<211> LENGTH: 141
<212> TYPE: PRT
<213> ORGANISM: Arabidopsis thaliana
<220> FEATURE:
<223> OTHER INFORMATION: G481 polypeptide

<400> SEQUENCE: 2

Met Ala Asp Thr Pro Ser Ser Pro Ala Gly Asp Gly Gly Glu Ser Gly
1               5                   10                  15

Gly Ser Val Arg Glu Gln Asp Arg Tyr Leu Pro Ile Ala Asn Ile Ser
            20                  25                  30

Arg Ile Met Lys Lys Ala Leu Pro Pro Asn Gly Lys Ile Gly Lys Asp
```

```
                    35                  40                  45
Ala Lys Asp Thr Val Gln Glu Cys Val Ser Glu Phe Ile Ser Phe Ile
 50                  55                  60

Thr Ser Glu Ala Ser Asp Lys Cys Gln Lys Glu Lys Arg Lys Thr Val
 65                  70                  75                  80

Asn Gly Asp Asp Leu Leu Trp Ala Met Ala Thr Leu Gly Phe Glu Asp
                 85                  90                  95

Tyr Leu Glu Pro Leu Lys Ile Tyr Leu Ala Arg Tyr Arg Glu Leu Glu
                100                 105                 110

Gly Asp Asn Lys Gly Ser Gly Lys Ser Gly Asp Gly Ser Asn Arg Asp
                115                 120                 125

Ala Gly Gly Gly Val Ser Gly Glu Glu Met Pro Ser Trp
                130                 135                 140

<210> SEQ ID NO 3
<211> LENGTH: 555
<212> TYPE: DNA
<213> ORGANISM: Glycine max
<220> FEATURE:
<223> OTHER INFORMATION: G3470

<400> SEQUENCE: 3
tcaccgggtt tgtgagatgt cggatgcacc ggcgagtccg agtcacgaga gtggtggcga      60
gcagagccct cgcggctcgt tgtccggcgc ggctagagag caggaccggt accttcccat     120
tgccaacatc agccgcatca tgaagaaggc tctgcctccc aatggcaaga ttgcgaagga     180
tgcaaaagac acaatgcaag aatgcgtttc tgaattcatc agcttcatta ccagcgaggc     240
gagtgagaaa tgccagaagg agaagagaaa gacaatcaat ggagacgatt tactatgggc     300
catggcaact ttagggtttg aagactacat tgagccgctt aaggtgtacc tggctaggta     360
cagagaggcg gagggtgaca ctaaaggatc tgctagaagt ggtgatggat ctgctagacc     420
agatcaagtt ggccttgcag gtcaaaatgc tcagcttgtt catcagggtt cgctgaacta     480
tattggtttg caggtgcaac cacaacatct ggttatgcct tcaatgcaag gccatgaata     540
gtttagatgc ttcta                                                      555

<210> SEQ ID NO 4
<211> LENGTH: 174
<212> TYPE: PRT
<213> ORGANISM: Glycine max
<220> FEATURE:
<223> OTHER INFORMATION: G3470 polypeptide

<400> SEQUENCE: 4

Met Ser Asp Ala Pro Ala Ser Pro Ser His Glu Ser Gly Gly Glu Gln
  1               5                  10                  15

Ser Pro Arg Gly Ser Leu Ser Gly Ala Ala Arg Glu Gln Asp Arg Tyr
                 20                  25                  30

Leu Pro Ile Ala Asn Ile Ser Arg Ile Met Lys Lys Ala Leu Pro Pro
                 35                  40                  45

Asn Gly Lys Ile Ala Lys Asp Ala Lys Asp Thr Met Gln Glu Cys Val
 50                  55                  60

Ser Glu Phe Ile Ser Phe Ile Thr Ser Glu Ala Ser Glu Lys Cys Gln
 65                  70                  75                  80

Lys Glu Lys Arg Lys Thr Ile Asn Gly Asp Asp Leu Leu Trp Ala Met
                 85                  90                  95

Ala Thr Leu Gly Phe Glu Asp Tyr Ile Glu Pro Leu Lys Val Tyr Leu
                100                 105                 110
```

```
Ala Arg Tyr Arg Glu Ala Glu Gly Asp Thr Lys Gly Ser Ala Arg Ser
        115                 120                 125
Gly Asp Gly Ser Ala Arg Pro Asp Gln Val Gly Leu Ala Gly Gln Asn
    130                 135                 140
Ala Gln Leu Val His Gln Gly Ser Leu Asn Tyr Ile Gly Leu Gln Val
145                 150                 155                 160
Gln Pro Gln His Leu Val Met Pro Ser Met Gln Gly His Glu
                165                 170
```

<210> SEQ ID NO 5
<211> LENGTH: 556
<212> TYPE: DNA
<213> ORGANISM: Glycine max
<220> FEATURE:
<223> OTHER INFORMATION: G3471

<400> SEQUENCE: 5

```
gtagggtttg tgagatgtcg gatgcgccac cgagcccgac tcatgagagt gggggcgagc      60
agagcccgcg cggttcgtcg tccggcgcga gggagcagga ccggtacctc ccgattgcca     120
acatcagccg cattatgaag aaggctctgc ctcccaacgg caagattgca aaggatgcca     180
aagacaccat gcaggaatgc gtttctgagt tcatcagctt cattaccagc gaggcgagtg     240
agaaatgcca gaaggagaag agaaagacaa tcaatggaga cgatttgcta tgggccatgg     300
ccactttagg atttgaagac tacatagagc cgcttaaggt gtacctggct aggtacagag     360
aggcggaggg tgacactaaa ggatctgcta gaagtggtga tggatctgct acaccagatc     420
aagttggcct tgcaggtcaa aattctcagc ttgttcatca gggttcgctg aactatattg     480
gtttgcaggt gcaaccacaa catctggtta tgccttcaat gcaaagccat gaatagttta     540
gatgcttcta cgcatc                                                     556
```

<210> SEQ ID NO 6
<211> LENGTH: 173
<212> TYPE: PRT
<213> ORGANISM: Glycine max
<220> FEATURE:
<223> OTHER INFORMATION: G3471 polypeptide

<400> SEQUENCE: 6

```
Met Ser Asp Ala Pro Pro Ser Pro Thr His Glu Ser Gly Gly Glu Gln
1               5                   10                  15
Ser Pro Arg Gly Ser Ser Gly Ala Arg Glu Gln Asp Arg Tyr Leu
            20                  25                  30
Pro Ile Ala Asn Ile Ser Arg Ile Met Lys Lys Ala Leu Pro Pro Asn
        35                  40                  45
Gly Lys Ile Ala Lys Asp Ala Lys Asp Thr Met Gln Glu Cys Val Ser
    50                  55                  60
Glu Phe Ile Ser Phe Ile Thr Ser Glu Ala Ser Glu Lys Cys Gln Lys
65                  70                  75                  80
Glu Lys Arg Lys Thr Ile Asn Gly Asp Asp Leu Leu Trp Ala Met Ala
                85                  90                  95
Thr Leu Gly Phe Glu Asp Tyr Ile Glu Pro Leu Lys Val Tyr Leu Ala
            100                 105                 110
Arg Tyr Arg Glu Ala Glu Gly Asp Thr Lys Gly Ser Ala Arg Ser Gly
        115                 120                 125
Asp Gly Ser Ala Thr Pro Asp Gln Val Gly Leu Ala Gly Gln Asn Ser
    130                 135                 140
```

Gln Leu Val His Gln Gly Ser Leu Asn Tyr Ile Gly Leu Gln Val Gln
145                 150                 155                 160

Pro Gln His Leu Val Met Pro Ser Met Gln Ser His Glu
                165                 170

<210> SEQ ID NO 7
<211> LENGTH: 818
<212> TYPE: DNA
<213> ORGANISM: Glycine max
<220> FEATURE:
<223> OTHER INFORMATION: G3875

<400> SEQUENCE: 7
cttaacattt ccctaaacat aactcacaca cccctcttct ctagggtttc aatttcacca    60
tgtttccctt tctcaaatta gggttccggc gagcatggcc gacggtccgg cgagtccagg   120
cggcggtagc cacgagagcg gcgagcacag ccctcgctct aacgtgcgcg agcaggacag   180
gtacctcccc atcgctaaca taagccgcat catgaagaag gcactacctg cgaacggtaa   240
aatcgccaag gacgccaaag agaccgttca ggaatgcgta tccgagttca tcagtttcat   300
caccagcgag gcctctgata agtgtcagag ggaaaagaga aagactatta acggtgatga   360
tttgctctgg gccatggcca ctcttggttt tgaggattat atcgatcctc ttaaaattta   420
cctcactaga tacagagaga tggagggtga tacgaagggt tcagccaagg gcggagactc   480
atcttctaag aaagatgttc agccaagtcc taatgctcag cttgctcatc aaggttcttt   540
ctcacaaggt gttagttaca caatttctca gggtcaacat atgatggttc caatgcaagg   600
cccggagtag gtatcaagtt tattaaccct cctgttgtaa cgtatgtttt ccacgccagt   660
taccaagtgc tcacggcata ttgaatgtct ttttatgtta tgtgaatact gacataggag   720
atggttcttg tgtcctttt ttttaaaaaa aaaagtaagg tttgtatatt atctttggag   780
tcgaattatt atttgaaagt tattatattg taaatcct                          818

<210> SEQ ID NO 8
<211> LENGTH: 171
<212> TYPE: PRT
<213> ORGANISM: Glycine max
<220> FEATURE:
<223> OTHER INFORMATION: G3875 polypeptide

<400> SEQUENCE: 8

Met Ala Asp Gly Pro Ala Ser Pro Gly Gly Gly Ser His Glu Ser Gly
1               5                   10                  15

Glu His Ser Pro Arg Ser Asn Val Arg Glu Gln Asp Arg Tyr Leu Pro
                20                  25                  30

Ile Ala Asn Ile Ser Arg Ile Met Lys Lys Ala Leu Pro Ala Asn Gly
            35                  40                  45

Lys Ile Ala Lys Asp Ala Lys Glu Thr Val Gln Glu Cys Val Ser Glu
        50                  55                  60

Phe Ile Ser Phe Ile Thr Ser Glu Ala Ser Asp Lys Cys Gln Arg Glu
65                  70                  75                  80

Lys Arg Lys Thr Ile Asn Gly Asp Asp Leu Leu Trp Ala Met Ala Thr
                85                  90                  95

Leu Gly Phe Glu Asp Tyr Ile Asp Pro Leu Lys Ile Tyr Leu Thr Arg
                100                 105                 110

Tyr Arg Glu Met Glu Gly Asp Thr Lys Gly Ser Ala Lys Gly Gly Asp
            115                 120                 125

Ser Ser Ser Lys Lys Asp Val Gln Pro Ser Pro Asn Ala Gln Leu Ala
        130                 135                 140

```
His Gln Gly Ser Phe Ser Gln Gly Val Ser Tyr Thr Ile Ser Gln Gly
145                 150                 155                 160

Gln His Met Met Val Pro Met Gln Gly Pro Glu
                165                 170
```

<210> SEQ ID NO 9
<211> LENGTH: 557
<212> TYPE: DNA
<213> ORGANISM: Zea mays
<220> FEATURE:
<223> OTHER INFORMATION: G3876

<400> SEQUENCE: 9

```
tataagtgca ggaggagctc atggcggaag ctccggcgag ccctggcggc ggcggcggga      60
gccacgagag cgggagcccc aggggaggcg gaggcggtgg cagcgtcagg gagcaggaca     120
ggttcctgcc catcgccaac atcagtcgca tcatgaagaa ggccatcccg ctaacggga     180 agatcgccaa ggacgctaag gagaccgtgc aggagtgcgt ctccgagttc atctccttca    240
tcactagcga agcgagtgac aagtgccaga gggagaagcg gaagaccatc aatggcgacg    300
atctgctgtg ggccatggcc acgctggggt ttgaagacta cattgaaccc ctcaaggtgt    360
acctgcagaa gtacagagag atggagggtg atagcaagtt aactgcaaaa tctagcgatg    420
gctcaattaa aaaggatgcc cttggtcatg tgggagcaag tagctcagct gcacaaggga    480
tgggccaaca gggagcatac aaccaaggaa tgggttatat gcaaccccag taccataacg    540
gggatatctc aaactaa                                                   557
```

<210> SEQ ID NO 10
<211> LENGTH: 178
<212> TYPE: PRT
<213> ORGANISM: Zea mays
<220> FEATURE:
<223> OTHER INFORMATION: G3876 polypeptide

<400> SEQUENCE: 10

```
Met Ala Glu Ala Pro Ala Ser Pro Gly Gly Gly Gly Ser His Glu
1               5                   10                  15

Ser Gly Ser Pro Arg Gly Gly Gly Gly Gly Ser Val Arg Glu Gln
                20                  25                  30

Asp Arg Phe Leu Pro Ile Ala Asn Ile Ser Arg Ile Met Lys Ala
            35                  40                  45

Ile Pro Ala Asn Gly Lys Ile Ala Lys Asp Ala Lys Glu Thr Val Gln
50                  55                  60

Glu Cys Val Ser Glu Phe Ile Ser Phe Ile Thr Ser Glu Ala Ser Asp
65                  70                  75                  80

Lys Cys Gln Arg Glu Lys Arg Lys Thr Ile Asn Gly Asp Asp Leu Leu
                85                  90                  95

Trp Ala Met Ala Thr Leu Gly Phe Glu Asp Tyr Ile Glu Pro Leu Lys
                100                 105                 110

Val Tyr Leu Gln Lys Tyr Arg Glu Met Glu Gly Asp Ser Lys Leu Thr
            115                 120                 125

Ala Lys Ser Ser Asp Gly Ser Ile Lys Lys Asp Ala Leu Gly His Val
        130                 135                 140

Gly Ala Ser Ser Ser Ala Ala Gln Gly Met Gly Gln Gln Gly Ala Tyr
145                 150                 155                 160

Asn Gln Gly Met Gly Tyr Met Gln Pro Gln Tyr His Asn Gly Asp Ile
                165                 170                 175
```

Ser Asn

<210> SEQ ID NO 11
<211> LENGTH: 819
<212> TYPE: DNA
<213> ORGANISM: Zea mays
<220> FEATURE:
<223> OTHER INFORMATION: G3434

<400> SEQUENCE: 11

```
tcgacaaggg ttgcggcgga ggcgcccggt cgctggcgat ggccgacgac ggcgggagcc    60
acgagggcag cggcggcggc ggaggcgtcc gggagcagga ccggttcctg cccatcgcca   120
acatcagccg gatcatgaag aaggccgtcc cggccaacgg caagatcgcc aaggacgcta   180
aggagaccct gcaggagtgc gtctccgagt tcatatcatt cgtgaccagc gaggccagcg   240
acaaatgcca gaaggagaaa cgaaagacaa tcaacgggga cgatttgctc tgggcgatgg   300
ccactttagg attcgaggag tacgtcgagc ctctcaagat ttacctacaa aagtacaaag   360
agatggaggg tgatagcaag ctgtctacaa aggctggcga gggctctgta aagaaggatg   420
caattagtcc ccatggtggc accagtagct caagtaatca gttggttcag catggagtct   480
acaaccaagg gatgggctat atgcagccac agtaccacaa tggggaaacc taacaaaggg   540
ctaatacagc agcaatttat gctagggaag tctctgcatt gcttaccatg tgtattggca   600
gaaaacagga ggcacttaca aagggtgtta atctctgcga tggctgcctc tcaggtgtaa   660
attggcttcg gttagcgct gcttttgtcc gtatatttag gatgatttga ctgttgctac   720
ttttggcaac cttttacatt tacagatatg tattattcag cataaatata atatagtagt   780
cctaggccta ataatggtg attaaaaaaa aaaaaaaaa                           819
```

<210> SEQ ID NO 12
<211> LENGTH: 164
<212> TYPE: PRT
<213> ORGANISM: Zea mays
<220> FEATURE:
<223> OTHER INFORMATION: G3434 polypeptide

<400> SEQUENCE: 12

```
Met Ala Asp Asp Gly Gly Ser His Glu Gly Ser Gly Gly Gly Gly Gly
1               5                   10                  15

Val Arg Glu Gln Asp Arg Phe Leu Pro Ile Ala Asn Ile Ser Arg Ile
            20                  25                  30

Met Lys Lys Ala Val Pro Ala Asn Gly Lys Ile Ala Lys Asp Ala Lys
        35                  40                  45

Glu Thr Leu Gln Glu Cys Val Ser Glu Phe Ile Ser Phe Val Thr Ser
    50                  55                  60

Glu Ala Ser Asp Lys Cys Gln Lys Glu Lys Arg Lys Thr Ile Asn Gly
65                  70                  75                  80

Asp Asp Leu Leu Trp Ala Met Ala Thr Leu Gly Phe Glu Glu Tyr Val
                85                  90                  95

Glu Pro Leu Lys Ile Tyr Leu Gln Lys Tyr Lys Glu Met Glu Gly Asp
            100                 105                 110

Ser Lys Leu Ser Thr Lys Ala Gly Glu Gly Ser Val Lys Lys Asp Ala
        115                 120                 125

Ile Ser Pro His Gly Gly Thr Ser Ser Ser Asn Gln Leu Val Gln
    130                 135                 140

His Gly Val Tyr Asn Gln Gly Met Gly Tyr Met Gln Pro Gln Tyr His
145                 150                 155                 160
```

Asn Gly Glu Thr

<210> SEQ ID NO 13
<211> LENGTH: 823
<212> TYPE: DNA
<213> ORGANISM: Arabidopsis thaliana
<220> FEATURE:
<223> OTHER INFORMATION: G1364

<400> SEQUENCE: 13

```
ctcttctctc gatctctctc cctctctgcc tcctctcttc ctccaatcaa caaacacctc      60
tctgtttcac tcccgccctt tttcgaattc ttctgatggc ggagtcgcag gccaagagtc     120
ccggaggctg tggaagccat gagagtggtg agatcaaag  tcccaggtcg ttacatgttc     180
gtgagcaaga taggtttctt ccgattgcta acataagccg tatcatgaaa agaggtcttc     240
ctgctaatgg gaaaatcgct aaagatgcta aggagattgt gcaggaatgt gtctctgaat     300
tcatcagttt cgtcaccagc gaagcgagtg ataaatgtca agagagaaa  aggaagacta     360
ttaatggaga tgatttgctt tgggcaatgg ctactttagg atttgaagac tacatggaac     420
ctctcaaggt ttacctgatg agatatagag agatggaggg tgacacaaag ggatcagcaa     480
aaggtgggga tccaaatgca agaaagatg  ggcaatcaag ccaaaatggc cagttctcgc     540
agcttgctca ccaaggtcct tatgggaact ctcaagctca gcagcatatg atggttccaa     600
tgccgggaac agactagtat gagaggagta ttcaactttg ttatgttcc  accaaaagag     660
gttatcttat ctgtatatta tttgtgttgt aagagttttg ctatgcagaa cttgtgacta     720
taatcatctc attgttttgt tttgtttttg tttccttgga tttgttctga atatgtcatc     780
aagtcagtca gtctatttat atatttggtt tgttgattat ttc                       823
```

<210> SEQ ID NO 14
<211> LENGTH: 173
<212> TYPE: PRT
<213> ORGANISM: Arabidopsis thaliana
<220> FEATURE:
<223> OTHER INFORMATION: G1364 polypeptide

<400> SEQUENCE: 14

```
Met Ala Glu Ser Gln Ala Lys Ser Pro Gly Gly Cys Gly Ser His Glu
1               5                   10                  15

Ser Gly Gly Asp Gln Ser Pro Arg Ser Leu His Val Arg Glu Gln Asp
            20                  25                  30

Arg Phe Leu Pro Ile Ala Asn Ile Ser Arg Ile Met Lys Arg Gly Leu
        35                  40                  45

Pro Ala Asn Gly Lys Ile Ala Lys Asp Ala Lys Glu Ile Val Gln Glu
    50                  55                  60

Cys Val Ser Glu Phe Ile Ser Phe Val Thr Ser Glu Ala Ser Asp Lys
65                  70                  75                  80

Cys Gln Arg Glu Lys Arg Lys Thr Ile Asn Gly Asp Asp Leu Leu Trp
                85                  90                  95

Ala Met Ala Thr Leu Gly Phe Glu Asp Tyr Met Glu Pro Leu Lys Val
            100                 105                 110

Tyr Leu Met Arg Tyr Arg Glu Met Glu Gly Asp Thr Lys Gly Ser Ala
        115                 120                 125

Lys Gly Gly Asp Pro Asn Ala Lys Lys Asp Gly Gln Ser Ser Gln Asn
    130                 135                 140

Gly Gln Phe Ser Gln Leu Ala His Gln Gly Pro Tyr Gly Asn Ser Gln
145                 150                 155                 160
```

```
Ala Gln Gln His Met Met Val Pro Met Pro Gly Thr Asp
            165                 170
```

<210> SEQ ID NO 15
<211> LENGTH: 600
<212> TYPE: DNA
<213> ORGANISM: Glycine max
<220> FEATURE:
<223> OTHER INFORMATION: G3475

<400> SEQUENCE: 15

```
tcgattatcc gtttgtcgat ggcggactcg dacaacgact ccggcggcgc gcacaacgcc    60
gggaagggga gcgagatgtc gccgcgggag caggaccggt tcctgccgat cgcgaacgtg   120
agccgcatca tgaagaaggc gctgccggcg aacgcgaaga tctcgaagga cgcgaaggag   180
acggtgcagg agtgcgtgtc ggagttcatc agcttcatca ccggcgaggc ctccgacaag   240
tgccagcggg agaagcgcaa gacgatcaac ggcgacgacc tgctctgggc gatgaccact   300
ctcggcttcg aggactacgt cgagcctctc aagggctacc tccagcgctt ccagaaaatg   360
gaaggagaga agacagtggc ggcgcgtgac aaggacgcgc tcctcctac caatgctacc   420 aacagtgcct acgagagtcc tagttatgct gctgctcctg gtggaatcat gatgcatcag   480
ggacacgtgt acggttctgc cggcttccat caagtggctg gtggtgctat aaagggtggg   540
cctgtttatc ccgggcctgg atccaatgcc ggtaggccca ggtagatggg cctatgttat   600
```

<210> SEQ ID NO 16
<211> LENGTH: 188
<212> TYPE: PRT
<213> ORGANISM: Glycine max
<220> FEATURE:
<223> OTHER INFORMATION: G3475 polypeptide

<400> SEQUENCE: 16

```
Met Ala Asp Ser Asp Asn Asp Ser Gly Gly Ala His Asn Ala Gly Lys
1               5                   10                  15

Gly Ser Glu Met Ser Pro Arg Glu Gln Asp Arg Phe Leu Pro Ile Ala
            20                  25                  30

Asn Val Ser Arg Ile Met Lys Lys Ala Leu Pro Ala Asn Ala Lys Ile
        35                  40                  45

Ser Lys Asp Ala Lys Glu Thr Val Gln Glu Cys Val Ser Glu Phe Ile
50                  55                  60

Ser Phe Ile Thr Gly Glu Ala Ser Asp Lys Cys Gln Arg Glu Lys Arg
65                  70                  75                  80

Lys Thr Ile Asn Gly Asp Asp Leu Leu Trp Ala Met Thr Thr Leu Gly
                85                  90                  95

Phe Glu Asp Tyr Val Glu Pro Leu Lys Gly Tyr Leu Gln Arg Phe Arg
            100                 105                 110

Glu Met Glu Gly Glu Lys Thr Val Ala Ala Arg Asp Lys Asp Ala Pro
        115                 120                 125

Pro Pro Thr Asn Ala Thr Asn Ser Ala Tyr Glu Ser Pro Ser Tyr Ala
130                 135                 140

Ala Ala Pro Gly Gly Ile Met Met His Gln Gly His Val Tyr Gly Ser
145                 150                 155                 160

Ala Gly Phe His Gln Val Ala Gly Gly Ala Ile Lys Gly Gly Pro Val
                165                 170                 175

Tyr Pro Gly Pro Gly Ser Asn Ala Gly Arg Pro Arg
            180                 185
```

<210> SEQ ID NO 17
<211> LENGTH: 684
<212> TYPE: DNA
<213> ORGANISM: Arabidopsis thaliana
<220> FEATURE:
<223> OTHER INFORMATION: G485

<400> SEQUENCE: 17

```
cctctctgat ccaacggacc caaaacatct atctctcttt ctcgaccttt tgtctcctcg      60
atctaaagat ggcggattcg gacaacgatt caggaggaca caaagacggt ggaaatgctt     120
cgacacgtga gcaagatagg tttctaccga tcgctaacgt tagcaggatc atgaagaaag     180
cacttcctgc gaacgcaaaa atctctaagg atgctaaaga aacggttcaa gagtgtgtat     240
cggaattcat aagtttcatc accggtgagg cttctgacaa gtgtcagaga gagaagagga     300
agacaatcaa cggtgacgat cttctttggg cgatgactac gctagggttt gaggactacg     360
tggagcctct caaggtttat ctgcaaaagt atagggaggt ggaaggagag aagactacta     420
cggcagggag acaaggcgat aaggaaggtg aggaggaggg cggtggagct ggaagtggaa     480
gtggaggagc tccgatgtac ggtggtggca tggtgactac gatgggacat caattttccc     540
atcattttc ttaattgtaa aatgataaaa gcaaattttc atttttatta attaatgata     600
tatatatata tatgtttaac ttttagtata atgtttacag aattttttt ttaaaactag     660
gttcaaccca ctaacgtaac agcg                                            684
```

<210> SEQ ID NO 18
<211> LENGTH: 161
<212> TYPE: PRT
<213> ORGANISM: Arabidopsis thaliana
<220> FEATURE:
<223> OTHER INFORMATION: G485 polypeptide

<400> SEQUENCE: 18

```
Met Ala Asp Ser Asp Asn Asp Ser Gly Gly His Lys Asp Gly Gly Asn
1               5                   10                  15

Ala Ser Thr Arg Glu Gln Asp Arg Phe Leu Pro Ile Ala Asn Val Ser
            20                  25                  30

Arg Ile Met Lys Lys Ala Leu Pro Ala Asn Ala Lys Ile Ser Lys Asp
        35                  40                  45

Ala Lys Glu Thr Val Gln Glu Cys Val Ser Glu Phe Ile Ser Phe Ile
    50                  55                  60

Thr Gly Glu Ala Ser Asp Lys Cys Gln Arg Glu Lys Arg Lys Thr Ile
65                  70                  75                  80

Asn Gly Asp Asp Leu Leu Trp Ala Met Thr Thr Leu Gly Phe Glu Asp
                85                  90                  95

Tyr Val Glu Pro Leu Lys Val Tyr Leu Gln Lys Tyr Arg Glu Val Glu
            100                 105                 110

Gly Glu Lys Thr Thr Thr Ala Gly Arg Gln Gly Asp Lys Glu Gly Gly
        115                 120                 125

Gly Gly Gly Gly Gly Ala Gly Ser Gly Ser Gly Ala Pro Met Tyr
    130                 135                 140

Gly Gly Gly Met Val Thr Thr Met Gly His Gln Phe Ser His His Phe
145                 150                 155                 160

Ser
```

<210> SEQ ID NO 19
<211> LENGTH: 528
<212> TYPE: DNA
<213> ORGANISM: Glycine max

```
<220> FEATURE:
<223> OTHER INFORMATION: G3476

<400> SEQUENCE: 19
ggattgattg tgaagatggc tgagtcggac aacgactcgg gaggggcgca gaacgcggga      60
aacagtggaa acttgagcga gttgtcgcct cgggaacagg accggtttct ccccatagcg     120
aacgtgagca ggatcatgaa gaaggccttg ccggcgaacg cgaagatctc gaaggacgcg     180
aaggagacgg tgcaggaatg cgtgtcggag ttcatcagct tcataacggg tgaggcgtcg     240
gacaagtgcc agagggagaa gcgcaagacc atcaacggcg acgatcttct ctgggccatg     300
acaaccctgg gattcgaaga gtacgtggag cctctgaaga tttacctcca gcgcttccgc     360
gagatggagg gagagaagac cgtggccgcc cgcgactctt ctaaggactc ggcctccgcc     420
tcctcctatc atcagggaca cgtgtacggc tcccctgcct accatcatca agtgcctggg     480
cccacttatc ctgcccctgg tagacccaga tgacgtgctc ctctattc                  528

<210> SEQ ID NO 20
<211> LENGTH: 165
<212> TYPE: PRT
<213> ORGANISM: Glycine max
<220> FEATURE:
<223> OTHER INFORMATION: G3476 polypeptide

<400> SEQUENCE: 20

Met Ala Glu Ser Asp Asn Asp Ser Gly Gly Ala Gln Asn Ala Gly Asn
1               5                   10                  15

Ser Gly Asn Leu Ser Glu Leu Ser Pro Arg Glu Gln Asp Arg Phe Leu
            20                  25                  30

Pro Ile Ala Asn Val Ser Arg Ile Met Lys Lys Ala Leu Pro Ala Asn
        35                  40                  45

Ala Lys Ile Ser Lys Asp Ala Lys Glu Thr Val Gln Glu Cys Val Ser
    50                  55                  60

Glu Phe Ile Ser Phe Ile Thr Gly Glu Ala Ser Asp Lys Cys Gln Arg
65                  70                  75                  80

Glu Lys Arg Lys Thr Ile Asn Gly Asp Asp Leu Leu Trp Ala Met Thr
                85                  90                  95

Thr Leu Gly Phe Glu Glu Tyr Val Glu Pro Leu Lys Ile Tyr Leu Gln
            100                 105                 110

Arg Phe Arg Glu Met Glu Gly Glu Lys Thr Val Ala Ala Arg Asp Ser
        115                 120                 125

Ser Lys Asp Ser Ala Ser Ala Ser Ser Tyr His Gln Gly His Val Tyr
    130                 135                 140

Gly Ser Pro Ala Tyr His His Gln Val Pro Gly Pro Thr Tyr Pro Ala
145                 150                 155                 160

Pro Gly Arg Pro Arg
                165

<210> SEQ ID NO 21
<211> LENGTH: 896
<212> TYPE: DNA
<213> ORGANISM: Oryza sativa
<220> FEATURE:
<223> OTHER INFORMATION: G2345

<400> SEQUENCE: 21
agatcagatc aaatctctct ctccatctcc gtcctcctcc tcaatcatca tttctctctc      60
cgtctcccgc tcttttttcga attctccttc ttcttcaggg tttctgagat ggccgaatcg    120
```

```
caaaccggtg gtggtggtgg tggaagccat gagagtggcg gtgatcagag cccgaggtct       180
ttgaatgttc gtgagcagga caggtttctt ccgattgcta acataagccg tatcatgaag       240
agaggtttac ctctaaatgg caaaatcgct aaagatgcta agagactat gcaggaatgt        300 gtctctgaat tcatcagctt cgtcaccagc gaggctagtg ataagtgcca agagagaaa        360 aggaagacca tcaatggaga tgatttgctt tgggctatgg ccactttagg attcgaagat       420
tacatcgatc ccctcaaggt ttacctgatg cgatatagag agatggaggg tgacactaaa      480
ggatcaggaa aaggcgggga atcgagtgca agagagatg gtcaaccaag ccaagtgtct       540
cagttctcgc aggttcctca acaaggctca ttctcacagg gtccttatgg aaactctcaa      600
ggttcgaata tgatggttca aatgccgggc acagagtagt actaggacac tattcatcac     660
aatcttccga gactcgacta tgcctgttgt gtctgagaat ctgagtgatc cactttccat     720
agatatggat tgtggtatct cagttttttgg gagagagaag attttgtatat gattgtgttg   780 tagggagaag agtttggttt gcttatgata agaattgaaa agcaccttttt ttttcttttg    840 actgttatgt ttcttaggtt ttggtcttaa gcagaagcta tttaccaaaa aaaaaa          896
```

<210> SEQ ID NO 22
<211> LENGTH: 176
<212> TYPE: PRT
<213> ORGANISM: Oryza sativa
<220> FEATURE:
<223> OTHER INFORMATION: G2345 polypeptide

<400> SEQUENCE: 22

```
Met Ala Glu Ser Gln Thr Gly Gly Gly Gly Gly Ser His Glu Ser
1               5                   10                  15

Gly Gly Asp Gln Ser Pro Arg Ser Leu Asn Val Arg Glu Gln Asp Arg
            20                  25                  30

Phe Leu Pro Ile Ala Asn Ile Ser Arg Ile Met Lys Arg Gly Leu Pro
        35                  40                  45

Leu Asn Gly Lys Ile Ala Lys Asp Ala Lys Glu Thr Met Gln Glu Cys
    50                  55                  60

Val Ser Glu Phe Ile Ser Phe Val Thr Ser Glu Ala Ser Asp Lys Cys
65                  70                  75                  80

Gln Arg Glu Lys Arg Lys Thr Ile Asn Gly Asp Asp Leu Leu Trp Ala
                85                  90                  95

Met Ala Thr Leu Gly Phe Glu Asp Tyr Ile Asp Pro Leu Lys Val Tyr
            100                 105                 110

Leu Met Arg Tyr Arg Glu Met Glu Gly Asp Thr Lys Gly Ser Gly Lys
        115                 120                 125

Gly Gly Glu Ser Ser Ala Lys Arg Asp Gly Gln Pro Ser Gln Val Ser
    130                 135                 140

Gln Phe Ser Gln Val Pro Gln Gln Gly Ser Phe Ser Gln Gly Pro Tyr
145                 150                 155                 160

Gly Asn Ser Gln Gly Ser Asn Met Met Val Gln Met Pro Gly Thr Glu
                165                 170                 175
```

<210> SEQ ID NO 23
<211> LENGTH: 553
<212> TYPE: DNA
<213> ORGANISM: Glycine max
<220> FEATURE:
<223> OTHER INFORMATION: G3474

<400> SEQUENCE: 23

```
gatatccatg gctgagtccg acaacgagtc aggaggtcac acggggaacg cgagcgggag       60
```

```
caacgagttg tccggttgca gggagcaaga caggttcctc ccaatagcaa acgtgagcag      120
gatcatgaag aaggcgttgc cggcgaacgc gaagatatcg aaggaggcga aggagacggt      180
gcaggagtgc gtgtcggagt tcatcagctt cataacagga gaggcttccg ataagtgcca      240
gaaggagaag aggaagacga tcaacggcga cgatcttctc tgggccatga ctaccctggg      300
cttcgaggac tacgtggatc ctctcaagat ttacctgcac aagtataggg agatggaggg      360
ggagaaaacc gctatgatgg gaaggccaca tgagagggat gagggttatg gccatggcca      420
tggtcatgca actcctatga tgacgatgat gatgggcat cagccccagc accagcacca      480
gcaccagcac cagggacacg tgtatggatc tggatcagca tcttctgcaa gaactagata      540
gcatgtgtca tct                                                         553
```

<210> SEQ ID NO 24
<211> LENGTH: 177
<212> TYPE: PRT
<213> ORGANISM: Glycine max
<220> FEATURE:
<223> OTHER INFORMATION: G3474 polypeptide

<400> SEQUENCE: 24

```
Met Ala Glu Ser Asp Asn Glu Ser Gly Gly His Thr Gly Asn Ala Ser
1               5                   10                  15

Gly Ser Asn Glu Leu Ser Gly Cys Arg Glu Gln Asp Arg Phe Leu Pro
            20                  25                  30

Ile Ala Asn Val Ser Arg Ile Met Lys Lys Ala Leu Pro Ala Asn Ala
        35                  40                  45

Lys Ile Ser Lys Glu Ala Lys Glu Thr Val Gln Glu Cys Val Ser Glu
    50                  55                  60

Phe Ile Ser Phe Ile Thr Gly Glu Ala Ser Asp Lys Cys Gln Lys Glu
65                  70                  75                  80

Lys Arg Lys Thr Ile Asn Gly Asp Asp Leu Leu Trp Ala Met Thr Thr
                85                  90                  95

Leu Gly Phe Glu Asp Tyr Val Asp Pro Leu Lys Ile Tyr Leu His Lys
            100                 105                 110

Tyr Arg Glu Met Glu Gly Glu Lys Thr Ala Met Met Gly Arg Pro His
        115                 120                 125

Glu Arg Asp Glu Gly Tyr Gly His Gly His Gly His Ala Thr Pro Met
    130                 135                 140

Met Thr Met Met Met Gly His Gln Pro Gln His Gln His Gln His Gln
145                 150                 155                 160

His Gln Gly His Val Tyr Gly Ser Gly Ser Ala Ser Ser Ala Arg Thr
                165                 170                 175

Arg
```

<210> SEQ ID NO 25
<211> LENGTH: 602
<212> TYPE: DNA
<213> ORGANISM: Glycine max
<220> FEATURE:
<223> OTHER INFORMATION: G3478

<400> SEQUENCE: 25

```
ttccgttagt cgatggcgga ctccgacaac gactccggcg gcgcgcacaa cggcggcaag      60
gggagcgaga tgtcgccgcg ggagcaggac cggtttctcc cgatcgcgaa cgtgagccgc     120
atcatgaaga aggcgctgcc ggcgaacgcg aagatctcga aggacgcgaa ggagacggtg     180
```

```
caggagtgcg tgtcagagtt catcagcttc atcaccggcg aggcctccga caagtgccag    240
cgcgagaagc gcaagacgat caacggcgac gacctgctct gggcgatgac cactctgggc    300
ttcgaggact acgtggagcc tctcaaaggc tacctccagc gcttccgaga aatggaagga    360
gagaagaccg tggcggcgcg tgacaaggac gcgcctcctc ttacgaatgc taccaacagt    420
gcctacgaga gtgctaatta tgctgctgct gctgctgttc ctggtggaat catgatgcat    480
cagggacacg tgtacggttc tgccggcttc atcaagtgg ctggcggggc tataaagggt     540
gggcctgctt atcctgggcc tggatccaat gccggtaggc ccagataaag agcctattat    600
ta                                                                   602
```

<210> SEQ ID NO 26
<211> LENGTH: 191
<212> TYPE: PRT
<213> ORGANISM: Glycine max
<220> FEATURE:
<223> OTHER INFORMATION: G3478 polypeptide

<400> SEQUENCE: 26

```
Met Ala Asp Ser Asp Asn Asp Ser Gly Gly Ala His Asn Gly Gly Lys
 1               5                  10                  15

Gly Ser Glu Met Ser Pro Arg Glu Gln Asp Arg Phe Leu Pro Ile Ala
            20                  25                  30

Asn Val Ser Arg Ile Met Lys Lys Ala Leu Pro Ala Asn Ala Lys Ile
        35                  40                  45

Ser Lys Asp Ala Lys Glu Thr Val Gln Glu Cys Val Ser Glu Phe Ile
    50                  55                  60

Ser Phe Ile Thr Gly Glu Ala Ser Asp Lys Cys Gln Arg Glu Lys Arg
65                  70                  75                  80

Lys Thr Ile Asn Gly Asp Asp Leu Leu Trp Ala Met Thr Thr Leu Gly
                85                  90                  95

Phe Glu Asp Tyr Val Glu Pro Leu Lys Gly Tyr Leu Gln Arg Phe Arg
           100                 105                 110

Glu Met Glu Gly Glu Lys Thr Val Ala Ala Arg Asp Lys Asp Ala Pro
       115                 120                 125

Pro Leu Thr Asn Ala Thr Asn Ser Ala Tyr Glu Ser Ala Asn Tyr Ala
   130                 135                 140

Ala Ala Ala Val Pro Gly Gly Ile Met Met His Gln Gly His Val
145                 150                 155                 160

Tyr Gly Ser Ala Gly Phe His Gln Val Ala Gly Gly Ala Ile Lys Gly
               165                 170                 175

Gly Pro Ala Tyr Pro Gly Pro Gly Ser Asn Ala Gly Arg Pro Arg
           180                 185                 190
```

<210> SEQ ID NO 27
<211> LENGTH: 1065
<212> TYPE: DNA
<213> ORGANISM: Arabidopsis thaliana
<220> FEATURE:
<223> OTHER INFORMATION: G482

<400> SEQUENCE: 27

```
tcgacccacg cgtccggaca cttaacaatt cacaccttct cttttactc ttcctaaaac     60 cctaaatttc ctcgcttcag tcttcccact caagtcaacc accaattgaa ttcgatttcg    120
aatcattgat ggaaatgatt tgaaaaaaga gtaaagttta ttttttatt ccttgtaatt     180 ttcagaaatg ggggattccg acagggattc cggtggaggg caaaacggga acaaccagaa    240
```

```
cggacagtcc tccttgtctc caagagagca agacaggttc ttgccgatcg ctaacgtcag        300
ccggatcatg aagaaggcct tgcccgccaa cgccaagatc tctaaagatg ccaaagagac        360
gatgcaggag tgtgtctccg agttcatcag cttcgtcacc ggagaagcat ctgataagtg        420
tcagaaggag aagaggaaga cgatcaacgg agacgatttg ctctgggcta tgactactct        480
aggttttgag gattatgttg agccattgaa agtttacttg cagaggttta gggagatcga        540
aggggagagg actggactag gaggccaca gactggtggt gaggtcggag agcatcagag        600
agatgctgtc ggagatggcg gtgggttcta cggtggtggt ggtgggatgc agtatcacca        660
acatcatcag tttcttcacc agcagaacca tatgtatgga gccacaggtg gcggtagcga        720
cagtggaggt ggagctgcct ccggtaggac aaggacttaa caaagattgg tgaagtggat        780
ctctctctgt atatagatac ataaatacat gtatacacat gcctattttt acgacccata        840
taaggtatct atcatgtgat agaacgaaca ttggtgttgg tgatgtaaaa tcagatgtgc        900
attaagggtt tagattttga ggctgtgtaa aagaagatca agtgtgcttt gttggacaat        960
aggattcact aacgaatctg cttcattgga tcttgtatgt aactaaagcc attgtattga       1020
atgcaaatgt tttcatttgg gatgctttaa aaaaaaaaaa aaaaa                       1065
```

<210> SEQ ID NO 28
<211> LENGTH: 190
<212> TYPE: PRT
<213> ORGANISM: Arabidopsis thaliana
<220> FEATURE:
<223> OTHER INFORMATION: G482 polypeptide

<400> SEQUENCE: 28

```
Met Gly Asp Ser Asp Arg Asp Ser Gly Gly Gly Gln Asn Gly Asn Asn
1               5                   10                  15

Gln Asn Gly Gln Ser Ser Leu Ser Pro Arg Glu Gln Asp Arg Phe Leu
            20                  25                  30

Pro Ile Ala Asn Val Ser Arg Ile Met Lys Lys Ala Leu Pro Ala Asn
        35                  40                  45

Ala Lys Ile Ser Lys Asp Ala Lys Glu Thr Met Gln Glu Cys Val Ser
    50                  55                  60

Glu Phe Ile Ser Phe Val Thr Gly Glu Ala Ser Asp Lys Cys Gln Lys
65                  70                  75                  80

Glu Lys Arg Lys Thr Ile Asn Gly Asp Asp Leu Leu Trp Ala Met Thr
                85                  90                  95

Thr Leu Gly Phe Glu Asp Tyr Val Glu Pro Leu Lys Val Tyr Leu Gln
            100                 105                 110

Arg Phe Arg Glu Ile Glu Gly Glu Arg Thr Gly Leu Gly Arg Pro Gln
        115                 120                 125

Thr Gly Gly Glu Val Gly Glu His Gln Arg Asp Ala Val Gly Asp Gly
    130                 135                 140

Gly Gly Phe Tyr Gly Gly Gly Gly Met Gln Tyr His Gln His His
145                 150                 155                 160

Gln Phe Leu His Gln Gln Asn His Met Tyr Gly Ala Thr Gly Gly Gly
                165                 170                 175

Ser Asp Ser Gly Gly Ala Ala Ser Gly Arg Thr Arg Thr
            180                 185                 190
```

<210> SEQ ID NO 29
<211> LENGTH: 735
<212> TYPE: DNA
<213> ORGANISM: Zea mays
<220> FEATURE:

<223> OTHER INFORMATION: G3435

<400> SEQUENCE: 29

```
cggcggtggc cttgagctga ggcggcggag cgatgccgga ctcggacaac gactccggcg      60
ggccgagcaa cgccggggc gagctgtcgt cgccgcggga gcaggaccgg ttcctgccca      120
tcgccaacgt gagccggatc atgaagaagg cgctcccggc caacgccaag atcagcaagg      180
acgccaagga cacggtgcag gagtgcgtgt ccgagttcat ctccttcatc accggcgagg      240
cctccgacaa gtgccagcgc gagaagcgca agaccatcaa cggcgacgac ctgctgtggg      300
ccatgaccac gctcggcttc gaggactacg tcgagccgct caagcactac ctgcacaagt      360
tccgcgagat cgagggcgag agggccgccg cgtccgccgg cgcctcgggc tcgcagcagc      420
agcagcagca gggcgagctg cccagaggcg ccgccaatgc cgccgggtac gccgggtacg      480
gcgcgcctgg ctccggcggc atgatgatga tgatgatggg cagcccatg tacggcggct      540
cgcagccgca gaacagccg ccgccgcctc agccgccaca gcagcagcag caacatcaac      600
agcatcacat ggcaatagga ggcagaggag gattcggcca acaaggcggc ggcggcggct      660
cctcgtcgtc gtcagggctt ggccggcaag acagggcgtg agttgcgacg atacgtcaga      720
atcagaatcg ctgat                                                      735
```

<210> SEQ ID NO 30
<211> LENGTH: 222
<212> TYPE: PRT
<213> ORGANISM: Zea mays
<220> FEATURE:
<223> OTHER INFORMATION: G3435 polypeptide

<400> SEQUENCE: 30

```
Met Pro Asp Ser Asp Asn Asp Ser Gly Gly Pro Ser Asn Ala Gly Gly
1               5                   10                  15

Glu Leu Ser Ser Pro Arg Glu Gln Asp Arg Phe Leu Pro Ile Ala Asn
            20                  25                  30

Val Ser Arg Ile Met Lys Lys Ala Leu Pro Ala Asn Ala Lys Ile Ser
        35                  40                  45

Lys Asp Ala Lys Glu Thr Val Gln Glu Cys Val Ser Glu Phe Ile Ser
    50                  55                  60

Phe Ile Thr Gly Glu Ala Ser Asp Lys Cys Gln Arg Glu Lys Arg Lys
65                  70                  75                  80

Thr Ile Asn Gly Asp Asp Leu Leu Trp Ala Met Thr Thr Leu Gly Phe
                85                  90                  95

Glu Asp Tyr Val Glu Pro Leu Lys His Tyr Leu His Lys Phe Arg Glu
            100                 105                 110

Ile Glu Gly Glu Arg Ala Ala Ala Ser Ala Gly Ala Ser Gly Ser Gln
        115                 120                 125

Gln Gln Gln Gln Gln Gly Glu Leu Pro Arg Gly Ala Ala Asn Ala Ala
    130                 135                 140

Gly Tyr Ala Gly Tyr Gly Ala Pro Gly Ser Gly Gly Met Met Met Met
145                 150                 155                 160

Met Met Gly Gln Pro Met Tyr Gly Gly Ser Gln Pro Gln Gln Pro
                165                 170                 175

Pro Pro Pro Gln Pro Gln Gln Gln Gln His Gln His His
            180                 185                 190

Met Ala Ile Gly Gly Arg Gly Gly Phe Gly Gln Gln Gly Gly Gly
        195                 200                 205

Gly Ser Ser Ser Ser Ser Gly Leu Gly Arg Gln Asp Arg Ala
```

<210> SEQ ID NO 31
<211> LENGTH: 547
<212> TYPE: DNA
<213> ORGANISM: Glycine max
<220> FEATURE:
<223> OTHER INFORMATION: G3472

<400> SEQUENCE: 31

```
taaggctagc tagctagcca tggctgagtc ggacaacgag tccggaggtc acacggggaa      60
cgcaagcgga agcaacgaat tctccggttg cagggagcaa gacaggttcc ttccgatagc     120
gaacgtgagc aggatcatga agaaggcgtt gccggcgaac gcgaagatct cgaaggaggc     180
gaaggagacg gtgcaggagt gcgtgtcgga gttcatcagc ttcataacag agaagcgtc      240
cgataagtgc cagaaggaga gaggaagac gatcaacggc gatgatctgc tgtgggccat      300
gaccacgctg ggattcgagg agtacgtgga gcctctcaag gtttatctgc ataagtatag     360
ggagctggaa ggggagaaaa ctgctatgat gggaaggcca catgagaggg atgagggtta     420
tggtcatgca actcctatga tgatcatgat ggggcatcaa cagcagcagc atcagggaca     480
cgtgtatgga tctggaacta ctactggatc agcatcttct gcaagaacta gataacaggt     540
ttatgca                                                               547
```

<210> SEQ ID NO 32
<211> LENGTH: 171
<212> TYPE: PRT
<213> ORGANISM: Glycine max
<220> FEATURE:
<223> OTHER INFORMATION: G3472 polypeptide

<400> SEQUENCE: 32

```
Met Ala Glu Ser Asp Asn Glu Ser Gly Gly His Thr Gly Asn Ala Ser
1               5                   10                  15

Gly Ser Asn Glu Phe Ser Gly Cys Arg Glu Gln Asp Arg Phe Leu Pro
            20                  25                  30

Ile Ala Asn Val Ser Arg Ile Met Lys Lys Ala Leu Pro Ala Asn Ala
        35                  40                  45

Lys Ile Ser Lys Glu Ala Lys Glu Thr Val Gln Glu Cys Val Ser Glu
    50                  55                  60

Phe Ile Ser Phe Ile Thr Gly Glu Ala Ser Asp Lys Cys Gln Lys Glu
65                  70                  75                  80

Lys Arg Lys Thr Ile Asn Gly Asp Asp Leu Leu Trp Ala Met Thr Thr
                85                  90                  95

Leu Gly Phe Glu Glu Tyr Val Glu Pro Leu Lys Val Tyr Leu His Lys
            100                 105                 110

Tyr Arg Glu Leu Glu Gly Glu Lys Thr Ala Met Met Gly Arg Pro His
        115                 120                 125

Glu Arg Asp Glu Gly Tyr Gly His Ala Thr Pro Met Met Ile Met Met
    130                 135                 140

Gly His Gln Gln Gln Gln His Gln Gly His Val Tyr Gly Ser Gly Thr
145                 150                 155                 160

Thr Thr Gly Ser Ala Ser Ser Ala Arg Thr Arg
                165                 170
```

<210> SEQ ID NO 33
<211> LENGTH: 803
<212> TYPE: DNA
<213> ORGANISM: Zea mays

<220> FEATURE:
<223> OTHER INFORMATION: G3436

<400> SEQUENCE: 33

| | | | | | |
|---|---|---|---|---|---|
| tttgacttga | ccggacagtg | ctgttcggtg | gctcggccgc | gatgccggac | tccgacaacg | 60 |
| agtccggcgg | gccgagcaac | gcggagttct | cgtcgccgcg | ggagcaggac | cggttcctgc | 120 |
| cgatcgcgaa | cgtgagccgg | atcatgaaga | aggcgctccc | ggccaacgcc | aagatctcca | 180 |
| aggacgccaa | ggagacggtg | caggagtgcg | tgtcggagtt | catctccttc | atcaccggcg | 240 |
| aggcctccga | caagtgccag | cgcgagaagc | gcaagaccat | caacggcgac | gacctactct | 300 |
| gggccatgac | cacgctcggc | ttcgaggact | acgtcgagcc | gctcaagctc | tacctccaca | 360 |
| agttccgcga | gctcgagggc | gagaaggcgg | ccacgacgag | cgcctcctcc | ggcccgcagc | 420 |
| cgccgctgca | cagggagacg | acgccgtcgt | cgtcaacgca | caatggcgcg | ggcgggcccg | 480 |
| tcggggata | cggcatgtac | ggcggcgcg | gcggggaag | cggtatgatc | atgatgatgg | 540 |
| gacagcccat | gtacggcggc | tccccgccgg | ccgcgtcgtc | cgggtcgtac | ccgcaccacc | 600 |
| agatggccat | gggcggaaaa | ggtggcgcct | atggctacgg | cggaggctcg | tcgtcgtcgc | 660 |
| cgtcagggct | cggcaggtag | gacaggttgt | gaccgtcgcc | gtccatgctt | gcatggccat | 720 |
| ggccatggca | tggctcccgc | cgccggcttc | ttgcttggtg | tcggtaatta | gcgctggtgg | 780 |
| cctgcgctgg | ttaagttcac | cat | | | | 803 |

<210> SEQ ID NO 34
<211> LENGTH: 212
<212> TYPE: PRT
<213> ORGANISM: Zea mays
<220> FEATURE:
<223> OTHER INFORMATION: G3436 polypeptide

<400> SEQUENCE: 34

Met Pro Asp Ser Asp Asn Glu Ser Gly Gly Pro Ser Asn Ala Glu Phe
1               5                   10                  15

Ser Ser Pro Arg Glu Gln Asp Arg Phe Leu Pro Ile Ala Asn Val Ser
                20                  25                  30

Arg Ile Met Lys Lys Ala Leu Pro Ala Asn Ala Lys Ile Ser Lys Asp
            35                  40                  45

Ala Lys Glu Thr Val Gln Glu Cys Val Ser Glu Phe Ile Ser Phe Ile
        50                  55                  60

Thr Gly Glu Ala Ser Asp Lys Cys Gln Arg Glu Lys Arg Lys Thr Ile
65                  70                  75                  80

Asn Gly Asp Asp Leu Leu Trp Ala Met Thr Thr Leu Gly Phe Glu Asp
                85                  90                  95

Tyr Val Glu Pro Leu Lys Leu Tyr Leu His Lys Phe Arg Glu Leu Glu
                100                 105                 110

Gly Glu Lys Ala Ala Thr Thr Ser Ala Ser Ser Gly Pro Gln Pro Pro
            115                 120                 125

Leu His Arg Glu Thr Thr Pro Ser Ser Ser Thr His Asn Gly Ala Gly
        130                 135                 140

Gly Pro Val Gly Gly Tyr Gly Met Tyr Gly Gly Ala Gly Gly Gly Ser
145                 150                 155                 160

Gly Met Ile Met Met Met Gly Gln Pro Met Tyr Gly Gly Ser Pro Pro
                165                 170                 175

Ala Ala Ser Ser Gly Ser Tyr Pro His His Gln Met Ala Met Gly Gly
            180                 185                 190

Lys Gly Gly Ala Tyr Gly Tyr Gly Gly Gly Ser Ser Ser Ser Pro Ser

```
                195                 200                 205

Gly Leu Gly Arg
    210

<210> SEQ ID NO 35
<211> LENGTH: 720
<212> TYPE: DNA
<213> ORGANISM: Oryza sativa
<220> FEATURE:
<223> OTHER INFORMATION: G3397

<400> SEQUENCE: 35
gcgtctgatt tgctgaagag gaggaggagg atgccggact cggacaacga ctccggcggg      60
ccgagcaact acgcgggagg ggagctgtcg tcgccgcggg agcaggacag gttcctgccg     120
atcgcgaacg tgagcaggat catgaagaag gcgctgccgg cgaacgccaa gatcagcaag     180
gacgccaagg agacggtgca ggagtgcgtc tccgagttca tctccttcat caccggcgag     240
gcctccgaca agtgccagcg cgagaagcgc aagaccatca cggcgacga cctgctctgg      300 gccatgacca ccctcggctt cgaggactac gtcgaccccc tcaagcacta cctccacaag     360
ttccgcgaga tcgagggcga gcgcgccgcc gcctccacca ccggcgccgg caccagcgcc     420
gcctccacca cgccgccgca gcagcagcac accgccaatg ccgccggcgg ctacgccggg     480
tacgccgccc cgggagccgg ccccggcggc atgatgatga tgatgggca gcccatgtac       540 ggctcgccgc caccgccgcc acagcagcag cagcagcaac accaccacat ggcaatggga     600
ggaagaggcg gcttcggtca tcatcccggc ggcggcggcg gcgggtcgtc gtcgtcgtcg     660
gggcacggtc ggcaaaacag gggcgcttga catcgctccg agacgagtag catgcaccat     720

<210> SEQ ID NO 36
<211> LENGTH: 219
<212> TYPE: PRT
<213> ORGANISM: Oryza sativa
<220> FEATURE:
<223> OTHER INFORMATION: G3397 polypeptide

<400> SEQUENCE: 36

Met Pro Asp Ser Asp Asn Asp Ser Gly Gly Pro Ser Asn Tyr Ala Gly
1               5                   10                  15

Gly Glu Leu Ser Ser Pro Arg Glu Gln Asp Arg Phe Leu Pro Ile Ala
            20                  25                  30

Asn Val Ser Arg Ile Met Lys Lys Ala Leu Pro Ala Asn Ala Lys Ile
        35                  40                  45

Ser Lys Asp Ala Lys Glu Thr Val Gln Glu Cys Val Ser Glu Phe Ile
    50                  55                  60

Ser Phe Ile Thr Gly Glu Ala Ser Asp Lys Cys Gln Arg Glu Lys Arg
65                  70                  75                  80

Lys Thr Ile Asn Gly Asp Asp Leu Leu Trp Ala Met Thr Thr Leu Gly
                85                  90                  95

Phe Glu Asp Tyr Val Asp Pro Leu Lys His Tyr Leu His Lys Phe Arg
            100                 105                 110

Glu Ile Glu Gly Glu Arg Ala Ala Ala Ser Thr Thr Gly Ala Gly Thr
        115                 120                 125

Ser Ala Ala Ser Thr Thr Pro Pro Gln Gln Gln His Thr Ala Asn Ala
    130                 135                 140

Ala Gly Gly Tyr Ala Gly Tyr Ala Ala Pro Gly Ala Gly Pro Gly Gly
145                 150                 155                 160

Met Met Met Met Met Gly Gln Pro Met Tyr Gly Ser Pro Pro Pro Pro
```

```
                165                 170                 175
Pro Gln Gln Gln Gln Gln His His His Met Ala Met Gly Gly Arg
        180                 185                 190

Gly Gly Phe Gly His His Pro Gly Gly Gly Gly Ser Ser Ser
        195                 200                 205

Ser Ser Gly His Gly Arg Gln Asn Arg Gly Ala
        210                 215

<210> SEQ ID NO 37
<211> LENGTH: 610
<212> TYPE: DNA
<213> ORGANISM: Oryza sativa
<220> FEATURE:
<223> OTHER INFORMATION: G3395

<400> SEQUENCE: 37
tggatctagg gttttggag ggcggcgcgg ggatggcgga cgcggggcac gacgagagcg      60
ggagcccgcc gaggagcggc ggggtgaggg agcaggacag gttcctgccc atcgccaaca     120
tcagccgcat catgaagaag gccgtcccgg cgaacggcaa gatcgccaag gacgccaagg     180
agaccctgca ggagtgcgtc tcggagttca tctccttcgt caccagcgag gcgagcgaca     240
aatgtcagaa ggagaagcgc aagaccatca cggggaaga tctcctcttt gcgatgggta      300
cgcttggctt tgaggagtac gttgatccgt tgaagatcta tttacacaag tacagagaga     360
tggagggtga tagtaagctg tcctcaaagg ctggtgatgg ttcagtaaag aaggatacaa     420
ttggtccgca cagtggcgct agtagctcaa gtgcgcaagg gatggttggg gcttacaccc     480
aagggatggg ttatatgcaa cctcagtatc ataatgggga cacctaaaga tgaggatagt     540
gaaaattttc agtaactggt gtcctctgtg agttattatc catctgttaa ggaagaaccc     600
acattagggc                                                           610

<210> SEQ ID NO 38
<211> LENGTH: 164
<212> TYPE: PRT
<213> ORGANISM: Oryza sativa
<220> FEATURE:
<223> OTHER INFORMATION: G3395 polypeptide

<400> SEQUENCE: 38

Met Ala Asp Ala Gly His Asp Glu Ser Gly Ser Pro Pro Arg Ser Gly
1               5                   10                  15

Gly Val Arg Glu Gln Asp Arg Phe Leu Pro Ile Ala Asn Ile Ser Arg
            20                  25                  30

Ile Met Lys Lys Ala Val Pro Ala Asn Gly Lys Ile Ala Lys Asp Ala
        35                  40                  45

Lys Glu Thr Leu Gln Glu Cys Val Ser Glu Phe Ile Ser Phe Val Thr
    50                  55                  60

Ser Glu Ala Ser Asp Lys Cys Gln Lys Glu Lys Arg Lys Thr Ile Asn
65                  70                  75                  80

Gly Glu Asp Leu Leu Phe Ala Met Gly Thr Leu Gly Phe Glu Glu Tyr
                85                  90                  95

Val Asp Pro Leu Lys Ile Tyr Leu His Lys Tyr Arg Glu Met Glu Gly
            100                 105                 110

Asp Ser Lys Leu Ser Ser Lys Ala Gly Asp Gly Ser Val Lys Lys Asp
        115                 120                 125

Thr Ile Gly Pro His Ser Gly Ala Ser Ser Ser Ala Gln Gly Met
    130                 135                 140
```

Val Gly Ala Tyr Thr Gln Gly Met Gly Tyr Met Gln Pro Gln Tyr His
145                 150                 155                 160

Asn Gly Asp Thr

<210> SEQ ID NO 39
<211> LENGTH: 761
<212> TYPE: DNA
<213> ORGANISM: Oryza sativa
<220> FEATURE:
<223> OTHER INFORMATION: G3398

<400> SEQUENCE: 39

```
cctctcctct tcgtcttcct cctcgccttc gcttcgactg cttcgatcga gggagatcga      60
ggttgcgatg ccggattcgg acaacgagtc agggggggccg agcaacgcgg gggagtacgc    120
gtcggcgagg gagcaggaca ggttcctgcc gatcgcgaac gtgagcagga tcatgaagag    180
ggcgctcccg gcgaacgcca agatcagcaa ggacgccaag gagacggtgc aggagtgcgt    240
ctcggagttc atctccttca tcaccggcga ggcctccgac aagtgccagc gggagaagcg    300
caagaccatc aacggcgacg acctcctctg ggcgatgacc acgctcggct cgaggactat    360
catcgacccg ctcaagctct acctccacaa gttccgcgag ctcgagggcg agaaggccat    420
cggcgccgcc ggcagcggcg gcggtggcgc cgcctcctcc ggcggctccg gctccggctc    480
cggctcgcac caccaccagg atgcttcccg gaacaatggc ggatacggca tgtacgcgg    540
cggcggcggc atgatcatga tgatgggaca gcctatgtac ggctcgccgc cggcgtcgtc    600
agctgggtac gcgcagccgc cgccgccccca ccaccaccac caccagatgg tgatgggagg    660
gaaaggtgcg tatggccatg cggcggcggc cggcggcggg ccctcccccgt cgtcgggata    720
cggccggcaa gacaggctat gagcttgctt tcttggttgg t                        761
```

<210> SEQ ID NO 40
<211> LENGTH: 224
<212> TYPE: PRT
<213> ORGANISM: Oryza sativa
<220> FEATURE:
<223> OTHER INFORMATION: G3398 polypeptide

<400> SEQUENCE: 40

Met Pro Asp Ser Asp Asn Glu Ser Gly Gly Pro Ser Asn Ala Gly Glu
1               5                   10                  15

Tyr Ala Ser Ala Arg Glu Gln Asp Arg Phe Leu Pro Ile Ala Asn Val
                20                  25                  30

Ser Arg Ile Met Lys Arg Ala Leu Pro Ala Asn Ala Lys Ile Ser Lys
            35                  40                  45

Asp Ala Lys Glu Thr Val Gln Glu Cys Val Ser Glu Phe Ile Ser Phe
50                  55                  60

Ile Thr Gly Glu Ala Ser Asp Lys Cys Gln Arg Glu Lys Arg Lys Thr
65                  70                  75                  80

Ile Asn Gly Asp Asp Leu Leu Trp Ala Met Thr Thr Leu Gly Phe Glu
                85                  90                  95

Asp Tyr Ile Asp Pro Leu Lys Leu Tyr Leu His Lys Phe Arg Glu Leu
            100                 105                 110

Glu Gly Glu Lys Ala Ile Gly Ala Ala Ser Gly Gly Gly Gly Ala
        115                 120                 125

Ala Ser Ser Gly Gly Ser Gly Ser Gly Ser His His His Gln
    130                 135                 140

Asp Ala Ser Arg Asn Asn Gly Gly Tyr Gly Met Tyr Gly Gly Gly Gly
145                 150                 155                 160

Gly Met Ile Met Met Met Gly Gln Pro Met Tyr Gly Ser Pro Pro Ala
            165                 170                 175

Ser Ser Ala Gly Tyr Ala Gln Pro Pro Pro His His His His His
        180                 185                 190

Gln Met Val Met Gly Gly Lys Gly Ala Tyr Gly His Gly Gly Gly
        195                 200                 205

Gly Gly Gly Pro Ser Pro Ser Ser Gly Tyr Gly Arg Gln Asp Arg Leu
    210                 215                 220

<210> SEQ ID NO 41
<211> LENGTH: 1205
<212> TYPE: DNA
<213> ORGANISM: Zea mays
<220> FEATURE:
<223> OTHER INFORMATION: G3866

<400> SEQUENCE: 41
cggtccggaa ttcccgggtc gacccacgcg tccgcgcacc ctcccgggcc gccttctctt      60
ctccagcgtc cgatctccca ctcccctccc tcaccgcagc tctcccacct ccgccctccc     120
cccgcacgcg ctcgccacct cgccctcccc tccacgttgc tcgcacccgc gcttatataa     180
gtgcaggagg agctcatggc ggaagctccg gcgagccctg gcggcggcgg cgggagccac     240
gagagcggga gccccagggg aggcggaggc ggtggcagcg tcaggagca ggacaggttc     300 ctgcccatcg ccaacatcag tcgcatcatg aagaaggcca tcccggctaa cgggaagacc     360
atcccggcta cgggaagat cgccaaggac gctaaggaga ccgtgcagga gtgcgtctcc     420
gagttcatct ccttcatcac tagcgaagcg agtgacaagt gccagaggga aagcggaag     480 accatcaatg cgacgatct gctgtgggcc atggccacgc tggggtttga agactacatt     540 gaaccccctca aggtgtacct gcagaagtac agagagatgg agggtgatag caagttaact     600
gcaaaatcta gcgatggctc aattaaaaag gatgccctttg gtcatgtggg agcaagtagc     660
tcagctgcac aagggatggg ccaacaggga gcatacaacc aaggaatggg ttatatgcaa     720
ccccagtacc ataacgggga tatctcaaac taatggaggt atggaccttt tctgcgacag     780
ctgctcttac ctgaggcgat ttttttttgtc ttagttattt actaagacac cttgcggtga     840
ccattaaaga gtaaccaatc gccctcaata ggtccgtttt tatctgccag aactgatgag     900
gtcgctcact aggagtaagt cgcttccctg ggaacggttg tcggctagca ccgctcttgt     960
atgtatatta agagtaactt aatgattggt cttttggctg cgatttgatt acatgtattt    1020
gtatcgggag gcataaatat tgtgtaattt tgtgttaaaga ctggtgtaat tgaactatgg    1080
gaagagctgc tttggttgta accatatttt gatgcccgta tattaggcaa aaatagaagg    1140
ctgtgggcgt gcacaacaaa aaaaaaaaaa aaaaaaaaaa aagggcggcc gctctagagg    1200
atcca                                                                1205

<210> SEQ ID NO 42
<211> LENGTH: 185
<212> TYPE: PRT
<213> ORGANISM: Zea mays
<220> FEATURE:
<223> OTHER INFORMATION: G3866 polypeptide

<400> SEQUENCE: 42

Met Ala Glu Ala Pro Ala Ser Pro Gly Gly Gly Gly Ser His Glu
1               5                   10                  15

Ser Gly Ser Pro Arg Gly Gly Gly Gly Gly Ser Val Arg Glu Gln
            20                  25                  30

```
Asp Arg Phe Leu Pro Ile Ala Asn Ile Ser Arg Ile Met Lys Lys Ala
            35                  40                  45

Ile Pro Ala Asn Gly Lys Thr Ile Pro Ala Asn Gly Lys Ile Ala Lys
 50                  55                  60

Asp Ala Lys Glu Thr Val Gln Glu Cys Val Ser Glu Phe Ile Ser Phe
 65                  70                  75                  80

Ile Thr Ser Glu Ala Ser Asp Lys Cys Gln Arg Glu Lys Arg Lys Thr
                 85                  90                  95

Ile Asn Gly Asp Asp Leu Leu Trp Ala Met Ala Thr Leu Gly Phe Glu
            100                 105                 110

Asp Tyr Ile Glu Pro Leu Lys Val Tyr Leu Gln Lys Tyr Arg Glu Met
            115                 120                 125

Glu Gly Asp Ser Lys Leu Thr Ala Lys Ser Ser Asp Gly Ser Ile Lys
        130                 135                 140

Lys Asp Ala Leu Gly His Val Gly Ala Ser Ser Ala Ala Gln Gly
145                 150                 155                 160

Met Gly Gln Gln Gly Ala Tyr Asn Gly Met Gly Tyr Met Gln Pro
                165                 170                 175

Gln Tyr His Asn Gly Asp Ile Ser Asn
            180                 185

<210> SEQ ID NO 43
<211> LENGTH: 837
<212> TYPE: DNA
<213> ORGANISM: Oryza sativa
<220> FEATURE:
<223> OTHER INFORMATION: G3396

<400> SEQUENCE: 43
gtcgagatcc ggcggccggt ggcgtcctcc tccctctccc tcctcccaa ccaacggcgc      60
tgatccctc cgccatctcc gtccatctcc gcctaaaaaa actaagcgat gtcggagggg     120
ttcgacggga cggagaacgg cggcggcggc ggcggaggcg gagtagggaa ggagcaggac    180
cggttcctgc cgatcgccaa catcggccgc atcatgcgcc gggccgtgcc ggagaacggc    240
aagatcgcca aggactccaa ggagtccgtc caggagtgcg tctccgagtt catcagcttc    300
atcaccagcg aagcaagcga caagtgcctc aaggagaagc gcaagaccat caatggggac    360
gacctgatct ggtcaatggg cacgctcgga ttcgaggact atgtcgagcc tctcaagctc    420
tacctcaggc tctaccggga gacggagggt gacacaaagg gttcaagagc ttctgaactg    480
ccagtaaaga aagatgttgt acttaatgga gatcctggat catcgtttga aggcatgtag    540
gacgaggagt gtgatagcat ctaggaagga gaaccatcgt ttttagggaa gaacgctcc     600
agcatcctgt tatgttgtaa gcaggatgct tctaaagttc caataccttg ttaccacgaa    660
tgttagtcgt cgttctttt gaaatgttct tgtgttagcc aggatgtcca aatttgttgt    720
aggttctagt tcagtcgtgt gttgtgtggt tgtgtctaac catatttggc cgtttccggc    780
tgtcctgcat atgctaaatt cagagggta aagagatcta agaaaaaaaa aaaaaaa       837

<210> SEQ ID NO 44
<211> LENGTH: 143
<212> TYPE: PRT
<213> ORGANISM: Oryza sativa
<220> FEATURE:
<223> OTHER INFORMATION: G3396 polypeptide

<400> SEQUENCE: 44

Met Ser Glu Gly Phe Asp Gly Thr Glu Asn Gly Gly Gly Gly Gly Gly
```

```
                 1               5                  10                 15
Gly Gly Val Gly Lys Glu Gln Asp Arg Phe Leu Pro Ile Ala Asn Ile
                    20                  25                  30

Gly Arg Ile Met Arg Arg Ala Val Pro Glu Asn Gly Lys Ile Ala Lys
                    35                  40                  45

Asp Ser Lys Glu Ser Val Gln Glu Cys Val Ser Glu Phe Ile Ser Phe
                50                  55                  60

Ile Thr Ser Glu Ala Ser Asp Lys Cys Leu Lys Glu Lys Arg Lys Thr
 65                  70                  75                  80

Ile Asn Gly Asp Asp Leu Ile Trp Ser Met Gly Thr Leu Gly Phe Glu
                    85                  90                  95

Asp Tyr Val Glu Pro Leu Lys Leu Tyr Leu Arg Leu Tyr Arg Glu Thr
                100                 105                 110

Glu Gly Asp Thr Lys Gly Ser Arg Ala Ser Glu Leu Pro Val Lys Lys
                115                 120                 125

Asp Val Val Leu Asn Gly Asp Pro Gly Ser Ser Phe Glu Gly Met
                130                 135                 140

<210> SEQ ID NO 45
<211> LENGTH: 920
<212> TYPE: DNA
<213> ORGANISM: Oryza sativa
<220> FEATURE:
<223> OTHER INFORMATION: G3429

<400> SEQUENCE: 45
ccaggtcatt gagacttgag agacatggca gggaacaaaa agcgtggtat agtagtatag        60
tcagtactag gattagtact tgataactag cacaacaaaa agctactatc atttttgcat       120
tcaaagtggt aattaagaat cggatgatca ttttgattgt cctcttcat ttgttttgga       180 tgtcaggtgg caggaacatg gatcaggtca agaaggcggc agtgagatcg gatggggtgg       240
gaggtagtgc gaccaacgcc gagctgccga tggccaacct cgtacgcctg ataaagaagg       300
tgctcccagg gaaagcgaag atcggggag cagccaaggg tctcacccat gattgcgcgg       360
tggagttcgt cgggttcgtc ggcgacgagg cctccgagaa ggccaaggca gagcaccgcc       420
gcaccgtagc gccggaagac tacttgggct cattcggcga ccttggcttc gatcgctacg       480
tcgaccccat ggatgcctac atccatggtt accgtgagtt tgagagggct ggtgggaata       540
ggagggtggc gccgcctcct ccggcggcag ctacaccgct gacgcccggt ggaccgacat       600
tcactgacgc agagctgcag tttctccggt cggtgatccc ctccagaagt gatgatgaat       660
atagcggctc atcaccagcc ataggcggct atggctatgg atatggctat ggaaaaaata       720
tgtgaacaac ttgatgcatg tgtgtgtgta cactgcatgc atgcgtggag ggtcaaacag       780
agtcaagact cttgtggtgg tttcaataag tctctagtga caatataagt tgtgtatcgt       840
tgtttccttt gtaaaaaaaa aaacgtcatg tatcgttgtg tgtcctcatc cggtaatcct       900
ttacgtgggt gggttatggc                                                   920

<210> SEQ ID NO 46
<211> LENGTH: 193
<212> TYPE: PRT
<213> ORGANISM: Oryza sativa
<220> FEATURE:
<223> OTHER INFORMATION: G3429 polypeptide

<400> SEQUENCE: 46

Met Ile Ile Leu Ile Val Pro Leu His Leu Phe Trp Met Ser Gly Gly
 1               5                  10                  15
```

```
Arg Asn Met Asp Gln Val Lys Lys Ala Ala Val Arg Ser Asp Gly Val
            20                  25                  30

Gly Gly Ser Ala Thr Asn Ala Glu Leu Pro Met Ala Asn Leu Val Arg
        35                  40                  45

Leu Ile Lys Lys Val Leu Pro Gly Lys Ala Lys Ile Gly Gly Ala Ala
    50                  55                  60

Lys Gly Leu Thr His Asp Cys Ala Val Glu Phe Val Gly Phe Val Gly
65                  70                  75                  80

Asp Glu Ala Ser Glu Lys Ala Lys Ala Glu His Arg Arg Thr Val Ala
                85                  90                  95

Pro Glu Asp Tyr Leu Gly Ser Phe Gly Asp Leu Gly Phe Asp Arg Tyr
            100                 105                 110

Val Asp Pro Met Asp Ala Tyr Ile His Gly Tyr Arg Glu Phe Glu Arg
        115                 120                 125

Ala Gly Gly Asn Arg Arg Val Ala Pro Pro Pro Ala Ala Ala Thr
    130                 135                 140

Pro Leu Thr Pro Gly Gly Pro Thr Phe Thr Asp Ala Glu Leu Gln Phe
145                 150                 155                 160

Leu Arg Ser Val Ile Pro Ser Arg Ser Asp Glu Tyr Ser Gly Ser
                165                 170                 175

Ser Pro Ala Ile Gly Tyr Tyr Gly Tyr Gly Tyr Gly Lys Asn
            180                 185                 190

Met

<210> SEQ ID NO 47
<211> LENGTH: 91
<212> TYPE: PRT
<213> ORGANISM: Arabidopsis thaliana
<220> FEATURE:
<223> OTHER INFORMATION: G481 conserved B domain

<400> SEQUENCE: 47

Arg Glu Gln Asp Arg Tyr Leu Pro Ile Ala Asn Ile Ser Arg Ile Met
1               5                   10                  15

Lys Lys Ala Leu Pro Pro Asn Gly Lys Ile Gly Lys Asp Ala Lys Asp
20                  25                  30

Thr Val Gln Glu Cys Val Ser Glu Phe Ile Ser Phe Ile Thr Ser Glu
35                  40                  45

Ala Ser Asp Lys Cys Gln Lys Glu Lys Arg Lys Thr Val Asn Gly Asp
50                  55                  60

Asp Leu Leu Trp Ala Met Ala Thr Leu Gly Phe Glu Asp Tyr Leu Glu
65                  70                  75                  80

Pro Leu Lys Ile Tyr Leu Ala Arg Tyr Arg Glu
85                  90

<210> SEQ ID NO 48
<211> LENGTH: 91
<212> TYPE: PRT
<213> ORGANISM: Glycine max
<220> FEATURE:
<223> OTHER INFORMATION: G3470 conserved B domain

<400> SEQUENCE: 48

Arg Glu Gln Asp Arg Tyr Leu Pro Ile Ala Asn Ile Ser Arg Ile Met
1               5                   10                  15

Lys Lys Ala Leu Pro Pro Asn Gly Lys Ile Ala Lys Asp Ala Lys Asp
            20                  25                  30
```

```
Thr Met Gln Glu Cys Val Ser Glu Phe Ile Ser Phe Ile Thr Ser Glu
        35                  40                  45

Ala Ser Glu Lys Cys Gln Lys Glu Lys Arg Lys Thr Ile Asn Gly Asp
    50                  55                  60

Asp Leu Leu Trp Ala Met Ala Thr Leu Gly Phe Glu Asp Tyr Ile Glu
65                  70                  75                  80

Pro Leu Lys Val Tyr Leu Ala Arg Tyr Arg Glu
                85                  90

<210> SEQ ID NO 49
<211> LENGTH: 91
<212> TYPE: PRT
<213> ORGANISM: Glycine max
<220> FEATURE:
<223> OTHER INFORMATION: G3471 conserved B domain

<400> SEQUENCE: 49

Arg Glu Gln Asp Arg Tyr Leu Pro Ile Ala Asn Ile Ser Arg Ile Met
1               5                   10                  15

Lys Lys Ala Leu Pro Pro Asn Gly Lys Ile Ala Lys Asp Ala Lys Asp
            20                  25                  30

Thr Met Gln Glu Cys Val Ser Glu Phe Ile Ser Phe Ile Thr Ser Glu
        35                  40                  45

Ala Ser Glu Lys Cys Gln Lys Glu Lys Arg Lys Thr Ile Asn Gly Asp
    50                  55                  60

Asp Leu Leu Trp Ala Met Ala Thr Leu Gly Phe Glu Asp Tyr Ile Glu
65                  70                  75                  80

Pro Leu Lys Val Tyr Leu Ala Arg Tyr Arg Glu
                85                  90

<210> SEQ ID NO 50
<211> LENGTH: 91
<212> TYPE: PRT
<213> ORGANISM: Glycine max
<220> FEATURE:
<223> OTHER INFORMATION: G3875 conserved B domain

<400> SEQUENCE: 50

Arg Glu Gln Asp Arg Tyr Leu Pro Ile Ala Asn Ile Ser Arg Ile Met
1               5                   10                  15

Lys Lys Ala Leu Pro Ala Asn Gly Lys Ile Ala Lys Asp Ala Lys Glu
            20                  25                  30

Thr Val Gln Glu Cys Val Ser Glu Phe Ile Ser Phe Ile Thr Ser Glu
        35                  40                  45

Ala Ser Asp Lys Cys Gln Arg Glu Lys Arg Lys Thr Ile Asn Gly Asp
    50                  55                  60

Asp Leu Leu Trp Ala Met Ala Thr Leu Gly Phe Glu Asp Tyr Ile Asp
65                  70                  75                  80

Pro Leu Lys Ile Tyr Leu Thr Arg Tyr Arg Glu
                85                  90

<210> SEQ ID NO 51
<211> LENGTH: 91
<212> TYPE: PRT
<213> ORGANISM: Zea mays
<220> FEATURE:
<223> OTHER INFORMATION: G3876 conserved B domain

<400> SEQUENCE: 51

Arg Glu Gln Asp Arg Phe Leu Pro Ile Ala Asn Ile Ser Arg Ile Met
1               5                   10                  15
```

```
Lys Lys Ala Ile Pro Ala Asn Gly Lys Ile Ala Lys Asp Ala Lys Glu
            20                  25                  30

Thr Val Gln Glu Cys Val Ser Glu Phe Ile Ser Phe Ile Thr Ser Glu
            35                  40                  45

Ala Ser Asp Lys Cys Gln Arg Glu Lys Arg Lys Thr Ile Asn Gly Asp
            50                  55                  60

Asp Leu Leu Trp Ala Met Ala Thr Leu Gly Phe Glu Asp Tyr Ile Glu
65                  70                  75                  80

Pro Leu Lys Val Tyr Leu Gln Lys Tyr Arg Glu
                85                  90

<210> SEQ ID NO 52
<211> LENGTH: 91
<212> TYPE: PRT
<213> ORGANISM: Zea mays
<220> FEATURE:
<223> OTHER INFORMATION: G3434 conserved B domain

<400> SEQUENCE: 52

Arg Glu Gln Asp Arg Phe Leu Pro Ile Ala Asn Ile Ser Arg Ile Met
1               5                   10                  15

Lys Lys Ala Val Pro Ala Asn Gly Lys Ile Ala Lys Asp Ala Lys Glu
            20                  25                  30

Thr Leu Gln Glu Cys Val Ser Glu Phe Ile Ser Phe Val Thr Ser Glu
            35                  40                  45

Ala Ser Asp Lys Cys Gln Lys Glu Lys Arg Lys Thr Ile Asn Gly Asp
            50                  55                  60

Asp Leu Leu Trp Ala Met Ala Thr Leu Gly Phe Glu Glu Tyr Val Glu
65                  70                  75                  80

Pro Leu Lys Ile Tyr Leu Gln Lys Tyr Lys Glu
                85                  90

<210> SEQ ID NO 53
<211> LENGTH: 91
<212> TYPE: PRT
<213> ORGANISM: Arabidopsis thaliana
<220> FEATURE:
<223> OTHER INFORMATION: G1364 conserved B domain

<400> SEQUENCE: 53

Arg Glu Gln Asp Arg Phe Leu Pro Ile Ala Asn Ile Ser Arg Ile Met
1               5                   10                  15

Lys Arg Gly Leu Pro Ala Asn Gly Lys Ile Ala Lys Asp Ala Lys Glu
            20                  25                  30

Ile Val Gln Glu Cys Val Ser Glu Phe Ile Ser Phe Val Thr Ser Glu
            35                  40                  45

Ala Ser Asp Lys Cys Gln Arg Glu Lys Arg Lys Thr Ile Asn Gly Asp
            50                  55                  60

Asp Leu Leu Trp Ala Met Ala Thr Leu Gly Phe Glu Asp Tyr Met Glu
65                  70                  75                  80

Pro Leu Lys Val Tyr Leu Met Arg Tyr Arg Glu
                85                  90

<210> SEQ ID NO 54
<211> LENGTH: 91
<212> TYPE: PRT
<213> ORGANISM: Glycine max
<220> FEATURE:
<223> OTHER INFORMATION: G3475 conserved B domain
```

-continued

<400> SEQUENCE: 54

Arg Glu Gln Asp Arg Phe Leu Pro Ile Ala Asn Val Ser Arg Ile Met
1               5                   10                  15

Lys Lys Ala Leu Pro Ala Asn Ala Lys Ile Ser Lys Asp Ala Lys Glu
            20                  25                  30

Thr Val Gln Glu Cys Val Ser Glu Phe Ile Ser Phe Ile Thr Gly Glu
        35                  40                  45

Ala Ser Asp Lys Cys Gln Arg Glu Lys Arg Lys Thr Ile Asn Gly Asp
    50                  55                  60

Asp Leu Leu Trp Ala Met Thr Thr Leu Gly Phe Glu Asp Tyr Val Glu
65                  70                  75                  80

Pro Leu Lys Gly Tyr Leu Gln Arg Phe Arg Glu
                85                  90

<210> SEQ ID NO 55
<211> LENGTH: 91
<212> TYPE: PRT
<213> ORGANISM: Arabidopsis thaliana
<220> FEATURE:
<223> OTHER INFORMATION: G485 conserved B domain

<400> SEQUENCE: 55

Arg Glu Gln Asp Arg Phe Leu Pro Ile Ala Asn Val Ser Arg Ile Met
1               5                   10                  15

Lys Lys Ala Leu Pro Ala Asn Ala Lys Ile Ser Lys Asp Ala Lys Glu
            20                  25                  30

Thr Val Gln Glu Cys Val Ser Glu Phe Ile Ser Phe Ile Thr Gly Glu
        35                  40                  45

Ala Ser Asp Lys Cys Gln Arg Glu Lys Arg Lys Thr Ile Asn Gly Asp
    50                  55                  60

Asp Leu Leu Trp Ala Met Thr Thr Leu Gly Phe Glu Asp Tyr Val Glu
65                  70                  75                  80

Pro Leu Lys Val Tyr Leu Gln Lys Tyr Arg Glu
                85                  90

<210> SEQ ID NO 56
<211> LENGTH: 91
<212> TYPE: PRT
<213> ORGANISM: Glycine max
<220> FEATURE:
<223> OTHER INFORMATION: G3476 conserved B domain

<400> SEQUENCE: 56

Arg Glu Gln Asp Arg Phe Leu Pro Ile Ala Asn Val Ser Arg Ile Met
1               5                   10                  15

Lys Lys Ala Leu Pro Ala Asn Ala Lys Ile Ser Lys Asp Ala Lys Glu
            20                  25                  30

Thr Val Gln Glu Cys Val Ser Glu Phe Ile Ser Phe Ile Thr Gly Glu
        35                  40                  45

Ala Ser Asp Lys Cys Gln Arg Glu Lys Arg Lys Thr Ile Asn Gly Asp
    50                  55                  60

Asp Leu Leu Trp Ala Met Thr Thr Leu Gly Phe Glu Glu Tyr Val Glu
65                  70                  75                  80

Pro Leu Lys Ile Tyr Leu Gln Arg Phe Arg Glu
                85                  90

<210> SEQ ID NO 57
<211> LENGTH: 91
<212> TYPE: PRT

```
<213> ORGANISM: Arabidopsis thaliana
<220> FEATURE:
<223> OTHER INFORMATION: G2345 conserved B domain

<400> SEQUENCE: 57

Arg Glu Gln Asp Arg Phe Leu Pro Ile Ala Asn Ile Ser Arg Ile Met
1               5                   10                  15

Lys Arg Gly Leu Pro Leu Asn Gly Lys Ile Ala Lys Asp Ala Lys Glu
            20                  25                  30

Thr Met Gln Glu Cys Val Ser Glu Phe Ile Ser Phe Val Thr Ser Glu
        35                  40                  45

Ala Ser Asp Lys Cys Gln Arg Glu Lys Arg Lys Thr Ile Asn Gly Asp
    50                  55                  60

Asp Leu Leu Trp Ala Met Ala Thr Leu Gly Phe Glu Asp Tyr Ile Asp
65                  70                  75                  80

Pro Leu Lys Val Tyr Leu Met Arg Tyr Arg Glu
                85                  90

<210> SEQ ID NO 58
<211> LENGTH: 91
<212> TYPE: PRT
<213> ORGANISM: Glycine max
<220> FEATURE:
<223> OTHER INFORMATION: G3474 conserved B domain

<400> SEQUENCE: 58

Arg Glu Gln Asp Arg Phe Leu Pro Ile Ala Asn Val Ser Arg Ile Met
1               5                   10                  15

Lys Lys Ala Leu Pro Ala Asn Ala Lys Ile Ser Lys Glu Ala Lys Glu
            20                  25                  30

Thr Val Gln Glu Cys Val Ser Glu Phe Ile Ser Phe Ile Thr Gly Glu
        35                  40                  45

Ala Ser Asp Lys Cys Gln Lys Glu Lys Arg Lys Thr Ile Asn Gly Asp
    50                  55                  60

Asp Leu Leu Trp Ala Met Thr Thr Leu Gly Phe Glu Asp Tyr Val Asp
65                  70                  75                  80

Pro Leu Lys Ile Tyr Leu His Lys Tyr Arg Glu
                85                  90

<210> SEQ ID NO 59
<211> LENGTH: 91
<212> TYPE: PRT
<213> ORGANISM: Glycine max
<220> FEATURE:
<223> OTHER INFORMATION: G3478 conserved B domain

<400> SEQUENCE: 59

Arg Glu Gln Asp Arg Phe Leu Pro Ile Ala Asn Val Ser Arg Ile Met
1               5                   10                  15

Lys Lys Ala Leu Pro Ala Asn Ala Lys Ile Ser Lys Asp Ala Lys Glu
            20                  25                  30

Thr Val Gln Glu Cys Val Ser Glu Phe Ile Ser Phe Ile Thr Gly Glu
        35                  40                  45

Ala Ser Asp Lys Cys Gln Arg Glu Lys Arg Lys Thr Ile Asn Gly Asp
    50                  55                  60

Asp Leu Leu Trp Ala Met Thr Thr Leu Gly Phe Glu Asp Tyr Val Glu
65                  70                  75                  80

Pro Leu Lys Gly Tyr Leu Gln Arg Phe Arg Glu
                85                  90
```

```
<210> SEQ ID NO 60
<211> LENGTH: 91
<212> TYPE: PRT
<213> ORGANISM: Arabidopsis thaliana
<220> FEATURE:
<223> OTHER INFORMATION: G482 conserved B domain

<400> SEQUENCE: 60

Arg Glu Gln Asp Arg Phe Leu Pro Ile Ala Asn Val Ser Arg Ile Met
1               5                   10                  15

Lys Lys Ala Leu Pro Ala Asn Ala Lys Ile Ser Lys Asp Ala Lys Glu
            20                  25                  30

Thr Met Gln Glu Cys Val Ser Glu Phe Ile Ser Phe Val Thr Gly Glu
        35                  40                  45

Ala Ser Asp Lys Cys Gln Lys Glu Lys Arg Lys Thr Ile Asn Gly Asp
    50                  55                  60

Asp Leu Leu Trp Ala Met Thr Thr Leu Gly Phe Glu Asp Tyr Val Glu
65                  70                  75                  80

Pro Leu Lys Val Tyr Leu Gln Arg Phe Arg Glu
                85                  90

<210> SEQ ID NO 61
<211> LENGTH: 91
<212> TYPE: PRT
<213> ORGANISM: Zea mays
<220> FEATURE:
<223> OTHER INFORMATION: G3435 conserved B domain

<400> SEQUENCE: 61

Arg Glu Gln Asp Arg Phe Leu Pro Ile Ala Asn Val Ser Arg Ile Met
1               5                   10                  15

Lys Lys Ala Leu Pro Ala Asn Ala Lys Ile Ser Lys Asp Ala Lys Glu
            20                  25                  30

Thr Val Gln Glu Cys Val Ser Glu Phe Ile Ser Phe Ile Thr Gly Glu
        35                  40                  45

Ala Ser Asp Lys Cys Gln Arg Glu Lys Arg Lys Thr Ile Asn Gly Asp
    50                  55                  60

Asp Leu Leu Trp Ala Met Thr Thr Leu Gly Phe Glu Asp Tyr Val Glu
65                  70                  75                  80

Pro Leu Lys His Tyr Leu His Lys Phe Arg Glu
                85                  90

<210> SEQ ID NO 62
<211> LENGTH: 91
<212> TYPE: PRT
<213> ORGANISM: Glycine max
<220> FEATURE:
<223> OTHER INFORMATION: G3472 conserved B domain

<400> SEQUENCE: 62

Arg Glu Gln Asp Arg Phe Leu Pro Ile Ala Asn Val Ser Arg Ile Met
1               5                   10                  15

Lys Lys Ala Leu Pro Ala Asn Ala Lys Ile Ser Lys Glu Ala Lys Glu
            20                  25                  30

Thr Val Gln Glu Cys Val Ser Glu Phe Ile Ser Phe Ile Thr Gly Glu
        35                  40                  45

Ala Ser Asp Lys Cys Gln Lys Glu Lys Arg Lys Thr Ile Asn Gly Asp
    50                  55                  60

Asp Leu Leu Trp Ala Met Thr Thr Leu Gly Phe Glu Glu Tyr Val Glu
65                  70                  75                  80
```

```
Pro Leu Lys Val Tyr Leu His Lys Tyr Arg Glu
                85                  90

<210> SEQ ID NO 63
<211> LENGTH: 91
<212> TYPE: PRT
<213> ORGANISM: Zea mays
<220> FEATURE:
<223> OTHER INFORMATION: G3436 conserved B domain

<400> SEQUENCE: 63

Arg Glu Gln Asp Arg Phe Leu Pro Ile Ala Asn Val Ser Arg Ile Met
1               5                   10                  15

Lys Lys Ala Leu Pro Ala Asn Ala Lys Ile Ser Lys Asp Ala Lys Glu
            20                  25                  30

Thr Val Gln Glu Cys Val Ser Glu Phe Ile Ser Phe Ile Thr Gly Glu
        35                  40                  45

Ala Ser Asp Lys Cys Gln Arg Glu Lys Arg Lys Thr Ile Asn Gly Asp
    50                  55                  60

Asp Leu Leu Trp Ala Met Thr Thr Leu Gly Phe Glu Asp Tyr Val Glu
65                  70                  75                  80

Pro Leu Lys Leu Tyr Leu His Lys Phe Arg Glu
                85                  90

<210> SEQ ID NO 64
<211> LENGTH: 91
<212> TYPE: PRT
<213> ORGANISM: Oryza sativa
<220> FEATURE:
<223> OTHER INFORMATION: G3397 conserved B domain

<400> SEQUENCE: 64

Arg Glu Gln Asp Arg Phe Leu Pro Ile Ala Asn Val Ser Arg Ile Met
1               5                   10                  15

Lys Lys Ala Leu Pro Ala Asn Ala Lys Ile Ser Lys Asp Ala Lys Glu
            20                  25                  30

Thr Val Gln Glu Cys Val Ser Glu Phe Ile Ser Phe Ile Thr Gly Glu
        35                  40                  45

Ala Ser Asp Lys Cys Gln Arg Glu Lys Arg Lys Thr Ile Asn Gly Asp
    50                  55                  60

Asp Leu Leu Trp Ala Met Thr Thr Leu Gly Phe Glu Asp Tyr Val Asp
65                  70                  75                  80

Pro Leu Lys His Tyr Leu His Lys Phe Arg Glu
                85                  90

<210> SEQ ID NO 65
<211> LENGTH: 91
<212> TYPE: PRT
<213> ORGANISM: Oryza sativa
<220> FEATURE:
<223> OTHER INFORMATION: G3395 conserved B domain

<400> SEQUENCE: 65

Arg Glu Gln Asp Arg Phe Leu Pro Ile Ala Asn Ile Ser Arg Ile Met
1               5                   10                  15

Lys Lys Ala Val Pro Ala Asn Gly Lys Ile Ala Lys Asp Ala Lys Glu
            20                  25                  30

Thr Leu Gln Glu Cys Val Ser Glu Phe Ile Ser Phe Val Thr Ser Glu
        35                  40                  45

Ala Ser Asp Lys Cys Gln Lys Glu Lys Arg Lys Thr Ile Asn Gly Glu
```

```
                50                  55                  60
Asp Leu Leu Phe Ala Met Gly Thr Leu Gly Phe Glu Glu Tyr Val Asp
 65                  70                  75                  80

Pro Leu Lys Ile Tyr Leu His Lys Tyr Arg Glu
                 85                  90

<210> SEQ ID NO 66
<211> LENGTH: 91
<212> TYPE: PRT
<213> ORGANISM: Oryza sativa
<220> FEATURE:
<223> OTHER INFORMATION: G3398 conserved B domain

<400> SEQUENCE: 66

Arg Glu Gln Asp Arg Phe Leu Pro Ile Ala Asn Val Ser Arg Ile Met
 1               5                  10                  15

Lys Arg Ala Leu Pro Ala Asn Ala Lys Ile Ser Lys Asp Ala Lys Glu
                20                  25                  30

Thr Val Gln Glu Cys Val Ser Glu Phe Ile Ser Phe Ile Thr Gly Glu
             35                  40                  45

Ala Ser Asp Lys Cys Gln Arg Glu Lys Arg Lys Thr Ile Asn Gly Asp
         50                  55                  60

Asp Leu Leu Trp Ala Met Thr Thr Leu Gly Phe Glu Asp Tyr Ile Asp
 65                  70                  75                  80

Pro Leu Lys Leu Tyr Leu His Lys Phe Arg Glu
                 85                  90

<210> SEQ ID NO 67
<211> LENGTH: 98
<212> TYPE: PRT
<213> ORGANISM: Zea mays
<220> FEATURE:
<223> OTHER INFORMATION: G3866 conserved B domain

<400> SEQUENCE: 67

Arg Glu Gln Asp Arg Phe Leu Pro Ile Ala Asn Ile Ser Arg Ile Met
 1               5                  10                  15

Lys Lys Ala Ile Pro Ala Asn Gly Lys Thr Ile Pro Ala Asn Gly Lys
                20                  25                  30

Ile Ala Lys Asp Ala Lys Glu Thr Val Gln Glu Cys Val Ser Glu Phe
             35                  40                  45

Ile Ser Phe Ile Thr Ser Glu Ala Ser Asp Lys Cys Gln Arg Glu Lys
         50                  55                  60

Arg Lys Thr Ile Asn Gly Asp Asp Leu Leu Trp Ala Met Ala Thr Leu
 65                  70                  75                  80

Gly Phe Glu Asp Tyr Ile Glu Pro Leu Lys Val Tyr Leu Gln Lys Tyr
                 85                  90                  95

Arg Glu

<210> SEQ ID NO 68
<211> LENGTH: 91
<212> TYPE: PRT
<213> ORGANISM: Oryza sativa
<220> FEATURE:
<223> OTHER INFORMATION: G3396 conserved B domain

<400> SEQUENCE: 68

Lys Glu Gln Asp Arg Phe Leu Pro Ile Ala Asn Ile Gly Arg Ile Met
 1               5                  10                  15

Arg Arg Ala Val Pro Glu Asn Gly Lys Ile Ala Lys Asp Ser Lys Glu
```

```
              20                  25                  30
Ser Val Gln Glu Cys Val Ser Glu Phe Ile Ser Phe Ile Thr Ser Glu
         35                  40                  45

Ala Ser Asp Lys Cys Leu Lys Glu Lys Arg Lys Thr Ile Asn Gly Asp
 50                  55                  60

Asp Leu Ile Trp Ser Met Gly Thr Leu Gly Phe Glu Asp Tyr Val Glu
65                  70                  75                  80

Pro Leu Lys Leu Tyr Leu Arg Leu Tyr Arg Glu
                 85                  90

<210> SEQ ID NO 69
<211> LENGTH: 89
<212> TYPE: PRT
<213> ORGANISM: Oryza sativa
<220> FEATURE:
<223> OTHER INFORMATION: G3429 conserved B domain

<400> SEQUENCE: 69

Thr Asn Ala Glu Leu Pro Met Ala Asn Leu Val Arg Leu Ile Lys Lys
1               5                  10                  15

Val Leu Pro Gly Lys Ala Lys Ile Gly Gly Ala Lys Gly Leu Thr
             20                  25                  30

His Asp Cys Ala Val Glu Phe Val Gly Phe Val Gly Asp Glu Ala Ser
         35                  40                  45

Glu Lys Ala Lys Ala Glu His Arg Arg Thr Val Ala Pro Glu Asp Tyr
 50                  55                  60

Leu Gly Ser Phe Gly Asp Leu Gly Phe Asp Arg Tyr Val Asp Pro Met
65                  70                  75                  80

Asp Ala Tyr Ile His Gly Tyr Arg Glu
                 85

<210> SEQ ID NO 70
<211> LENGTH: 831
<212> TYPE: DNA
<213> ORGANISM: artificial sequence
<220> FEATURE:
<223> OTHER INFORMATION: P46 expression vector (for preparing 35S::G481)

<400> SEQUENCE: 70
agcgtttcgt agaaaaattc gatttctcta aagccctaaa actaaaacga ctatccccaa      60
ttccaagttc tagggtttcc atcttcccca atctagtata aatggcggat acgccttcga     120
gcccagctgg agatggcgga gaaagcggcg gttccgttag ggagcaggat cgataccttc     180
ctatagctaa tatcagcagg atcatgaaga aagcgttgcc tcctaatggt aagattggaa     240
aagatgctaa ggatacagtt caggaatgcg tctctgagtt catcagcttc atcactagcg     300
aggccagtga taagtgtcaa aaagagaaaa ggaaaactgt gaatggtgat gatttgttgt     360
gggcaatggc aacattagga tttgaggatt acctggaacc tctaaagata tacctagcga     420
ggtacaggga gttggagggt gataataagg gatcaggaaa gagtggagat ggatcaaata     480
gagatgctgg tggcggtgtt tctggtgaag aaatgccgag ctggtaaaag aagttgcaag     540
tagtgattaa gaacaatcgc caaatgatca agggaaatta gagatcagtg agttgtttat     600
agttgagctg atcgacaact atttcgggtt tactctcaat ttcggttatg ttagtttgaa     660
cgtttggttt attgtttccg gtttagttgg ttgtatttaa agatttctct gttagatgtt     720
gagaacactt gaatgaagga aaatttgtc cacatcctgt tgttattttc gattcacttt     780
cggaatttca tagctaattt attctcattt aataccaaat ccttaaatta a              831
```

-continued

<210> SEQ ID NO 71
<211> LENGTH: 1183
<212> TYPE: DNA
<213> ORGANISM: artificial sequence
<220> FEATURE:
<223> OTHER INFORMATION: P5287 expression vector (LTP1::G481)

<400> SEQUENCE: 71

| gatatgacca | aaatgattaa | cttgcattac | agttgggaag | tatcaagtaa | acaacatttt | 60 |
| gttttttgttt | gatatcggga | atctcaaaac | caaagtccac | actagttttt | ggactatata | 120 |
| atgataaaag | tcagatatct | actaatacta | gttgatcagt | atattcgaaa | acatgactttt | 180 |
| ccaaatgtaa | gttatttact | ttttttttgc | tattataatt | aagatcaata | aaaatgtcta | 240 |
| agttttaaat | ctttatcatt | atatccaaac | aatcataatc | ttattgttaa | tctctcatca | 300 |
| acacacagtt | tttaaaataa | attaattacc | ctttgcatga | taccgaagag | aaacgaattc | 360 |
| gttcaaataa | ttttataaca | ggaaataaaa | tagataaccg | aaataaacga | tagaatgatt | 420 |
| tcttagtact | aactcttaac | aacagtttta | tttaaatgac | ttttgtaaaa | aaaacaaagt | 480 |
| taacttatac | acgtacacgt | gtcgaaaata | ttattgacaa | tggatagcat | gattcttatt | 540 |
| agagtcatgt | aaaagataaa | cacatgcaaa | tatatatatg | aataatatgt | tgttaagata | 600 |
| aactagacga | ttagaatata | tagcacatct | atagtttgta | aaataactat | ttctcaacta | 660 |
| gacttaagtc | ttcgaaatac | ataaataaac | aaaactataa | aaattcagaa | aaaaacatga | 720 |
| gagtacgtta | gtaaaatgta | tttttttggt | aaaataatca | cttttcatca | ggtcttttgt | 780 |
| aaagcagttt | tcatgttaga | taaacgagat | tttaattttt | tttaaaaaaa | gaagtaaaact | 840 |
| aactatgttc | ctatctacac | acctataatt | ttgaacaatt | acaaaacaac | aatgaaatgc | 900 |
| aaagaagacg | tagggcactg | tcacactaca | atacgattaa | taaatgtatt | ttggtcgaat | 960 |
| taataacttt | ccatacgata | aagttgaatt | aacatgtcaa | acaaagaga | tgagtggtcc | 1020 |
| tatacatagt | taggaattag | gaacctctaa | attaaatgag | tacaaccacc | aactactcct | 1080 |
| tccctctata | atctatcgca | ttcacaccac | ataacatata | cgtacctact | ctatataaca | 1140 |
| ctcactcccc | aaactctctt | catcatccat | cactacacac | atc | | 1183 |

<210> SEQ ID NO 72
<211> LENGTH: 831
<212> TYPE: DNA
<213> ORGANISM: artificial sequence
<220> FEATURE:
<223> OTHER INFORMATION: P6812 expression vector (opLexA::G481)

<400> SEQUENCE: 72

| agcgtttcgt | agaaaaattc | gatttctcta | aagccctaaa | actaaaacga | ctatccccaa | 60 |
| ttccaagttc | tagggtttcc | atcttcccca | atctagtata | aatggcggat | acgccttcga | 120 |
| gcccagctgg | agatggcgga | gaaagcggcg | gttccgttag | ggagcaggat | cgataccttc | 180 |
| ctatagctaa | tatcagcagg | atcatgaaga | aagcgttgcc | tcctaatggt | aagattggaa | 240 |
| aagatgctaa | ggatacagtt | caggaatgcg | tctctgagtt | catcagcttc | atcactagcg | 300 |
| aggccagtga | taagtgtcaa | aaagagaaaa | ggaaaactgt | gaatggtgat | gatttgttgt | 360 |
| gggcaatggc | aacattagga | tttgaggatt | acctggaacc | tctaaagata | tacctagcga | 420 |
| ggtacaggga | gttggagggt | gataataagg | gatcaggaaa | gagtggagat | ggatcaaata | 480 |
| gagatgctgg | tggcggtgtt | tctggtgaag | aaatgccgag | ctggtaaaag | aagttgcaag | 540 |
| tagtgattaa | gaacaatcgc | caaatgatca | agggaaatta | gagatcagtg | agttgtttat | 600 |

```
agttgagctg atcgacaact atttcggggtt tactctcaat ttcggttatg ttagtttgaa    660
cgtttggttt attgtttccg gtttagttgg ttgtatttaa agatttctct gttagatgtt    720
gagaacactt gaatgaagga aaaatttgtc cacatcctgt tgttattttc gattcacttt    780
cggaatttca tagctaattt attctcattt aataccaaat ccttaaatta a             831

<210> SEQ ID NO 73
<211> LENGTH: 847
<212> TYPE: DNA
<213> ORGANISM: artificial sequence
<220> FEATURE:
<223> OTHER INFORMATION: P21522 expression vector (SUC2::G481)

<400> SEQUENCE: 73
tcgacccacg cgtccgagcg tttcgtagaa aaattcgatt tctctaaagc cctaaaacta     60
aaacgactat ccccaattcc aagttctagg gtttccatct tccccaatct agtataaatg    120
gcggatacgc cttcgagccc agctggagat ggcggagaaa gcggcggttc cgttagggag    180
caggatcgat accttcctat agctaatatc agcaggatca tgaagaaagc gttgcctcct    240
aatggtaaga ttggaaaaga tgctaaggat acagttcagg aatgcgtctc tgagttcatc    300
agcttcatca ctagcgaggc cagtgataag tgtcaaaaag agaaaggaa aactgtgaat    360 ggtgatgatt tgttgtgggc aatggcaaca ttaggatttg aggattaccct ggaacctcta    420 aagatatacc tagcgaggta cagggagttg gagggtgata ataagggatc aggaaagagt    480
ggagatggat caaatagaga tgctggtggc ggtgtttctg gtgaagaaat gccgagctgg    540
taaaagaagt tgcaagtagt gattaagaac aatcgccaaa tgatcaaggg aaattagaga    600
tcagtgagtt gtttatagtt gagctgatcg acaactattt cgggtttact ctcaatttcg    660
gttatgttag tttgaacgtt tggttattg tttccggttt agttggttgt atttaaagat    720
ttctctgtta gatgttgaga acacttgaat gaaggaaaaa tttgtccaca tcctgttgtt    780
attttcgatt cactttcgga atttcatagc taatttattc tcatttaata ccaaatcctt    840
aaattaa                                                              847

<210> SEQ ID NO 74
<211> LENGTH: 2365
<212> TYPE: DNA
<213> ORGANISM: artificial sequence
<220> FEATURE:
<223> OTHER INFORMATION: P5311 expression vector (ARSK1::LexA-GAL4TA)

<400> SEQUENCE: 74
ggcgagtgat ggtatattta ttggttgggc ttaaatatat ttcagatgca aaccatatt     60 gaatcaataa attataaata catagcttcc ctaaccactt aaaccaccag ctacaaaacc    120
aataaacccg atcaatcatt atgttttcat aggatttcct gaacatacat taaattattt    180
ttcattttct tggtgctctt ttctgtctta ttcacgtttt aatggacata atcggtttca    240
tattgtaaat ctctttaacc taacgaacaa tttaatgacc ctagtaatag ataagaagg    300 tcgtgaaaaa tgaacgagaa aaacccacc aaaacactat ataagaaaga ccgaaaaagt    360
aaaaagggtg agccataaac caaaaacctt accagatgtt gtcaaagaac aaaaatcatc    420
atccatgatt aacctacgct tcactactaa gacaaggcga ttgtgtcccg gttgaaaagg    480
ttgtaaaaca gtttgaggat gctacaaaag tggatgttaa gtatgaagcg gctaaggttt    540
tggatttggt ctaggagcac attggttaag caatatcttc ggtggagatt gagtttttag    600
agatagtaga tactaattca tctatggaga catgcaaatt catcaaaatg cttggatgaa    660
```

-continued

```
ttagaaaaac taggtggaga atacagtaaa aaaattcaaa aagtgcatat tgtttggaca      720
acattaatat gtacaaatag tttacattta aatgtattat tttactaatt aagtacatat      780
aaagttgcta aactaaacta atataatttt tgcataagta aatttatcgt taaaagtttt      840
ctttctagcc actaaacaac aatacaaaat cgcccaagtc acccattaat taatttagaa      900
gtgaaaaaca aaatcttaat tatatggacg atcttgtcta ccatatttca agggctacag      960
gcctacagcc gccgaataaa tcttaccagc cttaaaccag aacaacggca ataagttca     1020 tgtggcggct ggtgatgatt cacaatttcc ccgacagttc tatgataatg aaactatata     1080
attattgtac gtacatacat gcatgcgacg aacaacactt caatttaatt gttagtatta     1140
aattacattt atagtgaagt atgttgggac gattagacgg atacaatgca cttatgttct     1200
ccggaaaatg aatcatttgt gttcagagca tgactccaag agtcaaaaaa gttattaaat     1260
ttatttgaat ttaaaactta aaaatagtgt aattttaac cacccgctgc cgcaaacgtt      1320
ggcggaagaa tacgcggtgt taaacaattt ttgtgatcgt tgtcaaacat ttgtaaccgc     1380
aatctctact gcacaatctg ttacgtttac aatttacaag ttagtataga agaacgttcg     1440
tacctgaaga ccaaccgacc tttagttatt gaataaatga ttatttagtt aagagtaaca     1500
aaatcaatgg ttcaaatttg tttctcttcc ttacttctta aattttaatc atggaagaaa     1560
caaagtcaac ggacatccaa ttatggccta atcatctcat tctcctttca acaaggcgaa     1620
tcaaatcttc tttatacgta atatttattt gccagcctga aatgtatacc aaatcatttt     1680
taaattaatt gcctaaatta ttagaacaaa aactattagt aaataactaa ttagtcttat     1740
gaaactagaa atcgagatag tggaatatag agagacacca ttaaattcac aaaatcattt     1800
ttaaattacc taaattatta caacaaaaac tattagacag aactaagtct ataatgaaac     1860
gagagatcgt atttggaatg tagagcgaga gacaattttc aattcattga atatataagc     1920
aaaattatat agcccgtaga ctttggtgag atgaagtcta agtacaaaca actgaatgaa     1980
tttataatca ataatattga ttatattgtg attagaaaaa gaaaacaact tgcgttattt     2040
ttcaatatta ttgtgaggat taatgtgaac atggaatcgt gtttctcctg aaaaaaatat     2100
cagcatagag cttagaacaa tataaatata tccaccaaaa ataacttcaa cattttata     2160 caactaatac aaaaaaaaaa aagcaaactt tttgtatata taaataaatt tgaaaactca     2220
aaggtcggtc agtacgaata agacacaaca actactataa attagaggac tttgaagaca     2280
agtaggttaa ctagaacatc cttaatttct aaacctacgc actctacaaa agattcatca     2340
aaaggagtaa aagactaact ttctc                                           2365
```

<210> SEQ ID NO 75
<211> LENGTH: 1510
<212> TYPE: DNA
<213> ORGANISM: artificial sequence
<220> FEATURE:
<223> OTHER INFORMATION: P9002 expression vector (RD29A::LexA-GAL4TA)

<400> SEQUENCE: 75

```
ggttgctatg gtagggacta tggggttttc ggattccggt ggaagtgagt ggggaggcag       60
tggcggaggt aagggagttc aagattctgg aactgaagat ttggggtttt gcttttgaat      120
gtttgcgttt ttgtatgatg cctctgtttg tgaactttga tgtatttat ctttgtgtga      180 aaaagagatt gggttaataa aatatttgct ttttggata agaaactctt ttagcggccc      240
attaataaag gttacaaatg caaaatcatg ttagcgtcag atatttaatt attcgaagat      300
gattgtgata gatttaaaat tatcctagtc aaaaagaaag agtaggttga gcagaaacag      360
```

```
tgacatctgt tgtttgtacc atacaaatta gtttagatta ttggttaaca tgttaaatgg      420
ctatgcatgt gacatttaga ccttatcgga attaatttgt agaattatta attaagatgt      480
tgattagttc aaacaaaaat tttatattaa aaaatgtaaa cgaatatttt gtatgttcag      540
tgaaagtaaa acaaattaaa ttaacaagaa acttatagaa gaaaattttt actatttaag      600
agaaagaaaa aaatctatca tttaatctga gtcctaaaaa ctgttatact taacagttaa      660
cgcatgattt gatggaggag ccatagatgc aattcaatca aactgaaatt tctgcaagaa      720
tctcaaacac ggagatctca aagtttgaaa gaaaatttat ttcttcgact caaaacaaac      780
ttacgaaatt taggtagaac ttatatacat tatattgtaa ttttttgtaa caaaatgttt      840
ttattattat tatagaatt tactggttaa attaaaaatg aatagaaaag gtgaattaag       900
aggagagagg aggtaaacat tttcttctat tttttcatat tttcaggata aattattgta      960
aaagtttaca agatttccat ttgactagtg taaatgagga atattctcta gtaagatcat     1020
tatttcatct acttctttta tcttctacca gtagaggaat aaacaatatt tagctccttt     1080
gtaaatacaa attaattttc cttcttgaca tcattcaatt ttaattttac gtataaaata     1140
aaagatcata cctattagaa cgattaagga gaaataacaat tcgaatgaga aggatgtgcc    1200
gtttgttata ataaacagcc acacgacgta aacgtaaaat gaccacatga tgggccaata     1260
gacatggacc gactactaat aatagtaagt tacattttag gatggaataa atatcatacc     1320
gacatcagtt ttgaaagaaa agggaaaaaa agaaaaaata aataaaagat atactaccga     1380
catgagttcc aaaaagcaaa aaaaaagatc aagccgacac agacacgcgt agagagcaaa     1440
atgactttga cgtcacacca cgaaaacaga cgcttcatac gtgtcccttt atctctctca     1500
gtctctctat                                                            1510

<210> SEQ ID NO 76
<211> LENGTH: 4801
<212> TYPE: DNA
<213> ORGANISM: artificial sequence
<220> FEATURE:
<223> OTHER INFORMATION: P5319 expression vector (AS1::LexA-GAL4TA)

<400> SEQUENCE: 76
ggaccgtgta atgggccatt gggccaagtt ttcttgatat aaaatctgaa atactactaa       60
attacaattt ttcttaaact cgatttcata attcatgtgg gactcagttc tccgcgtctt      120
atgacttaag agttaagagt aaagacaatt gattgtagtt tgcattatta aggttgtgat      180
tttaaaggct atattggccc aggcaaagtg gttatgaaag ttaaaggta ttattaaatg       240 tcgttatgga ctagctaaag aaaagagatg gatatagaaa cggatttgcc agtttgtgag      300
gttacgtact cgttactttc tattgcattt ttgtgtgtca ttgtgcttgt gatttctttta     360 gtatatgttt ttcttttgt caaactcttt agtacatgtt atgctttatt tcttgtttta      420
gcattgttat tgttatttg atccatgttc ttttacttaa tgtgtagagt gttcacgtac       480
gactctttat gatcgctata ctaatatact atgaaactcg aatgagaaca tgcatgtcat     540
aaatcaataa aacataacat acgacactta acctaaatca tacattcatt gattcatact     600
atcatgatcc tcatcacatt agtatcattt gtctttattt attacttagc tacttcgtta     660
tcttattata tctttacctg ttctgctggt catttgccat aaacaccaag tacaagcaac     720 tcttagtcc aatatcagac caaattaaca aacatttccc caatccaaaa cggaaattta      780
attataatta gcatttaaat aggttcgatt acaaaaaaaa atcaacaaag gaacaagtca     840
atttcataat ggtttgtcaa ttgtcacaca acgaaatggc tagccggatc aagcatgcat     900
```

```
gatccaaatt tcaacatttc catgataacc tgaattataa cgtctacata aaccatattt      960
aaataaatag gatggtcgaa agatatcatt aaaagaacga ttcaatattc tttattgttc     1020
aattgataca catgttattc tccttaacca gttatgaaca tgtcctacaa gtttcttgac     1080
ccaaactcat aatttcatat accataatcc caagttaagt tttttttttt tggggatcaa     1140
aatctcaagt taagttaagt tcaattattt agctgtaatg ctcggaaaaa agatcggatg     1200
aatatccaat tggttcaata tatccccaa tccggccaat ctccctatct ttatagctta      1260
attattagag aatggtcaat tcacgccatc agaaccagtt tcatatcttc atgaaccaaa     1320
acgcctacaa ccctattatt caagaaatca ctataattgt ccaagtaaaa ccattaatta     1380
accgagtcga tttttctatg gtcctatagg catgttgtta ctcaaactac tgattaatta     1440
ataagaagtt gtagtttgaa aaagaatcta gctgaaaaat actcctactc taagaattta     1500
agttagaata aaacatatta atacaaatat aaaaatttag ttattaaaaa agcgctacta     1560
ccaagacgtc ctaaagaaaa actagctttg tcttctaaaa gaaacctag cttaactacc      1620 caaaaaaatc tagttttaca aacactaaag acaaatttta ttttcaaca aatttaccaa      1680 ttaaagaaaa ttccatgtag gaatgtatcc aaattgaaaa tatccctaca tattttgtag     1740 gaaaaaggt ttttataaat attaaaaaaa cgagaaaaag aaaagagaaa agagaaaaaa      1800
aaaagccgga gagaatggag cacatgaggt aaaaggcaag agatggcaga gagaagatca     1860
gagaagggat ctgcctcaat ttgacaactc atatgtcatg tcatttccct cactactatt     1920
attttcctat ttcaaaaaca cctttctctg ataccatcac cttttacctt ctcttttttt     1980
ttactgtctt tgctctgttt cacattccct tctatatata cagtatagta tattttatcc     2040
ttcttttatt gttttgctta ctaaaagttt ttttcctccg gaatcaaaat tctaaaatgt     2100
atatcatgtt aggtcgcgag ggccatgcaa tattatgaac tatgcatgat gattaatgtc     2160
tgtggatcca tcacaaatat tattgaaggt tgatcagaga ctatggacca aaatggtccg     2220
aatcgcctga taataaaaaa ctattcattt ttattttta tttttttat taaacatgtg       2280 attaatgata gatcttacga ttcgcaactg ggaaacatgc actaactcaa acttaaaaca     2340
cacaatacta aaagttctat taaattttga atgtaaagag aaatatatta ggcaatcaaa     2400
cggtcaagta aatcatacac atcgataatt tattttttta tccttcaaag caggcccatc     2460
caaggcccac cactattctc atatcaacat acttttcttg ttttggttaa atcaacctac     2520
catgttggct gttctctccg ctcctctgtg taagatcaca ccaacaccac tgcataattt     2580
cttgtattat tttgagactt gagagtaaac tgattgacaa aaaaaaaaa aaaaaaaaa       2640 aattgagagt aaactagttt cttgaatatt gattttttca gcttaatttg ttggggaaag     2700
atattactac tattgctgta aaaaaaaaa aaaaaaaaa agatattatt actatatttg       2760
tagtgatttt attttgaaaa ttctcttcac tttttgtag ttaacattct aattttgtga      2820
aaagaacttt taatgtcagg tcatgtctct taaaagtttt gcatgatgaa atgatttaca     2880
aattacaata gaaaatggaa accattgcaa actaaatttt tatcaaaaaa aatcgaaaat     2940
aaaatgtatt gacttagtaa tgctgtgtct gctacgatta actattacac ataatgcaac     3000
actgaattat ccaaatacat tattagaata atagtattac agtatcacta ttacaacaac     3060
aatgtcaaca ataatcttat tataataata tataaataga ccttagtgac atcatatatt     3120
atagaaaaca tgtggttgcc taatttgtat aagctagata cttgggggtg atgagtgact     3180
agttgatgca atgataaaag agtgaaagtt ttgtctgcct gattatagac gtcggagaaa     3240
tactaaaata cgctatgaag attttggcgc atggtagcag aaaaaaaaaa cggagggtgt     3300
```

-continued

```
gagtgagtag tggtagtcgg atgtgatgga acaaagaaaa gtattttgg tagggttatg    3360
ggagagagaa ggggaccatt attacacact tacatgcttt ccccaaaaga taccattccc    3420
attttctgac acgtgtcccc ctcatcccca attactcata cgtcaaatcc aattttagc    3480
ctaaaagttt tttttatttg tttagccaaa tctattttac taattaaagt tttcaaatgg    3540
caaatagaaa gatcttctaa ggttttataa aattacttga ttatttctag ttttgctcat    3600
tttttaaata aaatttctct ttttttcttt gcaacattat tgatttttt tttgataggg    3660
agtaacatta gtgatgttct atctcttctc attgcaaaaa ctttattttc tcatctctat    3720
ttgatcatca ttgcgaaatc ttccatttc aacaaatact tttccatgtt aatatgctgt    3780
ttcaaaatat aagtgtttgg aaaataaatc aacaagttta aatgttaact attttatgc    3840
tattataatt atttttctta tgggtaagtg gaaattaatg ttactcaaat tggacataaa    3900
attctattgt ttgagtgaag gagtttataa atggagcatt attttcttga atggttagtt    3960
tttcttctat cattttgaca agtaaatgac ttttcagcca ctaaagtaca cactttttc    4020
attaaatttt aaagcatccc ctacattaga ttgtcatttt atttctcata atgttataga    4080
aaaatgaatt ttgagatccc aatgtagtaa atatatataa aaaaggttt aatattgtca    4140
atgacaaaca acgaacttat ggaatttcaa cttttcacct ccacgcgcct ctgtcagagt    4200
tttttttttc cccacttgtg atgtaaaaag gggaaaacgt ctgtgtctca gtcggtaaac    4260
ttttctctc ttttttttt taaagatttt attttaatta tgccgtctct gtggtctaat    4320
cgtgtacgtc gtctggtttt aaaagcctct ctcactttgg tcttttcgtt ttctctcttc    4380
cattttctcc aactatataa aaaaaaaaa gtgagagaga gagcaaatct gtgtgatgga    4440
agttgctctt gagtttggga ttattttatct tttcaatatc atttggtaag cattttatt    4500
ttgttttata gtaataattt taactctctt atcttcttaa taagtctttg cttaatagtg    4560
ttttggggtc agcattaatt tccctgttt ggtttccaga atataggttg tatagtgtga    4620
taataacaaa ttattccaag ttttgcttca aacattgtca aagttttgt cattttcatt    4680
tcttgaaacg gaaattttc agactttgta atttctaatt cgaaaattcg acagatcttg    4740
tagatttgtt tcgatctttt agagttttga attggagaga tttatgaaac gggttgattt    4800
t                                                                   4801
```

<210> SEQ ID NO 77
<211> LENGTH: 4276
<212> TYPE: DNA
<213> ORGANISM: artificial sequence
<220> FEATURE:
<223> OTHER INFORMATION: P6506 expression vector (35S::LexA-GAL4TA)

<400> SEQUENCE: 77

```
catgcctgca ggtcccaga ttagccttt caatttcaga aagaatgcta acccacagat      60
ggttagagag gcttacgcag caggtctcat caagacgatc tacccgagca ataatctcca    120
ggaaatcaaa taccttccca agaaggttaa agatgcagtc aaaagattca ggactaactg    180
catcaagaac acagagaaag atatatttct caagatcaga agtactattc agtatggac     240
gattcaaggc ttgcttcaca aaccaaggca agtaatagag attggagtct ctaaaaaggt    300
agttcccact gaatcaaagg ccatggagtc aaagattcaa atagaggacc taacagaact    360
cgccgtaaag actggcgaac agttcataca gagtctctta cgactcaatg acaagaagaa    420
aatcttcgtc aacatggtgg agcacgacac acttgtctac tccaaaaata tcaaagatac    480
agtctcagaa gaccaaaggg caattgagac ttttcaacaa agggtaatat ccggaaacct    540
```

```
cctcggattc cattgcccag ctatctgtca ctttattgtg aagatagtgg aaaaggaagg    600
tggctcctac aaatgccatc attgcgataa aggaaaggcc atcgttgaag atgcctctgc    660
cgacagtggt cccaaagatg accccccacc cacgaggagc atcgtggaaa agaagacgt    720
tccaaccacg tcttcaaagc aagtggattg atgtgatatc tccactgacg taagggatga    780
cgcacaatcc cactatcctt cggcggccgc aagacccttc ctctatataa ggaagttcat    840
ttcatttgga gaggacacgc tcgagtataa gagctcattt ttacaacaat taccaacaac    900
aacaaacaac aaacaacatt acaattacat ttacaattac catggaagcg ttaacggcca    960
ggcaacaaga ggtgtttgat ctcatccgtg atcacatcag ccagacaggt atgccgccga   1020
cgcgtgcgga aatcgcgcag cgtttggggt tccgttcccc aaacgcggct gaagaacatc   1080
tgaaggcgct ggcacgcaaa ggcgttattg aaattgtttc cggcgcatca cgcgggattc   1140
gtctgttgca ggaagaggaa gaagggttgc cgctggtagg tcgtgtggct gccggtgaac   1200
cacttctggc gcaacagcat attgaaggtc attatcaggt cgatccttcc ttattcaagc   1260
cgaatgctga tttcctgctg cgcgtcagcg ggatgtcgat gaaagatatc ggcattatgg   1320
atggtgactt gctggcagtg cataaaaactc aggatgtacg taacggtcag gtcgttgtcg   1380
cacgtattga tgacgaagtt accgttaagc gcctgaaaaa acagggcaat aaagtcgaac   1440
tgttgccaga aaatagcgag tttaaaccaa ttgtcgtaga tcttcgtcag cagagcttca   1500
ccattgaagg gctggcggtt ggggttattc gcaacggcga ctggctggaa ttccccaatt   1560
ttaatcaaag tgggaatatt gctgatagct cattgtcctt cactttcact aacagtagca   1620
acggtccgaa cctcataaca actcaaacaa attctcaagc gctttcacaa ccaattgcct   1680
cctctaacgt tcatgataac ttcatgaata atgaaatcac ggctagtaaa attgatgatg   1740
gtaataattc aaaaccactg tcacctggtt ggacggacca aactgcgtat aacgcgtttg   1800
gaatcactac agggatgttt aataccacta caatggatga tgtatataac tatctattcg   1860
atgatgaaga tacccccacca aacccaaaaa aagagtagct agagctttcg ttcgtatcat   1920
cggtttcgac aacgttcgtc aagttcaatg catcagtttc attgcgcaca caccagaatc   1980
ctactgagtt tgagtattat ggcattggga aaactgtttt tcttgtacca tttgttgtgc   2040
ttgtaattta ctgtgttttt tattcggttt tcgctatcga actgtgaaat ggaaatggat   2100
ggagaagagt taatgaatga tatggtcctt ttgttcattc tcaaattaat attatttgtt   2160
ttttctctta tttgttgtgt gttgaatttg aaattataag agatatgcaa acattttgtt   2220
ttgagtaaaa atgtgtcaaa tcgtggcctc taatgaccga agttaatatg aggagtaaaa   2280
cacttgtagt tgtaccatta tgcttattca ctaggcaaca aatatatttt cagacctaga   2340
aaagctgcaa atgttactga atacaagtat gtcctcttgt gttttagaca tttatgaact   2400
ttcctttatg taattttcca gaatccttgt cagattctaa tcattgcttt ataattatag   2460
ttatactcat ggatttgtag ttgagtatga aaatatttt taatgcattt tatgacttgc   2520
caattgattg acaacatgca tcaatctaga acatatccat atctaatctt acctcgactg   2580
ctgtatataa aaccagtggt tatatgtcca gtactgctgt atataaaacc agtggttata   2640
tgtacagtac gtcgatcgat cgacgactgc tgtatataaa accagtggtt atatgtacag   2700
tactgctgta tataaaacca gtggttatat gtacagtacg tcgagggat gatcaagacc   2760
cttcctctat ataaggaagt tcatttcatt tggagaggac acgctcgagt ataagagctc   2820
atttttacaa caattaccaa caacaacaaa caacaaacaa cattcaaatt acatttacaa   2880
ttaccatggt gagcaagggc gaggagctgt tcaccggggt ggtgcccatc ctggtcgagc   2940
```

```
tggacggcga cgtaaacggc cacaagttca gcgtgtccgg cgagggcgag ggcgatgcca   3000
cctacggcaa gctgaccctg aagttcatct gcaccaccgg caagctgccc gtgccctggc   3060
ccaccctcgt gaccaccctg acctacggcg tgcagtgctt cagccgctac cccgaccaca   3120
tgaagcagca cgacttcttc aagtccgcca tgcccgaagg ctacgtccag agcgcaccca   3180
tcttcttcaa ggacgacggc aactacaaga cccgcgccga ggtgaagttc gagggcgaca   3240
ccctggtgaa ccgcatcgag ctgaagggca tcgacttcaa ggaggacggc aacatcctgg   3300
ggcacaagct ggagtacaac tacaacagcc acaacgtcta tatcatggcc gacaagcaga   3360
agaacggcat caaggtgaac ttcaagatcc gccacaacat cgaggacggc agcgtgcagc   3420
tcgccgacca ctaccagcag aacaccccca tcggcgacgg ccccgtgctg ctgcccgaca   3480
accactacct gagcacccag tccgccctga gcaaagaccc caacgagaag cgcgatcaca   3540
tggtcctgct ggagttcgtg accgccgccg ggatcactct cggcatggac gagctgtaca   3600
agtccggagg gatcctctag ctagagcttt cgttcgtatc atcggtttcg acaacgttcg   3660
tcaagttcaa tgcatcagtt tcattgcgca cacaccagaa tcctactgag tttgagtatt   3720
atggcattgg gaaaactgtt tttcttgtac catttgttgt gcttgtaatt tactgtgttt   3780
tttattcggt tttcgctatc gaactgtgaa atggaaatgg atggagaaga gttaatgaat   3840
gatatggtcc ttttgttcat tctcaaatta atattatttg ttttttctct tatttgttgt   3900
gtgttgaatt tgaaattata agagatatgc aaacattttg ttttgagtaa aaatgtgtca   3960
aatcgtggcc tctaatgacc gaagttaata tgaggagtaa aacacttgta gttgtaccat   4020
tatgcttatt cactaggcaa caaatatatt ttcagaccta gaaaagctgc aaatgttact   4080
gaatacaagt atgtcctctt gtgttttaga catttatgaa ctttccttta tgtaattttc   4140
cagaatcctt gtcagattct aatcattgct ttataattat agttatactc atggatttgt   4200
agttgagtat gaaatatttt ttaatgcat tttatgactt gccaattgat tgacaacatg   4260
catcaatcga cctgca                                                  4276
```

<210> SEQ ID NO 78
<211> LENGTH: 1167
<212> TYPE: DNA
<213> ORGANISM: artificial sequence
<220> FEATURE:
<223> OTHER INFORMATION: P25281 expression vector (35S::G481-GFP fusion)

<400> SEQUENCE: 78

```
atggcggata cgccttcgag cccagctgga gatggcggag aaagcggcgg ttccgttagg     60
gagcaggatc gataccttcc tatagctaat atcagcagga tcatgaagaa agcgttgcct    120
cctaatggta agattggaaa agatgctaag gatacagttc aggaatgcgt ctctgagttc    180
atcagcttca tcactagcga ggccagtgat aagtgtcaaa agagaaaag gaaaactgtg    240 aatggtgatg atttgttgtg ggcaatggca acattaggat ttgaggatta cctggaacct    300
ctaaagatat acctagcgag gtacagggag ttggagggtg ataataaggg atcaggaaag    360
agtggagatg gatcaaatag agatgctggt ggcggtgttt ctggtgaaga aatgccgagc    420
tggtgcggcc gcatggtgag caagggcgag gagctgttca ccggggtggt gcccatcctg    480
gtcgagctgg acggcgacgt aaacggccac aagttcagcg tgtccggcga gggcgagggc    540
gatgccacct acggcaagct gaccctgaag ttcatctgca ccaccggcaa gctgcccgtg    600
ccctggccca cctcgtgac cacctgacc tacggcgtgc agtgcttcag ccgctacccc    660
gaccacatga gcagcacga cttcttcaag tccgccatgc ccgaaggcta cgtccaggag    720
```

| | |
|---|---|
| cgcaccatct tcttcaagga cgacggcaac tacaagaccc gcgccgaggt gaagttcgag | 780 |
| ggcgacaccc tggtgaaccg catcgagctg aagggcatcg acttcaagga ggacggcaac | 840 |
| atcctggggc acaagctgga gtacaactac aacagccaca acgtctatat catggccgac | 900 |
| aagcagaaga acggcatcaa ggtgaacttc aagatccgcc acaacatcga ggacggcagc | 960 |
| gtgcagctcg ccgaccacta ccagcagaac ccccccatcg gcgacggccc cgtgctgctg | 1020 |
| cccgacaacc actacctgag cacccagtcc gccctgagca agacccccaa cgagaagcgc | 1080 |
| gatcacatgg tcctgctgga gttcgtgacc gccgccggga tcactctcgg catggacgag | 1140 |
| ctgtacaagt ccggagggat cctctag | 1167 |

<210> SEQ ID NO 79
<211> LENGTH: 1034
<212> TYPE: DNA
<213> ORGANISM: artificial sequence
<220> FEATURE:
<223> OTHER INFORMATION: P47 expression vector (for preparing 35S::G482)

<400> SEQUENCE: 79

| | |
|---|---|
| acacttaaca attcacacct tctcttttta ctcttcctaa aaccctaaat ttcctcgctt | 60 |
| cagtcttccc actcaagtca accaccaatt gaattcgatt tcgaatcatt gatggaaatg | 120 |
| atttgaaaaa agagtaaagt ttatttttt attccttgta attttcagaa atggggggatt | 180 |
| ccgacaggga ttccggtgga gggcaaaacg ggaacaacca gaacggacag tcctccttgt | 240 |
| ctccaagaga gcaagacagg ttcttgccga tcgctaacgt cagccggatc atgaagaagg | 300 |
| ccttgcccgc caacgccaag atctctaaag atgccaaaga gacgatgcag gagtgtgtct | 360 |
| ccgagttcat cagcttcgtc accggagaag catctgataa gtgtcagaag gagaagagga | 420 |
| agacgatcaa cggagacgat ttgctctggg ctatgactac tctaggtttt gaggattatg | 480 |
| ttgagccatt gaaagtttac ttgcagaggt ttagggagat cgaaggggag aggactggac | 540 |
| tagggaggcc acagactggt ggtgaggtcg gagagcatca gagagatgct gtcggagatg | 600 |
| gcggtgggtt ctacggtggt ggtggtggga tgcagtatca ccaacatcat cagtttcttc | 660 |
| accagcagaa ccatatgtat ggagccacag gtggcgtag cgacagtgga ggtggagctg | 720 |
| cctccggtag gacaaggact taacaaagat tggtgaagtg gatctctctc tgtatataga | 780 |
| tacataaata catgtataca catgcctatt tttacgaccc atataaggta tctatcatgt | 840 |
| gatagaacga acattggtgt tggtgatgta aaatcagatg tgcattaagg gtttagattt | 900 |
| tgaggctgtg taaagaaga tcaagtgtgc tttgttggac aataggattc actaacgaat | 960 |
| ctgcttcatt ggatcttgta tgtaactaaa gccattgtat tgaatgcaaa tgttttcatt | 1020 |
| tgggatgctt taaa | 1034 |

<210> SEQ ID NO 80
<211> LENGTH: 1034
<212> TYPE: DNA
<213> ORGANISM: artificial sequence
<220> FEATURE:
<223> OTHER INFORMATION: P5072 expression vector (opLexA::G482)

<400> SEQUENCE: 80

| | |
|---|---|
| acacttaaca attcacacct tctcttttta ctcttcctaa aaccctaaat ttcctcgctt | 60 |
| cagtcttccc actcaagtca accaccaatt gaattcgatt tcgaatcatt gatggaaatg | 120 |
| atttgaaaaa agagtaaagt ttatttttt attccttgta attttcagaa atggggggatt | 180 |
| ccgacaggga ttccggtgga gggcaaaacg ggaacaacca gaacggacag tcctccttgt | 240 |

-continued

```
ctccaagaga gcaagacagg ttcttgccga tcgctaacgt cagccggatc atgaagaagg      300
ccttgcccgc caacgccaag atctctaaag atgccaaaga gacgatgcag gagtgtgtct      360
ccgagttcat cagcttcgtc accggagaag catctgataa gtgtcagaag gagaagagga      420
agacgatcaa cggagacgat ttgctctggg ctatgactac tctaggtttt gaggattatg      480
ttgagccatt gaaagtttac ttgcagaggt ttagggagat cgaaggggag aggactggac      540
tagggaggcc acagactggt ggtgaggtcg gagagcatca gagagatgct gtcggagatg      600
gcggtgggtt ctacggtggt ggtggtggga tgcagtatca ccaacatcat cagtttcttc      660
accagcagaa ccatatgtat ggagccacag gtggcggtag cgacagtgga ggtgagctg       720 cctccggtag gacaaggact aacaaagat tggtgaagtg gatctctctc tgtatataga       780
tacataaata catgtataca catgcctatt tttacgaccc atataaggta tctatcatgt       840
gatagaacga acattggtgt tggtgatgta aaatcagatg tgcattaagg gtttagattt       900
tgaggctgtg taaagaaga tcaagtgtgc tttgttggac aataggattc actaacgaat        960
ctgcttcatt ggatcttgta tgtaactaaa gccattgtat tgaatgcaaa tgttttcatt     1020
tgggatgctt taaa                                                       1034
```

<210> SEQ ID NO 81
<211> LENGTH: 682
<212> TYPE: DNA
<213> ORGANISM: artificial sequence
<220> FEATURE:
<223> OTHER INFORMATION: P1441 expression vector
      (for preparing 35S::G485)

<400> SEQUENCE: 81

```
tcctctctga tccaacggac ccaaaacatc tatctctctt tctcgacctt ttgtctcctc       60
gatctaaaga tggcggattc ggacaacgat tcaggaggac acaaagacgg tggaaatgct      120
tcgacacgtg agcaagatag gtttctaccg atcgctaacg ttagcaggat catgaagaaa      180
gcacttcctg cgaacgcaaa atctctaag gatgctaaag aaacggttca agagtgtgta      240
tcggaattca taagtttcat caccggtgag gcttctgaca agtgtcagag agagaagagg      300
aagacaatca acggtgacga tcttctttgg gcgatgacta cgctagggtt tgaggactac      360
gtggagcctc tcaaggttta tctgcaaaag tatagggagg tggaaggaga gaagactact      420
acggcaggga gacaaggcga taaggaaggt ggaggaggag gcggtggagc tggaagtgga      480
agtggaggag ctccgatgta cggtggtggc atggtgacta cgatgggaca tcaattttcc      540
catcattttt cttaattgta aaatgataaa agcaaatttt catttttatt aattaatgat      600
atatatatat atatgtttaa cttttagtat aatgtttaca gaattttttt tttaaaacta      660
ggttcaaccc actaacgtaa ca                                              682
```

<210> SEQ ID NO 82
<211> LENGTH: 685
<212> TYPE: DNA
<213> ORGANISM: artificial sequence
<220> FEATURE:
<223> OTHER INFORMATION: P4190 expression vector (opLexA::G485)

<400> SEQUENCE: 82

```
tcctctctga tccaacggac ccaaaacatc tatctctctt tctcgacctt ttgtctcctc       60
gatctaaaga tggcggattc ggacaacgat tcaggaggac acaaagacgg tggaaatgct      120
tcgacacgtg agcaagatag gtttctaccg atcgctaacg ttagcaggat catgaagaaa      180
gcacttcctg cgaacgcaaa atctctaag gatgctaaag aaacggttca agagtgtgta      240
```

```
tcggaattca taagtttcat caccggtgag gcttctgaca agtgtcagag agagaagagg    300
aagacaatca acggtgacga tcttctttgg gcgatgacta cgctagggtt tgaggactac    360
gtggagcctc tcaaggttta tctgcaaaag tataggaggt ggaaggagag aagactact    420 acggcaggga gacaaggcga taaggaaggt ggaggaggag gcggtggagc tggaagtgga    480
agtggaggag ctccgatgta cggtggtggc atggtgacta cgatgggaca tcaattttcc    540
catcattttt cttaattgta aaatgataaa agcaaatttt catttttatt aattaatgat    600 atatatat atatgtttaa cttttagtat aatgtttaca gaattttttt tttaaaacta     660
ggttcaaccc actaacgtaa cagcg                                         685

<210> SEQ ID NO 83
<211> LENGTH: 1230
<212> TYPE: DNA
<213> ORGANISM: artificial sequence
<220> FEATURE:
<223> OTHER INFORMATION: P26044 expression vector (35S::G485-(9A)-CFP)

<400> SEQUENCE: 83
atggcggatt cggacaacga ttcaggagga cacaaagacg gtggaaatgc ttcgacacgt    60
gagcaagata ggtttctacc gatcgctaac gttagcagga tcatgaagaa agcacttcct    120
gcgaacgcaa aaatctctaa ggatgctaaa gaaacggttc aagagtgtgt atcggaattc    180
ataagtttca tcaccggtga ggcttctgac aagtgtcaga gagagaagag gaagacaatc    240
aacggtgacg atcttctttg ggcgatgact acgctagggt ttgaggacta cgtggagcct    300
ctcaaggttt atctgcaaaa gtataggagg gtggaaggag agaagactac tacggcaggg    360
agacaaggcg ataaggaagg tggaggagga ggcggtggag ctggaagtgg aagtggagga    420
gctccgatgt acggtggtgg catggtgact acgatgggac atcaattttc ccatcatttt    480
tctgcggccg ctgccgctgc ggcagcggcc atggtgagca agggcgagga gctgttcacc    540
ggggtggtgc ccatcctggt cgagctggac ggcgacgtaa acggccacaa gttcagcgtg    600
tccggcgagg gcgagggcga tgccacctac ggcaagctga ccctgaagtt catctgcacc    660
accggcaagc tgcccgtgcc ctggcccacc ctcgtgacca ccctgacctg ggcgtgcag    720 tgcttcagcc gctaccccga ccacatgaag cagcacgact tcttcaagtc cgccatgccc    780
gaaggctacg tccaggagcg caccatcttc ttcaaggacg acggcaacta caagacccgc    840
gccgaggtga agttcgaggg cgacaccctg gtgaaccgca tcgagctgaa gggcatcgac    900
ttcaaggagg acggcaacat cctggggcac aagctggagt acaactacat cagccacaac    960
gtctatatca ccgccgacaa gcagaagaac ggcatcaagg ccaacttcaa gatccgccac    1020
aacatcgagg acggcagcgt gcagctcgcc gaccactacc agcagaacac ccccatcggc    1080
gacggccccg tgctgctgcc cgacaaccac tacctgagca cccagtccgc cctgagcaaa    1140 gacccccaacg agaagcgcga tcacatggtc ctgctggagt tcgtgaccgc cgccgggatc    1200
actctcggca tggacgagct gtacaagtaa                                    1230

<210> SEQ ID NO 84
<211> LENGTH: 1331
<212> TYPE: DNA
<213> ORGANISM: artificial sequence
<220> FEATURE:
<223> OTHER INFORMATION: P4357 expression vector (opLexA::G1364)

<400> SEQUENCE: 84
ttgtgttaat tgttgtaaag ttagggtttt tttttctttc tgagatggcg gagtcgcagg    60
```

```
ccaagagtcc cggaggctgt ggaagccatg agagtggtgg agatcaaagt cccaggtcgt    120
tacatgttcg tgagcaagat aggtttcttc cgattgctaa cataagccgt atcatgaaaa    180
gaggtcttcc tgctaatggg aaaatcgcta agatgctaa ggagattgtg caggaatgtg     240
tctctgaatt catcagtttc gtcaccagcg agtatgtctt ttttaacctt ttaacaatgc    300
tatgttgtgt ttgctcttgc tgaatgttta gaggcttgat aggaactttg agttttagtt    360
tcaagtctta aactttatag tgattttgg gttttcttaa actagtgaaa gttgaggcct     420
ttttagtcct tacattggtt actctttctt gttgttcatc tttgtttggc tttgatgttg    480
catatttgat gatgcaatgg tttttctatg acgttgatga gcagagcgag tgataaatgt    540
caaagagaga aaggaagac tattaatgga gatgatttgc tttgggcaat ggctacttta    600
ggatttgaag actacatgga acctctcaag gtttacctga tgagatatag agaggtatgt    660
tctgagtacg atgttattta gttatgctgt tgtgtgaaga gagtttttga atttcactaa    720
cttactctgt ttctcctttt cctttcttg ctctactacg tgaactggaa tatcacagat     780
ggaggtcagt ggttcttctt attctatttc ttgttcattc ctaaaacttg caacgatcta    840
tgatctttat ggcttccgtg aatcatctct ttttgtcaac ttatgtatca aactatttat    900
gctttcctta tccttttcaa tgatcaatag ggtgacacaa agggatcagc aaaaggtggg    960
gatccaaatg caaagaaaga tgggcaatca agccaaaatg ccaggtata tgtctcaaat    1020 ctcatgcctt tgaccatttt ttcgtcttcg cattcatctg cacgtattct ctcttccgct    1080
ttagctaagt tagtctgaca ttcatggggt ttgtttacca tttggcagtt ctcgcagctt    1140
gctcaccaag gtccttatgg gaactctcaa gtaacttttc ctctcttctc ttcacactca    1200
agcaatacgc atcattctct tctaatttgt taagaattga aaacttgtaa agcatcactt    1260
atgttataat ctatgaatac ctcaaaatct gtgaactaat ttgacattgg actcggtata    1320
attgtaggct c                                                         1331

<210> SEQ ID NO 85
<211> LENGTH: 1009
<212> TYPE: DNA
<213> ORGANISM: artificial sequence
<220> FEATURE:
<223> OTHER INFORMATION: P5284 expression vector (RBCS3::LexA-GAL4TA)

<400> SEQUENCE: 85
aaatggagta atatggataa tcaacgcaac tatatagaga aaaataata gcgctaccat     60 atacgaaaaa tagtaaaaaa ttataataat gattcagaat aaattattaa taactaaaaa    120
gcgtaaagaa ataaattaga gaataagtga tacaaaattg gatgttaatg gatacttctt    180
ataattgctt aaaaggaata caagatggga aataatgtgt tattattatt gatgtataaa    240
gaatttgtac aatttttgta tcaataaagt tccaaaaata atcttaaaa aataaaagta    300 cccttttatg aacttttat caaataaatg aaatccaata ttagcaaaac attgatatta    360
ttactaaata tttgttaaat taaaaatat gtcatttat ttttaacag atattttta     420 aagtaaatgt tataaattac gaaaaaggga ttaatgagta tcaaaacagc ctaaatggga    480
ggagacaata acagaaattt gctgtagtaa ggtggcttaa gtcatcattt aatttgatat    540
tataaaaatt ctaattagtt tatagtcttt cttttcctct tttgtttgtc ttgtatgcta    600
aaaaaggtat attatatcta taaattatgt agcataatga ccacatctgg catcatcttt    660
acacaattca cctaaaatatc tcaagcgaag ttttgccaaa actgaagaaa agatttgaac    720
aacctatcaa gtaacaaaaa tcccaaacaa tatagtcatc tatattaaat cttttcaatt    780
```

```
gaagaaattg tcaaagacac atacctctat gagttttttc atcaattttt ttttctttt      840 taaactgtat ttttaaaaaa atattgaata aaacatgtcc tattcattag tttgggaact     900
ttaagataag gagtgtgtaa tttcagaggc tattaattt gaaatgtcaa gagccacata     960
atccaatggt tatggttgct cttagatgag gttattgctt taggtgaaa               1009

<210> SEQ ID NO 86
<211> LENGTH: 1266
<212> TYPE: DNA
<213> ORGANISM: artificial sequence
<220> FEATURE:
<223> OTHER INFORMATION: P26108 expression vector (35S::G1364-(9A)-CFP
      fusion)

<400> SEQUENCE: 86
atggcggagt cgcaggccaa gagtcccgga ggctgtggaa gccatgagag tggtggagat      60
caaagtccca ggtcgttaca tgttcgtgag caagataggt ttcttccgat tgctaacata     120
agccgtatca tgaaaagagg tcttcctgct aatgggaaaa tcgctaaaga tgctaaggag     180
attgtgcagg aatgtgtctc tgaattcatc agtttcgtca ccagcgaagc gagtgataaa     240
tgtcaaagag agaaaaggaa gactattaat ggagatgatt tgctttgggc aatggctact     300
ttaggatttg aagactacat ggaacctctc aaggtttacc tgatgagata tagagagatg     360
gagggtgaca caagggatc agcaaaaggt ggggatccaa atgcaaagaa agatgggcaa     420
tcaagccaaa atggccagtt ctcgcagctt gctcaccaag gtccttatgg aactctcaa      480 gctcagcagc atatgatggt tccaatgccg ggaacagacg cggccgctgc cgctgcggca     540
gcggccatgg tgagcaaggg cgaggagctg ttcaccgggg tggtgcccat cctggtcgag     600
ctggacggcg acgtaaacgg ccacaagttc agcgtgtccg gcgagggcga gggcgatgcc     660
acctacggca agctgaccct gaagttcatc tgcaccaccg gcaagctgcc cgtgccctgg     720
cccaccctcg tgaccaccct gacctggggc gtgcagtgct tcagccgcta ccccgaccac     780
atgaagcagc acgacttctt caagtccgcc atgcccgaag gctacgtcca ggagcgcacc     840
atcttcttca aggacgacgg caactacaag acccgcgccg aggtgaagtt cgagggcgac     900
accctggtga accgcatcga gctgaagggc atcgacttca aggaggacgg caacatcctg     960
gggcacaagc tggagtacaa ctacatcagc cacaacgtct atatcaccgc cgacaagcag    1020
aagaacggca tcaaggccaa cttcaagatc cgccacaaca tcgaggacgg cagcgtgcag    1080
ctcgccgacc actaccagca gaacaccccc atcggcgacg gccccgtgct gctgcccgac    1140
aaccactacc tgagcaccca gtccgccctg agcaaagacc ccaacgagaa gcgcgatcac    1200
atggtcctgc tggagttcgt gaccgccgcc gggatcactc tcggcatgga cgagctgtac    1260
aagtaa                                                                1266

<210> SEQ ID NO 87
<211> LENGTH: 1820
<212> TYPE: DNA
<213> ORGANISM: artificial sequence
<220> FEATURE:
<223> OTHER INFORMATION: P8079 expression vector (opLexA::G2345)

<400> SEQUENCE: 87
ccgatttccc aatctctacc tgattatcta gggtttctga gatggccgaa tcgcaaaccg      60
gtggtggtgg tggtggaagc catgagagtg gcggtgatca gagcccgagg tctttgaatg     120
ttcgtgagca ggacaggttt cttccgattg ctaacataag ccgtatcatg aagagaggtt     180
```

```
tacctctaaa tggcaaaatc gctaaagatg ctaaagagac tatgcaggaa tgtgtctctg      240
aattcatcag cttcgtcacc agcgagtaat ttctttctct actttctcaa aaatgttacc      300
tttttgttgc tttggtggtt atagcgtgta aagccctctt ctttgttaag ttagattgat      360
gttatattca ttgggttgtt aagcaaagtc actatgtcga ttttggaata ttgttttgcc      420
ttttagggct agtgataagt gccaaagaga gaaaaggaag accatcaatg gagatgattt      480
gctttgggct atggccactt taggattcga agattacatc gatcccctca aggtttacct      540
gatgcgatat agagaggtat gttccacttc agattagtca gtttacattc tgctatacat      600
tcactgactc tctgttttc cttctcattt ccttgtctat gctatttgga ttggaatttt      660
gcagatggag gttcgtggtt ctcctctttc atttatcttt ctgatagtcg aattttgtac      720
gtggatcctt ttatgggta tatggtgtat gattgtatct aattaggatt gtctgctacc      780
ctttgctatt gttatctgtc tgatagggtg acactaaagg atcaggaaaa ggcggggaat      840
cgagtgcaaa gagagatggt caaccaagcc aagtgtctca ggtaatgact cggtcttctc      900
cagttgatat ggtcgtttac ctaagcatta gcttctccag ctaatttatt gtttccctgt      960
ctttactttc tgaacagttc tcgcaggttc ctcaacaagg ctcattctca cagggtcctt     1020
atggaaactc tcaagtaagt gttttccgac aaaagaaatg ttgatactta taaatgaatt     1080
cattctctac atagagcaga gccggggtat aagagagaa tattattaac aattaaagga     1140
tttaaggact ttaatagact cgataaaacc gtcatatatg cattatccac tttttgaaat     1200
ctagacatag gttctcatat gttccagtct ctgaggttcg gcaatagcat cgagcatctt     1260
gaagtgttaa tggtatttgt aatctatcaa tatgcagata attgattaaa ctcgtttgtg     1320
aatgtagggt tcgaatatga tggttcaaat gccgggcaca gagtagtact aggacactat     1380
tcatcacaat cttccgagac tcgactatgc ctgttgtgtc tgagaatctg agtgatccac     1440
tttccataga tatggattgt ggtatctcag ttttgggag agagaagatt tgtatatgat     1500
tgtgttgtag ggagaagagt ttggtttgct tatgataaga attgaaaagc acctttttt     1560 tcttttgact gttatgtttc ttaggttttg gtcttaagca gaagctattt atcaccactt     1620
cattggcctg ttgattcttt catgcaagtg agcccgtaac ttttataaaa caacatcatg     1680
atttataatt atctctttga ttttttggtc ctaaattcga gtttcatttg acatcatcca     1740
ttgataaaaa gaaacgaaac ttgatattga atcgttgtgg tgtggtaaaa ttcacgatct     1800
aagtttgtga taacactccg                                                 1820

<210> SEQ ID NO 88
<211> LENGTH: 610
<212> TYPE: DNA
<213> ORGANISM: artificial sequence
<220> FEATURE:
<223> OTHER INFORMATION: P21253 expression vector
      (for preparing 35S::G3395)

<400> SEQUENCE: 88
tggatctagg gtttttggag ggcggcgcgg ggatggcgga cgcggggcac gacgagagcg       60
ggagcccgcc gaggagcggc ggggtgaggg agcaggacag gttcctgccc atcgccaaca      120
tcagccgcat catgaagaag gccgtcccgg cgaacggcaa gatcgccaag gacgccaagg      180
agaccctgca ggagtgcgtc tcggagttca tctccttcgt caccagcgag gcgagcgaca      240
aatgtcagaa ggagaagcgc aagaccatca acggggaaga tctcctcttt gcgatgggta      300
cgcttggctt tgaggagtac gttgatccgt tgaagatcta tttacacaag tacagagaga      360
tggagggtga tagtaagctg tcctcaaagg ctggtgatgg ttcagtaaag aaggatacaa      420
```

```
ttggtccgca cagtggcgct agtagctcaa gtgcgcaagg gatggttggg gcttacaccc    480
aagggatggg ttatatgcaa cctcagtatc ataatgggga cacctaaaga tgaggatagt    540
gaaaattttc agtaactggt gtcctctgtg agttattatc catctgttaa ggaagaaccc    600
acattagggc                                                           610
```

<210> SEQ ID NO 89
<211> LENGTH: 468
<212> TYPE: DNA
<213> ORGANISM: artificial sequence
<220> FEATURE:
<223> OTHER INFORMATION: P23304 expression vector
      (for preparing 35S::G3396)

<400> SEQUENCE: 89

```
tcgacaaaaa ctaagcgatg tcggaggggt tcgacgggac ggagaacggc ggcggcggcg     60
gcggaggcgg agtagggaag gagcaggacc ggttcctgcc gatcgccaac atcggccgca    120
tcatgcgccg ggccgtgccg gagaacggca agatcgccaa ggactccaag gagtccgtcc    180
aggagtgcgt ctccgagttc atcagcttca tcaccagcga agcaagcgac aagtgcctca    240
aggagaagcg caagaccatc aatggggacg acctgatctg gtcaatgggc acgctcggat    300
tcgaggacta tgtcgagcct ctcaagctct acctcaggct ctaccgggag acggagggtg    360
acacaaaggg ttcaagagct tctgaactgc agtaaagaa agatgttgta cttaatggag    420
atcctggatc atcgtttgaa ggcatgtagg acgaggagtg tgatagct                 468
```

<210> SEQ ID NO 90
<211> LENGTH: 720
<212> TYPE: DNA
<213> ORGANISM: artificial sequence
<220> FEATURE:
<223> OTHER INFORMATION: P21265 expression vector
      (for preparing 35S::G3397)

<400> SEQUENCE: 90

```
gcgtctgatt tgctgaagag gaggaggagg atgccggact cggacaacga ctccggcggg     60
ccgagcaact acgcgggagg ggagctgtcg tcgccgcggg agcaggacag gttcctgccg    120
atcgcgaacg tgagcaggat catgaagaag gcgctgccgg cgaacgccaa gatcagcaag    180
gacgccaagg agacggtgca ggagtgcgtc tccgagttca tctccttcat caccggcgag    240
gcctccgaca gtgccagcg cgagaagcgc aagaccatca cggcgacga cctgctctgg     300 gccatgacca ccctcggctt cgaggactac gtcgaccccc tcaagcacta cctccacaag    360
ttccgcgaga tcgagggcga gcgcgccgcc gcctccacca ccggcgcgg caccagcgcc    420 gcctccacca cgccgccgca gcagcagcac accgccaatg ccgccggcgg ctacgccggg    480
tacgccgccc cggagccgg ccccggcggc atgatgatga tgatggggca gcccatgtac     540
ggctcgccgc caccgccgcc acagcagcag cagcagcaac accaccacat ggcaatggga    600
ggaagaggcg gcttcggtca tcatcccggc ggcggcggcg gcgggtcgtc gtcgtcgtcg    660
gggcacggtc ggcaaaacag gggcgcttga catcgctccg agacgagtag catgcaccat    720
```

<210> SEQ ID NO 91
<211> LENGTH: 761
<212> TYPE: DNA
<213> ORGANISM: artificial sequence
<220> FEATURE:
<223> OTHER INFORMATION: P21252 expression vector
      (for preparing 35S::G3398)

<400> SEQUENCE: 91

```
cctctcctct tcgtcttcct cctcgccttc gcttcgactg cttcgatcga gggagatcga        60
ggttgcgatg ccggattcgg acaacgagtc aggggggccg agcaacgcgg gggagtacgc       120
gtcggcgagg gagcaggaca ggttcctgcc gatcgcgaac gtgagcagga tcatgaagag       180
ggcgctcccg gcgaacgcca agatcagcaa ggacgccaag gagacggtgc aggagtgcgt       240
ctcggagttc atctccttca tcaccggcga ggcctccgac aagtgccagc gggagaagcg       300
caagaccatc aacggcgacg acctcctctg ggcgatgacc acgctcggct tcgaggacta       360
catcgacccg ctcaagctct acctccacaa gttccgcgag ctcgagggcg agaaggccat       420
cggcgccgcc ggcagcggcg gcggtggcgc cgcctcctcc ggcggctccg gctccggctc       480
cggctcgcac caccaccagg atgcttcccg gaacaatggc ggatacggca tgtacggcgg       540
cggcggcggc atgatcatga tgatgggaca gcctatgtac ggctcgccgc ggcgtcgtc        600
agctgggtac gcgcagccgc cgccgcccca ccaccaccac caccagatgg tgatgggagg       660
gaaaggtgcg tatggccatg gcggcggcgg cggcggcggg ccctccccgt cgtcgggata       720
cggccggcaa gacaggctat gagcttgctt tcttggttgg t                          761
```

<210> SEQ ID NO 92
<211> LENGTH: 633
<212> TYPE: DNA
<213> ORGANISM: artificial sequence
<220> FEATURE:
<223> OTHER INFORMATION: P21251 expression vector
      (for preparing 35S::G3429)

<400> SEQUENCE: 92

```
tgcattcaaa gtggtaatta agaatcggat gatcattttg attgttcctc ttcatttgtt        60
ttggatgtca ggtggcagga acatggatca ggtcaagaag gcggcagtga gatcggatgg       120
ggtgggaggt agtgcgacca acgccgagct gccgatggcc aacctcgtac gcctgataaa       180
gaaggtgctc ccagggaaag cgaagatcgg gggagcagcc aagggtctca cccatgattg       240
cgcggtggag ttcgtcgggt tcgtcggcga cgaggcctcc gagaaggcca aggcagagca       300
ccgccgcacc gtagcgccgg aagactactt gggctcattc ggcgaccttg gcttcgatcg       360
ctacgtcgac cccatggatg cctacatcca tggttaccgt gagtttgaga gggctggtgg       420
gaataggagg gtggcgccgc ctcctccggc ggcagctaca ccgctgacgc ccggtggacc       480
gacattcact gacgcagagc tgcagttctt ccggtcggtg atcccctcca gaagtgatga       540
tgaatatagc ggctcatcac cagccatagg cggctatggc tatggatatg gctatggaaa       600
aaatatgtga caacttgat gcatgtgtgt gtg                                    633
```

<210> SEQ ID NO 93
<211> LENGTH: 534
<212> TYPE: DNA
<213> ORGANISM: artificial sequence
<220> FEATURE:
<223> OTHER INFORMATION: P21466 expression vector
      (for preparing 35S::G3434)

<400> SEQUENCE: 93

```
tcgacaaggg ttgcggcgga ggcgcccggt cgctggcgat ggccgacgac ggcgggagcc        60
acgagggcag cggcggcggc ggaggcgtcc gggagcagga ccggttcctg cccatcgcca       120
acatcagccg gatcatgaag aaggccgtcc cggccaacgg caagatcgcc aaggacgcta       180
aggagaccct gcaggagtgc gtctccgagt tcatatcatt cgtgaccagc gaggccagcg       240
```

| | |
|---|---|
| acaaatgcca gaaggagaaa cgaaagacaa tcaacgggga cgatttgctc tgggcgatgg | 300 |
| ccactttagg attcgaggag tacgtcgagc ctctcaagat ttacctacaa aagtacaaag | 360 |
| agatggaggg tgatagcaag ctgtctacaa aggctggcga gggctctgta aagaaggatg | 420 |
| caattagtcc ccatggtggc accagtagct caagtaatca gttggttcag catggagtct | 480 |
| acaaccaagg gatgggctat atgcagccac agtaccacaa tggggaaacc tagc | 534 |

<210> SEQ ID NO 94
<211> LENGTH: 735
<212> TYPE: DNA
<213> ORGANISM: artificial sequence
<220> FEATURE:
<223> OTHER INFORMATION: P21314 expression vector
      (for preparing 35S::G3435)

<400> SEQUENCE: 94

| | |
|---|---|
| cggcggtggc cttgagctga ggcggcggag cgatgccgga ctcggacaac gactccggcg | 60 |
| ggccgagcaa cgccgggggc gagctgtcgt cgccgcggga gcaggaccgg ttcctgccca | 120 |
| tcgccaacgt gagccggatc atgaagaagg cgctcccggc caacgccaag atcagcaagg | 180 |
| acgcaaggga gacggtgcag gagtgcgtgt ccgagttcat ctccttcatc accggcgagg | 240 |
| cctccgacaa gtgccagcgc gagaagcgca agaccatcaa cggcgacgac ctgctgtggg | 300 |
| ccatgaccac gctcggcttc gaggactacg tcgagccgct caagcactac ctgcacaagt | 360 |
| tccgcgagat cgagggcgag agggccgccg cgtccgccgg cgcctcgggc tcgcagcagc | 420 |
| agcagcagca gggcgagctg cccagaggcg ccgccaatgc cgccgggtac gccgggtacg | 480 |
| gcgcgcctgg ctccggcggc atgatgatga tgatgatggg gcagcccatg tacggcggct | 540 |
| cgcagccgca gaacagccg ccgccgcctc agccgccaca gcagcagcag caacatcaac | 600 |
| agcatcacat ggcaatagga ggcagaggag gattcggcca acaaggcggc ggcggcggct | 660 |
| cctcgtcgtc gtcagggctt ggccggcaag acagggcgtg agttgcgacg atacgtcaga | 720 |
| atcagaatcg ctgat | 735 |

<210> SEQ ID NO 95
<211> LENGTH: 803
<212> TYPE: DNA
<213> ORGANISM: artificial sequence
<220> FEATURE:
<223> OTHER INFORMATION: P21381 expression vector
      (for preparing 35S::G3436)

<400> SEQUENCE: 95

| | |
|---|---|
| tttgacttga ccggacagtg ctgttcggtg gctcggccgc gatgccggac tccgacaacg | 60 |
| agtccggcgg gccgagcaac gcggagttct cgtcgccgcg ggagcaggac cggttcctgc | 120 |
| cgatcgcgaa cgtgagccgg atcatgaaga aggcgctccc ggccaacgcc aagatctcca | 180 |
| aggacgccaa ggagacggtg caggagtgcg tgtcggagtt catctccttc atcaccggcg | 240 |
| aggcctccga caagtgccag cgcgagaagc gcaagaccat caacggcgac gacctactct | 300 |
| gggccatgac cacgctcggc ttcgaggact acgtcgagcc gctcaagctc tacctccaca | 360 |
| agttccgcga gctcgagggc gagaaggcgg ccacgacgag cgcctcctcc ggcccgcagc | 420 |
| cgccgctgca cagggagacg acgccgtcgt cgtcaacgca caatggcgcg gcgggcccg | 480 |
| tcgggggata cggcatgtac ggcggcgcgg gcggggaag cggtatgatc atgatgatgg | 540 |
| gacagcccat gtacgcggc tcccgccgg ccgcgtcgtc cgggtcgtac ccgcaccacc | 600 |
| agatggccat gggcggaaaa ggtggcgcct atggctacgg cggaggctcg tcgtcgtcgc | 660 |

-continued

```
cgtcagggct cggcaggtag gacaggttgt gaccgtcgcc gtccatgctt gcatggccat      720
ggccatggca tggctcccgc cgccggcttc ttgcttggtg tcggtaatta gcgctggtgg      780
cctgcgctgg ttaagttaac ctt                                              803
```

```
<210> SEQ ID NO 96
<211> LENGTH: 555
<212> TYPE: DNA
<213> ORGANISM: artificial sequence
<220> FEATURE:
<223> OTHER INFORMATION: P21341 expression vector
      (for preparing 35S::G3470)

<400> SEQUENCE: 96
```

```
tcaccgggtt tgtgagatgt cggatgcacc ggcgagtccg agtcacgaga gtggtggcga       60
gcagagccct cgcggctcgt tgtccggcgc ggctagagag caggaccggt accttcccat      120
tgccaacatc agccgcatca tgaagaaggc tctgcctccc aatggcaaga ttgcgaagga      180
tgcaaaagac acaatgcaag aatgcgtttc tgaattcatc agcttcatta ccagcgaggc      240
gagtgagaaa tgccagaagg agaagagaaa gacaatcaat ggagacgatt tactatgggc      300
catggcaact ttagggtttg aagactacat tgagccgctt aaggtgtacc tggctaggta      360
cagagaggcg gagggtgaca ctaaaggatc tgctagaagt ggtgatggat ctgctagacc      420
agatcaagtt ggccttgcag tcaaaatgc tcagcttgtt catcagggtt cgctgaacta       480
tattggtttg caggtgcaac cacaacatct ggttatgcct tcaatgcaag gccatgaata      540
gtttagatgc ttcta                                                       555
```

```
<210> SEQ ID NO 97
<211> LENGTH: 568
<212> TYPE: DNA
<213> ORGANISM: artificial sequence
<220> FEATURE:
<223> OTHER INFORMATION: P21471 (for preparing 35S::G3470)

<400> SEQUENCE: 97
```

```
tcgacttgta gggtttgtga gatgtcggat gcaccggcga gtccgagtca cgagagtggt       60
ggcgagcaga gccctcgcgg ctcgttgtcc ggcgcggcta gagagcagga ccggtacctt      120
cccattgcca acatcagccg catcatgaag aaggctctgc ctcccaatgg caagattgcg      180
aaggatgcaa aagacacaat gcaagaatgc gtttctgaat tcatcagctt cattaccagc      240
gaggcgagtg agaaatgcca gaaggagaag agaaagacaa tcaatggaga cgatttacta      300
tgggccatgg caactttagg gtttgaagac tacattgagc cgcttaaggt gtacctggct      360
aggtacagag aggcggaggg tgacactaaa ggatctgcta gaagtggtga tggatctgct      420
agaccagatc aagttggcct tgcaggtcaa aatgctcagc ttgttcatca gggttcgctg      480
aactatattg gtttgcaggt gcaaccacaa catctggtta tgccttcaat gcaaggccat      540
gaatagttta gatgcttcta cgcatcgc                                         568
```

```
<210> SEQ ID NO 98
<211> LENGTH: 556
<212> TYPE: DNA
<213> ORGANISM: artificial sequence
<220> FEATURE:
<223> OTHER INFORMATION: P21342 (for preparing 35S::G3471)

<400> SEQUENCE: 98
```

```
gtagggtttg tgagatgtcg gatgcgccac cgagcccgac tcatgagagt ggggcgagc       60 agagcccgcg cggttcgtcg tccggcgcga gggagcagga ccggtacctc ccgattgcca      120
```

```
acatcagccg cattatgaag aaggctctgc ctcccaacgg caagattgca aaggatgcca   180
aagacaccat gcaggaatgc gtttctgagt tcatcagctt cattaccagc gaggcgagtg   240
agaaatgcca aaggagaaag agaaagacaa tcaatggaga cgatttgcta tgggccatgg   300
ccactttagg atttgaagac tacatagagc cgcttaaggt gtacctggct aggtacagag   360
aggcggaggg tgacactaaa ggatctgcta gaagtggtga tggatctgct acaccagatc   420
aagttggcct tgcaggtcaa aattctcagc ttgttcatca gggttcgctg aactatattg   480
gtttgcaggt gcaaccacaa catctggtta tgccttcaat gcaaagccat gaatagttta   540
gatgcttcta cgcatc                                                   556
```

<210> SEQ ID NO 99
<211> LENGTH: 547
<212> TYPE: DNA
<213> ORGANISM: artificial sequence
<220> FEATURE:
<223> OTHER INFORMATION: P21348 expression vector
(for preparing 35S::G3472)

<400> SEQUENCE: 99

```
taaggctagc tagctagcca tggctgagtc ggacaacgag tccggaggtc acacggggaa    60
cgcaagcgga agcaacgaat tctccggttg caggagcaa gacaggttcc ttccgatagc    120
gaacgtgagc aggatcatga agaaggcgtt gccggcgaac gcgaagatct cgaaggaggc   180
gaaggagacg gtgcaggagt gcgtgtcgga gttcatcagc ttcataacag gagaagcgtc   240
cgataagtgc cagaaggaga gaggaagac gatcaacggc gatgatctgc tgtgggccat    300
gaccacgctg ggattcgagg agtacgtgga gcctctcaag gtttatctgc ataagtatag   360
ggagctggaa ggggagaaaa ctgctatgat gggaaggcca catgagaggg atgagggtta   420
tggtcatgca actcctatga tgatcatgat ggggcatcaa cagcagcagc atcagggaca   480
cgtgtatgga tctggaacta ctactggatc agcatcttct gcaagaacta gataacaggt   540
ttatgca                                                             547
```

<210> SEQ ID NO 100
<211> LENGTH: 553
<212> TYPE: DNA
<213> ORGANISM: artificial sequence
<220> FEATURE:
<223> OTHER INFORMATION: P21344 expression vector
(for preparing 35S::G3474)

<400> SEQUENCE: 100

```
gatatccatg gctgagtccg acaacgagtc aggaggtcac acggggaacg cgagcgggag    60
caacgagttg tccggttgca gggagcaaga caggttcctc ccaatagcaa acgtgagcag   120
gatcatgaag aaggcgttgc cggcgaacgc gaagatatcg aaggaggcga aggagacggt   180
gcaggagtgc gtgtcggagt tcatcagctt cataacagga gaggcttccg ataagtgcca   240
gaaggagaag aggaagacga tcaacggcga cgatcttctc tgggccatga ctaccctggg   300
cttcgaggac tacgtggatc ctctcaagat ttacctgcac aagtataggg agatggaggg   360
ggagaaaacc gctatgatgg gaaggccaca tgagagggat gagggttatg ccatggcca    420 tggtcatgca actcctatga tgacgatgat gatgggggcat cagccccagc accagcacca   480
gcaccagcac cagggacacg tgtatggatc tggatcagca tcttctgcaa gaactagata   540
gcatgtgtca tct                                                      553
```

```
<210> SEQ ID NO 101
<211> LENGTH: 600
<212> TYPE: DNA
<213> ORGANISM: artificial sequence
<220> FEATURE:
<223> OTHER INFORMATION: P21347 expression vector
      (for preparing 35S::G3475)

<400> SEQUENCE: 101
tcgattatcc gtttgtcgat ggcggactcg gacaacgact ccggcggcgc gcacaacgcc     60
gggaagggga gcgagatgtc gccgcgggag caggaccggt tcctgccgat cgcgaacgtg    120
agccgcatca tgaagaaggc gctgccggcg aacgcgaaga tctcgaagga cgcgaaggag    180
acggtgcagg agtgcgtgtc ggagttcatc agcttcatca ccggcgaggc ctccgacaag    240
tgccagcggg agaagcgcaa gacgatcaac ggcgacgacc tgctctgggc gatgaccact    300
ctcggcttcg aggactacgt cgagcctctc aagggctacc tccagcgctt ccgagaaatg    360
gaaggagaga agacagtggc ggcgcgtgac aaggacgcgc ctcctcctac caatgctacc    420
aacagtgcct acgagagtcc tagttatgct gctgctcctg gtggaatcat gatgcatcag    480
ggacacgtgt acggttctgc cggcttccat caagtggctg gtggtgctat aaagggtggg    540
cctgtttatc ccgggcctgg atccaatgcc ggtaggccca ggtagatggg cctatgttat    600

<210> SEQ ID NO 102
<211> LENGTH: 528
<212> TYPE: DNA
<213> ORGANISM: artificial sequence
<220> FEATURE:
<223> OTHER INFORMATION: P21345 expression vector
      (for preparing 35S::G3476)

<400> SEQUENCE: 102
ggattgattg tgaagatggc tgagtcggac aacgactcgg aggggcgcga gaacgcggga     60
aacagtggaa acttgagcga gttgtcgcct cgggaacagg accggtttct ccccatagcg    120
aacgtgagca ggatcatgaa gaaggccttg ccggcgaacg cgaagatctc gaaggacgcg    180
aaggagacgg tgcaggaatg cgtgtcggag ttcatcagct tcataacggg tgaggcgtcg    240
gacaagtgcc agagggagaa gcgcaagacc atcaacggcg acgatcttct ctgggccatg    300
acaaccctgg gattcgaaga gtacgtggag cctctgaaga tttacctcca gcgcttccgc    360
gagatggagg gagagaagac cgtggccgcc cgcgactctt ctaaggactc ggcctccgcc    420
tcctcctatc atcagggaca cgtgtacggc tcccctgcct accatcatca agtgcctggg    480
cccacttatc ctgccctggt agacccaga tgacgtgctc ctctattc              528

<210> SEQ ID NO 103
<211> LENGTH: 602
<212> TYPE: DNA
<213> ORGANISM: artificial sequence
<220> FEATURE:
<223> OTHER INFORMATION: P21350 expression vector
      (for preparing 35S::G3478)

<400> SEQUENCE: 103
ttccgttagt cgatggcgga ctccgacaac gactccggcg gcgcgcacaa cggcggcaag     60
gggagcgaga tgtcgccgcg ggagcaggac cggtttctcc cgatcgcgaa cgtgagccgc    120
atcatgaaga aggcgctgcc ggcgaacgcg aagatctcga aggacgcgaa ggagacggtg    180
caggagtgcg tgtcagagtt catcagcttc atcaccggcg aggcctccga caagtgccag    240
cgcgagaagc gcaagacgat caacggcgac gacctgctct gggcgatgac cactctgggc    300
```

```
ttcgaggact acgtggagcc tctcaaaggc tacctccagc gcttccgaga aatggaagga      360
gagaagaccg tggcggcgcg tgacaaggac gcgcctcctc ttacgaatgc taccaacagt      420
gcctacgaga gtgctaatta tgctgctgct gctgctgttc ctggtggaat catgatgcat      480
cagggacacg tgtacggttc tgccggcttc atcaagtgg ctggcgggc tataaagggt       540 gggcctgctt atcctgggcc tggatccaat gccggtaggc ccagataaag agcctattat      600
ta                                                                    602

<210> SEQ ID NO 104
<211> LENGTH: 934
<212> TYPE: DNA
<213> ORGANISM: artificial sequence
<220> FEATURE:
<223> OTHER INFORMATION: P26587 expression vector (35S::G3866 fused at
      the C-terminus with the GAL4 TA)

<400> SEQUENCE: 104
tataagtgca ggaggagctc atggcggaag ctccggcgag ccctggcggc ggcggcggga       60
gccacgagag cgggagcccc aggggaggcg gaggcggtgg cagcgtcagg gagcaggaca      120
ggttcctgcc catcgccaac atcagtcgca tcatgaagaa ggccatcccg gctaacggga      180
agaccatccc ggctaacggg aagatcgcca aggacgctaa ggagaccgtg caggagtgcg      240
tctccgagtt catctccttc atcactagcg aagcgagtga caagtgccag agggagaagc      300
ggaagaccat caatggcgac gatctgctgt gggccatggc cacgctgggg tttgaagact      360
acattgaacc cctcaaggtg tacctgcaga agtacagaga gatggagggt gatagcaagt      420
taactgcaaa atctagcgat ggctcaatta aaaaggatgc ccttggtcat gtgggagcaa      480
gtagctcagc tgcacaaggg atgggccaac agggagcata caaccaagga atgggttata      540
tgcaacccca gtaccataac ggggatatct caaactgcgg ccgccccaat tttaatcaaa      600
gtgggaatat tgctgatagc tcattgtcct tcactttcac taacagtagc aacggtccga      660
acctcataac aactcaaaca aattctcaag cgctttcaca accaattgcc tcctctaacg      720
ttcatgataa cttcatgaat aatgaaatca cggctagtaa aattgatgat ggtaataatt      780
caaaaccact gtcacctggt tggacggacc aaactgcgta taacgcgttt ggaatcacta      840
cagggatgtt taataccact acaatggatg atgtatataa ctatctattc gatgatgaag      900 atacccacc aaacccaaaa aaagagtagt aagc                                   934

<210> SEQ ID NO 105
<211> LENGTH: 628
<212> TYPE: DNA
<213> ORGANISM: artificial sequence
<220> FEATURE:
<223> OTHER INFORMATION: P26609 expression vector
      (for preparing 35S::G3875)

<400> SEQUENCE: 105
attagggttc cggcgagcat ggccgacggt ccggcgagtc caggcggcgg tagccacgag       60
agcggcgagc acagccctcg ctctaacgtg cgcgagcagg acaggtacct ccccatcgct      120
aacataagcc gcatcatgaa gaaggcacta cctgcgaacg gtaaaatcgc caaggacgcc      180
aaagagaccg ttcaggaatg cgtatccgag ttcatcagtt tcatcaccag cgaggcctct      240
gataagtgtc agagggaaaa gagaaagact attaacggtg atgatttgct ctgggccatg      300
gccactcttg gttttgagga ttatatcgat cctcttaaaa tttacctcac tagatacaga      360
gagatggagg gtgatacgaa gggttcagcc aagggcggag actcatcttc taagaaagat      420
```

```
gttcagccaa gtcctaatgc tcagcttgct catcaaggtt ctttctcaca aggtgttagt    480
tacacaattt ctcagtgaat tctgggtgaa tgaaacaaat tcattgaagt atcttaagct    540
acaagggtac ctgatcctta aattggtcaa catatgatgg ttccaatgca aggcccggag    600
taggtatcaa gtttattaac cctcctgt                                      628
```

<210> SEQ ID NO 106
<211> LENGTH: 557
<212> TYPE: DNA
<213> ORGANISM: artificial sequence
<220> FEATURE:
<223> OTHER INFORMATION: P25657 expression vector
      (for preparing 35S::G3876)

<400> SEQUENCE: 106

```
tataagtgca ggaggagctc atggcggaag ctccggcgag ccctggcggc ggcggcggga     60
gccacgagag cgggagcccc aggggaggcg gaggcggtgg cagcgtcagg gagcaggaca    120
ggttcctgcc catcgccaac atcagtcgca tcatgaagaa ggccatcccg gctaacggga    180
agatcgccaa ggacgctaag gagaccgtgc aggagtgcgt ctccgagttc atctccttca    240
tcactagcga agcgagtgac aagtgccaga gggagaagcg gaagaccatc aatggcgacg    300
atctgctgtg ggccatggcc acgctggggt ttgaagacta cattgaaccc ctcaaggtgt    360
acctgcagaa gtacagagag atggagggtg atagcaagtt aactgcaaaa tctagcgatg    420
gctcaattaa aaaggatgcc cttggtcatg tgggagcaag tagctcagct gcacaaggga    480
tgggccaaca gggagcatac aaccaaggaa tgggttatat gcaaccccag taccataacg    540
gggatatctc aaactaa                                                  557
```

<210> SEQ ID NO 107
<211> LENGTH: 574
<212> TYPE: DNA
<213> ORGANISM: cauliflower mosaic virus
<220> FEATURE:
<223> OTHER INFORMATION: CaMV 35S constitutive promoter

<400> SEQUENCE: 107

```
gcggattcca ttgcccagct atctgtcact ttattgtgaa gatagtgaaa agaaggtgg     60 ctcctacaaa tgccatcatt gcgataaagg aaaggccatc gttgaagatg cctctgccga   120
cagtggtccc aaagatggac ccccacccac gaggagcatc gtggaaaaag aagacgttcc   180
aaccacgtct tcaaagcaag tggattgatg tgatggtccg attgagactt ttcaacaaag   240
ggtaatatcc ggaaacctcc tcggattcca ttgcccagct atctgtcact ttattgtgaa   300
gatagtggaa aaggaaggtg gctcctacaa atgccatcat tgcgataaag gaaaggccat   360
cgttgaagat gcctctgccg acagtggtcc caaagatgga ccccaccca cgaggagcat   420 cgtggaaaaa gaagacgttc caaccacgtc ttcaaagcaa gtggattgat gtgatatctc   480
cactgacgta agggatgacg cacaatccca ctatccttcg caagaccctt cctctatata   540
aggaagttca tttcatttgg agaggacacg ctga                               574
```

<210> SEQ ID NO 108
<211> LENGTH: 847
<212> TYPE: DNA
<213> ORGANISM: Arabidopsis thaliana
<220> FEATURE:
<223> OTHER INFORMATION: LTP1 (Lipid Transfer Protein 1) epidermal-
      specific promoter

<400> SEQUENCE: 108

-continued

```
tcgacccacg cgtccgagcg tttcgtagaa aaattcgatt tctctaaagc cctaaaacta     60
aaacgactat ccccaattcc aagttctagg gtttccatct tccccaatct agtataaatg    120
gcggatacgc cttcgagccc agctggagat ggcggagaaa gcggcggttc cgttagggag    180
caggatcgat accttcctat agctaatatc agcaggatca tgaagaaagc gttgcctcct    240
aatggtaaga ttggaaaaga tgctaaggat acagttcagg aatgcgtctc tgagttcatc    300
agcttcatca ctagcgaggc cagtgataag tgtcaaaaag agaaaggaa aactgtgaat    360 ggtgatgatt tgttgtgggc aatggcaaca ttaggatttg aggattacct ggaacctcta    420
aagatatacc tagcgaggta cagggagttg gagggtgata ataagggatc aggaaagagt    480
ggagatggat caaatagaga tgctggtggc ggtgtttctg gtgaagaaat gccgagctgg    540
taaaagaagt tgcaagtagt gattaagaac aatcgccaaa tgatcaaggg aaattagaga    600
tcagtgagtt gtttatagtt gagctgatcg acaactattt cgggtttact ctcaatttcg    660
gttatgttag tttgaacgtt tggtttattg tttccggttt agttggttgt atttaaagat    720
ttctctgtta gatgttgaga acacttgaat gaaggaaaaa tttgtccaca tcctgttgtt    780
attttcgatt cactttcgga atttcatagc taatttattc tcatttaata ccaaatcctt    840
aaattaa                                                              847
```

<210> SEQ ID NO 109
<211> LENGTH: 2244
<212> TYPE: DNA
<213> ORGANISM: Arabidopsis thaliana
<220> FEATURE:
<223> OTHER INFORMATION: SUC2 (Sucrose-proton Symporter) vascular-
      specific promoter

<400> SEQUENCE: 109

```
aactaggggt gcataatgat ggaacaaagc acaaatcttt taacgcaaac taactacaac     60
cttcttttgg ggtccccatc cccgacccta atgttttgga attaataaaa ctacaatcac    120
ttaccaaaaa ataaaagttc aaggccacta taatttctca tatgaaccta catttataaa    180
taaaatctgg tttcatatta atttcacaca ccaagttact ttctattatt aactgttata    240
atggaccatg aaatcatttg catatgaact gcaatgatac ataatccact ttgttttgtg    300
ggagacattt accagatttc ggtaaattgg tattccccct tttatgtgat ggtcattga    360 tcattgttag tggccagaca tttgaactcc cgttttttg tctataagaa ttcggaaaca    420
tatagtatcc tttgaaaacg gagaaacaaa taacaatgtg gacaaactag atataatttc    480
aacacaagac tatgggaatg attttaccca ctaattataa tccgatcaca aggtttcaac    540
gaactagttt tccagatatc aaccaaattt actttggaat taaactaact taaaactaat    600
tggttgttcg taaatggtgc tttttttttt tgcggatgtt agtaaagggt tttatgtatt    660
ttatattatt agttatctgt tttcagtgtt atgttgtctc atccataaag tttatatgtt    720
ttttctttgc tctataactt atatatatat atgagtttac agttatattt atacatttca    780
gatacttgat cggcatttt tttggtaaaa aatatatgca tgaaaactc aagtgtttct    840 ttttaagga attttaaat ggtgattata tgaatataat catatgtata tccgtatata    900
tatgtagcca gatagttaat tatttggggg atatttgaat tattaatgtt ataatattct    960
ttcttttgac tcgtctggtt aaattaaaga acaaaaaaaa cacatactt tactgttta    1020 aaaggttaaa ttaacataat ttattgatta caagtgtcaa gtccatgaca ttgcatgtag   1080
gttcgagact tcagagataa cggaagagat cgataattgt gatcgtaaca tccagatatg   1140
tatgtttaat tttcatttag atgtggatca gagaagataa gtcaaactgt cttcataatt   1200
```

-continued

```
taagacaacc tctttaata ttttcccaaa acatgtttta tgtaactact ttgcttatgt    1260
gattgcctga ggatactatt attctctgtc tttattctct tcacaccaca tttaaatagt    1320
ttaagagcat agaaattaat tattttcaaa aaggtgatta tatgcatgca aaatagcaca    1380
ccatttatgt ttatattttc aaattattta atacatttca atatttcata agtgtgattt    1440
tttttttttt tgtcaatttc ataagtgtga tttgtcattt gtattaaaca attgtatcgc    1500
gcagtacaaa taacagtgg gagaggtgaa aatgcagtta taaaactgtc caataattta    1560
ctaacacatt taaatatcta aaaagagtgt ttcaaaaaaa attcttttga aataagaaaa    1620
gtgatagata tttttacgct ttcgtctgaa aataaaacaa taatagttta ttagaaaaat    1680
gttatcaccg aaaattattc tagtgccact cgctcggatc gaaattcgaa agttatattc    1740
tttctcttta cctaatataa aaatcacaag aaaaatcaat ccgaatatat ctatcaacat    1800
agtatatgcc cttacatatt gtttctgact tttctctatc cgaatttctc gcttcatggt    1860
ttttttttaa catattctca tttaattttc attactatta tataactaaa agatggaaat    1920
aaaataaagt gtctttgaga atcgaacgtc catatcagta agatagtttg tgtgaaggta    1980
aaatctaaaa gatttaagtt ccaaaaacag aaaataatat attacgctaa aaagaagaa    2040 aataattaaa tacaaaacag aaaaaaataa tatacgacag acacgtgtca cgaagatacc    2100
ctacgctata gacacagctc tgttttctct tttctatgcc tcaaggctct cttaacttca    2160
ctgtctcctc ttcggataat cctatccttc tcttcctata aatacctctc cactcttcct    2220
cttcctccac cactacaacc acca                                           2244
```

<210> SEQ ID NO 110
<211> LENGTH: 2365
<212> TYPE: DNA
<213> ORGANISM: Arabidopsis thaliana
<220> FEATURE:
<223> OTHER INFORMATION: ARSK1 (Root-specific Kinase 1) root-specific promoter

<400> SEQUENCE: 110

```
ggcgagtgat ggtatattta ttggttgggc ttaaatatat ttcagatgca aaaccatatt      60
gaatcaataa attataaata catagcttcc ctaaccactt aaaccaccag ctacaaaacc     120
aataaacccg atcaatcatt atgttttcat aggatttcct gaacatacat taaattattt     180
ttcattttct tggtgctctt ttctgtctta ttcacgtttt aatggacata atcggtttca     240
tattgtaaat ctctttaacc taacgaacaa tttaatgacc ctagtaatag gataagaagg     300
tcgtgaaaaa tgaacgagaa aaacccacc aaaacactat ataagaaaga ccgaaaaagt     360 aaaagggtg agccataaac caaaaacctt accagatgtt gtcaaagaac aaaaatcatc     420
atccatgatt aacctacgct tcactactaa gacaaggcga ttgtgtcccg gttgaaaagg     480
ttgtaaaaca gtttgaggat gctacaaaag tggatgttaa gtatgaagcg ctaaggttt     540 tggatttggt ctaggagcac attggttaag caatatcttc ggtggagatt gagttttag     600 agatagtaga tactaattca tctatggaga catgcaaatt catcaaaatg cttggatgaa     660
ttagaaaaac taggtggaga atacagtaaa aaaattcaaa aagtgcatat tgtttggaca     720
acattaatat gtacaaatag tttacatta aatgtattat tttactaatt aagtacatat     780
aaagttgcta aactaaacta atataatttt tgcataagta aatttatcgt taaaagttt     840 cttctagcc actaaacaac aatacaaaat cgcccaagtc acccattaat taatttagaa     900 gtgaaaaca aaatcttaat tatatggacg atcttgtcta ccatatttca agggctacag    960
```

-continued

```
gcctacagcc gccgaataaa tcttaccagc cttaaaccag aacaacggca aataagttca    1020
tgtggcggct ggtgatgatt cacaatttcc ccgacagttc tatgataatg aaactatata    1080
attattgtac gtacatacat gcatgcgacg aacaacactt caatttaatt gttagtatta    1140
aattacattt atagtgaagt atgttgggac gattagacgg atacaatgca cttatgttct    1200
ccggaaaatg aatcatttgt gttcagagca tgactccaag agtcaaaaaa gttattaaat    1260
ttatttgaat ttaaaactta aaaatagtgt aattttttaac cacccgctgc cgcaaacgtt    1320
ggcggaagaa tacgcggtgt taaacaattt ttgtgatcgt tgtcaaacat ttgtaaccgc    1380
aatctctact gcacaatctg ttacgtttac aatttacaag ttagtataga agaacgttcg    1440
tacctgaaga ccaaccgacc tttagttatt gaataaatga ttatttagtt aagagtaaca    1500
aaatcaatgg ttcaaatttg tttctcttcc ttacttctta aattttaatc atggaagaaa    1560
caaagtcaac ggacatccaa ttatggccta atcatctcat tctcctttca acaaggcgaa    1620
tcaaatcttc tttatacgta atatttattt gccagcctga aatgtatacc aaatcatttt    1680
taaattaatt gcctaaatta ttagaacaaa aactattagt aaataactaa ttagtcttat    1740
gaaactagaa atcgagatag tggaatatag agagacacca ttaaattcac aaaatcattt    1800
ttaaattacc taaattatta caacaaaaac tattagacag aactaagtct ataatgaaac    1860
gagagatcgt atttggaatg tagagcgaga gacaattttc aattcattga atatataagc    1920
aaaattatat agcccgtaga cttggtgag atgaagtcta agtacaaaca actgaatgaa    1980
tttataatca ataatattga ttatattgtg attagaaaaa gaaaacaact tgcgttattt    2040
ttcaatatta ttgtgaggat taatgtgaac atggaatcgt gtttctcctg aaaaaaatat    2100
cagcatagag cttagaacaa tataaatata tccaccaaaa ataacttcaa cattttata     2160 caactaatac aaaaaaaaaa aagcaaactt tttgtatata taaataaatt tgaaaactca    2220
aaggtcggtc agtacgaata agacacaaca actactataa attagaggac tttgaagaca    2280
agtaggttaa ctagaacatc cttaatttct aaacctacgc actctacaaa agattcatca    2340
aaaggagtaa aagactaact ttctc                                           2365
```

<210> SEQ ID NO 111
<211> LENGTH: 1510
<212> TYPE: DNA
<213> ORGANISM: Arabidopsis thaliana
<220> FEATURE:
<223> OTHER INFORMATION: RD29A (Desiccation-responsive 29a) stress inducible promoter

<400> SEQUENCE: 111

```
ggttgctatg gtagggacta tggggttttc ggattccggt ggaagtgagt ggggaggcag      60
tggcggaggt aagggagttc aagattctgg aactgaagat ttggggtttt gcttttgaat     120
gtttgcgttt ttgtatgatg cctctgtttg tgaactttga tgtatttat ctttgtgtga     180 aaagagatt gggttaataa aatatttgct ttttggata agaaactctt ttagcggccc      240
attaataaag gttacaaatg caaaatcatg ttagcgtcag atatttaatt attcgaagat     300
gattgtgata gatttaaaat tatcctagtc aaaagaaag agtaggttga gcagaaacag     360
tgacatctgt tgtttgtacc atacaaatta gtttagatta ttggttaaca tgttaaatgg    420
ctatgcatgt gacatttaga ccttatcgga attaatttgt agaattatta attaagatgt    480
tgattagttc aaacaaaaat tttatattaa aaaatgtaaa cgaatatttt gtatgttcag    540
tgaaagtaaa acaaattaaa ttaacaagaa acttatagaa gaaaattttt actatttaag    600
agaaagaaaa aaatctatca tttaatctga gtcctaaaaa ctgttatact aacagttaa     660
```

```
cgcatgattt tgatggaggag ccatagatgc aattcaatca aactgaaatt tctgcaagaa    720
tctcaaacac ggagatctca aagtttgaaa gaaaatttat ttcttcgact caaaacaaac    780
ttacgaaatt taggtagaac ttatatacat tatattgtaa ttttttgtaa caaaatgttt    840
ttattattat tatagaattt tactggttaa attaaaaatg aatagaaaag gtgaattaag    900
aggagagagg aggtaaacat tttcttctat tttttcatat tttcaggata aattattgta    960
aaagtttaca agatttccat ttgactagtg taaatgagga atattctcta gtaagatcat   1020
tatttcatct acttctttta tcttctacca gtagaggaat aaacaatatt tagctccttt   1080
gtaaatacaa attaattttc cttcttgaca tcattcaatt ttaattttac gtataaaata   1140
aaagatcata cctattagaa cgattaagga gaaatacaat tcgaatgaga aggatgtgcc   1200
gtttgttata ataaacagcc acacgacgta aacgtaaaat gaccacatga tgggccaata   1260
gacatggacc gactactaat aatagtaagt tacattttag gatggaataa atatcatacc   1320
gacatcagtt ttgaaagaaa agggaaaaaa agaaaaaata aataaaagat atactaccga   1380
catgagttcc aaaaagcaaa aaaaaagatc aagccgacac agacacgcgt agagagcaaa   1440
atgactttga cgtcacacca cgaaaacaga cgcttcatac gtgtcccttt atctctctca   1500
gtctctctat                                                          1510

<210> SEQ ID NO 112
<211> LENGTH: 4801
<212> TYPE: DNA
<213> ORGANISM: Arabidopsis thaliana
<220> FEATURE:
<223> OTHER INFORMATION: AS1 (emergent leaf primordia-specific) promoter

<400> SEQUENCE: 112
ggaccgtgta atgggccatt gggccaagtt ttcttgatat aaaatctgaa atactactaa     60
attacaattt ttcttaaact cgatttcata attcatgtgg gactcagttc tccgcgtctt    120
atgacttaag agttaagagt aaagacaatt gattgtagtt tgcattatta aggttgtgat    180
tttaaaggct atattggccc aggcaaagtg gttatgaaag ttaaaaggta ttattaaatg    240
tcgttatgga ctagctaaag aaaagagatg gatatagaaa cggatttgcc agtttgtgag    300
gttacgtact cgttactttc tattgcattt ttgtgtgtca ttgtgcttgt gatttcttta    360
gtatatgttt ttcttttttgt caaactctttt agtacatgtt atgctttatt ttcttgttta    420
gcattgttat tgttattttg atccatgttc tttacttaa tgtgtagagt gttcacgtac    480
gactctttat gatcgctata ctaatatact atgaaactcg aatgagaaca tgcatgtcat    540
aaatcaataa aacataacat acgacactta acctaaatca tacattcatt gattcatact    600
atcatgatcc tcatcacatt agtatcattt gtctttattt attacttagc tacttcgtta    660
tcttattata tctttacctg ttctgctggt catttgccat aaacaccaag tacaagcaac    720
tctttagtcc aatatcagac caaattaaca aacatttccc caatccaaaa cggaaattta    780
attataatta gcatttaaat aggttcgatt acaaaaaaaa atcaacaaag gaacaagtca    840
atttcataat ggtttgtcaa ttgtcacaca acgaaatggc tagccggatc aagcatgcat    900
gatccaaatt tcaacatttc catgataacc tgaattataa cgtctacata aaccatattt    960 aaataaaatag gatggtcgaa agatatcatt aaaagaacga ttcaatattc tttattgttc   1020
aattgataca catgttattc tccttaacca gttatgaaca tgtcctacaa gtttcttgac   1080
ccaaactcat aatttcatat accataatcc caagttaagt tttttttttt tgggatcaa   1140 aatctcaagt taagttaagt tcaattattt agctgtaatg ctcggaaaaa agatcggatg   1200
```

-continued

```
aatatccaat tggttcaata tataccccaa tccggccaat ctccctatct ttatagctta    1260
attattagag aatggtcaat tcacgccatc agaaccagtt tcatatcttc atgaaccaaa    1320
acgcctacaa ccctattatt caagaaatca ctataattgt ccaagtaaaa ccattaatta    1380
accgagtcga ttttctatg gtcctatagg catgttgtta ctcaaactac tgattaatta     1440
ataagaagtt gtagtttgaa aaagaatcta gctgaaaaat actcctactc taagaattta    1500
agttagaata aaacatatta atacaaatat aaaaatttag ttattaaaaa agcgctacta    1560
ccaagacgtc ctaaagaaaa actagctttg tcttctaaaa gaaaacctag cttaactacc    1620
caaaaaaatc tagttttaca aacactaaag acaaatttta ttttcaaca aatttaccaa     1680 ttaaagaaaa ttccatgtag gaatgtatcc aaattgaaaa tatccctaca tattttgtag    1740
gaaaaaaggt tttataaat attaaaaaaa cgagaaaaag aaaagagaaa agagaaaaaa     1800
aaaagccgga gagaatggag cacatgaggt aaaaggcaag agatggcaga gagaagatca    1860
gagaagggat ctgcctcaat ttgacaactc atatgtcatg tcatttccct cactactatt    1920
attttcctat ttcaaaaaca cctttctctg ataccatcac cttttacctt ctcttttttt    1980
ttactgtctt tgctctgttt cacattccct tctatatata cagtatagta tattttatcc    2040
ttcttttatt gttttgctta ctaaaagttt ttttcctccg gaatcaaaat tctaaaatgt    2100
atatcatgtt aggtcgcgag ggccatgcaa tattatgaac tatgcatgat gattaatgtc    2160
tgtggatcca tcacaaatat tattgaaggt tgatcagaga ctatggacca aaatggtccg    2220
aatcgcctga taataaaaaa ctattcattt ttattttta ttttttttat taaacatgtg     2280
attaatgata gatcttacga ttcgcaactg ggaaacatgc actaactcaa acttaaaaca    2340
cacaatacta aaagttctat taaattttga atgtaaagag aaatatatta ggcaatcaaa    2400
cggtcaagta aatcatacac atcgataatt tattttttta tccttcaaag caggcccatc    2460
caaggcccac cactattctc atatcaacat acttttcttg ttttggttaa atcaacctac    2520
catgttggct gttctctccg ctcctctgtg taagatcaca ccaacaccac tgcataattt    2580
cttgtattat tttgagactt gagagtaaac tgattgacaa aaaaaaaaa aaaaaaaaa      2640 aattgagagt aaactagttt cttgaatatt gatttttca gcttaatttg ttggggaaag    2700
atattactac tattgctgta aaaaaaaaa aaaaaaaaa agatattatt actatatttg     2760
tagtgatttt attttgaaaa ttctcttcac ttttttgtag ttaacattct aattttgtga    2820
aaagaacttt taatgtcagg tcatgtctct taaaagtttt gcatgatgaa atgatttaca    2880
aattacaata gaaaatggaa accattgcaa actaaatttt tatcaaaaaa aatcgaaaat    2940
aaaatgtatt gacttagtaa tgctgtgtct gctacgatta actattacac ataatgcaac    3000
actgaattat ccaaatacat tattagaata atagtattac agtatcacta ttacaacaac    3060
aatgtcaaca ataatcttat tataataata tataaataga ccttagtgac atcatatatt    3120
atagaaaaca tgtggttgcc taatttgtat aagctagata cttgggggtg atgagtgact    3180
agttgatgca atgataaaag agtgaaagtt ttgtctgcct gattatagac gtcggagaaa    3240
tactaaaata cgctatgaag attttggcgc atggtagcag aaaaaaaaa cggagggtgt     3300 gagtgagtag tggtagtcgg atgtgatgga acaaagaaaa gtattttggg tagggttatg    3360
ggagagagaa ggggaccatt attacacact tacatgcttt ccccaaaaga taccattccc    3420
attttctgac acgtgtcccc ctcatcccca attactcata cgtcaaatcc aattttttagc   3480 ctaaaagttt ttttatttg tttagccaaa tctattttac taattaaagt tttcaaatgg     3540
caaatagaaa gatcttctaa ggttttataa aattacttga ttatttctag ttttgctcat    3600
```

```
tttttaaata aaatttctct ttttttcctt gcaacattat tgatttttt tttgataggg    3660
agtaacatta gtgatgttct atctcttctc attgcaaaaa ctttatttc tcatctctat    3720
ttgatcatca ttgcgaaatc ttccattttc aacaaatact tttccatgtt aatatgctgt    3780
ttcaaaatat aagtgtttgg aaaataaatc aacaagttta aatgttaact attttttatgc   3840
tattataatt attttttctta tgggtaagtg gaaattaatg ttactcaaat tggacataaa    3900
attctattgt ttgagtgaag gagtttataa atggagcatt attttcttga atggttagtt    3960
tttcttctat cattttgaca agtaaatgac ttttcagcca ctaaagtaca acactttttc    4020
atttaaattt aaagcatccc ctacattaga ttgtcatttt atttctcata atgttataga    4080
aaaatgaatt ttgagatccc aatgtagtaa atatatataa aaaaaggttt aatattgtca    4140
atgacaaaca acgaacttat ggaatttcaa ctttcaccct ccacgcgcct ctgtcagagt    4200
tttttttttc cccacttgtg atgtaaaaag gggaaaacgt ctgtgtctca gtcggtaaac    4260
ttttctctc tttttttttt taaagatttt attttaatta tgccgtctct gtggtctaat    4320
cgtgtacgtc gtctggtttt aaaagcctct ctcactttgg tcttttcgtt ttctctcttc    4380
cattttctcc aactatataa aaaaaaaaa gtgagagaga gagcaaatct gtgtgatgga    4440
agttgctctt gagtttggga ttatttatct tttcaatatc atttggtaag cattttatt    4500
ttgttttata gtaataattt taactctctt atcttcttaa taagtctttg cttaatagtg    4560
ttttggggtc agcattaatt tccctgttt ggtttccaga atataggttg tatagtgtga    4620
taataacaaa ttattccaag ttttgcttca aacattgtca aagttttgt cattttcatt    4680
tcttgaaacg gaaattttc agactttgta atttctaatt cgaaaattcg acagatcttg    4740
tagatttgtt tcgatctttt agagttttga attggagaga tttatgaaac gggttgattt    4800
t                                                                    4801

<210> SEQ ID NO 113
<211> LENGTH: 1009
<212> TYPE: DNA
<213> ORGANISM: Solanum lycopersicum
<220> FEATURE:
<223> OTHER INFORMATION: RBCS3 (Ribulose 1,5-bisphosphate carboxylase,
      small subunit 3) leaf-specific promoter

<400> SEQUENCE: 113
aaatggagta atatggataa tcaacgcaac tatatagaga aaaataata gcgctaccat      60
atacgaaaaa tagtaaaaaa ttataataat gattcagaat aaattattaa taactaaaaa     120
gcgtaaagaa ataaattaga gaataagtga tacaaaattg gatgttaatg gatacttctt     180
ataattgctt aaaaggaata caagatggga aataatgtgt tattattatt gatgtataaa     240
gaatttgtac aattttttgta tcaataaagt tccaaaaata atctttaaaa aataaaagta     300
cccttttatg aacttttttat caaataaatg aaatccaata ttagcaaaac attgatatta    360
ttactaaaata tttgttaaat taaaaaatat gtcatttat ttttaacag atattttta      420
aagtaaatgt tataaattac gaaaaaggga ttaatgagta tcaaaacagc ctaaatggga    480
ggagacaata acagaaattt gctgtagtaa ggtggcttaa gtcatcattt aatttgatat    540
tataaaaatt ctaattagtt tatagtctttt cttttcctct tttgtttgtc ttgtatgcta    600
aaaaaggtat attatatcta taaattatgt agcataatga ccacatctgg catcatcttt    660
acacaattca cctaaaatatc tcaagcgaag ttttgccaaa actgaagaaa agatttgaac    720
aacctatcaa gtaacaaaaa tcccaaacaa tatagtcatc tatattaaat cttttcaatt    780
```

-continued

```
gaagaaattg tcaaagacac atacctctat gagttttttc atcaattttt ttttctttttt      840 taaactgtat ttttaaaaaa atattgaata aaacatgtcc tattcattag tttgggaact       900
ttaagataag gagtgtgtaa tttcagaggc tattaatttt gaaatgtcaa gagccacata      960
atccaatggt tatggttgct cttagatgag gttattgctt taggtgaaa                   1009
```

<210> SEQ ID NO 114
<211> LENGTH: 9
<212> TYPE: PRT
<213> ORGANISM: Arabidopsis thaliana
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<223> OTHER INFORMATION: conserved residues within HFM and B domain, where Xaa can be any amino acid and-
 first Xaa is 19-26 re
sidues in length, second Xaa is 3 residues, third Xaa is 4 residues, fourth Xaa is 7 residues in length

<400> SEQUENCE: 114

Asn Xaa Lys Xaa Gln Xaa Glu Xaa Glu
1               5

<210> SEQ ID NO 115
<211> LENGTH: 16
<212> TYPE: PRT
<213> ORGANISM: Arabidopsis thaliana
<220> FEATURE:
<221> NAME/KEY: misc_feature
<222> LOCATION: (3)..(3)
<223> OTHER INFORMATION: Xaa can be K or R
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 115

Pro Lys Xaa Pro Ala Gly Arg Xaa Lys Phe Xaa Glu Thr Arg His Pro
1               5                   10                  15

<210> SEQ ID NO 116
<211> LENGTH: 5
<212> TYPE: PRT
<213> ORGANISM: Arabidopsis thaliana

<400> SEQUENCE: 116

Asp Ser Ala Trp Arg
1               5

What is claimed is:

1. A method of producing a transgenic plant having enhanced tolerance to cold, the method comprising:
   (a) introducing into a plant or plants a recombinant polynucleotide encoding a polypeptide that is at least 90% identical to SEQ ID NO: 10;
   (b) exposing the plant or plants to a cold stress; and
   (c) selecting from the plant or plants a transgenic plant that expresses the polypeptide which, when expressed in the transgenic plant, confers greater cold tolerance to the transgenic plant than the cold tolerance of a control plant that does not contain the recombinant polynucleotide.

2. The method of claim 1, wherein the polypeptide is at least 93% identical to SEQ ID NO: 10.

3. The method of claim 1, wherein the polypeptide is at least 96% identical to SEQ ID NO: 10.

4. The method of claim 1, wherein the polypeptide comprises SEQ ID NO: 10.

5. The method of claim 1, wherein the transgenic plant is more tolerant to 8° C. than the control plant.

6. The method of claim 1, wherein the transgenic plant is selected from the group consisting of a soy plant, a corn plant, and a rice plant.

7. The method of claim 1, wherein expression of the polypeptide in the transgenic plant is regulated by a constitutive, tissue-specific or inducible promoter.

8. The method of claim 1, wherein the transgenic plant is a transgenic seed comprising the nucleic acid construct.

9. The method of claim 1, wherein the transgenic plant is a host plant cell.

10. The method of claim 1, wherein the transgenic plant produces a greater yield than the control plant.

11. The method of claim 1, wherein the recombinant polynucleotide is introduced into the plant or plants by breeding with a parent plant comprising said recombinant polynucleotide.

12. A method of producing a transgenic plant having enhanced tolerance to cold, the method comprising:
   (a) introducing into a plant or plants a recombinant polynucleotide encoding a polypeptide that is at least 90% identical to SEQ ID NO: 10;
   (b) exposing the plant or plants to a cold stress; and
   (c) selecting from the plant or plants a transgenic plant that produces a greater yield than the control plant that does not contain the recombinant polynucleotide.

13. The method of claim 12, wherein the yield is selected from the group consisting of increased plant growth, increased crop growth, increased biomass, and increased plant product production.

14. The method of claim 12, wherein the polypeptide is at least 93% identical to SEQ ID NO: 10.

15. The method of claim 12, wherein the polypeptide is at least 96% identical to SEQ ID NO: 10.

16. The method of claim 12, wherein the polypeptide comprises SEQ ID NO: 10.

17. The method of claim 12, wherein the transgenic plant is more tolerant to 8° C. than the control plant.

18. The method of claim 12, wherein the transgenic plant is selected from the group consisting of a soy plant, a corn plant, and a rice plant.

19. The method of claim 12, wherein expression of the polypeptide in the transgenic plant is regulated by a constitutive, tissue-specific or inducible promoter.

20. The method of claim 12, wherein the transgenic plant is a transgenic seed comprising the nucleic acid construct.

21. The method of claim 12, wherein the transgenic plant is a host plant cell.

22. The method of claim 12, wherein the recombinant polynucleotide is introduced into the plant or plants by breeding with a parent plant comprising said recombinant polynucleotide.

* * * * *